(12) United States Patent
Bolli et al.

(10) Patent No.: US 9,150,566 B2
(45) Date of Patent: Oct. 6, 2015

(54) 2-(1,2,3-TRIAZOL-2-YL)BENZAMIDE AND 3-(1,2,3-TRIAZOL-2-YL)PICOLINAMIDE DERIVATIVES AS OREXIN RECEPTOR ANTAGONISTS

(71) Applicants: Martin Bolli, Allschwil (CH); Christoph Boss, Allschwil (CH); Christine Brotschi, Allschwil (CH); Bibia Heidmann, Allschwil (CH); Thierry Sifferlen, Allschwil (CH); Jodi T. Williams, Allschwil (CH)

(72) Inventors: Martin Bolli, Allschwil (CH); Christoph Boss, Allschwil (CH); Christine Brotschi, Allschwil (CH); Bibia Heidmann, Allschwil (CH); Thierry Sifferlen, Allschwil (CH); Jodi T. Williams, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 14/357,159

(22) PCT Filed: Nov. 7, 2012

(86) PCT No.: PCT/IB2012/056218
§ 371 (c)(1),
(2) Date: May 8, 2014

(87) PCT Pub. No.: WO2013/068935
PCT Pub. Date: May 16, 2013

(65) Prior Publication Data
US 2015/0158855 A1   Jun. 11, 2015

(30) Foreign Application Priority Data
Nov. 8, 2011   (WO) .................. PCT/IB2011/054976

(51) Int. Cl.
*C07D 413/10*   (2006.01)
*C07D 413/14*   (2006.01)
*C07D 417/14*   (2006.01)
*A61K 31/5377*   (2006.01)

(52) U.S. Cl.
CPC .......... *C07D 417/14* (2013.01); *A61K 31/5377* (2013.01); *C07D 413/10* (2013.01); *C07D 413/14* (2013.01)

(58) Field of Classification Search
CPC .. C07D 413/10; C07D 413/14; C07D 417/14; A61K 31/53777
See application file for complete search history.

(56) References Cited

U.S. PATENT DOCUMENTS

| 7,763,638 B2 | 7/2010 | Aissaoui et al. |
| 8,288,411 B2 | 10/2012 | Aissaoui et al. |
| 2009/0082394 A1 | 3/2009 | Jenck |
| 2010/0234420 A1 | 9/2010 | Jenck |

FOREIGN PATENT DOCUMENTS

| WO | WO 93/00313 A2 | 1/1993 |
| WO | WO 02/089800 A2 | 11/2002 |
| WO | WO 03/002559 A2 | 1/2003 |
| WO | WO 03/002561 A1 | 1/2003 |
| WO | WO 03/032991 A1 | 4/2003 |
| WO | WO 03/051368 A1 | 6/2003 |
| WO | WO 2008/008517 A2 | 1/2008 |
| WO | WO 2008/047109 A1 | 4/2008 |
| WO | WO 2008/069997 A1 | 6/2008 |
| WO | WO 2010/048010 A1 | 4/2010 |
| WO | WO 2010/048012 A1 | 4/2010 |
| WO | WO 2010/048013 A1 | 4/2010 |
| WO | WO 2010/063662 A1 | 6/2010 |
| WO | WO 2010/063663 A1 | 6/2010 |
| WO | WO 2011/050198 A1 | 4/2011 |
| WO | WO 2011/050200 A1 | 4/2011 |
| WO | WO 2011/050202 A1 | 4/2011 |

OTHER PUBLICATIONS

Adam, T.C., et al., "Stress, Eating and the Reward System", Physiology & Behavior, vol. 91, (2007), pp. 449-458, doi:10.1016j.physbeh.2007.04.011.

Aston-Jones, G., et al., "Lateral Hypothalamic Orexin/Hypocretin Neurons: A Role in Reward-Seeking and Addiction", Brain Research, (2009), doi:10.1016/j.brain.res.2009.09.106, (uncorrected proof).

(Continued)

*Primary Examiner* — Rebecca Anderson
(74) *Attorney, Agent, or Firm* — Hoxie & Associates LLC

(57) ABSTRACT

The present invention relates to 2-(1,2,3-triazol-2-yl)benzamide and 3-(1,2,3-triazol-2-yl)picolinamide derivatives of formula (I)

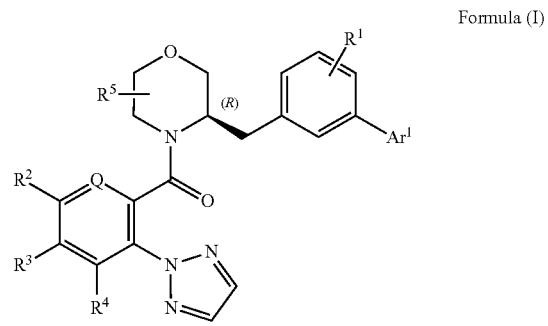

Formula (I)

wherein $Ar^1$, Q, and $R^1$ to $R^5$ are as described in the description, to their preparation, to pharmaceutically acceptable salts thereof, and to their use as pharmaceuticals, to pharmaceutical compositions containing one or more compounds of formula (I), and especially to their use as orexin receptor antagonists.

27 Claims, No Drawings

(56) References Cited

OTHER PUBLICATIONS

Berridge, C.W., et al., "Hypocretin/Orexin in Arousal and Stress", Brain Research, (Feb. 16, 2010), 1314C:91. doi:10.1016/j.brainres. 2009.09.019.

Borgland, S. L., et al., "Orexin A in the VTA is Critical for the Induction of Synaptic Plasticity and Behavioral Sensitization to Cocaine", Neuron., vol. 49, pp. 589-601, (Feb. 16, 2006), doi:10. 1016/j.neuron.2006.01.016.

Boutrel, B., et al., "Role for Hypocretin in Mediating Stress-Induced Reinstatement of Cocaine-Seeking Behavior Behavior", PNAS, vol. 102, No. 52, pp. 19168-19173, www.pnas.org/cgi/doi/10.1073/pnas. 0507480102 , 2005.

Brisbare-Roch, C., et al., "Promotion of Sleep by targeting the Orexin System in Rats, Dogs and Humans", Nature Medicine, (Advance Online Publication), published online Jan. 28, 2007; doi:10.1038/ nm1544.

Boss, C., et al., "Biomedical Application of Orexin/Hypocretin Receptor Ligands in Neuroscience", J. Med. Chem., (2009), vol. 52, No. 4, pp. 891-903, doi:10.1021/jm801296d, (published on Web Jan. 20, 2009).

Carter, M. E., et al., "The Brain Hypocretins and Their Receptors: Mediators of Allostatic Arousal", Current Opinion in Pharmacology, (2009), vol. 9, pp. 1-7, doi:10.1016/j.coph.2008.12.018.

Chemelli, R. M., et al., "Narcolepsy in Orexin Knockout Mice: Molecular Genetics of Sleep Regulation", Cell. vol. 98, pp. 437-451, (Aug. 20, 1999).

Chrousos, G. P., et al., "The Concepts of Stress and Stress System Disorders—Overview of Physical and Behavioral Homeostasis", JAMA, (1992), vol. 267, No. 9, pp. 1244-1252.

Dietrich, H., et al., "Intact Learning and Memory in Rats Following Treatment with the Dual Orexin Receptor Antagonist Almorexant", Psychopharmacology, (2010), vol. 212, pp. 145-154, doi:10.1007/ s00213-010-01933-5, (published online Jul. 15, 2010).

Feng, P., et al., "Changes in Brain Orexin Levels in a Rat Model of Depression Induced by Neonatal Administration of Clomipramine", Journal of Psychopharmacology, (2008), vol. 22, No. 7, pp. 784-791, doi:10.1177/0269881106082899.

Foulds Mathes, W., et al., "The Biology of Binge Eating", Appetite, vol. 52, (2009), pp. 545-553, doi:10.1016/j.appet.2009.03.005.

Furlong, T. M., et al., "Hypocretin/Orexin Contributes to the Expression of Some but Not All Forms of Stress and Arousal", European Journal of Neuroscience, pp. 1-12, (2009), doi: 10.1111/j.1460-9568. 2009.06952.x.

Gould, P. L., "Salt Selection for Basic Drugs", International Journal of Pharmaceutics, vol. 33, (1986), pp. 201-217.

Gozzi, A., et al., "Functional Magnetic Resonance Imaging Reveals Different Neural Substrates for the Effects of Orexin-1 and Orexin-2 Receptor Antagonists", PLoS ONE, (published Jan. 28, 2011), vol. 6, Issue 1, e16406, doi:10.1371/journal.pone.0016406, www.plosone. org.

Greenspan, P. D., et al., "Identification of Dipeptidyl Nitriles as Potent and Selective Inhibitors of Cathepsin B through Structure-Based Drug Design", J. Med. Chem., (2001), vol. 44, pp. 4524-4534, doi:10.1021/jm010206q, (published on Web Nov. 14, 2001).

Hollander, J. A., et al., "Insular Hypocretin Transmission Regulates Nicotine Reward" PNAS, vol. 105, (2008) No. 5, pp. 19479-19484, www.pnas.org/cgi/doi/10.1073/pnas.0808023105.

Hutcheson, D. M., et al., "Orexin-1 Receptor Antagonist SB-334867 Reduces the Acquisition and Expression of Cocaine-Conditioned Reinforcement and the Expression of Amphetamine-Conditioned Reward", Behavioural Pharmacology, (2011), doi:10.1097/FBP. 0b013e328343d761, (accepted as revised Dec. 15, 2010).

Kang, J., et al., "Amyloid-β Dynamics are Regulated by Orexin and the Sleep-Wake Cycle", Science Express, www.scienceexpress.org, Sep. 24, 2009, doi:10.1126/science.1180962.

Kayaba, Y., et al. "Attenuated Defense Response and Low Basal Blood Pressure in Orexin Knockout Mice", Am. J. Physiol. Regul. Integr. Comp. Physiol. vol. 285, pp. 8581-8598, (2003), (first published May 15, 2003), doi:10.1152/ajpregu.00671.2002.

Kazmierski, W. M., et al., "New, Potent P1/P2-Morpholinone-Based HIV-Protease Inhibitors", Bioorganic & Medicinal Chemistry Letters, vol. 16, (2006), pp. 5226-5230, doi: 10.1016/j.bmcl.2006.07. 014.

Koob, G. F., et al., "Neurobiological Mechanisms of Addiction: Focus on Corticotropin-Releasing Factor" , Current Opinion in Investigational Drugs, (2010), vol. 11, No. 1, pp. 63-71.

Langmead, C. J., et al., "Characterisation of the Binding of [$^3$H]-SB-674042, a Novel Nonpeptide Antagonist, to the Human Orexin-1 Receptor", British Journal of Pharmacology, (2004), vol. 141, pp. 340-346, (advance online publication Dec. 22, 2003), doi:10.1038/ sj.bjp.0705610.

Lawrence, A. J., et al., "The Orexin System Regulates Alcohol-Seeking in Rats", British Journal of Pharmacology, (2006), vol. 148, pp. 752-759, doi:10.1038/sj.bjp.0706789, (published online Jun. 5, 2006).

LeSage, M. G., et al., "Nicotine Self-Administration in the Rat: Effects of Hypocretin Antagonists and Changes in Hypocretin mRNA", Psychopharmacology, (2010), vol. 209, pp. 203-212, doi:10.1007/s00213-010-1792-0, (published online Feb. 24, 2010).

Liu, X., et al., "Insomnia and Hypersomnia Associated with Depressive Phenomenology and Comorbidity in Childhood Depression", SLEEP, (2007), vol. 30, No. 1, pp. 83-90.

Majzoub, J. A., "Corticotropin-Releasing Hormone Physiology", European Journal of Endocrinology, (2006), vol. 155, pp. S71-S76, doi:10.1530/eje.1.02247.

Moorthy, J. N., et al., "Photoinduced C-Br Homolysis of 2-Bromobenzophenones and Pschorr Ring Closure of 2-Aroylaryl Radicals to Fluorenones", J. Org. Chem. (2007), vol. 72, pp. 9786-9789, (published on Web Nov. 14, 2007), doi:10.1021/jo7017872.

Nollet, M., et al. "Activation of Orexin Neurons in Dorsomedial/ Perifornical Hypothalamus and Antidepressant Reversal in a Rodent Model of Depression", Neuropharmacology, (2011), doi:10.1016/j. neuropharm.2011.04.022.

Powers, J. J., et al., "Synthesis of methyl-, fluoro-, and chloro-substituted 6-hydroxyisoindolin-1-ones", Tetrahedron Letters, vol. 50, (2009), pp. 1267-1269, doi:1016/j.tetlet.2008.12.099, (available online Jan. 7, 2009).

Prud'Homme, M. J., et al., "Nutritional Status Modulates Behavioural and Olfactory Bulb Fos Responses to Isoamyl Acetate or Food Odour in Rats: Roles of Orexins and Leptin", Neuroscience, vol. 162, (2009), pp. 1287-1298, doi:10.1016/j.neuroscience.2009. 05.043.

Quarta, D., et al., "The Orexin-1 Receptor Antagonist SB-334867 Reduces Amphetamine-Evoked Dopamine Outflow in the Shell of the Nucleus Accumbens and Decreases the Expression of Amphetamine Sensitization", Neurochem. Int. (2009), doi:10.1016/j.neuint. 2009.08.012, (uncorrected proof).

Stickgold, R., "Sleep-Dependent Memory Consolidation", Nature, vol. 437, (Oct. 2005), doi:10.1038/nature04286, pp. 1272-1277.

Remington, The Science and Practice of Pharmacy, 21st Edition, 2005, Part 5, "Pharmaceutical Manufacturing", (front and back cover of book and Table of Contents).

Sakurai, T., et al., "Orexins and Orexin Receptors: A Family of Hypothalamic Neuropeptides and G Protein-Coupled Receptors that Regulate Feeding Behavior", Cell, vol. 92, pp. 573-585, (Feb. 20, 1998).

Salomon, R. M., et al., "Diurnal Variation of Cerebrospinal Fluid Hypocretin-1 (Orexin-A) Levels in Control and Depressed Subjects", Biol. Psychiatry, (2003), vol. 54, pp. 96-104, doi:10.1016/ S0006-3223(03)01740-7.

Sharf, R., et al., "Role of Orexin/Hypocretin in Dependence and Addiction", Brain Research, vol. 1314, pp. 130-138, (2010), (Available online Aug. 20, 2009), doi:10.1016/j.brainres.2009.08.028.

Smith, R. J., et al., "Orexin/Hypocretin Signaling at the $OX_1$ Receptor Regulates Cue-Elicited Cocaine-Seeking", Eur. J. Neurosci. (Aug. 2009), vol. 30, No. 3, pp. 493-503, doi:10.1111/j.1460-9568.2009. 06844x.

Smith, R. J., et al., "Orexin/Hypocretin is Necessary for Context-Driven Cocaine-Seeking", Neuropharmacology, (2009), doi:10. 1016/j.neuroopharm.2009.06.042, pp. 1-6, (uncorrected proof).

(56) References Cited

OTHER PUBLICATIONS

Spealman, R. D., et al., "Pharmacological and Environmental Determinants of Relapse to Cocaine-Seeking Behavior", Pharmacology Biochemistry and Behavior, vol. 64, No. 2, pp. 327-336, (1999).

Sutcliffe, J. G., et al., "The Hypocretins: Setting the Arousal Threshold", Nature Reviews, vol. 3, (May 2012), pp. 339-349, doi:10.1038/nrn808.

Shippenberg, T. S., et al., "Recent Advances in Animal Models of Drug Addiction", Neuropsychopharmacology: The Fifth Generation of Progress, Ch. 97: Recent Advances in Animal Models of Drug Addiction, pp. 1381-1397, (2002), Edited by K. L. Davis et al., American College of Neuropsychopharmacology.

Terashima, S., et al., "Synthetic Studies on Quinocarcin and Its Related Compounds. 3.[1,2] Synthesis of 5-Substituted- and 3,5-Disubstituted-2-formyl-pyrrolidine Derivatives, the Key D-Ring Fragments of Enantiomeric Pairs of Quinocarcin and 10-Decarboxyquinocarcin", Tetrahedron, vol. 50, No. 21, pp. 6221-6238, (1994).

Tsujino, N., et al, "Orexin-Hypocretin: A Neuropeptide at the Interface of Sleep, Energy Homeostasis, and Reward System", Pharmacol. Rev., vol. 61, No. 2, pp. 162-176, (2009), doi: 10.1124/pr.109.001321.

Winrow, C. J., et al., "Orexin Receptor Antagonism Prevents Transcriptional and Behavioral Plasticity Resulting from Stimulant Exposure", Neuropharmacology, (2009), doi:10.106/j.neuropharm.2009.07.008, pp. 1-10, (uncorrected proof).

Zhang, W., et al., "Multiple Components of the Defense Response Depend on Orexin: Evidence from Orexin Knockout Mice and Orexin Neuron-Ablated Mice", Autonomic Neuroscience: Basic and Clinical, vol. 126-127, (2006), pp. 139-145, doi:10.1016/j.autneu.2006.02.021.

U.S. Appl. No. 14/405,649, filed Dec. 4, 2014, Actelion Pharmaceuticals Ltd.

U.S. Appl. No. 14/434,997, filed Apr. 10, 2015, Actelion Pharmaceuticals Ltd.

2-(1,2,3-TRIAZOL-2-YL)BENZAMIDE AND 3-(1,2,3-TRIAZOL-2-YL)PICOLINAMIDE DERIVATIVES AS OREXIN RECEPTOR ANTAGONISTS

CROSS REFERENCE TO RELATED APPLICATIONS

This application is a United States Application under 35 U.S.C. 371 claiming benefit of PCT Application No. PCT/IB2012/056218, filed on Nov. 7, 2012, the contents of which are incorporated herein by reference, which claims the benefit of PCT Application No. PCT/IB2011/054976, filed on Nov. 8, 2011.

The present invention relates to novel 2-(1,2,3-triazol-2-yl)benzamide and 3-(1,2,3-triazol-2-yl)picolinamide derivatives of formula (I) and their use as pharmaceuticals. The invention also concerns related aspects including processes for the preparation of the compounds, pharmaceutical compositions containing one or more compounds of formula (I), and their use as orexin receptor antagonists, especially as orexin-1 receptor antagonists.

Orexins (orexin A or OX-A and orexinBor OX-B) are neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to the G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexin receptor antagonists are a novel type of nervous system or psychotropic drugs. Their mode of action in animals and humans involves either blockade of both orexin-1 and orexin-2 receptor (dual antagonists), or individual and selective blockade of either the orexin-1 or the orexin-2 receptor (selective antagonists) in the brain. Orexins were initially found to stimulate food consumption in rats suggesting a physiological role for these peptides as mediators in the central feedback mechanism that regulates feeding behaviour (Sakurai T. et al., Cell, 1998, 92, 573-585).

On the other hand, orexin neuropeptides and orexin receptors play an essential and central role in regulating circadian vigilance states. In the brain, orexin neurons collect sensory input about internal and external states and send short intra-hypothalamic axonal projections as well as long projections to many other brain regions. The particular distribution of orexin fibers and receptors in basal forebrain, limbic structures and brainstem regions—areas related to the regulation of waking, sleep and emotional reactivity-suggests that orexins exert essential functions as regulators of behavioral arousal; by activating wake-promoting cell firing, orexins contribute to orchestrate all brain arousal systems that regulate circadian activity, energy balance and emotional reactivity. This role opens large therapeutic opportunities for medically addressing numerous mental health disorders possibly relating to orexinergic dysfunctions [see for example: Tsujino N and Sakurai T, "Orexin/hypocretin: a neuropeptide at the interface of sleep, energy homeostasis, and reward systems.", Pharmacol Rev. 2009, 61:162-176; and Carter M E et al., "The brain hypocretins and their receptors: mediators of allostatic arousal.", Curr Op Pharmacol. 2009, 9: 39-45] that are described in the following sections. It was also observed that orexins regulate states of sleep and wakefulness opening potentially novel therapeutic approaches to insomnia and other sleep disorders (Chemelli R. M. et al., Cell, 1999, 98, 437-451).

Human memory is comprised of multiple systems that have different operating principles and different underlying neuronal substrates. The major distinction is between the capacity for conscious, declarative memory and a set of unconscious, non-declarative memory abilities. Declarative memory is further subdivided into semantic and episodic memory. Non-declarative memory is further subdivided into priming and perceptual learning, procedural memory for skills and habits, associative and non-associative learning, and some others. While semantic memory refers to the general knowledge about the world, episodic memory is autobiographical memory of events. Procedural memories refer to the ability to perform skill-based operations, as e.g. motor skills. Long-term memory is established during a multiple stage process through gradual changes involving diverse brain structures, beginning with learning, or memory acquisition, or formation. Subsequently, consolidation of what has been learned may stabilize memories. When long-term memories are retrieved, they may return to a labile state in which original content may be updated, modulated or disrupted. Subsequently, reconsolidation may again stabilize memories. At a late stage, long-term memory may be resistant to disruption. Long-term memory is conceptually and anatomically different from working memory, the latter of which is the capacity to maintain temporarily a limited amount of information in mind. Behavioural research has suggested that the human brain consolidates long-term memory at certain key time intervals. The initial phase of memory consolidation may occur in the first few minutes after we are exposed to a new idea or learning experience. The next, and possibly most important phase, may occur over a longer period of time, such as during sleep; in fact, certain consolidation processes have been suggested to be sleep-dependent [R. Stickgold et al., Sleep-dependent memory consolidation; Nature 2005, 437, 1272-1278]. Learning and memory processes are believed to be fundamentally affected in a variety of neurological and mental disorders, such as e.g. mental retardation, Alzheimer's disease or depression. Indeed, memory loss or impairment of memory acquisition is a significant feature of such diseases, and no effective therapy to prevent this detrimental process has emerged yet.

In addition, both anatomical and functional evidence from in vitro and in vivo studies suggest an important positive interaction of the endogenous orexin system with reward pathways of the brain [Aston-Jones G et al., Brain Res 2010, 1314, 74-90; Sharf R et al., Brain Res 2010, 1314, 130-138]. Selective pharmacological OXR-1 blockade reduced cue- and stress-induced reinstatement of cocaine seeking [Boutrel B, et al., "Role for hypocretin in mediating stress-induced reinstatement of cocaine-seeking behavior." Proc Natl Acad Sci 2005, 102(52), 19168-19173; Smith R J et al., "Orexin/hypocretin signaling at the orexin 1 receptor regulates cue-elicited cocaine-seeking." Eur J Neurosci 2009, 30(3), 493-503; Smith R J et al., "Orexin/hypocretin is necessary for context-driven cocaine-seeking." Neuropharmacology 2010, 58(1), 179-184], cue-induced reinstatement of alcohol seeking [Lawrence A J et al., Br J Pharmacol 2006, 148(6), 752-759] and nicotine self-administration [Hollander J A et al., Proc Natl Acad Sci 2008, 105(49), 19480-19485; LeSage M G et al., Psychopharmacology 2010, 209(2), 203-212]. Orexin-1 receptor antagonism also attenuated the expression of amphetamine- and cocaine-induced CPP [Gozzi A et al., PLoS One 2011, 6(1), e16406; Hutcheson D M et al., Behav Pharmacol 2011, 22(2), 173-181], and reduced the expression or development of locomotor sensitization to amphetamine and cocaine [Borgland S L et al., Neuron 2006, 49(4), 589-601; Quarta D et al., "The orexin-1 receptor antagonist SB-334867 reduces amphetamine-evoked dopamine outflow in the shell of the nucleus accumbens and decreases the expression of amphetamine sensitization." Neurochem Int 2010, 56(1), 11-15].

The effect of a drug to diminish addictions may be modelled in normal or particularly sensitive mammals used as animal models [see for example Spealman et al, Pharmacol. Biochem. Behav. 1999, 64, 327-336; or T. S. Shippenberg, G. F. Koob, "Recent advances in animal models of drug addiction" in Neuropsychopharmacology: The fifth generation of progress; K. L. Davis, D. Charney, J. T. Doyle, C. Nemeroff (eds.) 2002; chapter 97, pages 1381-1397].

Several converging lines of evidence furthermore demonstrate a direct role of the orexin system as modulator of the acute stress response. For instance, stress (i.e. psychological stress or physical stress) is associated with increased arousal and vigilance which in turn is controlled by orexins [Sutcliffe, J G et al., Nat Rev Neurosci 2002, 3(5), 339-349]. Orexin neurons are likely to be involved in the coordinated regulation of behavioral and physiological responses in stressful environments [Y. Kayaba et al., Am. J. Physiol. Regul. Integr. Comp. Physiol. 2003, 285:R581-593]. Hypocretin/orexin contributes to the expression of some but not all forms of stress and arousal [Furlong T M et al., Eur J Neurosci 2009, 30(8), 1603-1614]. Stress response may lead to dramatic, usually time-limited physiological, psychological and behavioural changes that may affect appetite, metabolism and feeding behavior [Chrousos, G P et al., *JAMA* 1992, 267(9), 1244-1252]. The acute stress response may include behavioural, autonomic and endocrinological changes, such as promoting heightened vigilance, decreased libido, increased heart rate and blood pressure, or a redirection of blood flow to fuel the muscles, heart and the brain [Majzoub, J A et al., European Journal of Endocrinology 2006, 155 (suppl_1) S71-S76].

As outlined above the orexin system regulates homeostatic functions such as sleep-wake cycle, energy balance, emotions and reward. Orexins are also involved in mediating the acute behavioral and autonomous nervous system response to stress [Zhang W et al., "Multiple components of the defense response depend on orexin: evidence from orexin knockout mice and orexin neuron-ablated mice." Auton Neurosci 2006, 126-127, 139-145]. Mood disorders including all types of depression and bipolar disorder are characterized by disturbed "mood" and feelings, as well as by sleeping problems (insomnia as well as hypersomnia), changes in appetite or weight and reduced pleasure and loss of interest in daily or once enjoyed activities [Liu X et al., Sleep 2007, 30(1): 83-90]. Thus, there is a strong rationale that disturbances in the orexin system may contribute to the symptoms of mood disorders. Evidence in humans, for instance, exists that depressed patients show blunted diurnal variation in CSF orexin levels [Salomon R M et al., Biol Psychiatry 2003, 54(2), 96-104]. In rodent models of depression, orexins were also shown to be involved. Pharmacological induction of a depressive behavioral state in rats, for instance, revealed an association with increased hypothalamic orexin levels [Feng P et al., J Psychopharmacol 2008, 22(7): 784-791]. A chronic stress model of depression in mice also demonstrated an association of molecular orexin system disturbances with depressed behavioral states and a reversal of these molecular changes by antidepressant treatment [Nollet et al., NeuroPharm 2011, 61(1-2):336-46].

The orexin system is also involved in stress-related appetitive/reward seeking behaviour (Berridge C W et al., Brain Res 2009, 1314, 91-102). In certain instances, a modulatory effect on stress may be complementary to an effect on appetitive/reward seeking behaviour as such. For instance, an $OX_1$ selective orexin receptor antagonist was able to prevent footshock stress induced reinstatement of cocaine seeking behaviour [Boutrel, B et al., Proc Natl Acad Sci 2005, 102(52), 19168-19173]. In addition, stress is also known to play an integral part in withdrawal which occurs during cessation of drug taking (Koob, G F et al., Curr Opin Investig Drugs 2010, 11(1), 63-71).

Orexins have been found to increase food intake and appetite [Tsujino, N, Sakurai, T, Pharmacol Rev 2009, 61(2) 162-176]. As an additional environmental factor, stress can contribute to binge eating behaviour, and lead to obesity [Adam, T C et al. Physiol Behav 2007, 91(4) 449-458]. Animal models that are clinically relevant models of binge eating in humans are described for example in W. Foulds Mathes et al.; Appetite 2009, 52, 545-553.

A number of recent studies report that orexins may play a role into several other important functions relating to arousal, especially when an organism must respond to unexpected stressors and challenges in the environment [Tsujino N and Sakurai T. Pharmacol Rev. 2009, 61:162-176; Carter M E, Borg J S and deLecea L., Curr Op Pharmacol. 2009, 9: 39-45; C Boss, C Brisbare-Roch, F Jenck, Journal of Medicinal Chemistry 2009, 52: 891-903]. The orexin system interacts with neural networks that regulate emotion, reward and energy homeostasis to maintain proper vigilance states. Dysfunctions in its function may thus relate to many mental health disorders in which vigilance, arousal, wakefulness or attention is disturbed.

The compound (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide (WO2005/118548), a dual orexin receptor antagonist, showed clinical efficacy in humans when tested for the indication primary insomnia. In the rat, the compound has been shown to decrease alertness, characterized by decreases in both active wake and locomotion; and to dose-dependently increase the time spent in both REM and NREM sleep [Brisbare et al., Nature Medicine 2007, 13, 150-155]. The compound further attenuated cardiovascular responses to conditioned fear and novelty exposure in rats [Furlong T M et al., Eur J Neurosci 2009, 30(8), 1603-1614]. It is also active in an animal model of conditioned fear: the rat fear-potentiated startle paradigm (WO2009/047723) which relates to emotional states of fear and anxiety diseases such as anxieties including phobias and post traumatic stress disorders (PTSDs). In addition, intact declarative and non-declarative learning and memory has been demonstrated in rats treated with this compound [WO2007/105177, H Dietrich, F Jenck, Psychopharmacology 2010, 212, 145-154]. Said compound furthermore decreased brain levels of amyloid-beta (Aβ) as well as AO plaque deposition after acute sleep restriction in amyloid precursor protein transgenic mice [J E Kang et al., "Amyloid-beta dynamics are regulated by orexin and the sleep-wake cycle.", Science 2009, 326(5955): 1005-1007]. The accumulation of the Aβ in the brain extracellular space is hypothesized to be a critical event in the pathogenesis of Alzheimer's disease. The so-called and generally known "amyloid cascade hypothesis" links Aβ to Alzheimer's disease and, thus, to the cognitive dysfunction, expressed as impairment of learning and memory. The compound has also been shown to induce antidepressant-like activity in a mouse model of depression, when administered chronically [Nollet et al., NeuroPharm 2011, 61(1-2):336-46]. Moreover, the compound has been shown to attenuate the natural activation induced by orexin A in fasted hungry rats exposed to food odors [M J Prud'homme et al., Neuroscience 2009, 162(4), 1287-1298]. The compound also displayed pharmacological activity in a rat model of nicotine self-administration [LeSage M G et al., Psychopharmacology 2010, 209(2), 203-212]. Another dual orexin receptor antagonist, N-biphenyl-2-yl-1-{[(1-methyl-1H-benzimidazol-2-yl)sulfanyl]acetyl}-L-prolinamide inhibited nicotine-reinstatement for a conditioned reinforcer and reduced behavioral (locomotor sensitization) and molecular (transcriptional responses) changes induced by repeated amphetamine administration in rodents [Winrow et al., Neuropharmacology 2009, 58(1), 185-94].

WO2003/002559 discloses N-aroyl cyclic amine derivatives encompassing morpholine derivatives as orexin receptor antagonists. A particular pyrrolidine derived orexin-1 selective compound within the scope of WO2003/002559 is disclosed in Langmead et. al, Brit. J. Pharmacol. 2004, 141, 340-346: 1-(5-(2-fluoro-phenyl)-2-methyl-thiazol-4-yl)-1-[(S)-2-(5-phenyl-[1,3,4]oxadiazol-2-ylmethyl)-pyrrolidin-1-yl)-methanone. The present compounds are different from the compounds disclosed in WO2003/002559 in view of the particular 2-(1,2,3-triazol-2-yl)benzamide and 3-(1,2,3-triazol-2-yl)picolinamide moiety and notably in view of the present particular benzyl substituent in position 3 of the morpholine moiety.

The present invention provides novel 2-(1,2,3-triazol-2-yl)benzamide and 3-(1,2,3-triazol-2-yl)picolinamide derivatives, which are non-peptide antagonists of human orexin receptors, especially the orexin-1 receptor. These compounds are in particular of potential use in the treatment of disorders relating to orexinergic dysfunctions, comprising especially anxiety disorders, addiction disorders, mood disorders, or appetite disorders, as well as cognitive dysfunctions or sleep disorders. The compounds of the present invention may notably be useful to treat mental health diseases or disorders relating to dysfunctions of the orexin 1 receptor.

1) A first aspect of the invention relates to compounds of the formula (I)

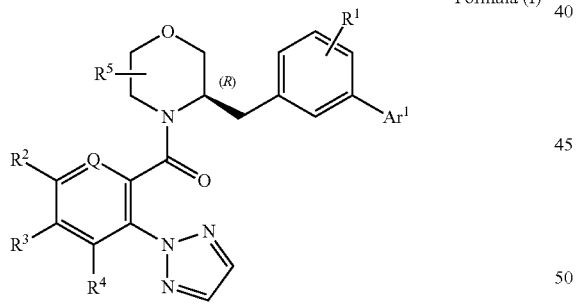

Formula (I)

wherein
Ar¹ represents a 5- or 6-membered heteroaryl selected from the group consisting of pyrrolyl, pyrazolyl, triazolyl, oxazolyl, thiazolyl, oxadiazolyl, thiophenyl, pyridinyl, pyrimidinyl, pyrazinyl, and pyridazinyl; wherein said heteroaryl is unsubstituted, mono-, or di-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;
R¹ represents one optional substituent selected from $(C_{1-4})$alkyl, $(C_{1-4})$alkoxy, hydroxy, and halogen;
R² represents hydrogen, $(C_{1-4})$alkyl, $(C_{1-4})$alkoxy, halogen, or cyano;
R³ represents hydrogen, $(C_{1-4})$alkyl, $(C_{1-4})$alkoxy, $(C_{1-3})$fluoroalkyl, or halogen;
R⁴ represents hydrogen, $(C_{1-4})$alkyl, $(C_{1-3})$fluoroalkyl, or halogen;
R⁵ represents one optional substituent on any ring carbon atom of the morpholine ring, wherein said substituent independently is methyl or ethyl; and
Q represents CR⁶; or, in case R² is $(C_{1-4})$alkyl or $(C_{1-4})$alkoxy, Q represents CR⁶ or N; wherein
R⁶ represents hydrogen, fluoro or methyl.

2) A second embodiment relates to compounds according to embodiment 1), wherein the morpholine ring of the compounds of formula (I):

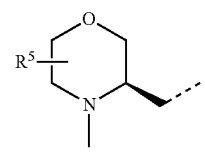

is a ring selected from the group consisting of:

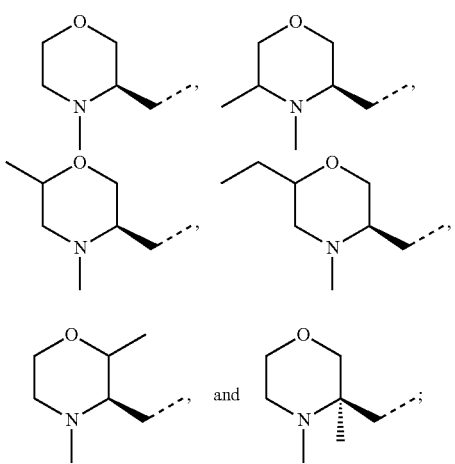

Ar¹ represents a 5- or 6-membered heteroaryl selected from the group consisting of pyrrolyl, pyrazolyl, triazolyl, oxazolyl, thiazolyl, oxadiazolyl, thiophenyl, pyridinyl, pyrimidinyl, pyrazinyl, and pyridazinyl; wherein said heteroaryl is unsubstituted or mono-substituted with $(C_{1-4})$alkyl (especially unsubstituted, or in case said heteroaryl is pyrimidinyl, optionally mono-substituted with methyl);
R¹ represents one optional substituent selected from methyl, methoxy, hydroxy, and halogen;
R² represents hydrogen, methyl, methoxy, halogen, or cyano;
R³ represents hydrogen, methyl, methoxy, trifluoroalkyl, or halogen;
R⁴ represents hydrogen, methyl, trifluoroalkyl, or halogen;
Q represents CR⁶; or, in case R² is methyl, Q represents CR⁶ or N; wherein
R⁶ represents hydrogen, fluoro or methyl.

3) A further embodiment relates to compounds according to embodiments 1) or 2), wherein the morpholine ring of the compounds of formula (I):

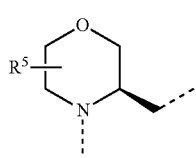

is a ring selected from the group consisting of:

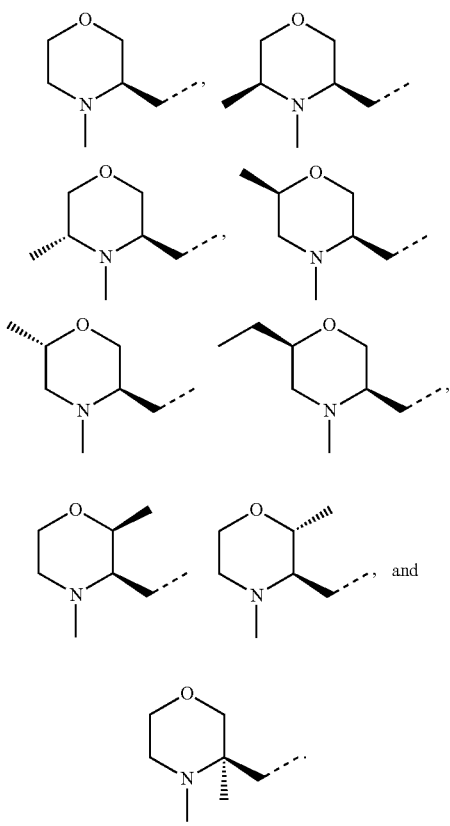

4) Another embodiment relates to compounds according to embodiments 1) or 2), wherein the morpholine ring of the compounds of formula (I):

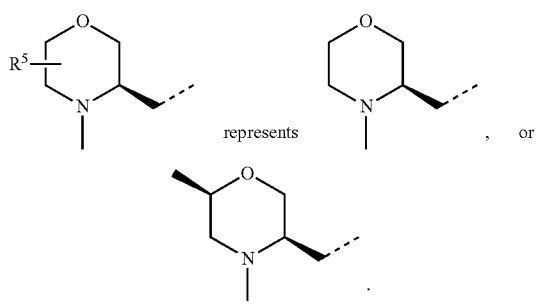

5) A further embodiment relates to compounds according to embodiments 1) or 2), wherein the morpholine ring of the compounds of formula (I):

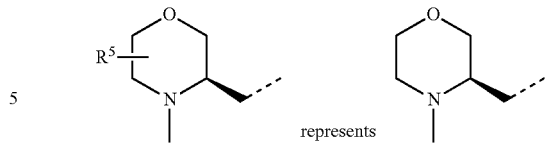 represents 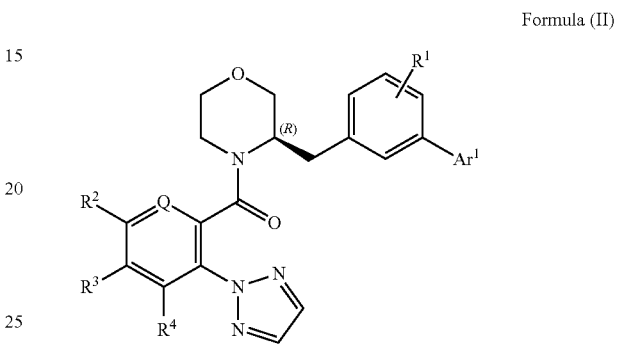.

6) A second aspect of the invention relates to compounds of formula (I) according to embodiment 1) which are also compounds of the formula (II)

Formula (II)

wherein
$Ar^1$ represents a 5- or 6-membered heteroaryl selected from the group consisting of pyrrolyl, pyrazolyl, triazolyl, oxazolyl, thiazolyl, oxadiazolyl, thiophenyl, pyridinyl, pyrimidinyl, pyrazinyl, and pyridazinyl; wherein said heteroaryl is unsubstituted, mono-, or di-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;
$R^1$ represents one optional substituent selected from $(C_{1-4})$alkyl, $(C_{1-4})$alkoxy, and halogen;
$R^2$ represents hydrogen, $(C_{1-4})$alkyl, $(C_{1-4})$alkoxy, halogen, or cyano;
$R^3$ represents hydrogen, $(C_{1-4})$alkyl, $(C_{1-4})$alkoxy, or halogen;
$R^4$ represents hydrogen, or halogen;
Q represents CH; or, in case $R^2$ is $(C_{1-4})$alkyl or $(C_{1-4})$alkoxy, Q represents CH, CF or N.

7) Another embodiment relates to compounds according to any one of embodiments 1) to 6), wherein $Ar^1$ represents pyrrol-1-yl, pyrazol-1-yl, [1,2,3]triazol-1-yl, [1,2,3]triazol-2-yl, [1,2,4]triazol-1-yl, oxazol-2-yl, thiazol-2-yl, [1,2,4]oxadiazol-3-yl, thiophen-2-yl, pyridin-2-yl, pyridin-3-yl, pyridin-4-yl, pyrimidin-2-yl, pyrazin-2-yl, and pyridazin-3-yl, which groups are unsubstituted or mono-substituted with $(C_{1-4})$alkyl (especially methyl)).

8) Another embodiment relates to compounds according to any one of embodiments 1) to 6), wherein $Ar^1$ represents pyrrol-1-yl, pyrazol-1-yl, [1,2,3]triazol-2-yl, oxazol-2-yl, thiophen-2-yl, pyridin-2-yl, pyridin-3-yl, pyrimidin-2-yl, pyrazin-2-yl, and pyridazin-3-yl, which groups are unsubstituted or mono-substituted, wherein the substituents are independently selected from $(C_{1-4})$alkyl.

9) Another embodiment relates to compounds according to any one of embodiments 1) to 6), wherein $Ar^1$ represents a 5- or 6-membered heteroaryl selected from the group consisting of pyrrolyl, pyrazolyl, triazolyl, oxadiazolyl, thiophenyl, 2-pyridinyl, pyrimidinyl, pyrazinyl, and pyridazinyl; wherein said heteroaryl is unsubstituted, or in case said heteroaryl is pyrimidinyl, optionally mono-substituted with methyl.

10) Another embodiment relates to compounds according to any one of embodiments 1) to 6), wherein $Ar^1$ represents a 5- or 6-membered heteroaryl selected from the group consisting of pyrazolyl, triazolyl, oxadiazolyl, and pyrimidinyl; wherein said heteroaryl is unsubstituted, or in case said heteroaryl is pyrimidinyl, optionally mono-substituted with methyl.

11) Another embodiment relates to compounds according to any one of embodiments 1) to 6), wherein $Ar^1$ represents pyrrol-1-yl, pyrazol-1-yl, [1,2,3]triazol-2-yl, [1,2,4]oxadiazol-3-yl, thiophen-2-yl, pyridin-2-yl, pyrimidin-2-yl, pyrazin-2-yl, and pyridazin-3-yl, which groups are unsubstituted, or in case of pyrimidin-2-yl, optionally mono-substituted with methyl.

12) A preferred embodiment relates to compounds according to any one of embodiments 1) to 6), wherein $Ar^1$ represents pyrazol-1-yl, [1,2,3]triazol-2-yl, [1,2,4]oxadiazol-3-yl, and pyrimidin-2-yl, which groups are unsubstituted, or in case of pyrimidin-2-yl, optionally mono-substituted with methyl.

13) Another preferred embodiment relates to compounds according to any one of embodiments 1) to 6), wherein $Ar^1$ represents unsubstituted [1,2,4]oxadiazol-3-yl, or unsubstituted [1,2,3]triazol-2-yl.

14) Another embodiment relates to compounds according to any one of embodiments 1) to 6), wherein $Ar^1$ represents unsubstituted pyrazol-1-yl, or unsubstituted [1,2,3]triazol-2-yl.

15) Another preferred embodiment relates to compounds according to any one of embodiments 1) to 6), wherein $Ar^1$ represents unsubstituted [1,2,3]triazol-2-yl.

16) Another embodiment relates to compounds according to any one of embodiments 1) to 15), wherein $R^1$ is absent, or $R^1$ represents $(C_{1-4})$alkoxy (especially methoxy).

17) Another embodiment relates to compounds according to any one of embodiments 1) to 15), wherein $R^1$ is absent, or $R^1$ represents methoxy in position 4 of the phenyl ring (i.e. in para position to the point of attachment of the —$CH_2$— group which links the phenyl ring to the rest of the molecule and ortho to the point of attachment of $Ar^1$).

18) Another embodiment relates to compounds according to any one of embodiments 1) to 15), wherein $R^1$ is absent; or $R^1$ represents halogen (especially fluoro or chloro) in position 2 or 3 of the phenyl ring; or $R^1$ represents methyl in position 2, 3, or 4 of the phenyl ring; or $R^1$ represents methoxy in position 4 of the phenyl ring [it being understood that the point of attachment of the —$CH_2$— group which links the phenyl ring to the rest of the molecule is position 1, and the point of attachment of $Ar^1$ is in position 5 of the phenyl ring].

19) Another embodiment relates to compounds according to any one of embodiments 1) to 15), wherein $R^1$ is absent, or $R^1$ represents halogen (especially fluoro or chloro) in position 2 of the phenyl ring (i.e. in para position to the point of attachment of $Ar^1$).

20) Another embodiment relates to compounds according to any one of embodiments 1) to 19), wherein $R^2$ represents hydrogen, methyl, methoxy, cyano, fluoro, or chloro; $R^3$ represents hydrogen, methyl, methoxy, or fluoro; $R^4$ represent hydrogen, or fluoro; and Q represents $CR^6$; or, in case $R^2$ is methyl, Q represents CH; or, in case $R^2$ is $(C_{1-4})$alkyl or $(C_{1-4})$alkoxy, Q represents CH, or N.

21) A preferred embodiment relates to compounds according to any one of embodiments 1) to 5), or 7) to 19); wherein $R^2$ represents hydrogen, methyl, methoxy, cyano, fluoro, or chloro; $R^3$ represents hydrogen, methyl, trifluoromethyl, fluoro, or chloro; $R^4$ represent hydrogen, methyl, trifluoromethyl, or fluoro; and Q represents $CR^6$; or, in case $R^2$ is methyl, Q represents $CR^6$ or N; wherein $R^6$ represents hydrogen, fluoro or methyl.

22) Another embodiment relates to compounds according to any one of embodiments 1) to 19), wherein $R^2$ represents hydrogen, methyl, methoxy, cyano, fluoro, or chloro.

23) Another embodiment relates to compounds according to any one of embodiments 1) to 19) or 21), wherein $R^2$ represents hydrogen, fluoro, or chloro.

24) Another embodiment relates to compounds according to any one of embodiments 1) to 5), 7) to 19), 21) or 23), wherein $R^3$ represents hydrogen, methyl, trifluoromethyl, or chloro.

25) Another embodiment relates to compounds according to any one of embodiments 1) to 19), or 22), wherein $R^3$ represents hydrogen, methyl, methoxy, or fluoro.

26) Another embodiment relates to compounds according to any one of embodiments 1) to 5), 7) to 19), 21), 23), or 24), wherein $R^4$ represents hydrogen or methyl.

27) Another embodiment relates to compounds according to any one of embodiments 1) to 19), 22) or 25), wherein $R^4$ represents hydrogen, or fluoro.

28) Another embodiment relates to compounds according to any one of embodiments 1) to 19), wherein $R^2$, $R^3$ and $R^4$ represent hydrogen; or $R^2$ represents methyl, and $R^3$ and $R^4$ represent hydrogen; or $R^2$ represents methoxy, and $R^3$ and $R^4$ represent hydrogen; or $R^2$ represents chloro, and $R^3$ and $R^4$ represent hydrogen; or $R^3$ represents methyl, and $R^2$ and $R^4$ represent hydrogen; or $R^2$ and $R^3$ represent methyl, and $R^4$ represents hydrogen; or $R^2$ represents methoxy, $R^3$ represents methyl or methoxy, and $R^4$ represents hydrogen.

29) Another embodiment relates to compounds according to any one of embodiments 1) to 28), wherein Q represents CH; or, in case $R^2$ is $(C_{1-4})$alkyl or $(C_{1-4})$alkoxy, Q represents CH, or N.

30) Another embodiment relates to compounds according to any one of embodiments 1) to 28), wherein $R^2$ is methyl and Q represents N.

31) Another embodiment relates to compounds according to any one of embodiments 1) to 5), 7) to 19), 21), 23), 24), or 26), wherein Q represents $CR^6$; wherein $R^6$ represents hydrogen, fluoro or methyl.

32) A preferred embodiment relates to compounds according to any one of embodiments 1) to 28), wherein Q represents CH.

33) Another preferred embodiment relates to compounds according to any one of embodiments 1) to 5), or 7) to 19), wherein $R^2$ represents hydrogen or chloro; $R^3$ represents hydrogen, chloro, methyl or trifluoromethyl, $R^4$ represent hydrogen or methyl; and Q represents CH.

34) Another preferred embodiment relates to compounds according to any one of the embodiments 1) to 5), or 7) to 19), wherein the group

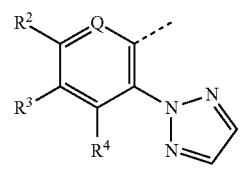

is a group independently selected from the following groups A) to F):

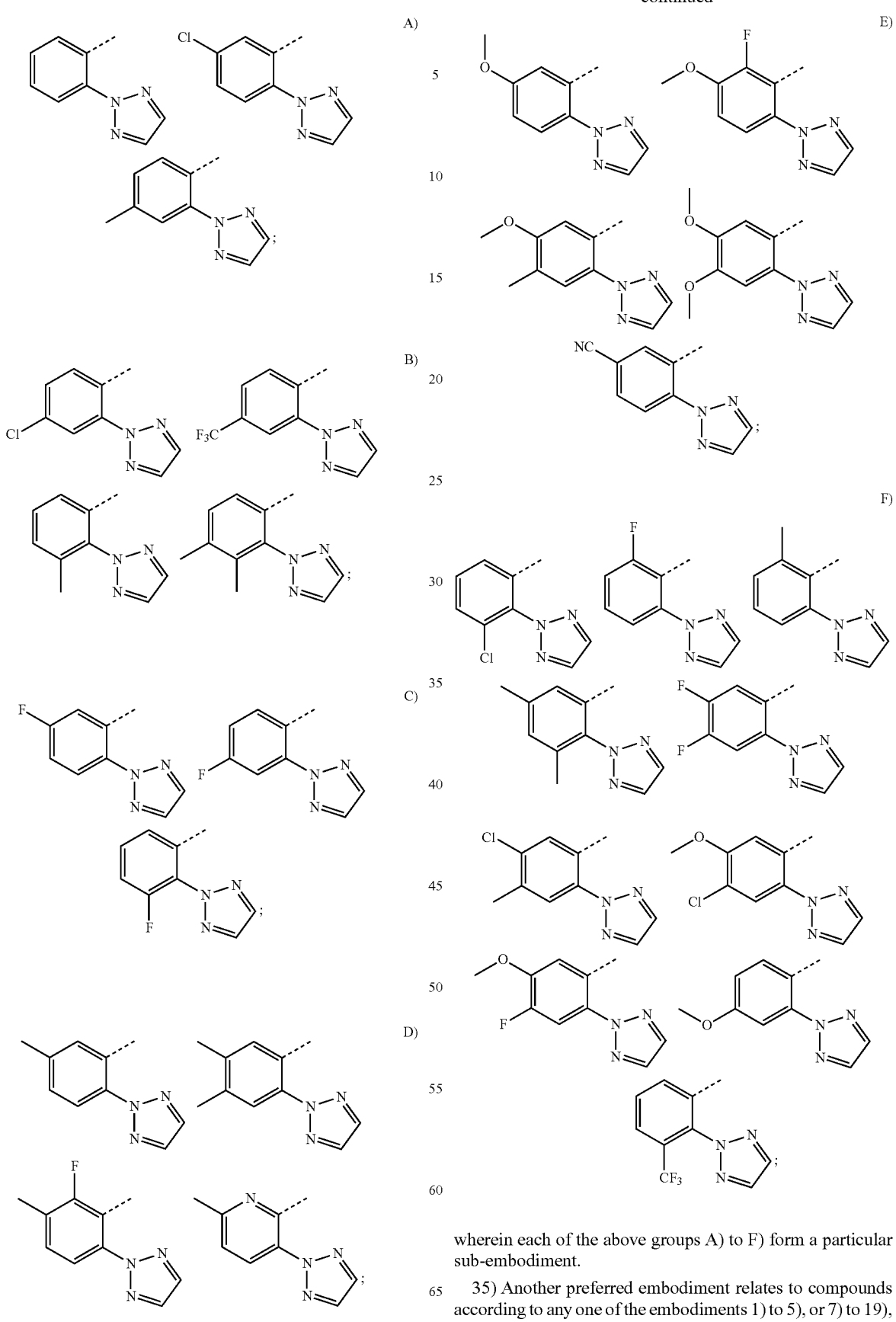
wherein each of the above groups A) to F) form a particular sub-embodiment.
35) Another preferred embodiment relates to compounds according to any one of the embodiments 1) to 5), or 7) to 19), wherein the group

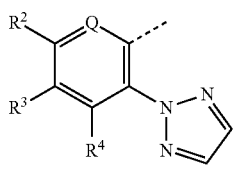

is a group selected from the group consisting of the following groups A) and B):

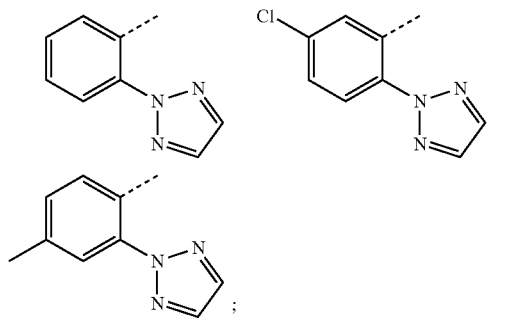

A)

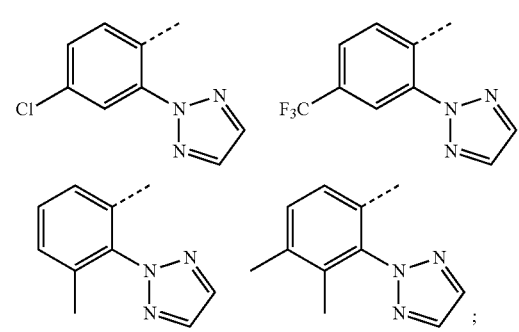

B)

wherein the groups A) and B) each form a particular sub-embodiment

36) Another embodiment relates to compounds according to any one of the embodiments 1) to 19) wherein the group

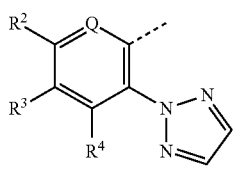

is a group selected from the group consisting of:

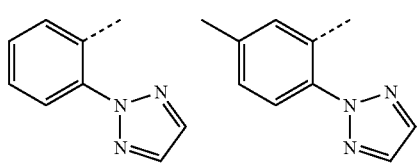

-continued

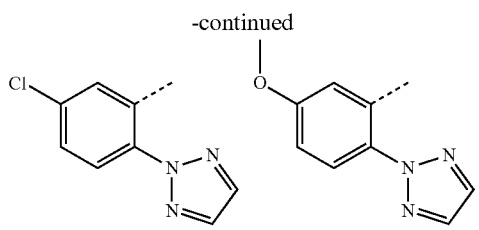

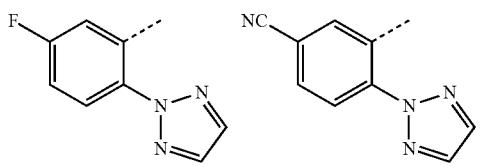

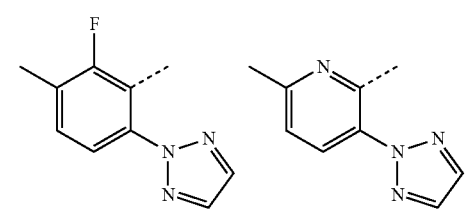

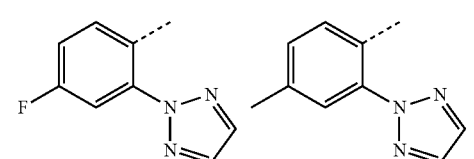

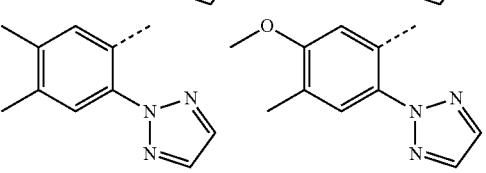

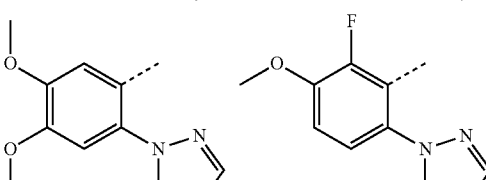

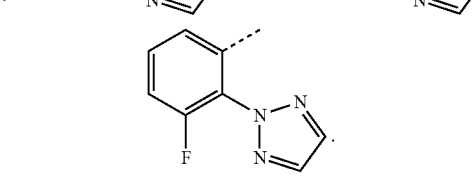

37) Another embodiment relates to compounds according to any one of the embodiments 1) to 5), or 20) to 36), wherein the group

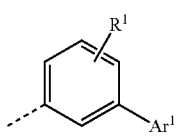

is a group independently selected from the following groups A) to H):

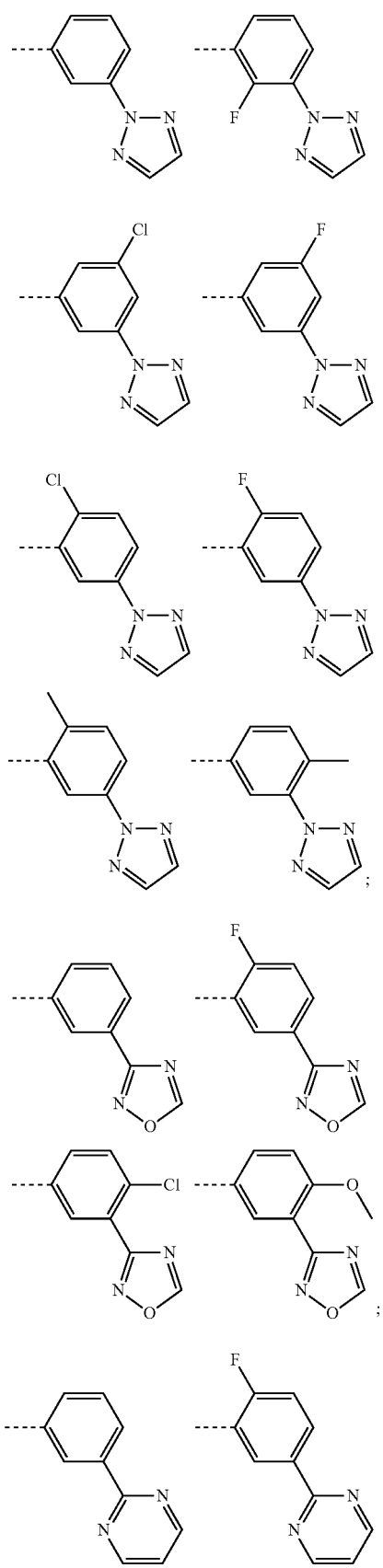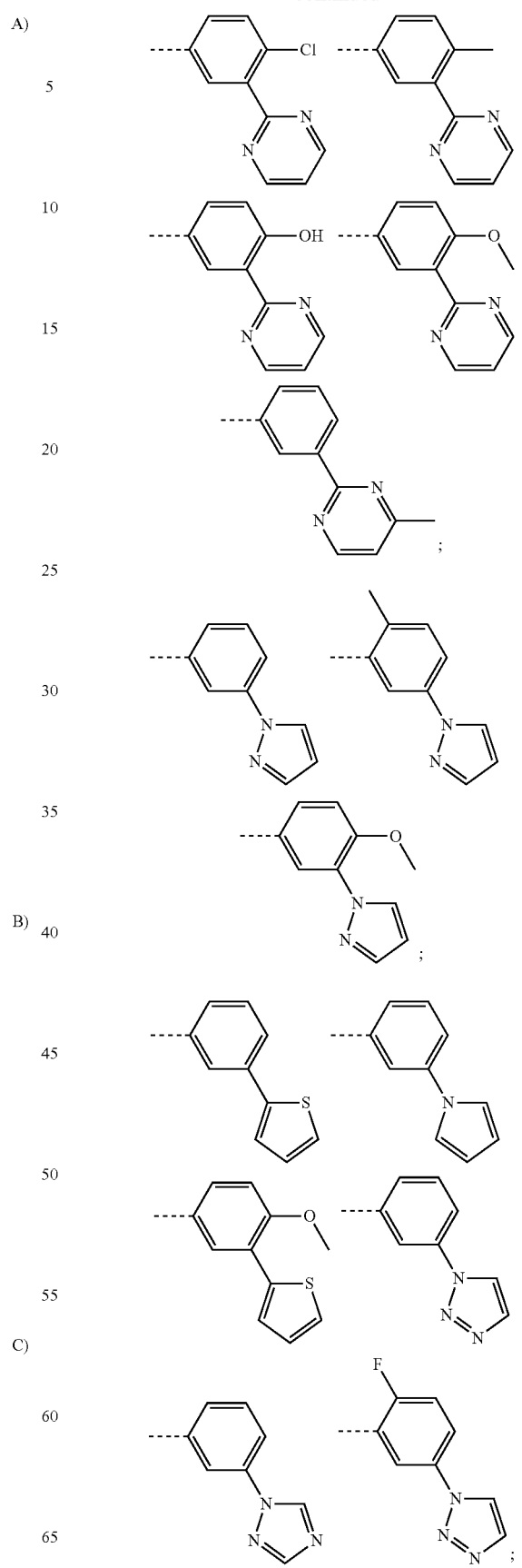

F)
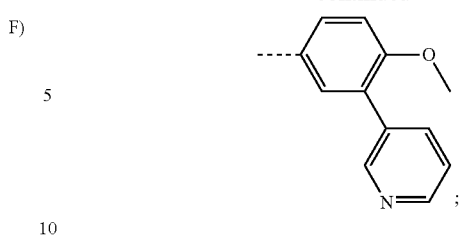
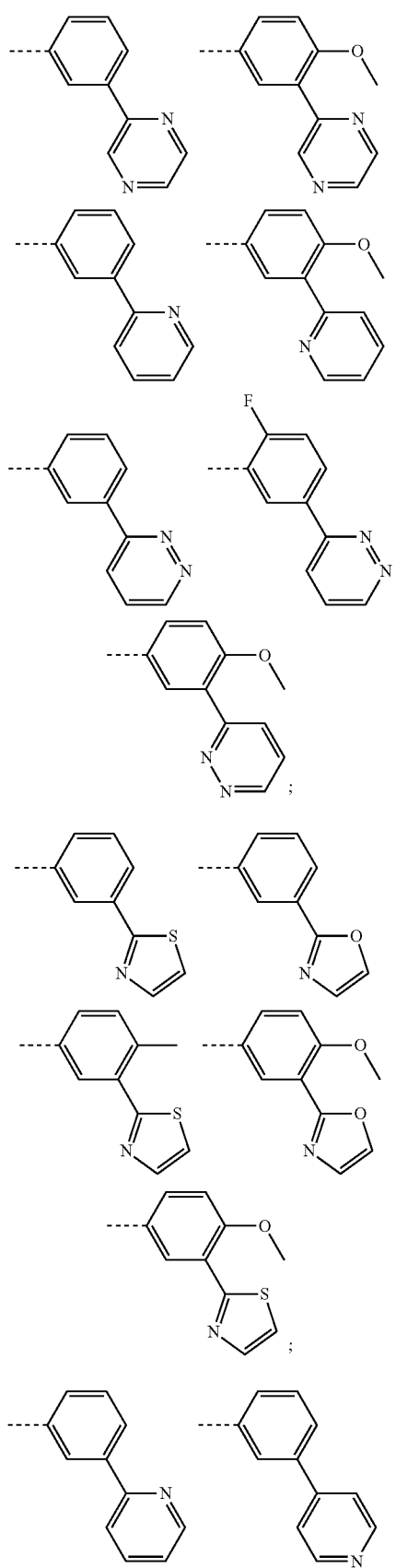
wherein the groups A) to F), and especially the groups A) to D), each form a preferred sub-embodiment.
38) Another embodiment relates to compounds according to any one of the embodiments 1) to 6), or 20) to 36), wherein the group
is a group independently selected from the group consisting of any one the following groups A), B) and C):
A)
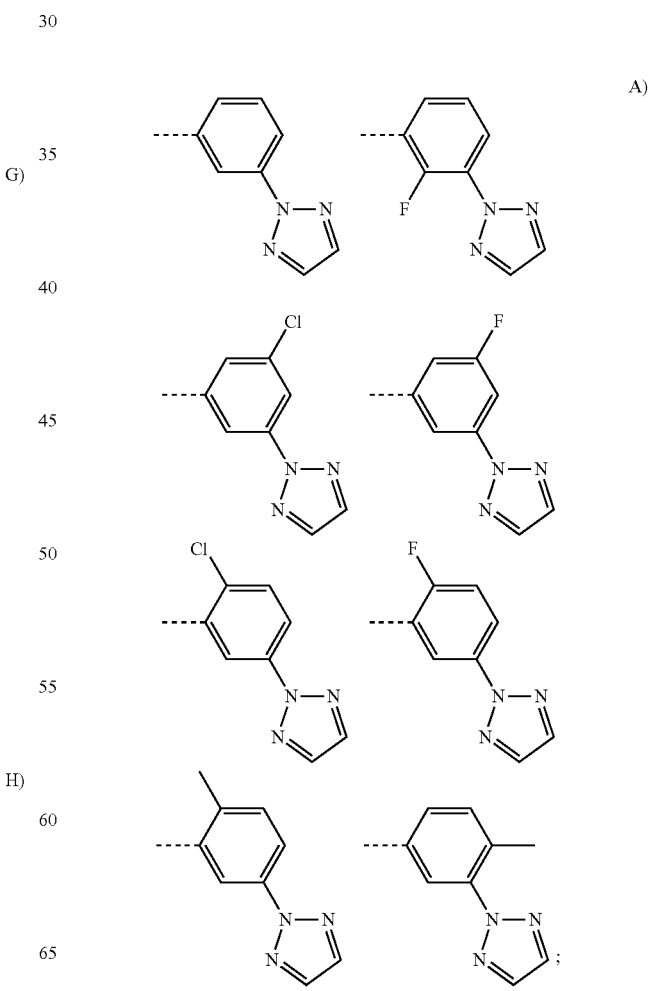

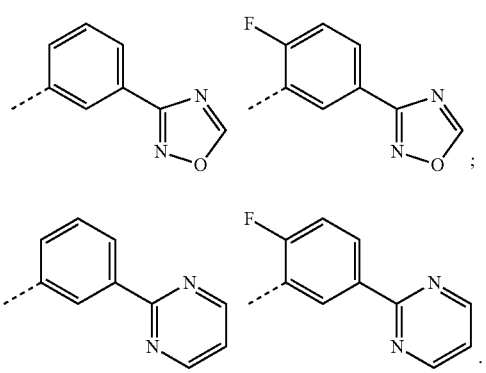

39) A preferred embodiment relates to compounds according to any one of the embodiments 1) to 6), or 20) to 36), wherein the group

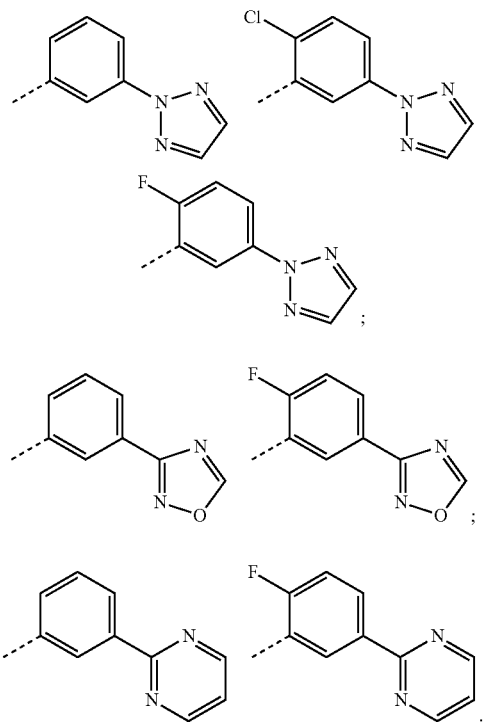

is a group independently selected from the group consisting of any one the following groups A), B) and C):

40) Another preferred embodiment relates to compounds according to any one of the embodiments 1) to 6), or 20) to 36), wherein the group

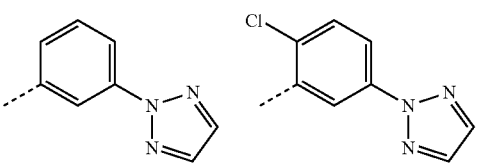

is a group selected from the group consisting of the following groups A) and B):

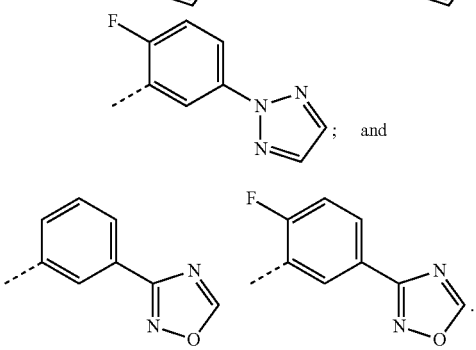

41) The invention, thus, relates to compounds of the formula (I) as defined in embodiment 1), compounds of the formula (II) as defined in embodiment 6); or to such compounds further limited by the characteristics of any one of embodiments 2) to 40), under consideration of their respective dependencies; to pharmaceutically acceptable salts thereof; and to the use of such compounds as medicaments especially in the treatment of mental health disorders relating to orexinergic dysfunctions, which disorders are as defined below and which are especially selected from anxiety disorders, addiction disorders, mood disorders, and appetite disorders. For avoidance of any doubt, especially the following embodiments relating to the compounds of formula (I) and (II) are thus possible and intended and herewith specifically disclosed in individualized form:

2+1, 5+1, 7+1, 7+2+1, 7+5+1, 12+1, 12+2+1, 12+5+1, 13+1, 13+2+1, 13+5+1, 15+1, 15+2+1, 15+5+1, 19+1, 19+2+1, 19+5+1, 19+7+1, 19+7+2+1, 19+7+5+1, 19+12+1, 19+12+2+1, 19+12+5+1, 19+13+1, 19+13+2+1, 19+13+5+1, 19+15+1, 19+15+2+1, 19+15+5+1, 21+1, 21+2+1, 21+5+1, 21+7+1, 21+7+2+1, 21+7+5+1, 21+12+1, 21+12+2+1, 21+12+5+1, 21+13+1, 21+13+2+1, 21+13+5+1, 21+15+1, 21+15+2+1, 21+15+5+1, 21+19+1, 21+19+2+1, 21+19+5+1, 21+19+7+1, 21+19+7+2+1, 21+19+7+5+1, 21+19+12+1, 21+19+12+2+1, 21+19+12+5+1, 21+19+13+1, 21+19+13+2+1, 21+19+13+5+1, 21+19+15+1, 21+19+15+2+1, 21+19+15+5+1, 32+1, 32+2+1, 32+5+1, 32+7+1, 32+7+2+1, 32+7+5+1, 32+12+1, 32+12+2+1, 32+12+5+1, 32+13+1, 32+13+2+1, 32+13+5+1, 32+15+1, 32+15+2+1, 32+15+5+1, 32+19+1, 32+19+2+1, 32+19+5+1, 32+19+7+1, 32+19+7+2+1, 32+19+7+5+1, 32+19+12+1, 32+19+12+2+1, 32+19+12+5+1, 32+19+13+1, 32+19+13+2+1, 32+19+13+5+1, 32+19+15+1, 32+19+15+2+1, 32+19+15+5+1, 32+21+1, 32+21+2+1, 32+21+5+1, 32+21+7+1, 32+21+7+2+1, 32+21+7+5+1, 32+21+12+1, 32+21+12+2+1, 32+21+12+5+

1, 32+21+13+1, 32+21+13+2+1, 32+21+13+5+1, 32+21+15+1, 32+21+15+2+1, 32+21+15+5+1, 32+21+19+1, 32+21+19+2+1, 32+21+19+5+1, 32+21+19+7+1, 32+21+19+7+2+1, 32+21+19+7+5+1, 32+21+19+12+1, 32+21+19+12+2+1, 32+21+19+12+5+1, 32+21+19+13+1, 32+21+19+13+2+1, 32+21+19+13+5+1, 32+21+19+15+1, 32+21+19+15+2+1, 32+21+19+15+5+1, 33+1, 33+2+1, 33+5+1, 33+7+1, 33+7+2+1, 33+7+5+1, 33+12+1, 33+12+2+1, 33+12+5+1, 33+13+1, 33+13+2+1, 33+13+5+1, 33+15+1, 33+15+2+1, 33+15+5+1, 33+19+1, 33+19+2+1, 33+19+5+1, 33+19+7+1, 33+19+7+2+1, 33+19+7+5+1, 33+19+12+1, 33+19+12+2+1, 33+19+12+5+1, 33+19+13+1, 33+19+13+2+1, 33+19+13+5+1, 33+19+15+1, 33+19+15+2+1, 33+19+15+5+1, 34+1, 34+2+1, 34+5+1, 34+7+1, 34+7+2+1, 34+7+5+1, 34+12+1, 34+12+2+1, 34+12+5+1, 34+13+1, 34+13+2+1, 34+13+5+1, 34+15+1, 34+15+2+1, 34+15+5+1, 34+19+1, 34+19+2+1, 34+19+5+1, 34+19+7+1, 34+19+7+2+1, 34+19+7+5+1, 34+19+12+1, 34+19+12+2+1, 34+19+12+5+1, 34+19+13+1, 34+19+13+2+1, 34+19+13+5+1, 34+19+15+1, 34+19+15+2+1, 34+19+15+5+1, 35+1, 35+2+1, 35+5+1, 35+7+1, 35+7+2+1, 35+7+5+1, 35+12+1, 35+12+2+1, 35+12+5+1, 35+13+1, 35+13+2+1, 35+13+5+1, 35+15+1, 35+15+2+1, 35+15+5+1, 35+19+1, 35+19+2+1, 35+19+5+1, 35+19+7+1, 35+19+7+2+1, 35+19+7+5+1, 35+19+12+1, 35+19+12+2+1, 35+19+12+5+1, 35+19+13+1, 35+19+13+2+1, 35+19+13+5+1, 35+19+15+1, 35+19+15+2+1, 35+19+15+5+1;
37+1, 37+2+1, 37+5+1, 37+21+1, 37+21+2+1, 37+21+5+1, 37+32+1, 37+32+2+1, 37+32+5+1, 37+33+1, 37+33+2+1, 37+33+5+1, 37+34+1, 37+34+2+1, 37+34+5+1, 37+35+1, 37+35+2+1, 37+35+5+1, 38+1, 38+2+1, 38+5+1, 38+21+1, 38+21+2+1, 38+21+5+1, 38+32+1, 38+32+2+1, 38+32+5+1, 38+33+1, 38+33+2+1, 38+33+5+1, 38+34+1, 38+34+2+1, 38+34+5+1, 38+35+1, 38+35+2+1, 38+35+5+1, 40+1, 40+2+1, 40+5+1, 40+21+1, 40+21+2+1, 40+21+5+1, 40+32+1, 40+32+2+1, 40+32+5+1, 40+33+1, 40+33+2+1, 40+33+5+1, 40+34+1, 40+34+2+1, 40+34+5+1, 40+35+1, 40+35+2+1, 40+35+5+1;
6+1, 7+6+1, 14+6+1, 20+6+1, 20+7+6+1, 20+14+6+1, 22+6+1, 22+7+6+1, 22+14+6+1, 25+6+1, 25+7+6+1, 25+14+6+1, 25+22+6+1, 25+22+7+6+1, 25+22+14+6+1, 27+6+1, 27+7+6+1, 27+14+6+1, 27+22+6+1, 27+22+7+6+1, 27+22+14+6+1, 27+25+6+1, 27+25+7+6+1, 27+25+14+6+1, 27+25+22+6+1, 27+25+22+7+6+1, 27+25+22+14+6+1, 28+6+1, 28+7+6+1, 28+14+6+1, 32+6+1, 32+7+6+1, 32+14+6+1, 32+22+6+1, 32+22+7+6+1, 32+22+14+6+1, 32+25+6+1, 32+25+7+6+1, 32+25+14+6+1, 32+25+22+6+1, 32+25+22+7+6+1, 32+25+22+14+6+1, 32+27+6+1, 32+27+7+6+1, 32+27+14+6+1, 32+27+22+6+1, 32+27+22+7+6+1, 32+27+22+14+6+1, 32+27+25+6+1, 32+27+25+7+6+1, 32+27+25+14+6+1, 32+27+25+22+6+1, 32+27+25+22+7+6+1, 32+27+25+22+14+6+1, 32+28+6+1, 32+28+7+6+1, 32+28+14+6+1, 36+6+1, 36+7+6+1, 36+14+6+1.

In the list above the numbers refer to the embodiments according to their numbering provided hereinabove whereas "+" indicates the dependency from another embodiment. The different individualized embodiments are separated by commas. In other words, "40+35+5+1" for example refers to embodiment 40) depending on embodiment 35), depending on embodiment 5), depending on embodiment 1), i.e. embodiment "40+35+5+1" corresponds to the compounds of embodiment 1) further limited by all the features of the embodiments 5), 35), and 40).

The compounds of formula (I) and (II) contain at least one stereogenic center which is situated in position 3 of the morpholine moiety. It is understood that the absolute configuration of said chiral center is as depicted in formula (I) and (II), i.e. it is in absolute (R) configuration.

In addition, the compounds of formula (I) (especially compounds of formula (I) in case $R^5$ is other than hydrogen) and (II) may contain one or more stereogenic or asymmetric centers, such as one or more asymmetric carbon atoms. The compounds of formula (I) and (II) may thus be present as mixtures of stereoisomers or preferably as pure stereoisomers. Mixtures of stereoisomers may be separated in a manner known to a person skilled in the art.

The present invention also includes isotopically labelled, especially $^2$H (deuterium) labelled compounds of formula (I) and (II), which compounds are identical to the compounds of formula (I) and (II) except that one or more atoms have each been replaced by an atom having the same atomic number but an atomic mass different from the atomic mass usually found in nature. Isotopically labelled, especially $^2$H (deuterium) labelled compounds of formula (I) and (II) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) and (II) are not isotopically labelled, or they are labelled only with one or more deuterium atoms. In a sub-embodiment, the compounds of formula (I) and (II) are not isotopically labelled at all. Isotopically labelled compounds of formula (I) and (II) may be prepared in analogy to the methods described hereinafter, but using the appropriate isotopic variation of suitable reagents or starting materials.

In this patent application, a dotted line shows the point of attachment of the radical drawn. For example, the radical drawn below

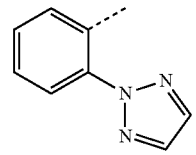

represents a 2-([1,2,3]triazol-2-yl)-phenyl group.

Where the plural form is used for compounds, salts, pharmaceutical compositions, diseases and the like, this is intended to mean also a single compound, salt, or the like.

Any reference to compounds of formula (I) or (II) is to be understood as referring also to the salts (and especially the pharmaceutically acceptable salts) of such compounds, as appropriate and expedient.

The term "pharmaceutically acceptable salts" refers to non-toxic, inorg. or organic acid and/or base addition salts. Reference can be made to "Salt selection for basic drugs", *Int. J. Pharm.* (1986), 33, 201-217.

Definitions provided herein are intended to apply uniformly to the compounds of formula (I) and (II) as defined in any one of embodiments 1) to 41), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "halogen" means fluorine, chlorine, or bromine, preferably fluorine or chlorine.

The term "alkyl", used alone or in combination, refers to a saturated straight or branched chain alkyl group containing one to six carbon atoms. The term "$(C_{x-y})$alkyl" (x and y each being an integer), refers to an alkyl group as defined before, containing x to y carbon atoms. For example a $(C_{1-4})$alkyl group contains from one to four carbon atoms. Examples of alkyl groups are methyl, ethyl, propyl, isopropyl, n-butyl, isobutyl, sec.-butyl and tert.-butyl. Preferred are methyl and ethyl. Most preferred is methyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are methoxy, ethoxy, n-propoxy, isopropoxy, n-butoxy, isobutoxy, sec.-butoxy and tert.-butoxy. Preferred are ethoxy and especially methoxy.

The term "fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$ fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $(C_1)$fluoroalkyl groups such as trifluoromethyl.

The term "fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $(C_1)$fluoroalkoxy groups such as trifluoromethoxy and difluoromethoxy.

Particular examples of $Ar^1$ representing a

"5- or 6-membered heteroaryl selected from the group consisting of pyrrolyl, pyrazolyl, triazolyl, oxazolyl, thiazolyl, oxadiazolyl, thiophenyl, pyridinyl, pyrimidinyl, pyrazinyl, and pyridazinyl; wherein said heteroaryl is unsubstituted, mono-, or di-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$ fluoroalkoxy" are notably pyrrolyl (in particular pyrrol-1-yl), pyrazolyl (in particular pyrazol-1-yl), triazolyl (in particular [1,2,3]triazol-1-yl, [1,2,3]triazol-2-yl, [1,2,4]triazol-1-yl), oxazolyl (in particular oxazol-2-yl), thiazolyl (in particular thiazol-2-yl), oxadiazolyl (in particular [1,2,4]oxadiazol-3-yl), thiophenyl (in particular thiophen-2-yl), pyridinyl (in particular pyridin-2-yl, pyridin-3-yl, pyridin-4-yl), pyrimidinyl (in particular pyrimidin-2-yl), pyrazinyl (in particular pyrazin-2-yl), and pyridazinyl (in particular pyridazin-3-yl). In a sub-embodiment, particular examples are pyrrol-1-yl, pyrazol-1-yl, [1,2,3]triazol-2-yl, oxazol-2-yl, thiophen-2-yl, pyridin-2-yl, pyridin-3-yl, pyrimidin-2-yl, pyrazin-2-yl, and pyridazin-3-yl. In a further sub-embodiment, particular examples are pyrazol-1-yl, and especially [1,2,3]triazol-2-yl. The above mentioned groups may be unsubstituted or substituted as explicitly defined. Notably, they are unsubstituted, mono-, or di-substituted, wherein the substituents are independently selected from $(C_{1-4})$alkyl. In a sub-embodiment, the above mentioned groups are unsubstituted or mono-substituted with $(C_{1-4})$alkyl (especially methyl). In a further sub-embodiment, the above mentioned groups are unsubstituted, or, in the case of pyrimidinyl groups, unsubstituted or mono-substituted with $(C_{1-4})$alkyl (especially methyl).

42) A further embodiment relates to particular compounds of formula (I) according to embodiment 1) which are selected from the following compounds:

[(R)-3-(3-[1,2,4]Oxadiazol-3-yl-benzyl)-morpholin-4-yl]-(2-[1,2,3]triazol-2-yl-phenyl)-methanone;
(5-Methyl-2-[1,2,3]triazol-2-yl-phenyl)-[(R)-3-(3-[1,2,4] oxadiazol-3-yl-benzyl)-morpholin-4-yl]-methanone;
[(R)-3-(4-Methoxy-3-pyridin-2-yl-benzyl)-morpholin-4-yl]-(2-[1,2,3]triazol-2-yl-phenyl)-methanone;
[(R)-3-(4-Methoxy-3-pyridin-3-yl-benzyl)-morpholin-4-yl]-(2-[1,2,3]triazol-2-yl-phenyl)-methanone;
[(R)-3-(4-Methoxy-3-pyrimidin-2-yl-benzyl)-morpholin-4-yl]-(2-[1,2,3]triazol-2-yl-phenyl)-methanone;
[(R)-3-(4-Methoxy-3-pyrazin-2-yl-benzyl)-morpholin-4-yl]-(2-[1,2,3]triazol-2-yl-phenyl)-methanone;
[(R)-3-(4-Methoxy-3-pyridazin-3-yl-benzyl)-morpholin-4-yl]-(2-[1,2,3]triazol-2-yl-phenyl)-methanone;
[(R)-3-(4-Methoxy-3-thiazol-2-yl-benzyl)-morpholin-4-yl]-(2-[1,2,3]triazol-2-yl-phenyl)-methanone;
[(R)-3-(4-Methoxy-3-oxazol-2-yl-benzyl)-morpholin-4-yl]-(2-[1,2,3]triazol-2-yl-phenyl)-methanone;
[(R)-3-(4-Methoxy-3-thiophen-2-yl-benzyl)-morpholin-4-yl]-(2-[1,2,3]triazol-2-yl-phenyl)-methanone;
(5-Methyl-2-[1,2,3]triazol-2-yl-phenyl)-[(R)-3-(3-[1,2,3] triazol-2-yl-benzyl)-morpholin-4-yl]-methanone;
[(R)-3-(3-[1,2,3]Triazol-2-yl-benzyl)-morpholin-4-yl]-(2-[1,2,3]triazol-2-yl-phenyl)-methanone;
[(S)-3-(3-[1,2,3]Triazol-2-yl-benzyl)-morpholin-4-yl]-(2-[1,2,3]triazol-2-yl-phenyl)-methanone;
[(R)-3-(4-Methoxy-3-pyrazol-1-yl-benzyl)-morpholin-4-yl]-(2-[1,2,3]triazol-2-yl-phenyl)-methanone;
(5-Methyl-2-[1,2,3]triazol-2-yl-phenyl)-[(R)-3-(3-[1,2,3] triazol-1-yl-benzyl)-morpholin-4-yl]-methanone;
[(R)-3-(3-Pyrazol-1-yl-benzyl)-morpholin-4-yl]-(2-[1,2,3] triazol-2-yl-phenyl)-methanone;
(5-Methyl-2-[1,2,3]triazol-2-yl-phenyl)-[(R)-3-(3-pyrimidin-2-yl-benzyl)-morpholin-4-yl]-methanone;
[(R)-3-(3-Pyrimidin-2-yl-benzyl)-morpholin-4-yl]-(2-[1,2,3]triazol-2-yl-phenyl)-methanone;
(5-Methyl-2-[1,2,3]triazol-2-yl-phenyl)-[(R)-3-(3-pyrazol-1-yl-benzyl)-morpholin-4-yl]-methanone;
(5-Fluoro-2-[1,2,3]triazol-2-yl-phenyl)-[(R)-3-(3-pyrazol-1-yl-benzyl)-morpholin-4-yl]-methanone;
(2-Fluoro-3-methyl-6-[1,2,3]triazol-2-yl-phenyl)-[(R)-3-(3-pyrazol-1-yl-benzyl)-morpholin-4-yl]-methanone;
(4-Methyl-2-[1,2,3]triazol-2-yl-phenyl)-[(R)-3-(3-pyrazol-1-yl-benzyl)-morpholin-4-yl]-methanone;
(5-Methyl-2-[1,2,3]triazol-2-yl-phenyl)-[(R)-3-(3-[1,2,4] triazol-1-yl-benzyl)-morpholin-4-yl]-methanone;
(5-Methyl-2-[1,2,3]triazol-2-yl-phenyl)-[(R)-3-(3-pyridin-2-yl-benzyl)-morpholin-4-yl]-methanone;
(5-Methyl-2-[1,2,3]triazol-2-yl-phenyl)-[(R)-3-(3-pyridin-3-yl-benzyl)-morpholin-4-yl]-methanone;
(5-Fluoro-2-[1,2,3]triazol-2-yl-phenyl)-[(R)-3-(3-[1,2,3] triazol-2-yl-benzyl)-morpholin-4-yl]-methanone;
(4-Methyl-2-[1,2,3]triazol-2-yl-phenyl)-[(R)-3-(3-[1,2,3] triazol-2-yl-benzyl)-morpholin-4-yl]-methanone;

(5-Methyl-2-[1,2,3]triazol-2-yl-phenyl)-[(R)-3-(3-pyridin-4-yl-benzyl)-morpholin-4-yl]-methanone;
(2-Fluoro-3-methyl-6-[1,2,3]triazol-2-yl-phenyl)-[(R)-3-(3-[1,2,3]triazol-2-yl-benzyl)-morpholin-4-yl]-methanone;
(5-Chloro-2-[1,2,3]triazol-2-yl-phenyl)-[(R)-3-(3-[1,2,3]triazol-2-yl-benzyl)-morpholin-4-yl]-methanone;
4-[1,2,3]Triazol-2-yl-3-[(R)-3-(3-[1,2,3]triazol-2-yl-benzyl)-morpholine-4-carbonyl]-benzonitrile;
(5-Methoxy-2-[1,2,3]triazol-2-yl-phenyl)-[(R)-3-(3-[1,2,3]triazol-2-yl-benzyl)-morpholin-4-yl]-methanone;
(2-Fluoro-3-methoxy-6-[1,2,3]triazol-2-yl-phenyl)-[(R)-3-(3-[1,2,3]triazol-2-yl-benzyl)-morpholin-4-yl]-methanone;
(4,5-Dimethoxy-2-[1,2,3]triazol-2-yl-phenyl)-[(R)-3-(3-[1,2,3]triazol-2-yl-benzyl)-morpholin-4-yl]-methanone;
(4,5-Dimethyl-2-[1,2,3]triazol-2-yl-phenyl)-[(R)-3-(3-[1,2,3]triazol-2-yl-benzyl)-morpholin-4-yl]-methanone;
(4-Fluoro-2-[1,2,3]triazol-2-yl-phenyl)-[(R)-3-(3-[1,2,3]triazol-2-yl-benzyl)-morpholin-4-yl]-methanone;
(5-Methoxy-4-methyl-2-[1,2,3]triazol-2-yl-phenyl)-[(R)-3-(3-[1,2,3]triazol-2-yl-benzyl)-morpholin-4-yl]-methanone;
(5-Methyl-2-[1,2,3]triazol-2-yl-phenyl)-[(R)-3-(3-pyrrol-1-yl-benzyl)-morpholin-4-yl]-methanone;
{(R)-3-[3-(4-Methyl-pyrimidin-2-yl)-benzyl]-morpholin-4-yl}-(5-methyl-2-[1,2,3]triazol-2-yl-phenyl)-methanone;
{(R)-3-[3-(4-Methyl-pyrimidin-2-yl)-benzyl]-morpholin-4-yl}-(2-[1,2,3]triazol-2-yl-phenyl)-methanone;
(5-Methyl-2-[1,2,3]triazol-2-yl-phenyl)-[(R)-3-(3-pyrazin-2-yl-benzyl)-morpholin-4-yl]-methanone;
[(R)-3-(3-Oxazol-2-yl-benzyl)-morpholin-4-yl]-(2-[1,2,3]triazol-2-yl-phenyl)-methanone;
(5-Methyl-2-[1,2,3]triazol-2-yl-phenyl)-[(R)-3-(3-thiazol-2-yl-benzyl)-morpholin-4-yl]-methanone;
[(R)-3-(3-Thiazol-2-yl-benzyl)-morpholin-4-yl]-(2-[1,2,3]triazol-2-yl-phenyl)-methanone;
(5-Methyl-2-[1,2,3]triazol-2-yl-phenyl)-[(R)-3-(3-thiophen-2-yl-benzyl)-morpholin-4-yl]-methanone;
[(R)-3-(3-Thiophen-2-yl-benzyl)-morpholin-4-yl]-(2-[1,2,3]triazol-2-yl-phenyl)-methanone;
(5-Methyl-2-[1,2,3]triazol-2-yl-phenyl)-[(R)-3-(3-pyridazin-3-yl-benzyl)-morpholin-4-yl]-methanone;
[(R)-3-(3-Pyridazin-3-yl-benzyl)-morpholin-4-yl]-(2-[1,2,3]triazol-2-yl-phenyl)-methanone;
(2-Fluoro-3-methyl-6-[1,2,3]triazol-2-yl-phenyl)-[(R)-3-(3-pyrimidin-2-yl-benzyl)-morpholin-4-yl]-methanone;
(5-Methoxy-2-[1,2,3]triazol-2-yl-phenyl)-[(R)-3-(3-pyrimidin-2-yl-benzyl)-morpholin-4-yl]-methanone;
(5-Chloro-2-[1,2,3]triazol-2-yl-phenyl)-[(R)-3-(3-pyrimidin-2-yl-benzyl)-morpholin-4-yl]-methanone;
(6-Methyl-3-[1,2,3]triazol-2-yl-pyridin-2-yl)-[(R)-3-(3-pyrazol-1-yl-benzyl)-morpholin-4-yl]-methanone;
(6-Methyl-3-[1,2,3]triazol-2-yl-pyridin-2-yl)-[(R)-3-(3-[1,2,3]triazol-2-yl-benzyl)-morpholin-4-yl]-methanone; and
(3-Fluoro-2-[1,2,3]triazol-2-yl-phenyl)-[(R)-3-(3-[1,2,3]triazol-2-yl-benzyl)-morpholin-4-yl]-methanone.

43) In addition to the above-listed compounds, further particular compounds of formula (I) according to embodiment 1) are selected from the group consisting of:
[(R)-3-(4-Hydroxy-3-pyrimidin-2-yl-benzyl)-morpholin-4-yl]-(2-[1,2,3]triazol-2-yl-phenyl)-methanone;
[(R)-3-(2-Fluoro-5-[1,2,3]triazol-2-yl-benzyl)-morpholin-4-yl]-(5-methyl-2-[1,2,3]triazol-2-yl-phenyl)-methanone;
[(R)-3-(2-Fluoro-5-[1,2,3]triazol-2-yl-benzyl)-morpholin-4-yl]-(2-[1,2,3]triazol-2-yl-phenyl)-methanone;
[(R)-3-(4-Methoxy-3-[1,2,4]oxadiazol-3-yl-benzyl)-morpholin-4-yl]-(5-methyl-2-[1,2,3]triazol-2-yl-phenyl)-methanone;
[(R)-3-(4-Methoxy-3-[1,2,4]oxadiazol-3-yl-benzyl)-morpholin-4-yl]-(2-[1,2,3]triazol-2-yl-phenyl)-methanone;
[(R)-3-(4-Methoxy-3-[1,2,4]oxadiazol-3-yl-benzyl)-morpholin-4-yl]-(4-methyl-2-[1,2,3]triazol-2-yl-phenyl)-methanone;
(4-Fluoro-2-[1,2,3]triazol-2-yl-phenyl)-[(R)-3-(4-methoxy-3-[1,2,4]oxadiazol-3-yl-benzyl)-morpholin-4-yl]-methanone;
[(R)-3-(2-Fluoro-5-[1,2,3]triazol-2-yl-benzyl)-morpholin-4-yl]-(4-methyl-2-[1,2,3]triazol-2-yl-phenyl)-methanone;
[(R)-3-(4-Methoxy-3-[1,2,4]oxadiazol-3-yl-benzyl)-morpholin-4-yl]-(2-methyl-6-[1,2,3]triazol-2-yl-phenyl)-methanone;
(3-Methyl-2-[1,2,3]triazol-2-yl-phenyl)-[(R)-3-(3-[1,2,3]triazol-2-yl-benzyl)-morpholin-4-yl]-methanone;
[(R)-3-(4-Methyl-3-[1,2,3]triazol-2-yl-benzyl)-morpholin-4-yl]-(5-methyl-2-[1,2,3]triazol-2-yl-phenyl)-methanone;
[(R)-3-(4-Methyl-3-[1,2,3]triazol-2-yl-benzyl)-morpholin-4-yl]-(2-[1,2,3]triazol-2-yl-phenyl)-methanone;
[(R)-3-(4-Methyl-3-[1,2,3]triazol-2-yl-benzyl)-morpholin-4-yl]-(4-methyl-2-[1,2,3]triazol-2-yl-phenyl)-methanone;
[(3R,5R)-3-Methyl-5-(3-[1,2,3]triazol-2-yl-benzyl)-morpholin-4-yl]-(2-[1,2,3]triazol-2-yl-phenyl)-methanone;
[(3R,5R)-3-Methyl-5-(3-[1,2,3]triazol-2-yl-benzyl)-morpholin-4-yl]-(4-methyl-2-[1,2,3]triazol-2-yl-phenyl)-methanone;
[(3R,5R)-3-Methyl-5-(3-[1,2,3]triazol-2-yl-benzyl)-morpholin-4-yl]-(3-methyl-2-[1,2,3]triazol-2-yl-phenyl)-methanone;
[(3S,5R)-3-Methyl-5-(3-[1,2,3]triazol-2-yl-benzyl)-morpholin-4-yl]-(4-methyl-2-[1,2,3]triazol-2-yl-phenyl)-methanone;
[(3S,5R)-3-Methyl-5-(3-[1,2,3]triazol-2-yl-benzyl)-morpholin-4-yl]-(3-methyl-2-[1,2,3]triazol-2-yl-phenyl)-methanone;
[(3S,5R)-3-Methyl-5-(3-[1,2,3]triazol-2-yl-benzyl)-morpholin-4-yl]-(5-methyl-2-[1,2,3]triazol-2-yl-phenyl)-methanone;
(4,5-Dimethyl-2-[1,2,3]triazol-2-yl-phenyl)-[(3S,5R)-3-methyl-5-(3-[1,2,3]triazol-2-yl-benzyl)-morpholin-4-yl]-methanone;
(3,5-Dimethyl-2-[1,2,3]triazol-2-yl-phenyl)-[(R)-3-(3-[1,2,3]triazol-2-yl-benzyl)-morpholin-4-yl]-methanone;
[(R)-3-(3-[1,2,3]Triazol-2-yl-benzyl)-morpholin-4-yl]-(2-[1,2,3]triazol-2-yl-4-trifluoromethyl-phenyl)-methanone;
(4-Chloro-2-[1,2,3]triazol-2-yl-phenyl)-[(R)-3-(3-[1,2,3]triazol-2-yl-benzyl)-morpholin-4-yl]-methanone;
(4-Fluoro-5-methoxy-2-[1,2,3]triazol-2-yl-phenyl)-[(R)-3-(3-[1,2,3]triazol-2-yl-benzyl)-morpholin-4-yl]-methanone;
(4,5-Dimethyl-2-[1,2,3]triazol-2-yl-phenyl)-[(R)-3-(4-methyl-3-[1,2,4]oxadiazol-3-yl-benzyl)-morpholin-4-yl]-methanone;
(4,5-Difluoro-2-[1,2,3]triazol-2-yl-phenyl)-[(R)-3-(3-[1,2,4]oxadiazol-3-yl-benzyl)-morpholin-4-yl]-methanone;
(4-Methyl-2-[1,2,3]triazol-2-yl-phenyl)-[(R)-3-(3-[1,2,4]oxadiazol-3-yl-benzyl)-morpholin-4-yl]-methanone;
(3-Fluoro-2-[1,2,3]triazol-2-yl-phenyl)-[(R)-3-(3-[1,2,4]oxadiazol-3-yl-benzyl)-morpholin-4-yl]-methanone;
(3-Methyl-2-[1,2,3]triazol-2-yl-phenyl)-[(R)-3-(3-[1,2,4]oxadiazol-3-yl-benzyl)-morpholin-4-yl]-methanone;
(5-Chloro-2-[1,2,3]triazol-2-yl-phenyl)-[(R)-3-(3-[1,2,4]oxadiazol-3-yl-benzyl)-morpholin-4-yl]-methanone;

(4,5-Dimethyl-2-[1,2,3]triazol-2-yl-phenyl)-[(R)-3-(3-[1,2,4]oxadiazol-3-yl-benzyl)-morpholin-4-yl]-methanone;
(4-Chloro-2-[1,2,3]triazol-2-yl-phenyl)-[(R)-3-(3-[1,2,4]oxadiazol-3-yl-benzyl)-morpholin-4-yl]-methanone;
[(R)-3-(3-[1,2,4]Oxadiazol-3-yl-benzyl)-morpholin-4-yl]-(2-[1,2,3]triazol-2-yl-4-trifluoromethyl-phenyl)-methanone;
(5-Fluoro-2-[1,2,3]triazol-2-yl-phenyl)-[(R)-3-(3-[1,2,4]oxadiazol-3-yl-benzyl)-morpholin-4-yl]-methanone;
(3,5-Dimethyl-2-[1,2,3]triazol-2-yl-phenyl)-[(R)-3-(3-[1,2,4]oxadiazol-3-yl-benzyl)-morpholin-4-yl]-methanone;
[(R)-3-(4-Chloro-3-[1,2,4]oxadiazol-3-yl-benzyl)-morpholin-4-yl]-(2-[1,2,3]triazol-2-yl-phenyl)-methanone;
(4,5-Difluoro-2-[1,2,3]triazol-2-yl-phenyl)-[(R)-3-(3-[1,2,3]triazol-2-yl-benzyl)-morpholin-4-yl]-methanone;
(3,4-Dimethyl-2-[1,2,3]triazol-2-yl-phenyl)-[(R)-3-(3-[1,2,3]triazol-2-yl-benzyl)-morpholin-4-yl]-methanone;
(4-Methoxy-2-[1,2,3]triazol-2-yl-phenyl)-[(R)-3-(3-[1,2,3]triazol-2-yl-benzyl)-morpholin-4-yl]-methanone;
(3,4-Dimethyl-2-[1,2,3]triazol-2-yl-phenyl)-[(R)-3-(2-fluoro-5-[1,2,3]triazol-2-yl-benzyl)-morpholin-4-yl]-methanone;
[(R)-3-(2-Fluoro-5-[1,2,3]triazol-2-yl-benzyl)-morpholin-4-yl]-(4-methoxy-2-[1,2,3]triazol-2-yl-phenyl)-methanone;
[(2S,5R)-2-Methyl-5-(3-[1,2,3]triazol-2-yl-benzyl)-morpholin-4-yl]-(4-methyl-2-[1,2,3]triazol-2-yl-phenyl)-methanone;
[(2R,5R)-2-Methyl-5-(3-[1,2,3]triazol-2-yl-benzyl)-morpholin-4-yl]-(3-methyl-2-[1,2,3]triazol-2-yl-phenyl)-methanone;
(4,5-Dimethyl-2-[1,2,3]triazol-2-yl-phenyl)-[(2R,5R)-2-methyl-5-(3-[1,2,3]triazol-2-yl-benzyl)-morpholin-4-yl]-methanone;
(3,4-Dimethyl-2-[1,2,3]triazol-2-yl-phenyl)-[(2R,5R)-2-methyl-5-(3-[1,2,3]triazol-2-yl-benzyl)-morpholin-4-yl]-methanone;
[(2R,5R)-2-Methyl-5-(3-[1,2,3]triazol-2-yl-benzyl)-morpholin-4-yl]-(2-[1,2,3]triazol-2-yl-phenyl)-methanone;
[(2R,5R)-2-Methyl-5-(3-[1,2,3]triazol-2-yl-benzyl)-morpholin-4-yl]-(4-methyl-2-[1,2,3]triazol-2-yl-phenyl)-methanone;
[(R)-3-Methyl-3-(3-[1,2,3]triazol-2-yl-benzyl)-morpholin-4-yl]-(5-methyl-2-[1,2,3]triazol-2-yl-phenyl)-methanone;
(5-Chloro-4-methyl-2-[1,2,3]triazol-2-yl-phenyl)-[(R)-3-(3-[1,2,3]triazol-2-yl-benzyl)-morpholin-4-yl]-methanone;
(4-Chloro-5-methoxy-2-[1,2,3]triazol-2-yl-phenyl)-[(R)-3-(3-[1,2,3]triazol-2-yl-benzyl)-morpholin-4-yl]-methanone;
[(R)-3-(3-Chloro-5-[1,2,3]triazol-2-yl-benzyl)-morpholin-4-yl]-(4-methyl-2-[1,2,3]triazol-2-yl-phenyl)-methanone;
[(R)-3-(3-Chloro-5-[1,2,3]triazol-2-yl-benzyl)-morpholin-4-yl]-(3-methyl-2-[1,2,3]triazol-2-yl-phenyl)-methanone;
(3-Chloro-2-[1,2,3]triazol-2-yl-phenyl)-[(R)-3-(3-[1,2,3]triazol-2-yl-benzyl)-morpholin-4-yl]-methanone;
[(2R,5R)-2-Methyl-5-(3-pyrimidin-2-yl-benzyl)-morpholin-4-yl]-(2-[1,2,3]triazol-2-yl-phenyl)-methanone;
[(2R,5R)-2-Methyl-5-(3-pyrimidin-2-yl-benzyl)-morpholin-4-yl]-(5-methyl-2-[1,2,3]triazol-2-yl-phenyl)-methanone;
[(2R,5R)-2-Methyl-5-(3-pyrimidin-2-yl-benzyl)-morpholin-4-yl]-(4-methyl-2-[1,2,3]triazol-2-yl-phenyl)-methanone;
[(2R,5R)-2-Methyl-5-(3-pyrimidin-2-yl-benzyl)-morpholin-4-yl]-(3-methyl-2-[1,2,3]triazol-2-yl-phenyl)-methanone;
(3,4-Dimethyl-2-[1,2,3]triazol-2-yl-phenyl)-[(2R,5R)-2-methyl-5-(3-pyrimidin-2-yl-benzyl)-morpholin-4-yl]-methanone;
(5-Chloro-2-[1,2,3]triazol-2-yl-phenyl)-[(2R,5R)-2-methyl-5-(3-pyrimidin-2-yl-benzyl)-morpholin-4-yl]-methanone;
(4-Chloro-2-[1,2,3]triazol-2-yl-phenyl)-[(2R,5R)-2-methyl-5-(3-pyrimidin-2-yl-benzyl)-morpholin-4-yl]-methanone;
[(2R,5R)-5-(2-Fluoro-5-[1,2,3]triazol-2-yl-benzyl)-2-methyl-morpholin-4-yl]-(5-methyl-2-[1,2,3]triazol-2-yl-phenyl)-methanone;
[(2R,5R)-5-(2-Fluoro-5-[1,2,3]triazol-2-yl-benzyl)-2-methyl-morpholin-4-yl]-(2-[1,2,3]triazol-2-yl-phenyl)-methanone;
[(2R,5R)-5-(2-Fluoro-5-[1,2,3]triazol-2-yl-benzyl)-2-methyl-morpholin-4-yl]-(4-methyl-2-[1,2,3]triazol-2-yl-phenyl)-methanone;
[(2R,5R)-5-(2-Fluoro-5-[1,2,3]triazol-2-yl-benzyl)-2-methyl-morpholin-4-yl]-(3-methyl-2-[1,2,3]triazol-2-yl-phenyl)-methanone;
[(R)-3-(2-Methyl-5-[1,2,3]triazol-2-yl-benzyl)-morpholin-4-yl]-(5-methyl-2-[1,2,3]triazol-2-yl-phenyl)-methanone;
[(R)-3-(2-Chloro-5-[1,2,3]triazol-2-yl-benzyl)-morpholin-4-yl]-(4-methyl-2-[1,2,3]triazol-2-yl-phenyl)-methanone;
[(R)-3-(2-Methyl-5-[1,2,3]triazol-2-yl-benzyl)-morpholin-4-yl]-(2-[1,2,3]triazol-2-yl-phenyl)-methanone;
[(R)-3-(2-Chloro-5-[1,2,3]triazol-2-yl-benzyl)-morpholin-4-yl]-(3-methyl-2-[1,2,3]triazol-2-yl-phenyl)-methanone;
[(R)-3-(2-Methyl-5-[1,2,3]triazol-2-yl-benzyl)-morpholin-4-yl]-(4-methyl-2-[1,2,3]triazol-2-yl-phenyl)-methanone;
[(R)-3-(2-Methyl-5-[1,2,3]triazol-2-yl-benzyl)-morpholin-4-yl]-(3-methyl-2-[1,2,3]triazol-2-yl-phenyl)-methanone;
[(R)-3-(2-Chloro-5-[1,2,3]triazol-2-yl-benzyl)-morpholin-4-yl]-(5-methyl-2-[1,2,3]triazol-2-yl-phenyl)-methanone;
[(R)-3-(2-Chloro-5-[1,2,3]triazol-2-yl-benzyl)-morpholin-4-yl]-(2-[1,2,3]triazol-2-yl-phenyl)-methanone;
[(R)-3-(2-Fluoro-5-[1,2,3]triazol-2-yl-benzyl)-morpholin-4-yl]-(3-methyl-2-[1,2,3]triazol-2-yl-phenyl)-methanone;
(4,5-Dimethyl-2-[1,2,3]triazol-2-yl-phenyl)-[(R)-3-(2-fluoro-5-[1,2,3]triazol-2-yl-benzyl)-morpholin-4-yl]-methanone;
(5-Chloro-2-[1,2,3]triazol-2-yl-phenyl)-[(R)-3-(2-fluoro-5-[1,2,3]triazol-2-yl-benzyl)-morpholin-4-yl]-methanone;
(4-Chloro-2-[1,2,3]triazol-2-yl-phenyl)-[(R)-3-(2-fluoro-5-[1,2,3]triazol-2-yl-benzyl)-morpholin-4-yl]-methanone;
[(R)-3-(2-Fluoro-5-[1,2,3]triazol-2-yl-benzyl)-morpholin-4-yl]-(5-methoxy-2-[1,2,3]triazol-2-yl-phenyl)-methanone;
(2-Fluoro-3-methyl-6-[1,2,3]triazol-2-yl-phenyl)-[(R)-3-(2-fluoro-5-[1,2,3]triazol-2-yl-benzyl)-morpholin-4-yl]-methanone;
(2-Fluoro-3-methoxy-6-[1,2,3]triazol-2-yl-phenyl)-[(R)-3-(2-fluoro-5-[1,2,3]triazol-2-yl-benzyl)-morpholin-4-yl]-methanone;
[(R)-3-(2-Fluoro-5-[1,2,3]triazol-2-yl-benzyl)-morpholin-4-yl]-(5-methoxy-4-methyl-2-[1,2,3]triazol-2-yl-phenyl)-methanone;
(3-Chloro-2-[1,2,3]triazol-2-yl-phenyl)-[(R)-3-(2-fluoro-5-[1,2,3]triazol-2-yl-benzyl)-morpholin-4-yl]-methanone;
[(R)-3-(2-Fluoro-5-[1,2,3]triazol-2-yl-benzyl)-morpholin-4-yl]-(2-fluoro-6-[1,2,3]triazol-2-yl-phenyl)-methanone;
(4,5-Difluoro-2-[1,2,3]triazol-2-yl-phenyl)-[(R)-3-(2-fluoro-5-[1,2,3]triazol-2-yl-benzyl)-morpholin-4-yl]-methanone;
[(R)-3-(2-Fluoro-5-[1,2,3]triazol-2-yl-benzyl)-morpholin-4-yl]-(2-[1,2,3]triazol-2-yl-4-trifluoromethyl-phenyl)-methanone;

(4-Chloro-5-methoxy-2-[1,2,3]triazol-2-yl-phenyl)-[(R)-3-(2-fluoro-5-[1,2,3]triazol-2-yl-benzyl)-morpholin-4-yl]-methanone;
[(2R,5R)-5-(2-Fluoro-5-[1,2,3]triazol-1-yl-benzyl)-2-methyl-morpholin-4-yl]-(5-methyl-2-[1,2,3]triazol-2-yl-phenyl)-methanone;
[(2R,5R)-5-(2-Fluoro-5-[1,2,3]triazol-1-yl-benzyl)-2-methyl-morpholin-4-yl]-(4-methyl-2-[1,2,3]triazol-2-yl-phenyl)-methanone;
[(2R,5R)-2-Ethyl-5-(3-[1,2,3]triazol-2-yl-benzyl)-morpholin-4-yl]-(5-methyl-2-[1,2,3]triazol-2-yl-phenyl)-methanone;
[(2R,5R)-2-Ethyl-5-(3-[1,2,3]triazol-2-yl-benzyl)-morpholin-4-yl]-(2-[1,2,3]triazol-2-yl-phenyl)-methanone;
[(2R,5R)-2-Ethyl-5-(3-[1,2,3]triazol-2-yl-benzyl)-morpholin-4-yl]-(4-methyl-2-[1,2,3]triazol-2-yl-phenyl)-methanone;
[(R)-3-(3-Fluoro-5-[1,2,3]triazol-2-yl-benzyl)-morpholin-4-yl]-(2-[1,2,3]triazol-2-yl-phenyl)-methanone;
[(R)-3-(3-Fluoro-5-[1,2,3]triazol-2-yl-benzyl)-morpholin-4-yl]-(4-methyl-2-[1,2,3]triazol-2-yl-phenyl)-methanone;
[(2R,5R)-5-(2-Fluoro-5-pyrimidin-2-yl-benzyl)-2-methyl-morpholin-4-yl]-(5-methyl-2-[1,2,3]triazol-2-yl-phenyl)-methanone;
[(2R,5R)-5-(2-Fluoro-5-pyrimidin-2-yl-benzyl)-2-methyl-morpholin-4-yl]-(2-[1,2,3]triazol-2-yl-phenyl)-methanone;
[(2R,5R)-5-(2-Fluoro-5-pyrimidin-2-yl-benzyl)-2-methyl-morpholin-4-yl]-(4-methyl-2-[1,2,3]triazol-2-yl-phenyl)-methanone;
[(2R,5R)-5-(2-Fluoro-5-pyrimidin-2-yl-benzyl)-2-methyl-morpholin-4-yl]-(3-methyl-2-[1,2,3]triazol-2-yl-phenyl)-methanone;
(3,4-Dimethyl-2-[1,2,3]triazol-2-yl-phenyl)-[(2R,5R)-5-(2-fluoro-5-pyrimidin-2-yl-benzyl)-2-methyl-morpholin-4-yl]-methanone;
(5-Chloro-2-[1,2,3]triazol-2-yl-phenyl)-[(2R,5R)-5-(2-fluoro-5-pyrimidin-2-yl-benzyl)-2-methyl-morpholin-4-yl]-methanone;
(4-Chloro-2-[1,2,3]triazol-2-yl-phenyl)-[(2R,5R)-5-(2-fluoro-5-pyrimidin-2-yl-benzyl)-2-methyl-morpholin-4-yl]-methanone;
(3-Chloro-2-[1,2,3]triazol-2-yl-phenyl)-[(2R,5R)-5-(2-fluoro-5-pyrimidin-2-yl-benzyl)-2-methyl-morpholin-4-yl]-methanone;
[(R)-3-(2-Fluoro-5-pyrimidin-2-yl-benzyl)-morpholin-4-yl]-(5-methyl-2-[1,2,3]triazol-2-yl-phenyl)-methanone;
[(R)-3-(2-Fluoro-5-pyrimidin-2-yl-benzyl)-morpholin-4-yl]-(4-methyl-2-[1,2,3]triazol-2-yl-phenyl)-methanone;
[(R)-3-(2-Fluoro-5-pyrimidin-2-yl-benzyl)-morpholin-4-yl]-(3-methyl-2-[1,2,3]triazol-2-yl-phenyl)-methanone;
(3,4-Dimethyl-2-[1,2,3]triazol-2-yl-phenyl)-[(R)-3-(2-fluoro-5-pyrimidin-2-yl-benzyl)-morpholin-4-yl]-methanone;
(5-Chloro-2-[1,2,3]triazol-2-yl-phenyl)-[(R)-3-(2-fluoro-5-pyrimidin-2-yl-benzyl)-morpholin-4-yl]-methanone;
(4-Chloro-2-[1,2,3]triazol-2-yl-phenyl)-[(R)-3-(2-fluoro-5-pyrimidin-2-yl-benzyl)-morpholin-4-yl]-methanone;
(3-Chloro-2-[1,2,3]triazol-2-yl-phenyl)-[(R)-3-(2-fluoro-5-pyrimidin-2-yl-benzyl)-morpholin-4-yl]-methanone;
[(2S,3R)-2-Methyl-3-(3-[1,2,3]triazol-2-yl-benzyl)-morpholin-4-yl]-(5-methyl-2-[1,2,3]triazol-2-yl-phenyl)-methanone;
[(2S,3R)-2-Methyl-3-(3-[1,2,3]triazol-2-yl-benzyl)-morpholin-4-yl]-(4-methyl-2-[1,2,3]triazol-2-yl-phenyl)-methanone;
[(2S,3R)-2-Methyl-3-(3-[1,2,3]triazol-2-yl-benzyl)-morpholin-4-yl]-(3-methyl-2-[1,2,3]triazol-2-yl-phenyl)-methanone;
[(2R,5R)-5-(2-Fluoro-5-pyridazin-3-yl-benzyl)-2-methyl-morpholin-4-yl]-(4-methyl-2-[1,2,3]triazol-2-yl-phenyl)-methanone;
[(R)-3-(2-Fluoro-5-pyridazin-3-yl-benzyl)-morpholin-4-yl]-(4-methyl-2-[1,2,3]triazol-2-yl-phenyl)-methanone;
[(2R,3R)-2-Methyl-3-(3-[1,2,3]triazol-2-yl-benzyl)-morpholin-4-yl]-(5-methyl-2-[1,2,3]triazol-2-yl-phenyl)-methanone;
[(2R,3R)-2-Methyl-3-(3-[1,2,3]triazol-2-yl-benzyl)-morpholin-4-yl]-(4-methyl-2-[1,2,3]triazol-2-yl-phenyl)-methanone;
[(R)-3-(2-Chloro-5-[1,2,3]triazol-2-yl-benzyl)-morpholin-4-yl]-(3,4-dimethyl-2-[1,2,3]triazol-2-yl-phenyl)-methanone;
[(R)-3-(2-Chloro-5-[1,2,3]triazol-2-yl-benzyl)-morpholin-4-yl]-(4-chloro-2-[1,2,3]triazol-2-yl-phenyl)-methanone;
[(R)-3-(2-Chloro-5-[1,2,3]triazol-2-yl-benzyl)-morpholin-4-yl]-(3-chloro-2-[1,2,3]triazol-2-yl-phenyl)-methanone;
(3-Chloro-2-[1,2,3]triazol-2-yl-phenyl)-[(2R,5R)-2-methyl-5-(3-[1,2,3]triazol-2-yl-benzyl)-morpholin-4-yl]-methanone;
(3-Chloro-2-[1,2,3]triazol-2-yl-phenyl)-[(2R,5R)-5-(2-fluoro-5-[1,2,3]triazol-2-yl-benzyl)-2-methyl-morpholin-4-yl]-methanone;
[(R)-3-(2-Fluoro-5-[1,2,4]oxadiazol-3-yl-benzyl)-morpholin-4-yl]-(5-methyl-2-[1,2,3]triazol-2-yl-phenyl)-methanone;
[(R)-3-(2-Fluoro-5-[1,2,4]oxadiazol-3-yl-benzyl)-morpholin-4-yl]-(4-methyl-2-[1,2,3]triazol-2-yl-phenyl)-methanone;
(5-Chloro-2-[1,2,3]triazol-2-yl-phenyl)-[(R)-3-(2-fluoro-5-[1,2,4]oxadiazol-3-yl-benzyl)-morpholin-4-yl]-methanone;
[(R)-3-(2-Fluoro-5-[1,2,4]oxadiazol-3-yl-benzyl)-morpholin-4-yl]-(3-methyl-2-[1,2,3]triazol-2-yl-phenyl)-methanone;
(4-Chloro-2-[1,2,3]triazol-2-yl-phenyl)-[(R)-3-(2-fluoro-5-[1,2,4]oxadiazol-3-yl-benzyl)-morpholin-4-yl]-methanone;
(4,5-Dimethyl-2-[1,2,3]triazol-2-yl-phenyl)-[(R)-3-(2-fluoro-5-[1,2,4]oxadiazol-3-yl-benzyl)-morpholin-4-yl]-methanone;
(3-Chloro-2-[1,2,3]triazol-2-yl-phenyl)-[(R)-3-(2-fluoro-5-[1,2,4]oxadiazol-3-yl-benzyl)-morpholin-4-yl]-methanone;
(3,4-Dimethyl-2-[1,2,3]triazol-2-yl-phenyl)-[(R)-3-(2-fluoro-5-[1,2,4]oxadiazol-3-yl-benzyl)-morpholin-4-yl]-methanone;
[(R)-3-(3-[1,2,3]Triazol-2-yl-benzyl)-morpholin-4-yl]-(2-[1,2,3]triazol-2-yl-3-trifluoromethyl-phenyl)-methanone;
[(R)-3-(2-Fluoro-3-[1,2,3]triazol-2-yl-benzyl)-morpholin-4-yl]-(4-methyl-2-[1,2,3]triazol-2-yl-phenyl)-methanone;
(5-Chloro-2-[1,2,3]triazol-2-yl-phenyl)-[(2R,5R)-2-methyl-5-(3-[1,2,3]triazol-2-yl-benzyl)-morpholin-4-yl]-methanone;
(4-Chloro-2-[1,2,3]triazol-2-yl-phenyl)-[(2R,5R)-2-methyl-5-(3-[1,2,3]triazol-2-yl-benzyl)-morpholin-4-yl]-methanone;
(5-Chloro-2-[1,2,3]triazol-2-yl-phenyl)-[(2R,5R)-5-(2-fluoro-5-[1,2,3]triazol-2-yl-benzyl)-2-methyl-morpholin-4-yl]-methanone;
(4-Chloro-2-[1,2,3]triazol-2-yl-phenyl)-[(2R,5R)-5-(2-fluoro-5-[1,2,3]triazol-2-yl-benzyl)-2-methyl-morpholin-4-yl]-methanone;

[(R)-3-(2-Methyl-5-pyrazol-1-yl-benzyl)-morpholin-4-yl]-(5-methyl-2-[1,2,3]triazol-2-yl-phenyl)-methanone;
[(R)-3-(2-Methyl-5-pyrazol-1-yl-benzyl)-morpholin-4-yl]-(4-methyl-2-[1,2,3]triazol-2-yl-phenyl)-methanone;
[(R)-3-(2-Methyl-5-pyrazol-1-yl-benzyl)-morpholin-4-yl]-(3-methyl-2-[1,2,3]triazol-2-yl-phenyl)-methanone;
(4-Chloro-2-[1,2,3]triazol-2-yl-phenyl)-[(R)-3-(2-methyl-5-[1,2,3]triazol-2-yl-benzyl)-morpholin-4-yl]-methanone;
[(R)-3-(4-Methyl-3-pyrimidin-2-yl-benzyl)-morpholin-4-yl]-(2-[1,2,3]triazol-2-yl-phenyl)-methanone;
[(R)-3-(4-Methyl-3-thiazol-2-yl-benzyl)-morpholin-4-yl]-(2-[1,2,3]triazol-2-yl-phenyl)-methanone; and
[(R)-3-(4-Chloro-3-pyrimidin-2-yl-benzyl)-morpholin-4-yl]-(2-[1,2,3]triazol-2-yl-phenyl)-methanone.

44) A further embodiment relates to particular compounds of formula (I) according to embodiment 1) are selected from the group consisting of:
(4-Chloro-2-[1,2,3]triazol-2-yl-phenyl)-[(R)-3-(3-[1,2,3]triazol-2-yl-benzyl)-morpholin-4-yl]-methanone;
(4-Methyl-2-[1,2,3]triazol-2-yl-phenyl)-[(R)-3-(3-[1,2,3]triazol-2-yl-benzyl)-morpholin-4-yl]-methanone;
[(R)-3-(3-[1,2,3]Triazol-2-yl-benzyl)-morpholin-4-yl]-(2-[1,2,3]triazol-2-yl-4-trifluoromethyl-phenyl)-methanone;
(4-Chloro-2-[1,2,3]triazol-2-yl-phenyl)-[(R)-3-(2-fluoro-5-[1,2,3]triazol-2-yl-benzyl)-morpholin-4-yl]-methanone;
(3,4-Dimethyl-2-[1,2,3]triazol-2-yl-phenyl)-[(R)-3-(3-[1,2,3]triazol-2-yl-benzyl)-morpholin-4-yl]-methanone;
[(R)-3-(2-Chloro-5-[1,2,3]triazol-2-yl-benzyl)-morpholin-4-yl]-(4-methyl-2-[1,2,3]triazol-2-yl-phenyl)-methanone;
[(R)-3-(2-Fluoro-5-[1,2,3]triazol-2-yl-benzyl)-morpholin-4-yl]-(4-methyl-2-[1,2,3]triazol-2-yl-phenyl)-methanone;
[(R)-3-(3-[1,2,4]Oxadiazol-3-yl-benzyl)-morpholin-4-yl]-(2-[1,2,3]triazol-2-yl-4-trifluoromethyl-phenyl)-methanone;
(5-Chloro-2-[1,2,3]triazol-2-yl-phenyl)-[(R)-3-(3-[1,2,3]triazol-2-yl-benzyl)-morpholin-4-yl]-methanone;
(3-Methyl-2-[1,2,3]triazol-2-yl-phenyl)-[(R)-3-(3-[1,2,3]triazol-2-yl-benzyl)-morpholin-4-yl]-methanone;
(3,4-Dimethyl-2-[1,2,3]triazol-2-yl-phenyl)-[(R)-3-(2-fluoro-5-[1,2,3]triazol-2-yl-benzyl)-morpholin-4-yl]-methanone;
[(R)-3-(3-[1,2,3]Triazol-2-yl-benzyl)-morpholin-4-yl]-(2-[1,2,3]triazol-2-yl-phenyl)-methanone; and
[(2R,5R)-5-(2-Fluoro-5-[1,2,3]triazol-2-yl-benzyl)-2-methyl-morpholin-4-yl]-(2-[1,2,3]triazol-2-yl-phenyl)-methanone.

The compounds of formula (I) and (II) according to any one of embodiments 1) to 44) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) and (II) according to any one of embodiments 1) to 44).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

For avoidance of any doubt, if compounds are described as useful for the prevention or treatment of certain diseases, such compounds are likewise suitable for use in the preparation of a medicament for the prevention or treatment of said diseases.

The compounds of formula (I) and (II) according to any one of embodiments 1) to 44) are useful for the prevention or treatment of disorders relating to orexinergic dysfunctions.

Such disorders relating to orexinergic dysfunctions are diseases or disorders where an antagonist of a human orexin receptor is required, notably mental health diseases or disorders relating to orexinergic dysfunctions, notably of the orexin 1 receptor. The above mentioned disorders may in particular be defined as comprising anxiety disorders, addiction disorders, mood disorders, or appetite disorders, as well as cognitive dysfunctions or sleep disorders. Especially, the above mentioned disorders comprise anxiety disorders, addiction disorders and mood disorders, notably anxiety disorders and addiction disorders.

In addition, further disorders relating to orexinergic dysfunctions are selected from treating, controlling, ameliorating or reducing the risk of epilepsy, including absence epilepsy; treating or controlling pain, including neuropathic pain; treating or controlling Parkinson's disease; treating or controlling psychosis including acute mania and bipolar disorder; treating or controlling stroke, particularly ischemic or haemorrhagic stroke; blocking an emetic response i.e. nausea and vomiting; and treating or controlling agitation, in isolation or co-morbid with another medical condition.

Anxiety disorders can be distinguished by the primary object or specificity of threat, ranging from rather diffuse as in generalized anxiety disorder, to circumscribed as encountered in phobic anxieties (PHOBs) or post-traumatic stress disorders (PTSDs). Anxiety disorders may, thus, be defined as comprising generalized anxiety disorders (GAD), obsessive compulsive disorders (OCDs), acute stress disorders, post-traumatic stress disorders (PTSDs), panic anxiety disorders (PADs) including panic attacks, phobic anxieties (PHOBs), specific phobia, social phobia (social anxiety disorder), avoidance, somatoform disorders including hypochondriasis, separation anxiety disorder, anxiety disorders due to a general medical condition, and substance induced anxiety disorders. In a sub-embodiment, particular examples of circumscribed threat induced anxiety disorders are phobic anxieties or post-traumatic stress disorders. Anxiety disorders especially include generalized anxiety disorders, post-traumatic stress disorders, obsessive compulsive disorders, panic attacks, phobic anxieties, and avoidance.

Addiction disorders may be defined as addictions to one or more rewarding stimuli, notably to one rewarding stimulus. Such rewarding stimuli may be of either natural or synthetic origin. Examples of such rewarding stimuli are substances/drugs {of either natural or synthetic origin; such as cocaine, amphetamines, opiates [of natural or (semi-)synthetic origin such as morphine or heroin], cannabis, ethanol, mescaline, nicotine, and the like}, which substances/drugs may be consumed alone or in combination; or other rewarding stimuli {of either natural origin (such as food, sweet, fat, or sex, and the like), or synthetic origin [such as gambling, or internet/IT (such as immoderate gaming, or inappropriate involvement in online social networking sites or blogging), and the like]}. In a sub-embodiment, addiction disorders relating to psychoactive substance use, abuse, seeking and reinstatement are defined as all types of psychological or physical addictions and their related tolerance and dependence components. Substance-related addiction disorders especially include substance use disorders such as substance dependence, substance craving and substance abuse; substance-induced disorders such as substance intoxication, substance withdrawal, and substance-induced delirium. The expression "prevention or treatment of addictions" (i.e. preventive or curative treatment of patients who have been diagnosed as having an addiction, or as being at risk of developing addictions) refers to diminishing addictions, notably diminishing the onset of addictions, to weakening their maintenance, to facilitating withdrawal, to facilitating abstinence, or to attenuating, decreasing or preventing the occurrence of reinstatement of addiction (especially to diminishing the onset of addictions, to facilitating withdrawal, or to attenuating, decreasing or preventing the occurrence of reinstatement of addiction).

Mood disorders include major depressive episode, manic episode, mixed episode and hypomanic episode; depressive disorders including major depressive disorder, dysthymic disorders; bipolar disorders including bipolar I disorder, bipolar II disorder (recurrent major depressive episodes with hypomanic episodes), cyclothymic disorder; mood disorders including mood disorder due to a general medical condition (including the subtypes with depressive features, with major depressive-like episode, with manic features, and with mixed features), substance-induced mood disorder (including the subtypes with depressive features, with manic features, and with mixed features). Such mood disorders are especially major depressive episode, major depressive disorder, mood disorder due to a general medical condition; and substance-induced mood disorder.

Appetite disorders comprise eating disorders and drinking disorders. Eating disorders may be defined as comprising eating disorders associated with excessive food intake and complications associated therewith; anorexias; compulsive eating disorders; obesity (due to any cause, whether genetic or environmental); obesity-related disorders including overeating and obesity observed in Type 2 (non-insulin-dependent) diabetes patients; bulimias including bulimia nervosa; cachexia; and binge eating disorder. Particular eating disorders comprise metabolic dysfunction; dysregulated appetite control; compulsive obesities; bulimia or anorexia nervosa. In a sub-embodiment, eating disorders may be defined as especially comprising anorexia nervosa, bulimia, cachexia, binge eating disorder, or compulsive obesities. Drinking disorders include polydipsias in psychiatric disorders and all other types of excessive fluid intake. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance.

Cognitive dysfunctions include deficits in attention, learning and especially memory functions occurring transiently or chronically in psychiatric, neurologic, neurodegenerative, cardiovascular and immune disorders, and also occurring transiently or chronically in the normal, healthy, young, adult, or especially aging population. Cognitive dysfunctions especially relate to the enhancement or maintenance of memory in patients who have been diagnosed as having, or being at risk of developing, diseases or disorders in which diminished memory (notably declarative or procedural) is a symptom [in particular dementias such as frontotemporal dementia, or dementia with Lewy bodies, or (especially) Alzheimer's disease]. Especially, the term "prevention or treatment of cognitive dysfunctions" relates to the enhancement or maintenance of memory in patients who have a clinical manifestation of a cognitive dysfunction, especially expressed as a deficit of declarative memory, linked to dementias such as frontotemporal dementia, or dementia with Lewy bodies, or (especially) Alzheimer's disease. Furthermore, the term "prevention or treatment of cognitive dysfunctions" also relates to improving memory consolidation in any of the above mentioned patient populations.

Sleep disorders comprise dyssomnias, parasomnias, sleep disorders associated with a general medical condition and substance-induced sleep disorders. In particular, dyssomnias include intrinsic sleep disorders (especially insomnias, breathing-related sleep disorders, periodic limb movement disorder, and restless leg syndrome), extrinsic sleep disorders, and circadian-rhythm sleep disorders. Dyssomnias notably include insomnia, primary insomnia, idiopathic insomnia, insomnias associated with depression, emotional/mood disorders, aging, Alzheimer's disease or cognitive impairment; REM sleep interruptions; breathing-related sleep disorders; sleep apnea; periodic limb movement disorder (nocturnal myoclonus), restless leg syndrome, circadian rhythm sleep disorder; shift work sleep disorder; and jet-lag syndrome. Parasomnias include arousal disorders and sleep-wake transition disorders; notably parasomnias include nightmare disorder, sleep terror disorder, and sleepwalking disorder. Sleep disorders associated with a general medical condition are in particular sleep disorders associated with diseases such as mental disorders, neurological disorders, neuropathic pain, and heart and lung diseases. Substance-induced sleep disorders include especially the subtypes insomnia type, parasomnia type and mixed type, and notably include conditions due to drugs which cause reductions in REM sleep as a side effect. Sleep disorders especially include all types of insomnias, sleep-related dystonias; restless leg syndrome; sleep apneas; jet-lag syndrome; shift work sleep disorder, delayed or advanced sleep phase syndrome, or insomnias related to psychiatric disorders. In addition, sleep disorders further include sleep disorders associated with aging; intermittent treatment of chronic insomnia; situational transient insomnia (new environment, noise) or short-term insomnia due to stress; grief; pain or illness.

In the context of the present invention, it is to be understood that, in case certain environmental conditions such as stress or fear (wherein stress may be of social origin (e.g. social stress) or of physical origin (e.g. physical stress), including stress caused by fear) facilitate or precipitate any of the disorders or diseases as defined before, the present compounds may be particularly useful for the treatment of such environmentally conditioned disorder or disease.

The present invention also relates to the compounds of formula (I) and (II), and/or to pharmaceutical compositions comprising, as active principle, one or more compounds of formula (I) and/or (II) for use in the treatment of the above-mentioned disorders relating to orexinergic dysfunctions, in combination with one or more further pharmaceutically active ingredients.

Preparation of Compounds of Formula (I):

The compounds of formula (I) can be prepared by the methods given below, by the methods given in the experimental part below or by analogous methods. Optimum reaction conditions may vary with the particular reactants or solvents used, but such conditions can be determined by a person skilled in the art by routine optimisation procedures. In some cases the final product may be further modified, for example, by manipulation of substituents to give a new final product.

These manipulations may include, but are not limited to, reduction, oxidation, alkylation, acylation, and hydrolysis reactions which are commonly known to those skilled in the art. In some cases the order of carrying out the following reaction schemes, and/or reaction steps, may be varied to facilitate the reaction or to avoid unwanted reaction products.

Compounds of formula (I) of the present invention can be prepared according to the general sequence of reactions outlined below wherein Q, $Ar^1$, $R^1$, $R^2$, $R^3$, $R^4$ and $R^5$ are as defined for formula (I).

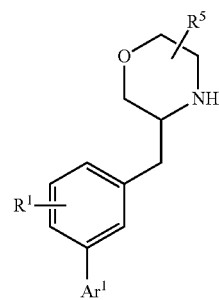

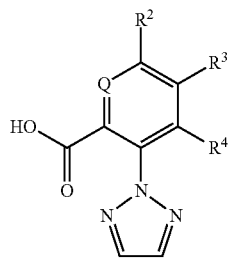

Compounds of formula (I) are prepared by reaction of an amine of Structure 1, or a salt such as a hydrochloride salt thereof, with an acid of Structure 2 in the presence of an amide-coupling reagent such as TBTU, HATU, EDC, DCC or PyBOP and a base like DIPEA or TEA in a solvent such as MeCN or DMF. Alternatively, coupling can be achieved via the corresponding acid chloride of Structure 2, prepared conventionally using a chlorinating reagent like oxalyl chloride or thionyl chloride.

Compounds of Structure 1 may be prepared by one of the synthetic pathways described below.

Reaction Scheme A

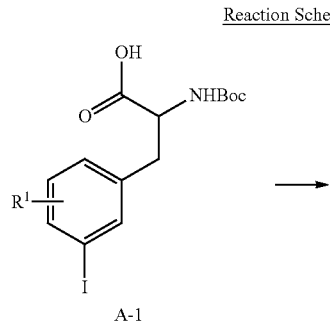

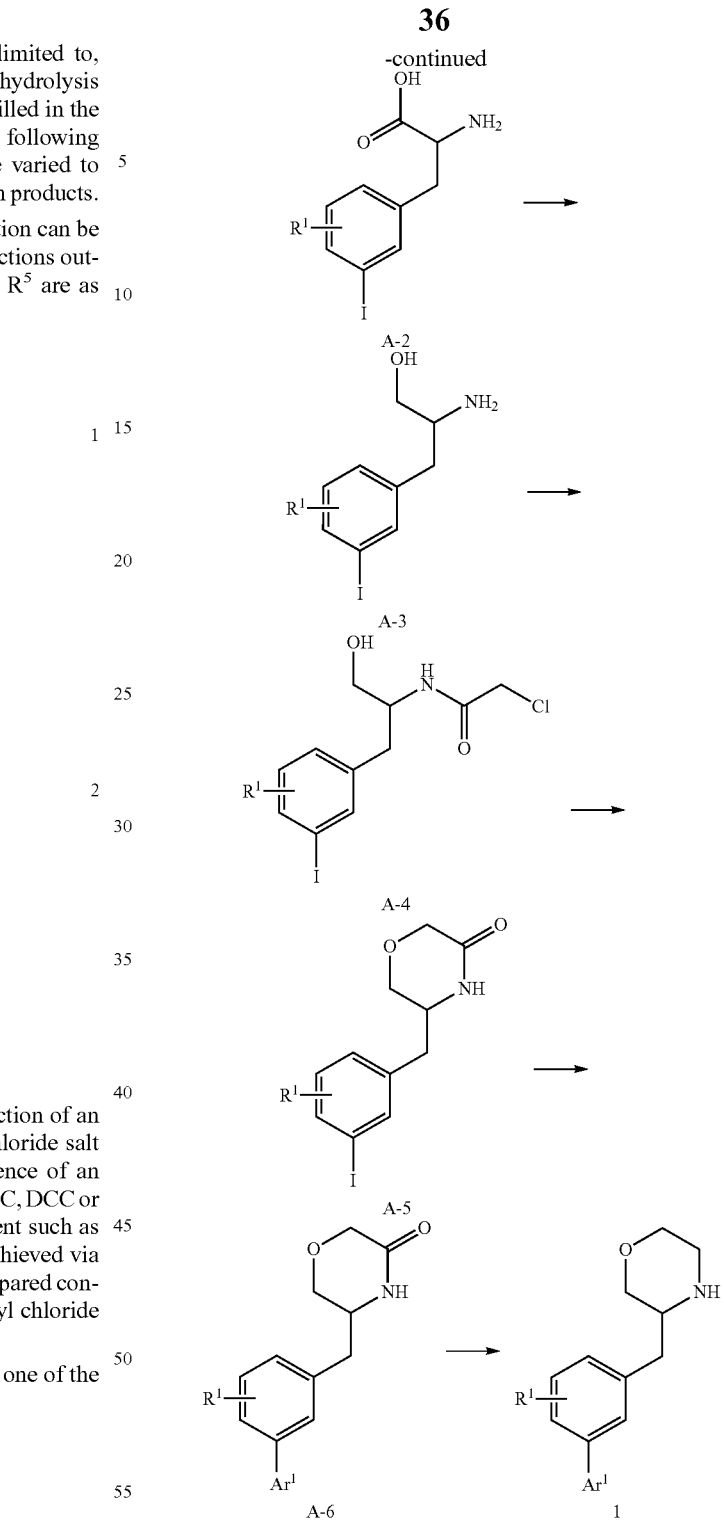

Compounds of Structure 1 may be prepared in analogy to the procedure described in WO2008047109 and as illustrated in Reaction Scheme A. A Boc-protected iodophenyl alanine derivative A-1, racemic or enantiomerically enriched, either commercially available or prepared following the procedure described by Greenspan et al. in J. Med. Chem. 2001, 44, 4524-4534, can be Boc-deprotected by treatment with 4M HCl in dioxane or with TFA to give the corresponding iodophenyl alanine as its HCl or TFA salt A-2. Iodophenyl alanine A-2, racemic or enantiomerically enriched, either commercially available or prepared as described above can be reduced with borane in a solvent like THF to furnish the corresponding amino alcohol A-3. Acylation of A-3 with chloroacetyl chloride furnishes amide A-4 which upon treatment with a base like sodium hydride or potassium tertbutoxide in a solvent like THF affords morpholinone A-5. Arylation of A-5 can be accomplished under metal catalysed conditions employing for example copper, palladium or zinc catalysts to give intermediates of type A-6. Alternatively, conversion of A-5 into it's corresponding boronic acid or ester followed by a Suzuki reaction gives intermediates of type A-6. Reduction of A-6 with borane in a solvent like THF furnishes compounds of Structure 1.

Reaction Scheme B

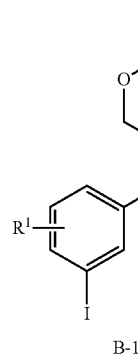

B-1

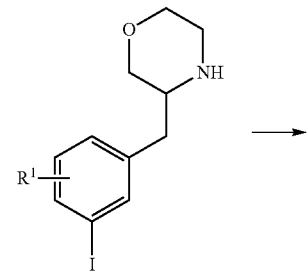

B-2

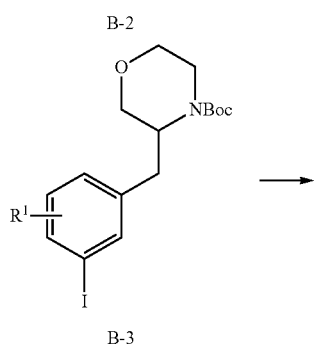

B-3

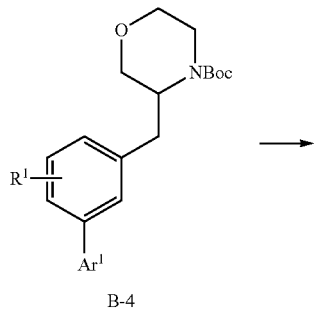

B-4

-continued

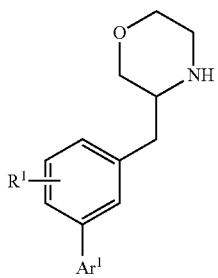

1

Compounds of Structure 1 may also be prepared as illustrated in Reaction Scheme B. Reduction of morpholinone B-1 with borane in a solvent like THF gives the corresponding morpholine B-2 which can be boc-protected under standard conditions to furnish intermediates of type B-3. Arylation of B-3 can be achieved by following one of several methods. For example, under metal catalysed conditions as described above, or alternatively, conversion of B-3 into it's corresponding boronic pinacol ester by treatment with bis(pinacolato) diboron in a solvent like DMSO followed by a Suzuki reaction. Intermediates of type B-3 can also be converted into their corresponding cyano derivatives by treatment with zinc cyanide under palladium catalysed conditions in a solvent like 1,4-dioxane followed by treatment with hydroxylamine and subsequent ring closure in trimethyl orthoformate to give intermediates of type B-4 where Ar¹ is a 1,2,4-oxadiazole. Boc-deprotection of B-4 by treatment with 4M HCl in dioxane or with TFA leads to compounds of Structure 1.

Reaction Scheme C

C-1

C-2

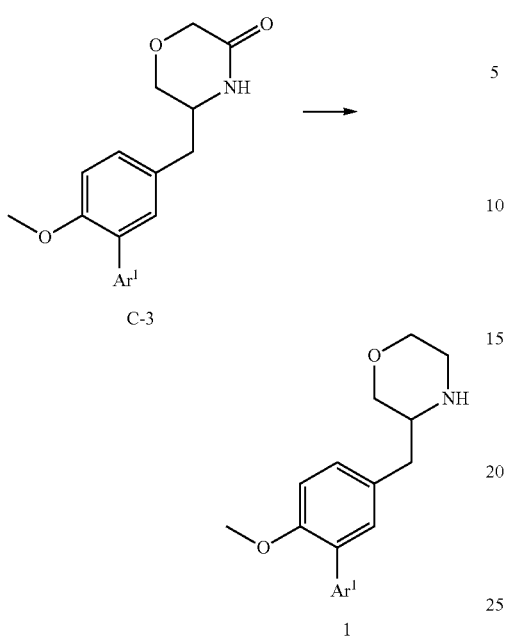

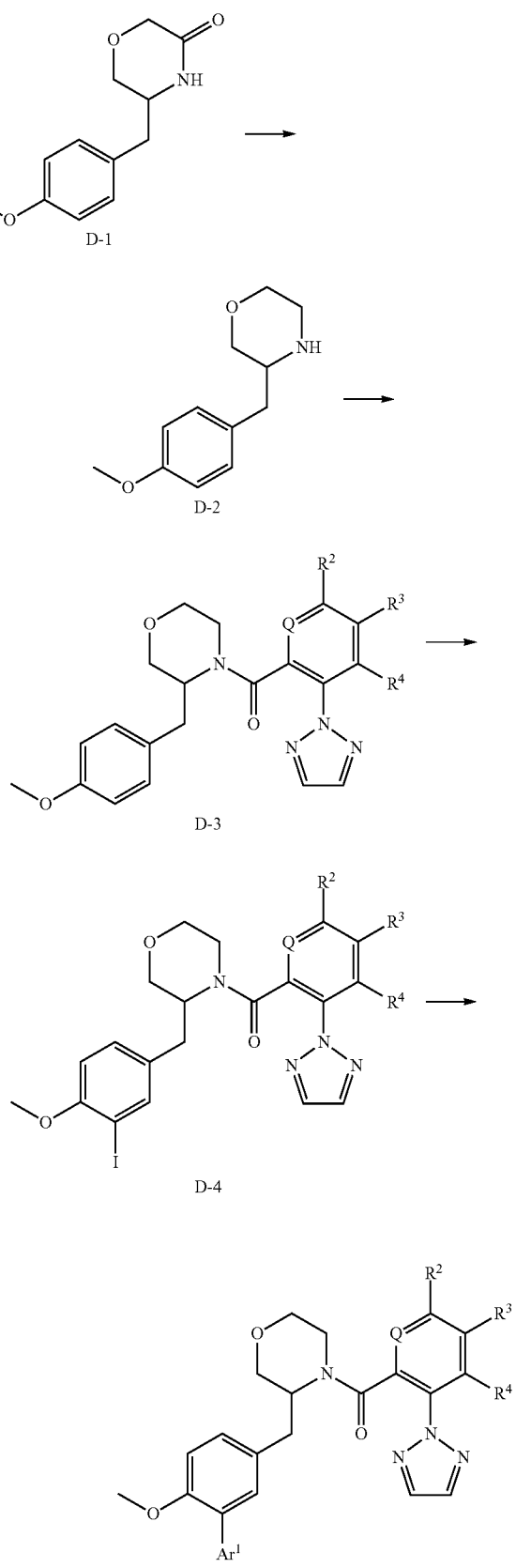

Reaction Scheme D

Compounds of Structure 1 may also be prepared as illustrated in Reaction Scheme C. Intermediate C-1 can be prepared from p-methoxyphenyl alanine in analogy to the sequence of reactions described in Reaction Scheme A. Iodination of morpholinone C-1 with NIS in the presence of an acid like triflic acid in a solvent like DCM or MeCN gives the corresponding morpholinone C-2. Arylation of C-2 can be accomplished under metal catalysed conditions employing for example copper or palladium catalysts to give intermediates of type C-3. Alternatively, conversion of C-2 into it's corresponding boronic pinacol ester by treatment with bis (pinacolato) diboron in a solvent like DMSO followed by a Suzuki reaction with the appropriate aryl halide furnishes intermediates of type C-3. Reduction of C-3 with borane in a solvent like THF furnishes compounds of Structure 1.

Final compounds of the present invention may be prepared as illustrated in Reaction Scheme D. For example, intermediate D-1 can be prepared from p-methoxyphenyl alanine in analogy to the sequence of reactions described in Reaction Scheme A. Reduction of morpholinone D-1 with borane in a solvent like THF gives the corresponding morpholine D-2. Reaction of D-2 with an acid of Structure 2 in the presence of an amide-coupling reagent such as TBTU, HATU or EDC, and a base like DIPEA or TEA in a solvent such as MeCN or DMF furnishes intermediates of type D-3. Iodination of D-3 in the presence of an acid like triflic acid in a solvent like DCM or MeCN gives intermediates of type D-4. Arylation of D-4 can be accomplished under metal catalysed conditions employing for example copper or palladium catalysts to give final compounds. Alternatively, conversion of D-4 into it's corresponding boronic pinacol ester by treatment with bis (pinacolato) diboron in a solvent like DMSO followed by a Suzuki reaction with the appropriate aryl halide furnishes final compounds.

Reaction Scheme G

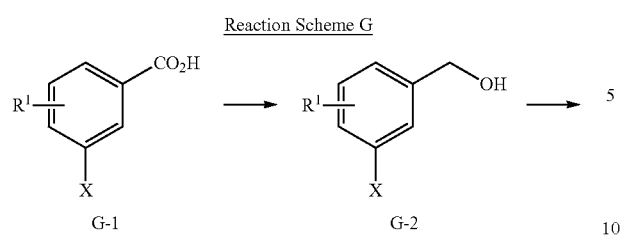

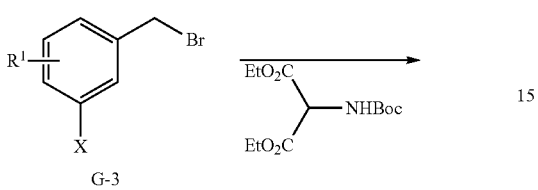

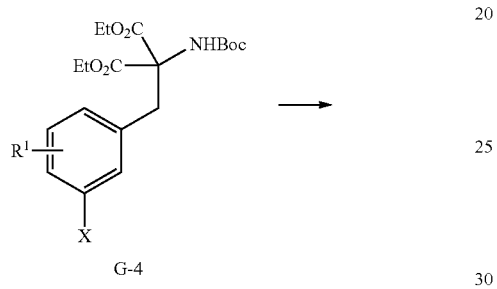

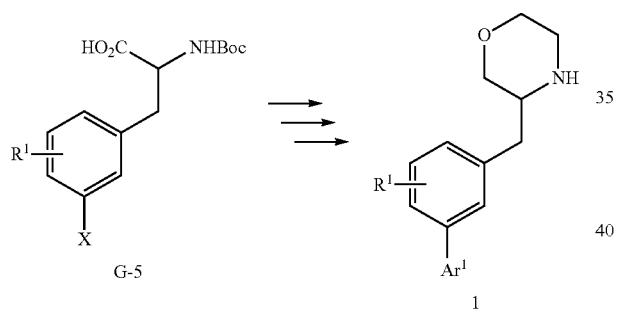

Compounds of Structure 1 may also be prepared as illustrated in Reaction Scheme G. Reduction of commercially available m-halobenzoic acid (X=Br or I) G-1 with borane in a solvent like THF gives the corresponding benzyl alcohol G-2 which can be brominated under standard conditions with phosphorus tribromide in a solvent like DCM to furnish benzyl bromides of type G-3. Subsequent Boc-aminomalonate alkylation chemistry with benzyl bromide G-3 as described by Greenspan et al. in J. Med. Chem. 2001, 44, 4524-4534, furnishes Boc-protected halophenyl alanine derivative G-5. Conversion of G-5 into compounds of Structure 1 can be accomplished by following the sequence of transformations as described in Reaction Scheme A.

Reaction Scheme H

-continued

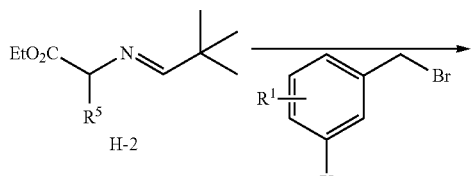

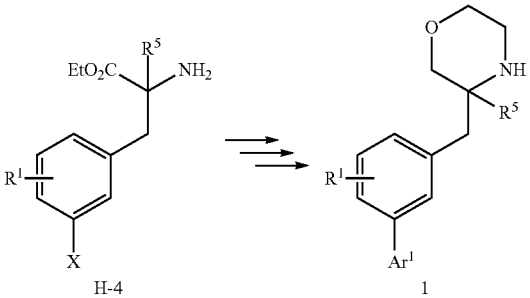

Compounds of Structure 1 may also be prepared as illustrated in Reaction Scheme H. Reaction of commercially available α-aminoester H-1 with trimethylacetaldehyde in a solvent like DCM in the presence of a dehydrating agent like $MgSO_4$ gives the corresponding imine H-2. Alkylation of H-2 with benzyl bromides H-3, prepared as described in Reaction Scheme G, in a solvent like toluene gives after imine hydrolysis intermediates of type H-4. Conversion of H-4 into compounds of Structure 1 can be accomplished by following the sequence of transformations as described in Reaction Scheme A.

Reaction Scheme I

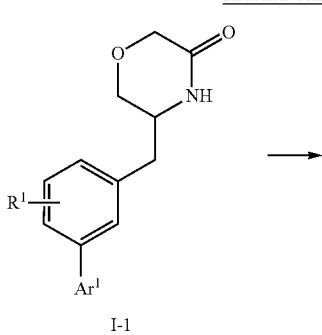

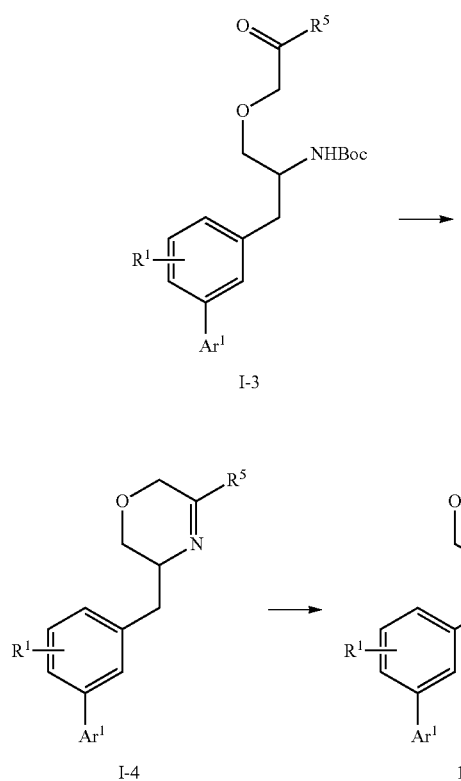

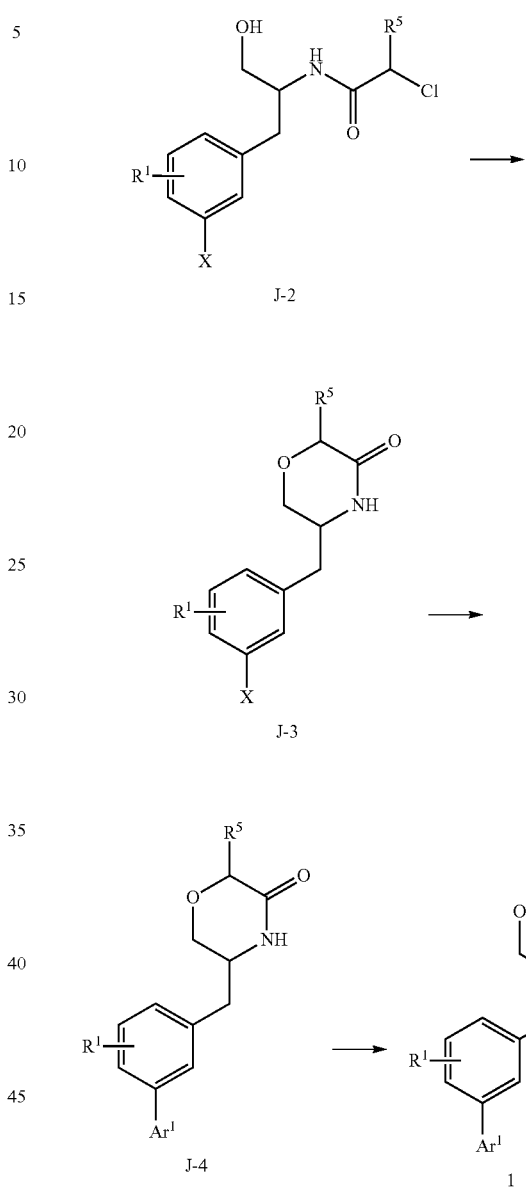

Compounds of Structure 1 may also be prepared as illustrated in Reaction Scheme I. Intermediate I-1, prepared according to Reaction Schemes A, C or G can be Boc-protected following the procedure described by Terashima et al. in Tetrahedron, 1994, 50, 6221-6238 to give Boc-morpholinone I-2. Reaction of I-2 with an appropriate alkyl-metal reagent like alkyl lithium reagents in a solvent like THF at a temperature of −78° C. gives the ring-opened ketone I-3. Boc-deprotection of I-3 by treatment with 4M HCl in dioxane or with TFA leads to cyclic imines of type I-4 that can be subsequently reduced with NaBH$_4$ in a solvent like MeOH to furnish compounds of Structure 1.

Reaction Scheme J

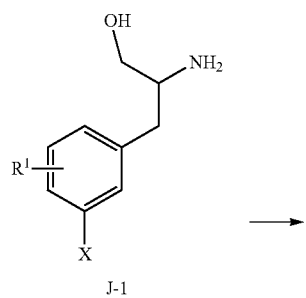

Compounds of Structure 1 may also be prepared as illustrated in Reaction Scheme J. In analogy to the procedure described by Kazmierski et al. in Bioorg. Med. Chem. Lett. 2006, 16, 5226-5230, amino alcohol J-1, prepared according to Reaction Scheme A can be acylated with chloroacetyl chloride derivatives to furnish amide J-2 which upon treatment with a base like sodium hydride or potassium tertbutoxide in a solvent like THF affords morpholinone J-3 as a single cis-diastereomer. Arylation of J-3 can be accomplished under metal catalysed conditions employing for example copper, palladium or zinc catalysts to give intermediates of type J-4. Alternatively, conversion of J-3 into it's corresponding boronic acid or ester followed by a Suzuki reaction gives intermediates of type J-4. Reduction of J-4 with borane in a solvent like THF furnishes compounds of Structure 1.

Reaction Scheme K

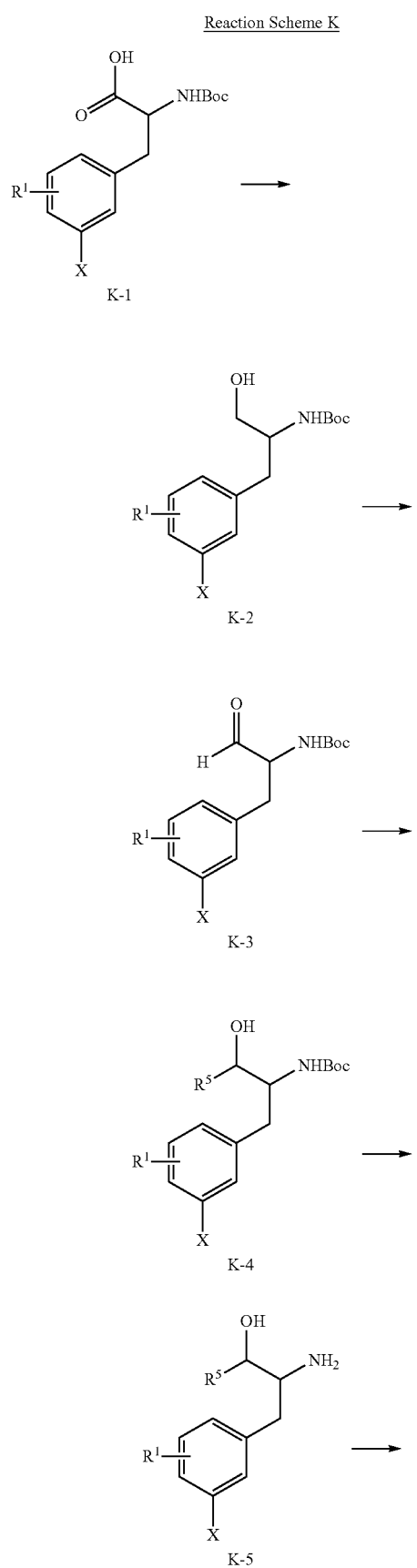

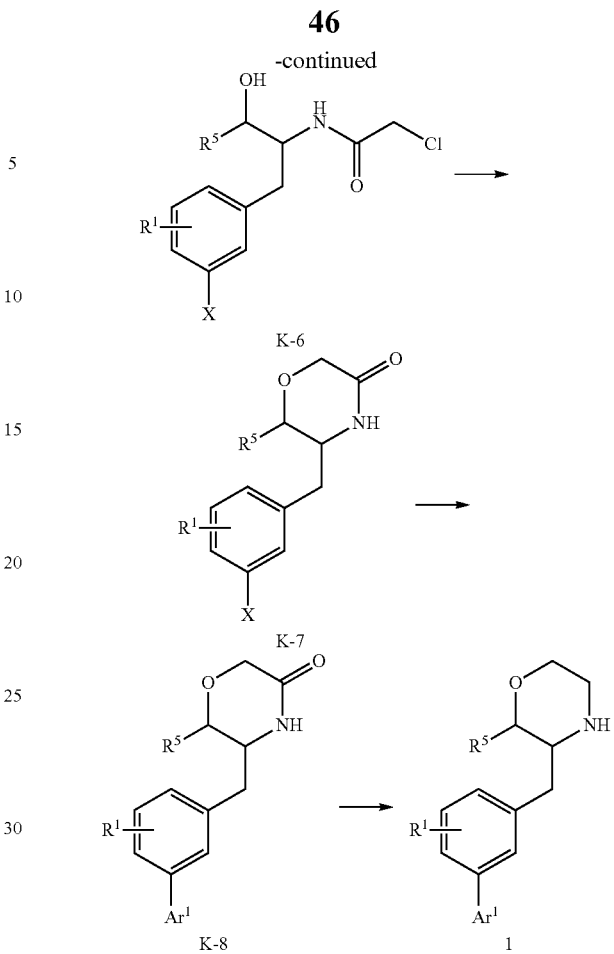

Compounds of Structure 1 may also be prepared as illustrated in Reaction Scheme K. A Boc-protected halophenyl alanine derivative (X=Br or I) K-1, racemic or enantiomerically enriched, either commercially available or prepared as illustrated in Reaction Scheme G can be reduced with NaBH$_4$ via its mixed anhydride in a solvent like THF to afford Boc-protected amino alcohol K-2. Dess-Martin oxidation of K-2 gives the corresponding aldehyde K-3 which can be alkylated with an alkyl zinc or magnesium reagent to give the 2° alcohol K-4. Boc-deprotection of K-4 by treatment with 4M HCl in dioxane or with TFA leads to the amino alcohol K-5 which can be converted into compounds of Structure 1 by following the sequence of transformations described above in Reaction Scheme A.

Reaction Scheme L

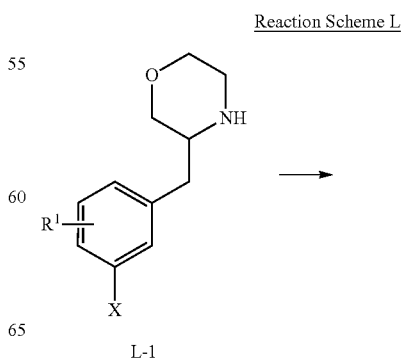

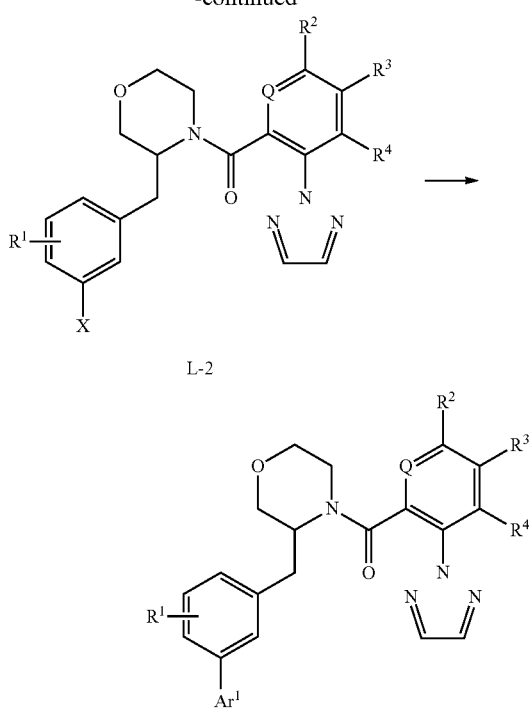

Final compounds of the present invention may also be prepared as illustrated in Reaction Scheme L. For example, intermediate L-1 (X=Br or I), prepared according to Reaction Scheme B can be coupled with an acid of Structure 2 in the presence of an amide-coupling reagent such as TBTU, HATU or EDC, and a base like DIPEA or TEA in a solvent such as MeCN or DMF to furnish intermediates of type L-2. Arylation of L-2 can be accomplished under metal catalysed conditions employing for example copper or palladium catalysts to give final compounds. Alternatively, conversion of L-2 into it's corresponding boronic pinacol ester by treatment with bis(pinacolato) diboron in a solvent like DMSO followed by a Suzuki reaction with the appropriate aryl halide furnishes final compounds.

Carboxylic acid derivatives of Structure 2 are well known in the art and can be especially prepared following the procedures reported in WO2008069997, WO2008008517, WO2010048012, WO2010063662, WO2010063663, WO2011050198, WO2011050200 and WO2011050202. In addition, they may be prepared in analogy to the methods given in the experimental part.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm), IC (5 μm) or AD-H (5 μm) column. Typical conditions of chiral HPLC are an isocratic mixture of eluent A (EtOH, in presence or absence of an amine such as triethylamine or diethylamine) and eluent B (heptane), at a flow rate of 0.8 to 150 mL/min.

The following examples are provided to illustrate the invention. These examples are illustrative only and should not be construed as limiting the invention in any way.

Experimental Part

I. Chemistry

All temperatures are stated in ° C. Commercially available starting materials were used as received without further purification. Unless otherwise specified, all reactions were carried out in oven-dried glassware under an atmosphere of nitrogen. Compounds were purified by flash column chromatography on silica gel or by preparative HPLC. Compounds described in the invention are characterised by LC-MS data (retention time $t_R$ is given in min; molecular weight obtained from the mass spectrum is given in g/mol) using the conditions listed below. In cases where compounds of the present invention appear as a mixture of conformational isomers, particularly visible in their LC-MS spectra, the retention time of the most abundant conformer is given.

LC-MS with Acidic Conditions

Method A:

Agilent 1100 series with mass spectrometry detection (MS: Finnigan single quadrupole). Column: Zorbax SB-aq (3.5 μm, 4.6×50 mm). Conditions: MeCN [eluent A]; water+0.04% TFA [eluent B]. Gradient: 95% B→5% B over 1.5 min (flow: 4.5 mL/min). Detection: UV/Vis+MS.

Method B:

Agilent 1100 series with mass spectrometry detection (MS: Finnigan single quadrupole). Column: Waters XBridge C18 (2.5 μm, 4.6×30 mm). Conditions: MeCN [eluent A]; water+0.04% TFA [eluent B]. Gradient: 95% B→5% B over 1.5 min (flow: 4.5 mL/min). Detection: UV/Vis+MS.

LC-MS with Basic Conditions

Method C:

Agilent 1100 series with mass spectrometry detection (MS: Finnigan single quadrupole). Column: Zorbax Extend C18 (5 μm, 4.6×50 mm). Conditions: MeCN [eluent A]; 13 mmol/L $NH_3$ in water [eluent B]. Gradient: 95% B→5% B over 1.5 min (flow: 4.5 mL/min). Detection: UV/Vis+MS.

Method D:

Agilent 1100 series with mass spectrometry detection (MS: Finnigan single quadrupole). Column: Waters XBridge C18 (5 μm, 4.6×50 mm). Conditions: MeCN [eluent A]; 13 mmol/L $NH_3$ in water [eluent B]. Gradient: 95% B→5% B over 1.5 min (flow: 4.5 mL/min). Detection: UV/Vis+MS.

Preparative HPLC with Acidic Conditions

Method E:

Column: Waters XBridge (10 μm, 75×30 mm). Conditions: MeCN [eluent A]; water+0.5% HCOOH [eluent B]; Gradient: 90% B→5% B over 6.4 min (flow: 75 mL/min). Detection: UV/Vis+MS.

Preparative HPLC with Basic Conditions

Method F:

Column: Waters XBridge (10 μm, 75×30 mm). Conditions: MeCN [eluent A]; water+0.5% $NH_4OH$ (25% aq.) [eluent B]; Gradient: 90% B→5% B over 6.5 min (flow: 75 mL/min). Detection: UV/Vis+MS.

Preparative HPLC for Chiral Separations

Final compounds that are obtained in racemic form are separated into their enantiomers using the following conditions:column:(R,R)Whelk-01 21×250 mm, 5 μM, 15% MeCN in MTBE+0.1% DEA (flow: 16 mL/min). Detection: UV/Vis.

ABBREVIATIONS

As Used Hereinbefore or Hereinafter acac acetylacetonate
aq. aqueous
atm atmosphere
BSA bovine serum albumin
Boc butyloxycarbonyl CDI carbonyl diimidazole
d days
dba dibenzylidene acetone
DCC dicyclohexyl carbodiimide
DCM dichloromethane
DEA diethylamine
DIPEA diisopropyl-ethylamine, Hünig's base, ethyl-diisopropylamine
DMAP 4-dimethylaminopyridne
DMCDA trans-N,N'-dimethylcyclohexane-1,2-diamine
DMF dimethylformamide
DMP Dess-Martin periodinane
DMSO dimethylsulfoxide
dppf 1,1'-bis(diphenylphosphino)ferrocene
EDC N-(3-dimethylaminopropyl)-N'-ethyl-carbodiimide
eq. equivalent(s)
Et ethyl
$Et_2O$ diethyl ether
EtOAc ethyl acetate
Ex. example(s)
h hour(s)
HBTU O-(benzotriazol-1-yl)-N,N,N',N'-tetramethyluronium hexafluorophosphate
HOBt 1-hydroxybenzotriazole
HPLC high performance liquid chromatography
HV high vacuum conditions
$^iBu$ isobutyl
$^iPr$ isopropyl
$KO^tBu$ potassium tert-butoxide
LC-MS liquid chromatography-mass spectrometry
Lit. Literature
Me methyl
MeCN acetonitrile
MeOH methanol
MeLi methyl lithium
MTBE methyl-tertbutyl ether
min minute(s)
NaOAc sodium acetate
$^nBuLi$ n-butyl-lithium
NIS N-iodo succinimide
$^nPr$ n-propyl
OAc acetate
$Pd(dppf)Cl_2.DCM$ [1,1'-bis(diphenylphosphino)-ferrocene] dichloropalladium (II) complex with dichloromethane
Ph phenyl
$PPh_3$ triphenyl phosphine
prep. Preparative
PyBOP benzotriazol-1-yl-oxy-tris-pyrrolidino-phosphonium-hexafluoro-phosphate
rac racemic
RT room temperature
s second(s)
sat. saturated
soln. solution
TBTU 2-(1H-benzotriazole-1-yl)-1,2,3,3-tetramethyluronium tetrafluoroborate
TEA triethylamine
TFA trifluoroacetic acid
TFAA trifluoroacetic anhydride
THF tetrahydrofuran
TLC thin layer chromatography
TMS trimethylsilyl
$t_R$ retention time General Method A for the Synthesis of 3-Benzyl Morpholines of Structure 1

(R)-2-Amino-3-(3-iodo-phenyl)-propionic acid hydrochloride (A-7)

A solution of Boc-3-iodo-D-phenylalanine (5 g, 12.8 mmol, available from Matrix Scientific and 3BSC) in 4M HCl in dioxane (63.9 mL, 256 mmol) under argon was stirred at RT for 15 h. The resulting suspension was filtered, washed with $Et_2O$ and dried in vacuo to give the title compound as a white solid. LC-MS B: $t_R$=0.42 min; $[M+H]^+$=291.98.

(R)-2-Amino-3-(3-iodo-phenyl)-propan-1-ol (A-8)

Borane.THF complex 1M soln. (197 mL, 0.197 mol) was added dropwise to a 0° C. suspension of (R)-2-amino-3-(3-iodo-phenyl)-propionic acid hydrochloride A-7 (21.5 g, 65.8 mmol) in THF (200 mL) under argon and after complete addition the reaction mixture was heated to 70° C. for 2 h. The reaction mixture was cooled to 0° C. and quenched with MeOH and after stirring for 5 min the reaction mixture was evaporated in vacuo. The residue was partitioned between 2M aq. HCl and MeOH and stirred for 30 min before being concentrated in vacuo. The remaining aqueous phase was diluted with additional water and extracted once with DCM. The layers were separated and the organic phase was re-washed with 2M aq. HCl before being discarded. The acidic aq. phases were combined and basified with 5M aq. NaOH and extracted with DCM (3×). The combined organic extracts were dried over $Na_2SO_4$, filtered and evaporated in vacuo to give the title compound as a cream solid that was used further without purification. LC-MS B: $t_R$=0.45 min; $[M+H]^+$=278.03.

2-Chloro-N—[(R)-1-hydroxymethyl-2-(3-iodo-phenyl)-ethyl]-acetamide (A-9)

Chloroacetylchloride (1.05 mL, 13.1 mmol) was added dropwise to a 0° C. solution of (R)-2-amino-3-(3-iodo-phenyl)-propan-1-ol A-8 (3.03 g, 10.9 mmol) and $Et_3N$ (1.98 mL, 14.2 mmol) in THF (50 mL) under argon and the resulting suspension was warmed to RT and stirred for 30 min. The reaction mixture was cooled back to 0° C. before being quenched with water and concentrated in vacuo. The remaining aq. phase was extracted with EtOAc (2×) and the combined organic extracts were washed with brine, dried over $Na_2SO_4$, filtered and evaporated in vacuo to give the title compound as a cream solid that was used further without purification. LC-MS B: $t_R$=0.71 min; $[M(^{35}Cl)+H]^+$=353.75.

(R)-5-(3-Iodo-benzyl)-morpholin-3-one (A-10)

NaH 60% Dispersion in mineral oil (0.93 g, 23.2 mmol) was added portionwise to a 0° C. solution of 2-chloro-N—[(R)-1-hydroxymethyl-2-(3-iodo-phenyl)-ethyl]-acetamide A-9 (3.72 g, 10.5 mmol) in THF (100 mL) under argon and the resulting suspension was warmed to RT and stirred for 1 h. The reaction mixture was cooled back to 0° C. before being quenched with water and concentrated in vacuo. The remaining aqueous phase was extracted with DCM (3×) and the combined organic extracts were washed with brine, dried over Na$_2$SO$_4$, filtered and evaporated in vacuo to give the crude product that was purified by flash chromatography (eluting with a gradient of 50% to 100% EtOAc in hexane) to give the title compound as a white solid. LC-MS B: $t_R$=0.72 min; [M+H+MeCN]$^+$=359.01; $^1$H NMR (CDCl$_3$) δ$_H$: 7.64 (d, J=7.9 Hz, 1H), 7.59 (s, 1H), 7.18 (m, 1H), 7.10 (t, J=7.7 Hz, 1H), 6.25 (s, 1H), 4.20 (s, 2H), 3.91 (dd, J$_1$=11.7 Hz, J$_2$=3.7 Hz, 1H), 3.76 (m, 1H), 3.60 (dd, J$_1$=11.7 Hz, J$_2$=6.1 Hz, 1H), 2.87 (dd, J$_1$=13.6 Hz, J$_2$=6.0 Hz, 1H), 2.72 (dd, J$_1$=13.6 Hz, J$_2$=8.5 Hz, 1H).

(R)-5-(3-Pyrazol-1-yl-benzyl)-morpholin-3-one (A-11)

A mixture of (R)-5-(3-iodo-benzyl)-morpholin-3-one A-10 (1.0 g, 3.15 mmol), pyrazole (322 mg, 4.73 mmol), K$_2$CO$_3$ (872 mg, 6.31 mmol), copper(I) chloride (31 mg, 0.32 mmol) and L-proline (73 mg, 0.63 mmol) in DMF (8 mL) was heated under argon to 110° C. for 24 h. The reaction mixture was cooled to RT and partitioned between water and DCM before being filtered through a celite plug. The layers were separated and the aqueous phase was re-extracted with DCM (2×). The combined organic phases were washed with brine, dried over Na$_2$SO$_4$, filtered and evaporated in vacuo to give the crude product that was purified by flash chromatography (eluting with a gradient of 50% to 100% EtOAc in hexane) to give the title compound as a white solid. LC-MS B: $t_R$=0.51 min; [M+H]$^+$=257.86.

(R)-3-(3-Pyrazol-1-yl-benzyl)-morpholine (A-12)

Borane.THF complex 1M soln. (5.83 mL, 5.83 mmol) was added dropwise to a 0° C. solution of (R)-5-(3-pyrazol-1-yl-benzyl)-morpholin-3-one A-11 (500 mg, 1.94 mmol) in THF (7 mL) under argon and after complete addition the reaction mixture was heated to 70° C. for 2.5 h. The reaction mixture was cooled to 50° C. and quenched with MeOH and 2M aq. HCl before being re-heated to 70° C. for a further 1 h. The reaction mixture was evaporated in vacuo and the residue was partitioned between 2M aq. HCl and EtOAC. The layers were separated and the organic phase was re-washed with 2M aq. HCl before being discarded. The acidic aq. phases were combined and basified with 5M aq. NaOH and extracted with EtOAC (3×). The combined organic extracts were dried over Na$_2$SO$_4$, filtered and evaporated in vacuo to give the title compound as a colourless oil that was used further without purification. LC-MS B: $t_R$=0.41 min; [M+H]$^+$=244.07.

(R)-5-(3-[1,2,3]Triazol-2-yl-benzyl)-morpholin-3-one (A-13) and (R)-5-(3-[1,2,3]triazol-1-yl-benzyl)-morpholin-3-one (A-14)

A mixture of (R)-5-(3-iodo-benzyl)-morpholin-3-one A-10 (3.94 g, 12.4 mmol), 1H-1,2,3-triazole (1.08 mL, 18.6 mmol), K$_2$CO$_3$ (3.43 g, 24.8 mmol), copper(I) chloride (123 mg, 1.24 mmol) and L-proline (286 mg, 2.48 mmol) in DMF (30 mL) was heated under argon to 110° C. for 190 h. The reaction mixture was cooled to RT and partitioned between water and DCM before being filtered through a celite plug. The layers were separated and the aqueous phase was re-extracted with DCM (2×). The combined organic phases were washed with brine, dried over Na$_2$SO$_4$, filtered and evaporated in vacuo to give the crude product that was purified by flash chromatography (eluting with a gradient of 50% to 100% EtOAc in hexane) to give the first title compound as a white solid. LC-MS B: $t_R$=0.55 min; [M+H]$^+$=259.19; $^1$H NMR (CDCl$_3$) δ$_H$: 8.04 (m, 1H), 7.96 (m, 1H), 7.85 (s, 2H), 7.50 (m, 1H), 7.22 (m, 1H), 6.19 (s, 1H), 4.21 (s, 2H), 3.95 (dd, J$_1$=11.7 Hz, J$_2$=3.7 Hz, 1H), 3.86 (m, 1H), 3.64 (m, 1H), 3.02 (m, 1H), 2.89 (m, 1H). Continued elution with 95:5 DCM:MeOH afforded the second title compound as an orange solid. LC-MS B: $t_R$=0.43 min; [M+H]$^+$=259.20; $^1$H NMR (CDCl$_3$) δ$_H$: 8.04 (s, 1H), 7.89 (s, 1H), 7.71 (s, 1H), 7.65 (m, 1H), 7.54 (t, J=7.8 Hz, 1H), 7.31 (d, J=7.6 Hz, 1H), 6.12 (s, 1H), 4.21 (s, 2H), 3.95 (dd, J$_1$=11.7 Hz, J$_2$=3.6 Hz, 1H), 3.85 (m, 1H), 3.66 (dd, J$_1$=11.7 Hz, J$_2$=5.8 Hz, 1H), 3.04 (dd, J$_1$=13.6 Hz, J$_2$=5.7 Hz, 1H), 2.91 (dd, J$_1$=13.6 Hz, J$_2$=8.6 Hz, 1H).

(R)-3-(3-[1,2,3]Triazol-2-yl-benzyl)-morpholine (A-15)

The title compound was prepared from A-13 in analogy to the procedure described for A-12. LC-MS A: $t_R$=0.52 min; [M+H]$^+$=245.18.

(R)-3-(3-[1,2,3]Triazol-1-yl-benzyl)-morpholine (A-16)

The title compound was prepared from A-14 in analogy to the procedure described for A-12. LC-MS A: $t_R$=0.46 min; [M+H]$^+$=245.18.

(R)-5-(3-[1,2,4]Triazol-1-yl-benzyl)-morpholin-3-one (A-17)

The title compound was prepared from A-10 and 1H-1,2,4-triazole in analogy to the procedure described for A-13. LC-MS B: $t_R$=0.42 min; [M+H]$^+$=258.96.

(R)-3-(3-[1,2,4]Triazol-1-yl-benzyl)-morpholine (A-18)

The title compound was prepared from A-17 in analogy to the procedure described for A-12. LC-MS B: $t_R$=0.34 min; [M+H]$^+$=245.08.

(R)-5-(3-Pyrrol-1-yl-benzyl)-morpholin-3-one (A-19)

The title compound was prepared from A-10 and pyrrole in analogy to the procedure described for A-13. LC-MS B: $t_R$=0.64 min; [M+H]$^+$=257.08.

(R)-3-(3-Pyrrol-1-yl-benzyl)-morpholine (A-20)

The title compound was prepared from A-19 in analogy to the procedure described for A-12. LC-MS B: $t_R$=0.51 min; [M+H]$^+$=242.94.

(S)-2-Amino-3-(3-iodo-phenyl)-propionic acid hydrochloride (A-21)

The title compound was prepared from Boc-3-iodo-L-phenylalanine (Matrix Scientific) in analogy to the procedure described for A-7. LC-MS A: $t_R$=0.49 min; [M+H+MeCN]$^+$=333.88.

(S)-2-Amino-3-(3-iodo-phenyl)-propan-1-ol (A-22)

The title compound was prepared from A-21 in analogy to the procedure described for A-8. LC-MS A: $t_R$=0.52 min; [M+H+MeCN]$^+$=319.06.

2-Chloro-N—[(S)-1-hydroxymethyl-2-(3-iodo-phenyl)-ethyl]-acetamide (A-23)

The title compound was prepared from A-22 in analogy to the procedure described for A-9. LC-MS A: $t_R$=0.71 min; [M($^{35}$Cl)+H]$^+$=353.70.

(S)-5-(3-Iodo-benzyl)-morpholin-3-one (A-24)

The title compound was prepared from A-23 in analogy to the procedure described for A-10. LC-MS A: $t_R$=0.72 min; [M+H+MeCN]$^+$=359.01.

(S)-5-(3-[1,2,3]Triazol-2-yl-benzyl)-morpholin-3-one (A-25)

The title compound was prepared from A-24 in analogy to the procedure described for A-13. LC-MS A: $t_R$=0.65 min; [M+H]$^+$=259.18.

(S)-3-(3-[1,2,3]Triazol-2-yl-benzyl)-morpholine (A-26)

The title compound was prepared from A-25 in analogy to the procedure described for A-12. LC-MS B: $t_R$=0.42 min; [M+H]$^+$=245.19.

Listed in Table 1 below are morpholinones of type A-6 prepared from the corresponding Boc-protected halophenyl alanine derivative G-5, in analogy to the sequence of reactions described for A-13. In most cases the isolated racemic morpholinone was subsequently separated into its R- and S-enantiomers by prep. chiral HPLC.

TABLE 1

| No. | Starting material | Intermediate | $t_R$ [min] LC-MS Method | MS-data m/z [M+ H]$^+$ |
|---|---|---|---|---|
| A-27 | G-30 | (R)-5-(2-Fluoro-5-[1,2,3]triazol-2-yl-benzyl)-morpholin-3-one | 0.68 A | 277.08 |
| A-28 | G-31 | (R)-5-(2-Chloro-5-[1,2,3]triazol-2-yl-benzyl)-morpholin-3-one | 0.72 A | ($^{35}$Cl) 293.07 |
| A-29 | G-32 | (R)-5-(2-Methyl-5-[1,2,3]triazol-2-yl-benzyl)-morpholin-3-one | 0.70 A | 273.13 |
| A-30 | G-33 | (R)-5-(3-Chloro-5-[1,2,3]triazol-2-yl-benzyl)-morpholin-3-one | 0.64 B | ($^{35}$Cl) 293.07 |
| A-31 | G-34 | rac-5-(3-Fluoro-5-[1,2,3]triazol-2-yl-benzyl)-morpholin-3-one | 0.70 A | 277.12 |
| A-32 | G-35 | rac-5-(2-Fluoro-3-[1,2,3]triazol-2-yl-benzyl)-morpholin-3-one | 0.50 B | 277.21 |
| A-33 | G-36 | (R)-5-(4-Methyl-3-[1,2,3]triazol-2-yl-benzyl)-morpholin-3-one | 0.56 B | 273.31 |

Listed in Table 2 below are compounds of Structure 1 prepared from the corresponding intermediates of type A-6, in analogy to the procedure described for A-12.

TABLE 2

| No. | Starting material | Morpholine 1 | $t_R$ [min] LC-MS Method | MS-data m/z [M + H]$^+$ |
|---|---|---|---|---|
| A-34 | A-27 | (R)-3-(2-Fluoro-5-[1,2,3]triazol-2-yl-benzyl)-morpholine | 0.53 A | 263.10 |
| A-35 | A-28 | (R)-3-(2-Chloro-5-[1,2,3]triazol-2-yl-benzyl)-morpholine | 0.56 A | ($^{35}$Cl) 279.10 |
| A-36 | A-29 | (R)-3-(2-Methyl-5-[1,2,3]triazol-2-yl-benzyl)-morpholine | 0.56 A | 259.18 |
| A-37 | A-30 | (R)-3-(3-Chloro-5-[1,2,3]triazol-2-yl-benzyl)-morpholine | 0.58 A | 320.09 [M($^{35}$Cl) + H + MeCN]$^+$ |
| A-38 | A-31 | rac-3-(3-Fluoro-5-[1,2,3]triazol-2-yl-benzyl)-morpholine | 0.54 A | 304.13 [M + H + MeCN]$^+$ |
| A-39 | A-32 | rac-3-(2-Fluoro-3-[1,2,3]triazol-2-yl-benzyl)-morpholine | 0.39 B | 263.22 |
| A-40 | A-33 | (R)-3-(4-Methyl-3-[1,2,3]triazol-2-yl-benzyl)-morpholine | 0.44 B | 259.02 |

(R)-5-(2-Methyl-5-pyrazol-1-yl-benzyl)-morpholin-3-one (A-41)

The title compound was prepared from G-32 in analogy to the sequence of reactions described for A-11 followed by prep. chiral HPLC. LC-MS A: $t_R$=0.68 min; [M+H]$^+$=272.14.

(R)-3-(2-Methyl-5-pyrazol-1-yl-benzyl)-morpholine (A-42)

The title compound was prepared from A-41 in analogy to the procedure described for A-12. LC-MS A: $t_R$=0.55 min; [M+H]$^+$=257.99.

General Method B for the Synthesis of 3-Benzyl Morpholines of Structure 1

(R)-3-(3-Iodo-benzyl)-morpholine (B-5)

The title compound was prepared from A-10 in analogy to the procedure described for A-13. LC-MS B: $t_R$=0.50 min; [M+H+MeCN]$^+$=345.02.

(R)-3-(3-Iodo-benzyl)-morpholine-4-carboxylic acid tert-butyl ester (B-6)

A solution of Boc$_2$O (635 mg, 2.91 mmol) in DCM (4 mL) was added dropwise to a RT solution of (R)-3-(3-iodo-benzyl)-morpholine B-5 (864 mg, 2.85 mmol) and Et$_3$N (0.4 mL, 2.99 mmol) in DCM (4 mL) under argon and the resulting mixture was stirred for 3 h. The reaction mixture was quenched with 1M aq. citric acid and stirred for another 10 min. The layers were separated and the aq. layer was re-extracted once with DCM. The combined organic extracts were washed with 1M aq. citric acid and water (2×), dried over Na$_2$SO$_4$, filtered and evaporated in vacuo to give the title compound that was used further without purification. LC-MS B: $t_R$=0.95 min; [M-Me]$^+$=388.82.

(R)-3-[3-(4,4,5,5-Tetramethyl-[1,3,2]dioxaborolan-2-yl)-benzyl]-morpholine-4-carboxylic acid tert-butyl ester (B-7)

Bis(pinacolato)diboron (732 mg, 2.88 mmol) followed by potassium acetate (772 mg, 7.86 mmol) were added in one portion to a RT solution of (R)-3-(3-iodo-benzyl)-morpholine-4-carboxylic acid tert-butyl ester B-6 (1.06 g, 2.62 mmol) in DMSO (10 mL) and argon was bubbled through the resulting suspension for 1 min. Pd(dppf)Cl$_2$.DCM (128 mg, 0.16 mmol) was then added in one portion and the suspension was heated to 80° C. for 20 min. The reaction mixture was cooled back to RT, diluted with Et$_2$O and filtered through a celite plug rinsing with Et$_2$O and a little MeOH. The volatiles were removed in vacuo and the residue was dissolved in Et$_2$O and washed with water (2×) and sat. aq. NH$_4$Cl soln. The organic phase was dried over Na$_2$SO$_4$, filtered through a second celite plug and evaporated in vacuo to give the title compound that was used further without purification. LC-MS B: $t_R$=1.01 min; [M+H-$^t$Bu]$^+$=348.18.

(R)-3-(3-Pyrimidin-2-yl-benzyl)-morpholine-4-carboxylic acid tert-butyl ester (B-8)

2-Bromopyrimidine (43 mg, 0.27 mmol) was added in one portion to a RT solution of (R)-3-[3-(4,4,5,5-tetramethyl-[1,3,2]dioxaborolan-2-yl)-benzyl]-morpholine-4-carboxylic acid tert-butyl ester B-7 (100 mg, 0.25 mmol) in dioxane (0.76 mL) under argon. EtOH (0.38 mL) was then added followed by 2M aq. Na$_2$CO$_3$ (0.38 mL, 0.74 mmol) and argon was bubbled through the resulting suspension for 1 min. Pd(dppf)Cl$_2$.DCM (12 mg, 6 mol %) was added in one portion and the resulting mixture was heated to 80° C. for 2 h. The reaction mixture was cooled to RT, quenched into water and filtered through a celite plug washing with TBME. The layers were separated and the aqueous phase was extracted with TBME (3×). The combined organic extracts were washed with brine, dried over Na$_2$SO$_4$, filtered through a second celite plug and evaporated in vacuo to give the crude product that was purified by prep. HPLC (method E) to give the title compound as a yellow oil. LC-MS B: $t_R$=0.79 min; [M+H]$^+$=356.05.

Listed in Table 3 below are intermediates of type B-4, prepared from (R)-3-[3-(4,4,5,5-tetramethyl-[1,3,2]dioxaborolan-2-yl)-benzyl]-morpholine-4-carboxylic acid tert-butyl ester B-7 according to the procedure described for B-8.

TABLE 3

| No. | Aryl halide | Intermediate | $t_R$ [min] LC-MS Method | MS-data m/z [M + H]$^+$ |
|---|---|---|---|---|
| B-9 | 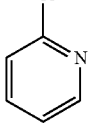 | (R)-3-(3-Pyridin-2-yl-benzyl)-morpholine-4-carboxylic acid tert-butyl ester | 0.60 B | 355.03 |
| B-10 | 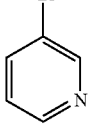 | (R)-3-(3-Pyridin-3-yl-benzyl)-morpholine-4-carboxylic acid tert-butyl ester | 0.59 B | 355.11 |
| B-11 | 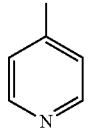 | (R)-3-(3-Pyridin-4-yl-benzyl)-morpholine-4-carboxylic acid tert-butyl ester | 0.57 B | 355.14 |
| B-12 | 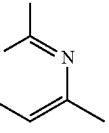 | (R)-3-[3-(4-Methyl-pyrimidin-2-yl)-benzyl]-morpholine-4-carboxylic acid tert-butyl ester | 0.85 B | 369.51 |
| B-13 | 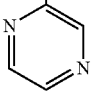 | (R)-3-(3-Pyrazin-2-yl-benzyl)-morpholine-4-carboxylic acid tert-butyl ester | 0.77 B | 356.03 |
| B-14 | 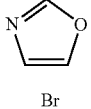 | (R)-3-(3-Oxazol-2-yl-benzyl)-morpholine-4-carboxylic acid tert-butyl ester | 0.79 B | 345.04 |
| B-15 | 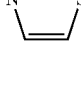 | (R)-3-(3-Thiazol-2-yl-benzyl)-morpholine-4-carboxylic acid tert-butyl ester | 0.84 B | 361.01 |

TABLE 3-continued

| No. | Aryl halide | Intermediate | $t_R$ [min] LC-MS Method | MS-data m/z $[M + H]^+$ |
|---|---|---|---|---|
| B-16 | Br, thiophene | (R)-3-(3-Thiophen-2-yl-benzyl)-morpholine-4-carboxylic acid tert-butyl ester | 0.97 B | 345.00 $[M - Me]^+$ |
| B-17 | Br, pyridazine | (R)-3-(3-Pyridazin-3-yl-benzyl)-morpholine-4-carboxylic acid tert-butyl ester | 0.68 B | 356.05 |

Listed in Table 4 below are compounds of Structure 1 prepared from the corresponding intermediates of type B-4, in analogy to the procedure described for A-7.

TABLE 4

| No. | Starting material | Morpholine 1 | $t_R$ [min] LC-MS Method | MS-data m/z $[M + H]^+$ |
|---|---|---|---|---|
| B-18 | B-8 | (R)-3-(3-Pyrimidin-2-yl-benzyl)-morpholine hydrochloride | 0.40 B | 256.18 |
| B-19 | B-9 | (R)-3-(3-Pyridin-2-yl-benzyl)-morpholine hydrochloride | 0.31 B | 255.08 |
| B-20 | B-10 | (R)-3-(3-Pyridin-3-yl-benzyl)-morpholine hydrochloride | 0.28 B | 296.11 $[M + H + MeCN]^+$ |
| B-21 | B-11 | (R)-3-(3-Pyridin-4-yl-benzyl)-morpholine hydrochloride | 0.27 B | 255.16 |
| B-22 | B-12 | (R)-3-[3-(4-Methyl-pyrimidin-2-yl)-benzyl]-morpholine hydrochloride | 0.44 B | 270.08 |
| B-23 | B-13 | (R)-3-(3-Pyrazin-2-yl-benzyl)-morpholine hydrochloride | 0.39 B | 256.07 |
| B-24 | B-14 | (R)-3-(3-Oxazol-2-yl-benzyl)-morpholine hydrochloride | 0.41 B | 245.08 |
| B-25 | B-15 | (R)-3-(3-Thiazol-2-yl-benzyl)-morpholine hydrochloride | 0.45 B | 261.19 |
| B-26 | B-16 | (R)-3-(3-Thiophen-2-yl-benzyl)-morpholine hydrochloride | 0.56 B | 301.19 $[M + H + MeCN]^+$ |
| B-27 | B-17 | (R)-3-(3-Pyridazin-3-yl-benzyl)-morpholine hydrochloride | 0.35 B | 297.23 |

[(R)-3-(3-Iodo-benzyl)-morpholin-4-yl]-(2-[1,2,3]triazol-2-yl-phenyl)-methanone (B-28)

A solution of (R)-3-(3-iodo-benzyl)-morpholine B-5 (100 mg, 0.33 mmol) and DIPEA (57 μL, 0.33 mmol) in DMF (1.5 mL) was added to a RT solution of 2-(2H-1,2,3-triazol-2-yl)benzoic acid E-2 (62 mg, 0.33 mmol), TBTU (111 mg, 0.35 mmol) and DIPEA (57 μL, 0.33 mmol) in DMF (1.5 ml) under argon and the resulting mixture was stirred for 22 h. The reaction mixture was quenched with sat. aq. NaHCO₃ and stirred for 10 min before being diluted with water and extracted with DCM (3×). The combined organic extracts were washed with 2M aq. NaOH (1×), 2M aq. HCl (1×) and brine (1×), dried over Na₂SO₄, filtered and evaporated in vacuo. The crude product was purified by prep. HPLC (method F) to give the title compound as a white solid. LC-MS D: $t_R$=0.93 min; $[M+H]^+$=474.91.

3-[(R)-4-(2-[1,2,3]Triazol-2-yl-benzoyl)-morpholin-3-ylmethyl]-benzonitrile (B-29)

Pd₂(dba)₃ (11 mg, 0.01 mmol), dppf (7 mg, 0.01 mmol), H₂O (45 μL, 2.49 mmol) and zinc cyanide (73 mg, 0.62 mmol) were added to a RT solution of [(R)-3-(3-iodo-benzyl)-morpholin-4-yl]-(2-[1,2,3]triazol-2-yl-phenyl)-methanone B-28 (118 mg, 0.25 mmol) in DMF (2.49 mL, ~0.1M soln.) and argon was bubbled through the reaction mixture for 5 min before it was heated to 90° C. for 17 h. The reaction mixture was cooled to RT and quenched with sat. aq. NH₄Cl before being extracted with EtOAc (3×). The combined organic extracts were dried over Na₂SO₄, filtered and evaporated in vacuo to give the crude product that was purified by flash chromatography (eluting with a gradient of 25% to 75% EtOAc in hexane) to give the title compound as a yellow solid. LC-MS D: $t_R$=0.81 min; $[M+H]^+$=374.05.

[(R)-3-(3-Iodo-benzyl)-morpholin-4-yl]-(5-methyl-2-[1,2,3]triazol-2-yl-phenyl)-methanone (B-30)

The title compound was prepared from B-5 and E-3 in analogy to the procedure described for B-28. LC-MS D: $t_R$=0.94 min; $[M+H]^+$=488.85.

3-[(R)-4-(5-Methyl-2-[1,2,3]triazol-2-yl-benzoyl)-morpholin-3-ylmethyl]-benzonitrile (B-31)

The title compound was prepared from B-30 in analogy to the procedure described for B-29. LC-MS D: $t_R$=0.85 min; $[M+H]^+$=388.04.

(R)-3-(3-Iodo-4-methoxy-benzyl)-morpholine (B-32)

The title compound was prepared from C-7 in analogy to the procedure described for A-12. LC-MS B: $t_R$=0.48 min; $[M+H]^+$=334.06.

(R)-3-(3-Iodo-4-methoxy-benzyl)-morpholine-4-carboxylic acid tert-butyl ester (B-33)

The title compound was prepared from B-32 in analogy to the procedure described for B-6. LC-MS B: $t_R$=0.91 min; $[M-Me]^+$=418.86.

(R)-3-(3-Cyano-4-methoxy-benzyl)-morpholine-4-carboxylic acid tert-butyl ester (B-34)

The title compound was prepared from B-33 in analogy to the procedure described for B-29. LC-MS B: $t_R$=0.76 min; $[M-Me]^+$=318.13.

(R)-3-(4-Methoxy-3-[1,2,4]oxadiazol-3-yl-benzyl)-morpholine-4-carboxylic acid tert-butyl ester (B-35)

The title compound was prepared from B-34 in analogy to the procedure described for Example 1. LC-MS B: $t_R$=0.72 min; $[M+H-^tBu]^+$=320.04.

(R)-3-(4-Methoxy-3-[1,2,4]oxadiazol-3-yl-benzyl)-morpholine hydrochloride (B-36)

The title compound was prepared from B-35 in analogy to the procedure described for A-7. LC-MS B: $t_R$=0.37 min; $[M+H]^+$=276.11.

(R)-3-(3-Cyano-benzyl)-morpholine-4-carboxylic acid tert-butyl ester (B-37)

The title compound was prepared from B-6 in analogy to the procedure described for B-29. LC-MS B: $t_R$=0.77 min; [M-Me]$^+$=288.18.

(R)-3-(3-[1,2,4]Oxadiazol-3-yl-benzyl)-morpholine-4-carboxylic acid tert-butyl ester (B-38)

The title compound was prepared from B-37 in analogy to the procedure described for Example 1. LC-MS A: $t_R$=0.88 min; [M+H-$^t$Bu]$^+$=290.01.

(R)-3-(3-[1,2,4]Oxadiazol-3-yl-benzyl)-morpholine hydrochloride (B-39)

The title compound was prepared from B-38 in analogy to the procedure described for A-7. LC-MS B: $t_R$=0.37 min; [M+H]$^+$=276.11.

(R)-3-(2-Fluoro-5-[1,2,4]oxadiazol-3-yl-benzyl)-morpholine hydrochloride (B-40)

The title compound was prepared from (R)-2-amino-3-(5-bromo-2-fluorophenyl)propan-1-ol (Chiral Quest), in analogy to the sequence of reactions described for the preparation of B-39. LC-MS A: $t_R$=0.51 min; [M+H]$^+$=264.13.

Rac-3-(4-Methyl-3-[1,2,4]oxadiazol-3-yl-benzyl)-morpholine hydrochloride (B-41)

The title compound was prepared from G-36 in analogy to the sequence of reactions described for the preparation of B-39. LC-MS A: $t_R$=0.54 min; [M+H]$^+$=260.21.

Rac-3-(4-Chloro-3-[1,2,4]oxadiazol-3-yl-benzyl)-morpholine hydrochloride (B-42)

The title compound was prepared from G-37 in analogy to the sequence of reactions described for the preparation of B-39. LC-MS A: $t_R$=0.53 min; [M($^{35}$Cl)+H]$^+$=321.13.

(R)-3-(2-Fluoro-5-pyrimidin-2-yl-benzyl)-morpholine hydrochloride (B-43)

The title compound was prepared from (R)-2-amino-3-(5-bromo-2-fluorophenyl)propan-1-ol (Chiral Quest) or G-30, in analogy to the sequence of reactions described for the preparation of B-18. LC-MS A: $t_R$=0.52 min; [M+H]$^+$=273.85.

(R)-3-(2-Fluoro-5-(pyridazin-3-yl)benzyl)morpholine hydrochloride (B-44)

The title compound was prepared from (R)-2-amino-3-(5-bromo-2-fluorophenyl)propan-1-ol (Chiral Quest) or G-30, in analogy to the sequence of reactions described for the preparation of B-18, substituting 2-bromopyrimidine for 3-bromopyridazine hydrobromide. LC-MS A: $t_R$=0.48 min; [M+H+MeCN]$^+$=315.22.

EXAMPLE COMPOUNDS 1 AND 2

Example 1

[(R)-3-(3-[1,2,4]Oxadiazol-3-yl-benzyl)-morpholin-4-yl]-(2-[1,2,3]triazol-2-yl-phenyl)-methanone Step 1:
Hydroxylamine~50% in H$_2$O (72 µL, 1.17 mmol) was added to a RT suspension of 3-[(R)-4-(2-[1,2,3]triazol-2-yl-benzoyl)-morpholin-3-ylmethyl]-benzonitrile B-29 (30 mg, 0.08 mmol) in EtOH (1 mL) and the resulting suspension was heated to 70° C. for 45 min. The volatiles were removed in vacuo and the crude hydroxyamidine intermediate was used directly in step 2.

Step 2:
p-Toluenesulfonic acid monohydrate (1 mg, 5 mol %) was added to a solution of crude hydroxyamidine from step 1 in trimethyl orthoformate (1 mL) and the resulting mixture was heated to 100° C. for 15 min. The reaction mixture was cooled to RT and filtered through a silica plug (eluting with EtOAc) to give the crude product that was subsequently purified by prep. HPLC (method F) to give the title compound as a white solid. LC-MS D: $t_R$=0.82 min; [M+H]$^+$=417.03.

Example 2

(5-Methyl-2-[1,2,3]triazol-2-yl-phenyl)-[(R)-3-(3-[1,2,4]oxadiazol-3-yl-benzyl)-morpholin-4-yl]-methanone The title compound was prepared from B-31 in analogy to the procedure described for Example 1. LC-MS D: $t_R$=0.82 min; [M+H]$^+$=431.02.

General Method C for the Synthesis of 3-Benzyl Morpholines of Structure 1

(R)-2-Amino-3-(4-methoxy-phenyl)-propan-1-ol (C-4)

The title compound was prepared from p-methoxy-D-phenyl alanine in analogy to the procedure described for A-8. LC-MS A: $t_R$=0.43 min; [M+H]$^+$=182.29.

2-Chloro-N—[(R)-1-hydroxymethyl-2-(4-methoxy-phenyl)-ethyl]-acetamide (C-5)

The title compound was prepared from C-4 in analogy to the procedure described for A-9. LC-MS A: $t_R$=0.61 min; [M($^{35}$Cl)+H]$^+$=257.88.

(R)-5-(4-Methoxy-benzyl)-morpholin-3-one (C-6)

The title compound was prepared from C-5 in analogy to the procedure described for A-10. LC-MS A: $t_R$=0.62 min; [M+H+MeCN]$^+$=263.17.

(R)-5-(3-Iodo-4-methoxy-benzyl)-morpholin-3-one (C-7)

A solution of NIS (559 mg, 2.49 mmol) in DCM (3 mL) was added dropwise to a RT solution of (R)-5-(4-methoxy-benzyl)-morpholin-3-one C-6 (500 mg, 2.26 mmol) and trifluoromethanesulfonic acid (220 µL, 2.49 mmol) in DCM (3 mL) under argon and the resulting mixture was stirred for 40 min. The reaction was quenched with sat. aq. NaHCO$_3$ and the layers were separated. The organic layer was washed with water (2×), dried over Na$_2$SO$_4$, filtered and evaporated in vacuo to give the crude product that was purified by flash chromatography (eluting with a gradient of 50% to 100% EtOAc in hexane) to give the title compound as a pale yellow solid. LC-MS B: t$_R$=0.62 min; [M+H+MeCN]$^+$=388.95.

(R)-5-(4-Methoxy-3-pyrazol-1-yl-benzyl)-morpholin-3-one (C-8)

A mixture of (R)-5-(3-iodo-4-methoxy-benzyl)-morpholin-3-one C-7 (60 mg, 0.17 mmol), pyrazole (18 mg, 0.30 mmol), K$_2$CO$_3$ (48 mg, 0.35 mmol), copper(I) chloride (1.7 mg, 0.02 mmol) and L-proline (4 mg, 0.04 mmol) in DMF (1 mL) was heated under argon to 110° C. for 168 h. The reaction mixture was cooled to RT and partitioned between water and DCM before being filtered through a celite plug. The layers were separated and the aqueous phase was re-extracted with DCM (2×). The combined organic phases were washed with brine, dried over Na$_2$SO$_4$, filtered and evaporated in vacuo to give the crude product that was purified by flash chromatography (Biotage SP1, 10 g SNAP-cartridge eluting with 95:5 DCM:MeOH) to give the title compound as a brown oil. LC-MS B: t$_R$=0.53 min; [M+H]$^+$=288.16.

(R)-3-(4-Methoxy-3-pyrazol-1-yl-benzyl)-morpholine (C-9)

The title compound was prepared from C-8 in analogy to the procedure described for A-12. LC-MS B: t$_R$=0.44 min; [M+H]$^+$=273.91.

General Method D for the Synthesis of Example Compounds of Formula (I)

(R)-3-(4-Methoxy-benzyl)-morpholine (D-5)

The title compound was prepared from C-6 in analogy to the procedure described for A-12. LC-MS B: t$_R$=0.38 min; [M+H]$^+$=208.27.

[(R)-3-(4-Methoxy-benzyl)-morpholin-4-yl]-(2-[1,2,3]triazol-2-yl-phenyl)-methanone (D-6)

The title compound was prepared from D-5 and E-2 in analogy to the procedure described for B-28. LC-MS B: t$_R$=0.72 min; [M+H]$^+$=378.99.

[(R)-3-(3-Iodo-4-methoxy-benzyl)-morpholin-4-yl]-(2-[1,2,3]triazol-2-yl-phenyl)-methanone (D-7)

The title compound was prepared from D-6 in analogy to the procedure described for C-7. LC-MS B: t$_R$=0.80 min; [M+H]$^+$=504.81.

{(R)-3-[4-Methoxy-3-(4,4,5,5-tetramethyl-[1,3,2]dioxaborolan-2-yl)-benzyl]-morpholin-4-yl}-(2-[1,2,3]triazol-2-yl-phenyl)-methanone (D-8)

The title compound was prepared from D-7 in analogy to the procedure described for B-7. LC-MS B: t$_R$=0.81 min; [M+H]$^+$=505.02.

Example Compounds 3 to 10

The aryl halide (0.20 mmol) followed by K$_2$CO$_3$ (82 mg, 0.60 mmol) were added successively in one portion to a RT solution of {(R)-3-[4-methoxy-3-(4,4,5,5-tetramethyl-[1,3,2]dioxaborolan-2-yl)-benzy]-morpholin-4-yl}-(2-[1,2,3]triazol-2-yl-phenyl)-methanone D-8 (100 mg, 0.20 mmol) in dioxane (1.8 mL) and H$_2$O (0.9 mL) under argon. The resulting mixture was degassed with argon for 1 min before Pd(PPh$_3$)$_4$ (12 mg, 0.01 mmol) was added and the reaction mixture was heated to 90° C. for 1 h. The reaction mixture was cooled to RT and quenched with water. The resulting suspension was passed through a phase separator filter extracting with DCM (2×). The combined organic extracts were filtered through a celite plug and evaporated in vacuo. The crude product was purified by prep. HPLC (method E) to furnish the desired product.

Listed in Table 5 below are example compounds, prepared from D-8 according to the above Suzuki procedure.

TABLE 5

| Example No. | Aryl halide | Compound of Formula (I) | t$_R$ [min] LC-MS Method | MS-data m/z [M + H]$^+$ |
|---|---|---|---|---|
| 3 | Br-pyridin-2-yl | [(R)-3-(4-Methoxy-3-pyridin-2-yl-benzyl)-morpholin-4-yl]-(2-[1,2,3]triazol-2-yl-phenyl)-methanone | 0.54 B | 455.94 |
| 4 | Br-pyridin-3-yl | [(R)-3-(4-Methoxy-3-pyridin-3-yl-benzyl)-morpholin-4-yl]-(2-[1,2,3]triazol-2-yl-phenyl)-methanone | 0.56 B | 455.95 |
| 5 | Br-pyrimidin-2-yl | [(R)-3-(4-Methoxy-3-pyrimidin-2-yl-benzyl)-morpholin-4-yl]-(2-[1,2,3]triazol-2-yl-phenyl)-methanone | 0.59 B | 456.93 |

TABLE 5-continued

| Example No. | Aryl halide | Compound of Formula (I) | $t_R$ [min] LC-MS Method | MS-data m/z [M + H]$^+$ |
|---|---|---|---|---|
| 6 | Cl-pyrazine | [(R)-3-(4-Methoxy-3-pyrazin-2-yl-benzyl)-morpholin-4-yl]-(2-[1,2,3]triazol-2-yl-phenyl)-methanone | 0.66 B | 456.93 |
| 7 | Br-pyridazine | [(R)-3-(4-Methoxy-3-pyridazin-3-yl-benzyl)-morpholin-4-yl]-(2-[1,2,3]triazol-2-yl-phenyl)-methanone | 0.61 B | 456.94 |
| 8 | Br-thiazole | [(R)-3-(4-Methoxy-3-thiazol-2-yl-benzyl)-morpholin-4-yl]-(2-[1,2,3]triazol-2-yl-phenyl)-methanone | 0.74 B | 461.90 |
| 9 | Br-oxazole | [(R)-3-(4-Methoxy-3-oxazol-2-yl-benzyl)-morpholin-4-yl]-(2-[1,2,3]triazol-2-yl-phenyl)-methanone | 0.63 B | 445.92 |
| 10 | Br-thiophene | [(R)-3-(4-Methoxy-3-thiophen-2-yl-benzyl)-morpholin-4-yl]-(2-[1,2,3]triazol-2-yl-phenyl)-methanone | 0.85 B | 460.91 |

General Method E for the Synthesis of o-triazolocarboxylic Acids of Structure 2

2-Fluoro-3-methyl-6-(2H-1,2,3-triazol-2-yl)benzoic acid (E-1)

The title compound was prepared in analogy to the procedure described in WO2008/069997. $Cs_2CO_3$ (6.98 g, 21.4 mmol) was added portionwise to a RT solution of 2-fluoro-6-iodo-3-methyl-benzoic acid (3.0 g, 10.7 mmol) in DMF (15 mL) under argon followed by 1H-1,2,3-triazole (1.24 mL, 21.4 mmol) and Cu(I)I (103 mg, 0.536 mmol) and the resulting blue suspension was stirred at 80° C. overnight. The reaction mixture was quenched with 2M aq. HCl and filtered through a celite plug before being extracted with DCM (3×). The combined organic layers were dried over $Na_2SO_4$, filtered and evaporated in vacuo to give the crude product that was purified by prep. HPLC (method E) to give the title compound as a pale yellow solid. LC-MS B: $t_R$=0.55 min; [M+H]$^+$=222.01.

Listed in Table 6 below are o-triazolocarboxylic acids of Structure 2, unless otherwise stated, prepared from the corresponding commercially available iodo-carboxylic acid according to the above procedures.

TABLE 6

| No. | Carboxylic Acid 2 | $t_R$ [min] LC-MS Method | MS-data m/z [M + H]$^+$ |
|---|---|---|---|
| E-2 | 2-(2H-1,2,3-Triazol-2-yl)benzoic acid | 0.55 A | 190.08 |
| E-3 | 5-Methyl-2-(2H-1,2,3-triazol-2-yl)benzoic acid | 0.53 B | 204.13 |
| E-4 | 4-Methyl-2-(2H-1,2,3-triazol-2-yl)benzoic acid | 0.53 B | 204.23 |
| E-5 | 5-Chloro-2-(2H-1,2,3-triazol-2-yl)benzoic acid | 0.66 A | ($^{35}$Cl) 224.3 |
| E-6 | 4,5-Dimethyl-2-(2H-1,2,3-triazol-2-yl)benzoic acid | 0.59 B | 218.09 |
| E-7 | 5-Fluoro-2-(2H-1,2,3-triazol-2-yl)benzoic acid | 0.49 B | 208.32 |
| E-8$^\#$ | 4-Fluoro-2-(2H-1,2,3-triazol-2-yl)benzoic acid | 0.51 B | 208.16 |
| E-9 | 2-Fluoro-3-methoxy-6-(2H-1,2,3-triazol-2-yl)benzoic acid | 0.48 B | 238.01 |

TABLE 6-continued

| No. | Carboxylic Acid 2 | $t_R$ [min] LC-MS Method | MS-data m/z [M + H]$^+$ |
|---|---|---|---|
| E-10 | 5-Methoxy-2-(2H-1,2,3-triazol-2-yl)benzoic acid | 0.49 B | 220.19 |
| E-11[#‡] | 5-Methoxy-4-methyl-2-(2H-1,2,3-triazol-2-yl)benzoic acid | 0.68 A | 234.05 |
| E-12 | 4,5-Dimethoxy-2-(2H-1,2,3-triazol-2-yl)benzoic acid | 0.46 B | 250.03 |
| E-13 | 5-Cyano-2-(2H-1,2,3-triazol-2-yl)benzoic acid | 0.46 B | No ionisation |
| E-14 | 6-Methyl-3-(2H-1,2,3-triazol-2-yl)picolinic acid | 0.30 B | 205.35 |
| E-15[#] | 3-Fluoro-2-(2H-1,2,3-triazol-2-yl)benzoic acid | 0.56 A | 208.08 |
| E-16[#] | 3,5-Dimethyl-2-(2H-1,2,3-triazol-2-yl)benzoic acid | 0.66 A | 218.10 |
| E-17 | 4-Chloro-2-(2H-1,2,3-triazol-2-yl)benzoic acid | 0.66 A | ($^{35}$Cl) 224.10 |
| E-18[#] | 4-Methoxy-2-(2H-1,2,3-triazol-2-yl)benzoic acid | 0.60 A | 220.05 |
| E-19[#‡] | 4-Fluoro-5-methoxy-2-(2H-1,2,3-triazol-2-yl)benzoic acid | 0.64 A | 238.1 |
| E-20 | 3,4-Dimethyl-2-(2H-1,2,3-triazol-2-yl)benzoic acid | 0.65 A | 218.30 |
| E-21[#] | 2-(2H-1,2,3-triazol-2-yl)-4-(trifluoromethyl)benzoic acid | 0.72 A | No ionisation |
| E-22[#‡] | 4-Chloro-5-methoxy-2-(2H-1,2,3-triazol-2-yl)benzoic acid | 0.70 A | ($^{35}$Cl) 254.01 |
| E-23[#] | 3-Chloro-2-(2H-1,2,3-triazol-2-yl)benzoic acid | 0.61 A | ($^{35}$Cl) 224.09 |
| E-24[#] | 4,5-Difluoro-2-(2H-1,2,3-triazol-2-yl)benzoic acid | 0.56 B | No ionisation |
| E-25 | 2-Methyl-6-(2H-1,2,3-triazol-2-yl)benzoic acid | 0.51 B | 204.41 |
| E-26 | 2-Fluoro-6-(2H-1,2,3-triazol-2-yl)benzoic acid | 0.46 B | 208.21 |

[#]Prepared from the corresponding o-bromo-carboxylic acid
[‡]Corresponding o-bromo-carboxylic acid was prepared according to the procedure described below Synthesis of 2-bromo-substituted benzoic acids was performed in analogy to described methods (Tetrahedron Letters, 2009, 50, 1267-1269, J. Org. Chem, 2007, 72, 9786-9789).

2-Bromo-5-methoxy-4-methyl-benzoic acid

Br$_2$ (0.74 mL, 14.4 mmol) was added to a RT suspension of 3-methoxy-4-methylbenzoic acid (2.0 g, 12 mmol) in acetic acid (15 mL) and water (15 mL) and the resulting mixture was heated to 60° C. for 2 h. The reaction mixture was cooled to RT and filtered rinsing with cold water (40 mL) to yield 2-bromo-5-methoxy-4-methylbenzoic acid as a white solid that was used further without purification. LC-MS A: $t_R$=0.76 min, [M+H]$^+$=No ionisation. $^1$H NMR (DMSO) $\delta_H$: 7.49 (s, 1H), 7.29 (s, 1H), 3.82 (s, 3H), 2.17 (s, 3H).

2-Bromo-4-fluoro-5-methoxy-benzoic acid

The title compound was prepared from 4-fluoro-3-methoxybenzoic acid in analogy to the above described method. LC-MS A: $t_R$=0.72 min, [M+H]$^+$=No ionisation. $^1$H NMR (DMSO) $\delta_H$: 13.52 (bs, 1H), 7.77 (dd, 1H), 7.44 (dd, 1H), 4.01 (s, 3H).

2-Bromo-3,5-dimethyl-benzoic acid

The title compound was prepared from 3,5-dimethyl-benzoic acid in analogy to the above described method. LC-MS A: $t_R$=0.75 min, [M+H]$^+$=No ionisation. $^1$H NMR (DMSO) $\delta_H$: 7.56 (s, 1H), 7.28 (m, 2H), 2.36 (s, 3H), 2.27 (s, 3H).

2-Bromo-4-chloro-5-methoxybenzoic acid

The title compound was prepared from 4-chloro-3-methoxybenzoic acid in analogy to the above described method. LC-MS A: $t_R$=0.77 min, [M+H]$^+$=No ionisation. $^1$H NMR (DMSO) $\delta_H$: 13.60 (bs, 1H), 7.82 (s, 1H), 7.47 (s, 1H), 3.91 (s, 3H).

3-Methyl-2-(2H-1,2,3-triazol-2-yl)benzoic acid (E-27)

Step 1:
K$_2$CO$_3$ (8.18 g, 59.2 mmol) was added to a RT solution of 2-fluoro-3-methylbenzonitrile (4.0 g, 29.6 mmol) and 1H-1,2,3-triazole (1.72 mL, 29.6 mmol) in DMF (80 mL) and the resulting suspension was heated to 120° C. for 4 h. The reaction mixture was cooled to RT and quenched with water before being extracted with EtOAc (3×). The combined organic extracts were washed with brine, dried over Na$_2$SO$_4$, filtered and evaporated in vacuo to give the crude product that was purified by flash chromatography (eluting with a gradient of 33% to 50% EtOAc in hexane) to give 3-methyl-2-(2H-1,2,3-triazol-2-yl)benzonitrile as a white solid. LC-MS B: $t_R$=0.62 min; [M+H]$^+$=185.16.

Step 2:
4M aq. NaOH (10 mL, 40.2 mmol) was added to a RT solution of 3-methyl-2-(2H-1,2,3-triazol-2-yl)benzonitrile (1.48 g, 8.04 mmol) in MeOH (15 mL) and the resulting mixture was heated to 90° C. for 50 h. The reaction mixture was cooled to RT and diluted with water before the organic solvent was removed in vacuo. The remaining aqueous phase was acidified with 1M aq. HCl and extracted with EtOAc (3×). The combined organic phases were washed with brine, dried over Na$_2$SO$_4$, filtered and evaporated in vacuo to give the title compound that was used further without purification. LC-MS B: $t_R$=0.50 min; [M+H]$^+$=186.17.

5-Chloro-4-methyl-2-(2H-1,2,3-triazol-2-yl)benzoic acid (E-28)

Cs$_2$CO$_3$ (742 mg, 2.28 mmol) was added portionwise to a RT solution of 2-bromo-5-chloro-4-methyl-benzoic acid methyl ester (300 mg, 1.14 mmol) in DMF (3 mL) followed by 1H-1,2,3-triazole (0.1 mL, 1.71 mmol), Cu(I)I (13 mg, 0.068 mmol) and DMCDA (40 μL, 0.23 mmol). The resulting suspension was heated to 120° C. for 4 h. The reaction mixture was cooled to RT, quenched with 2M aq. HCl and extracted with EtOAc (3×). The combined organic layers were dried over Na$_2$SO$_4$, filtered and evaporated in vacuo to give the crude product that was purified by prep. HPLC (method E) to give the title compound as a pale yellow solid. LC-MS A: $t_R$=0.72 min; [M($^{35}$Cl)+H]$^+$=238.01.

2-(2H-1,2,3-Triazol-2-yl)-3-(trifluoromethyl)benzoic acid (E-29)

The title compound was prepared from 2-iodo-3-(trifluoromethyl)benzonitrile in analogy to the procedure described for E-27. LC-MS A: $t_R$=0.68 min; [M+H]$^+$=No ionisation; $^1$H NMR (DMSO) $\delta_H$: 12.01 (m, 1H), 8.20 (m, 2H), 8.10 (s, 2H), 7.95 (m, 1H).

General Method G for the Synthesis of 3-Benzyl Morpholines of Structure 1

(2-Fluoro-5-iodo-phenyl)-methanol (G-6)

Borane.THF complex 1M soln. (94 mL, 94 mmol) was added dropwise to a 0° C. suspension of 2-fluoro-5-iodobenzoic acid (10 g, 37.6 mmol) in THF (60 mL) under argon and after complete addition the reaction mixture was heated to 70° C. for 2 h. The reaction mixture was cooled to 0° C. and quenched with MeOH and after stirring for 5 min the reaction mixture was evaporated in vacuo. The residue was partitioned between 2M aq. HCl and MeOH and stirred for 30 min at 50° C. before being concentrated in vacuo. The remaining aqueous phase was diluted with additional water and extracted with DCM (3×). The combined organic extracts were dried (Na$_2$SO$_4$), filtered and evaporated in vacuo to give the title compound as a yellow solid that was used further without purification. LC-MS B: $t_R$=0.66 min; [M+H+Na]$^+$=275.99; $^1$H NMR (DMSO) $\delta_H$: 7.77 (dd, J$_1$=7.0 Hz, J$_2$=2.3 Hz, 1H), 7.64 (m, 1H), 7.01 (dd, J$_1$=10.1 Hz, J$_2$=8.6 Hz, 1H), 5.38 (t, J=5.8 Hz, 1H), 4.52 (d, J=5.8 Hz, 2H).

Listed in Table 7 below are intermediates of type G-2, prepared from the corresponding commercially available carboxylic acid according to the above procedure.

TABLE 7

| No. | Intermediate | $t_R$ [min] LC-MS Method | MS-data m/z [M + H + Na]$^+$ |
|---|---|---|---|
| G-7 | (2-Chloro-5-iodo-phenyl)-methanol | 0.79 A | No ionisation |
| G-8 | (5-Iodo-2-methyl-phenyl)-methanol | 0.77 A | 272.09 |

TABLE 7-continued

| No. | Intermediate | $t_R$ [min] LC-MS Method | MS-data m/z [M + H + Na]$^+$ |
|---|---|---|---|
| G-9 | (3-Chloro-5-iodo-phenyl)-methanol | 0.75 B | No ionisation |
| G-10 | (3-Bromo-5-fluoro-phenyl)-methanol | 0.72 A | No ionisation |
| G-11 | (2-Fluoro-3-iodo-phenyl)-methanol | 0.64 B | 276.04 |
| G-12 | (3-Iodo-4-methyl-phenyl)-methanol | 0.70 B | 272.14 |
| G-13 | (4-Chloro-3-iodo-phenyl)-methanol | 0.70 B | ($^{35}$Cl) 291.83 |

2-Bromomethyl-1-fluoro-4-iodo-benzene (G-14)

Phosphorus tribromide 1.0 M soln. in DCM (18.9 mL, 18.9 mmol) was added dropwise to a 0° C. solution of (2-fluoro-5-iodo-phenyl)-methanol G-6 (9.52 g, 37.8 mmol) in DCM (215 mL) and the resulting mixture was stirred for 1 h before being quenched with water. The layers were separated and the aqueous phase was re-extracted with DCM (2×). The combined organic extracts were washed with brine, dried over Na$_2$SO$_4$, filtered and evaporated in vacuo to give the crude product that was purified by flash chromatography (eluting with 5% EtOAc in hexane) to give the title compound as a white solid. LC-MS B: $t_R$=0.92 min; No ionisation; $^1$H NMR (DMSO) $\delta_H$: 7.93 (dd, J$_1$=7.1 Hz, J$_2$=2.3 Hz, 1H), 7.74 (ddd, J$_1$=8.6 Hz, J$_2$=4.9 Hz, J$_3$=2.3 Hz, 1H), 7.10 (dd, J$_1$=10.0 Hz, J$_2$=8.7 Hz, 1H), 4.66 (s, 2H).

Listed in Table 8 below are intermediates of type G-3, prepared from the corresponding benzyl alcohol G-2, according to the above procedure.

TABLE 8

| No. | Intermediate | $t_R$ [min] LC-MS Method | MS-data m/z [M + H]$^+$ |
|---|---|---|---|
| G-15 | 2-Bromomethyl-1-chloro-4-iodo-benzene | 0.96 A | No ionisation |
| G-16 | 2-Bromomethyl-4-iodo-1-methyl-benzene | 0.96 A | No ionisation |
| G-17 | 1-Bromomethyl-3-chloro-5-iodo-benzene | 1.01 B | No ionisation |
| G-18 | 1-Bromo-3-bromomethyl-5-fluoro-benzene | 0.92 A | No ionisation |
| G-19 | 1-Bromomethyl-2-fluoro-3-iodo-benzene | 0.90 B | No ionisation |
| G-20 | 4-Bromomethyl-2-iodo-1-methyl-benzene | 0.97 B | No ionisation |
| G-21 | 4-Bromomethyl-1-chloro-2-iodo-benzene | 0.94 A | No ionisation |

2-tert-Butoxycarbonylamino-2-(2-fluoro-5-iodo-benzyl)-malonic acid diethyl ester (G-22)

A solution of diethyl(Boc-amino)malonate (6.96 g, 25.3 mmol, either commercially available or prepared by conventional Boc-protection of diethylaminomalonate hydrochloride) in DMF (7 mL) was added dropwise to a 0° C. suspension of sodium hydride (0.926 g, 23.2 mmol) in DMF (45 mL)

under N$_2$ and then a solution of 2-bromomethyl-1-fluoro-4-iodo-benzene G-14 (6.62 g, 21.1 mmol) in DMF (30 mL) was added to the suspension. The resulting solution was warmed to RT and stirred for 1 h. The reaction was quenched by the addition of water and the mixture was extracted with DCM (3×). The combined organic extracts were washed with brine, dried over Na$_2$SO$_4$, filtered and evaporated in vacuo to give the crude product as a white solid that was used further without purification. LC-MS B: t$_R$=1.05 min; [M+H]$^+$=510.02.

Listed in Table 9 below are intermediates of type G-4, prepared from the corresponding benzyl bromide G-3, according to the above procedure.

TABLE 9

| No. | Intermediate | t$_R$ [min] LC-MS Method | MS-data m/z [M + H]$^+$ |
|---|---|---|---|
| G-23 | 2-tert-Butoxycarbonylamino-2-(2-chloro-5-iodo-benzyl)-malonic acid diethyl ester | 1.07 A | ($^{35}$Cl) 526.02 |
| G-24 | 2-tert-Butoxycarbonylamino-2-(5-iodo-2-methyl-benzyl)-malonic acid diethyl ester | 1.07 A | 506.00 |
| G-25 | 2-tert-Butoxycarbonylamino-2-(3-chloro-5-iodo-benzyl)-malonic acid diethyl ester | 1.12 B | ($^{35}$Cl) 526.14 |
| G-26 | 2-(3-Bromo-5-fluoro-benzyl)-2-tert-butoxycarbonylamino-malonic acid diethyl ester | 1.05 A | No ionisation |
| G-27 | 2-tert-Butoxycarbonylamino-2-(2-fluoro-3-iodo-benzyl)-malonic acid diethyl ester | 1.03 B | 509.92 |
| G-28 | 2-tert-Butoxycarbonylamino-2-(3-iodo-4-methyl-benzyl)-malonic acid diethyl ester | 1.08 B | 506.04 |
| G-29 | 2-tert-Butoxycarbonylamino-2-(4-chloro-3-iodo-benzyl)-malonic acid diethyl ester | 1.06 A | ($^{35}$Cl) 469.88 |

Rac-2-tert-Butoxycarbonylamino-3-(2-fluoro-5-iodo-phenyl)-propionic acid (G-30)

A suspension of 2-tert-butoxycarbonylamino-2-(2-fluoro-5-iodo-benzyl)-malonic acid diethyl ester G-22 in EtOH (113 mL) was heated to 40° C. and water (50 mL) was then added giving an easily stirrable emulsion. 1M aq. NaOH (93 mL) was carefully added and reaction mixture was heated to 100° C. for 16 h. The reaction mixture was cooled to RT and the volatiles were removed in vacuo. The remaining aqueous phase was extracted once with TBME and this extract was discarded. The aqueous layer was acidified with 25% aq. HCl and extracted with TBME (2×). The combined organic layers were washed with water, dried over Na$_2$SO$_4$, filtered and evaporated in vacuo to give the crude product that was purified by flash chromatography (eluting with a gradient of 25% to 50% EtOAc in hexane) to give the title compound as a white solid. LC-MS B: t$_R$=0.80 min; [M-Me]$^+$=394.95.

Listed in Table 10 below are intermediates of type G-5, prepared from the corresponding malonic acid derivative G-4, according to the above procedure.

TABLE 10

| No. | Intermediate | t$_R$ [min] LC-MS Method | MS-data m/z [M − Me]$^+$ |
|---|---|---|---|
| G-31 | rac-2-tert-Butoxycarbonylamino-3-(2-chloro-5-iodo-phenyl)-propionic acid | 0.88 A | ($^{35}$Cl) 410.85 |
| G-32 | rac-2-tert-Butoxycarbonylamino-3-(5-iodo-2-methyl-phenyl)-propionic acid | 0.88 A | 390.91 |

TABLE 10-continued

| No. | Intermediate | t$_R$ [min] LC-MS Method | MS-data m/z [M − Me]$^+$ |
|---|---|---|---|
| G-33 | rac-2-tert-Butoxycarbonylamino-3-(3-chloro-5-iodo-phenyl)-propionic acid | 0.87 B | ($^{35}$Cl) 410.80 |
| G-34 | rac-3-(3-Bromo-5-fluoro-phenyl)-2-tert-butoxycarbonylamino-propionic acid | 0.85 A | ($^{79}$Br) 347.01 |
| G-35 | rac-2-tert-Butoxycarbonylamino-3-(2-fluoro-3-iodo-phenyl)-propionic acid | 0.79 B | 394.92 |
| G-36 | rac-2-tert-Butoxycarbonylamino-3-(3-iodo-4-methyl-phenyl)-propionic acid | 0.84 B | 391.00 |
| G-37 | rac-2-tert-Butoxycarbonylamino-3-(4-chloro-3-iodo-phenyl)-propionic acid | 0.84 B | ($^{35}$Cl) 410.87 |

General Method H for the Synthesis of 3-Benzyl Morpholines of Structure 1

Rac-2-Amino-3-(3-iodo-phenyl)-2-methyl-propionic acid ethyl ester (H-5)

Step 1:

A suspension of DL-alanine ethyl ester hydrochloride (10 g, 65.1 mmol) in DCM (150 mL) was washed with 2M aq. NaOH and the layers were separated. The organic phase was dried over Na$_2$SO$_4$, filtered and the filtrate was cooled to 0° C. before MgSO$_4$ hydrate (11.3 g) followed by pivalaldeyde (7.72 g, 89.6 mmol) were added and the resulting mixture was warmed to RT and stirred for 16 h. The reaction mixture was filtered and evaporated in vacuo to give rac-ethyl 2-((2,2-dimethylpropylidene)amino)propanoate that was used further without purification.

Step 2:

3-Iodobenzyl bromide (14.4 g, 48.6 mmol) was added to a RT solution of rac-ethyl 2-((2,2-dimethylpropylidene)amino) propanoate (10 g, 48.6 mmol) from above in toluene (100 mL) under argon and the resulting mixture was cooled to −10° C. before KO$^t$Bu (10.9 g, 97.2 mmol) was added portionwise. The reaction mixture was stirred at 0° C. for 4 h before being quenched with water. The toluene was evaporated in vacuo and the remaining aqueous phase was extracted with EtOAC (3×). The combined organic extracts were dried over Na$_2$SO$_4$, filtered and evaporated in vacuo. The residue was stirred in 1M aq. HCl overnight after which LCMS showed the desired product. EtOAc was added and the mixture stirred for 30 min before the layers were separated. The organic phase was discarded and the aqueous phase was basified with 2M aq. NaOH and re-extracted with EtOAc (3×). The combined organic extracts were dried over Na$_2$SO$_4$, filtered and evaporated in vacuo to give the title compound that was used further without purification. LC-MS D: t$_R$=0.88 min; [M+H+MeCN]$^+$=375.06.

Rac-2-Amino-3-(3-iodo-phenyl)-2-methyl-propan-1-ol (H-6)

BH$_3$.THF Complex 1 M soln. in THF (9 mL, 9 mmol) was added dropwise to a 0° C. solution of rac-2-amino-3-(3-iodo-phenyl)-2-methyl-propionic acid ethyl ester H-5 (1.2 g, 3.6 mol) in THF (10 mL) under argon and the resulting mixture was stirred for 5 min at 0° C. before being warmed to RT and stirred overnight. The reaction mixture was cooled to 0° C. and quenched with MeOH before being evaporated in vacuo. The residue was partioned between 2M aq. HCl and TBME and stirred for 30 min. The phases were separated and the aqueous phase was re-extracted with TBME (2×) and the combined organic extracts were discarded. The aqueous layer was basified with 2M aq. NaOH and re-extracted with DCM (3×). The combined DCM extracts were washed with brine, dried over $Na_2SO_4$, filtered and evaporated in vacuo to give the title compound as a white solid. LC-MS D: $t_R$=0.74 min; $[M+H+MeCN]^+$=333.02.

rac-2-Chloro-N-[1-hydroxymethyl-2-(3-iodo-phenyl)-1-methyl-ethyl]-acetamide (H-7)

NaOH 1M aq. soln. (10 mL) followed by NaOH 32% (270 µL) were added to a 0° C. solution of rac-2-amino-3-(3-iodo-phenyl)-2-methyl-propan-1-ol H-6 (850 mg, 2.92 mmol) in DCM (10 mL). After 10 min a solution of chloroacetyl chloride (261 mL, 3.21 mmol) in DCM (10 mL) was added dropwise to the reaction mixture maintaining the temperature below 5° C. The resulting suspension was heated to 35° C. for 30 min after which complete formation of product was observed by LCMS. The layers were separated and the aqueous layer extracted with DCM (2×). The combined organic extracts were washed with brine, dried over $Na_2SO_4$, filtered and evaporated in vacuo to give the title compound that was used further without purification. LC-MS A: $t_R$=0.79 min; $[M(^{35}Cl)+H]^+$=367.91.

Rac-5-(3-Iodo-benzyl)-5-methyl-morpholin-3-one (H-8)

A solution of rac-2-chloro-N-[1-hydroxymethyl-2-(3-iodo-phenyl)-1-methyl-ethyl]-acetamide H-7 (1.0 g, 2.7 mmol) in THF (13 mL) was added dropwise to a RT solution of KO$^t$Bu (6.8 mL, 6.8 mmol, 1M soln. in THF) under argon and the reaction mixture was stirred for 20 min. The reaction was quenched with 1M aq. HCl, diluted with water and concentrated in vacuo. The remaining aqueous phase was extracted with DCM (3×) and the combined organic extracts were dried over $Na_2SO_4$, filtered and evaporated in vacuo to give the title compound that was used further without purification. LC-MS A: $t_R$=0.75 min; $[M+H+MeCN]^+$=373.02.

Rac-5-Methyl-5-(3-[1,2,3]triazol-2-yl-benzyl)-morpholin-3-one (H-9)

DMCDA (85 µL, 0.538 mmol) followed by 1H-1,2,3-triazole (0.31 mL, 5.38 mmol) were added to a mixture of rac-5-(3-iodo-benzyl)-5-methyl-morpholin-3-one H-8 (890 mg, 2.69 mmol), $Cs_2CO_3$ (1.75 g, 5.38 mmol) and CuI (77 mg, 0.40 mmol) in DMF (5 mL) under argon and the resulting blue suspension was heated to 120° C. for 18 h. The reaction mixture was cooled to RT before being quenched with water and filtered over celite rinsing with water and DCM. The layers were separated and the aqueous phase was re-extracted with DCM (2×). The combined organic extracts were washed with brine, dried over $Na_2SO_4$, filtered and evaporated in vacuo. The crude product was purified by flash chromatography (eluting with a gradient of 75% to 100% EtOAc in hexane) to give the title compound as a pale brown solid. LC-MS A: $t_R$=0.69 min; $[M+H]^+$=273.21.

Rac-3-Methyl-3-(3-[1,2,3]triazol-2-yl-benzyl)-morpholine (H-10)

The title compound was prepared from H-9 in analogy to the procedure described for A-12. LC-MS A: $t_R$=0.55 min; $[M+H]^+$=259.07.

General Method I for the Synthesis of 3-Benzyl Morpholines of Structure 1

(R)-3-Oxo-5-(3-[1,2,3]triazol-2-yl-benzyl)-morpholine-4-carboxylic acid tert-butyl ester (I-5)

$Boc_2O$ (1.79 g, 8.19 mmol) was added in one portion to a RT solution of (R)-5-(3-[1,2,3]triazol-2-yl-benzyl)-morpholin-3-one A-13 (1.06 g, 4.09 mmol) and DMAP (51 mg, 0.41 mmol) in $Et_3N$:MeCN 3:1 (16 mL) under Argon and the resulting mixture was stirred for 1.5 h. The reaction mixture was diluted with EtOAc, transferred to a separating funnel and washed successively with 3% aq. HCl, sat. aq. $NaHCO_3$ and brine. The organic phase was dried over $Na_2SO_4$, filtered and evaporated in vacuo to give the title compound that was used further without purification. LC-MS B: $t_R$=0.81 min; $[M+H-Boc]^+$=259.17.

[(R)-2-(2-Oxo-propoxy)-1-(3-[1,2,3]triazol-2-yl-benzyl)-ethyl]-carbamic acid tert-butyl ester (I-6)

MeLi 1.6 M in $Et_2O$ (3.6 mL, 5.82 mmol) was added dropwise to a −78° C. solution of (R)-3-oxo-5-(3-[1,2,3]triazol-2-yl-benzyl)-morpholine-4-carboxylic acid tert-butyl ester I-5 (1.49 g, 4.16 mmol) in THF (15 mL) and the resulting mixture was stirred at −78° C. for 3 h. The reaction mixture was quenched with sat. aq. $NH_4Cl$, warmed to RT and the solvent was removed in vacuo. The remaining aqueous layer was extracted with EtOAc (3×) and the combined organic extracts were washed with brine, dried over $Na_2SO_4$, filtered and evaporated in vacuo. The crude product was purified by flash chromatography (eluting with 20% to 50% EtOAc in hexane) to give the title compound as a yellow solid. LC-MS B: $t_R$=0.81 min; $[M+H-Boc]^+$=259.17.

(3R,5R)-3-Methyl-5-(3-[1,2,3]triazol-2-yl-benzyl)-morpholine (I-7) and (3S,5R)-3-Methyl-5-(3-[1,2,3]triazol-2-yl-benzyl)-morpholine (I-8)

Step 1:
[(R)-2-(2-Oxo-propoxy)-1-(3-[1,2,3]triazol-2-yl-benzyl)-ethyl]-carbamic acid tert-butyl ester (I-6) (500 mg, 1.34 mmol) was dissolved in TFA (5 mL) at 0° C. and stirred for 1 h. The reaction mixture was evaporated in vacuo and used directly in Step 2.
Step 2:
The Boc-cleaved intermediate from above was dissolved in MeOH (10 mL) and cooled to 0° C. Sodium borohydride (52 mg, 1.37 mmol) was then added and the resulting mixture was stirred for 1 h. The reaction mixture was quenched with water and the solvent was evaporated in vacuo. The remaining aqueous phase was extracted once with DCM and this extract was discarded. The aqueous layer was basified with 5M aq. NaOH and re-extracted with DCM (3×). The combined basic organic extracts were washed with brine, dried over $Na_2SO_4$, filtered and evaporated in vacuo to give the crude product that was purified by flash chromatography (eluting with 95:5 DCM:MeOH) to give the first title compound as a colourless oil. LC-MS A: $t_R$=0.55 min; $[M+H]^+$=259.20. Continued elution afforded the second title compound (major product) as a colourless oil. LC-MS A: $t_R$=0.54 min; $[M+H]^+$=259.21.

General Method J for the Synthesis of 3-Benzyl Morpholines of Structure 1

(R)—N—[(R)-1-(3-Iodo-benzyl)-2-hydroxy-ethyl]-2-chloro-propionamide and (S)—N—[(R)-1-(3-Iodo-benzyl)-2-hydroxy-ethyl]-2-chloro-propionamide (J-5)

The title compounds were prepared as a mixture of diastereomers from A-8 and rac-2-chloropropanoyl chloride in analogy to the procedure described for H-7. LC-MS A: $t_R$=0.76 min; [M($^{35}$Cl)+H]$^+$=367.98.

(2R,5R)-5-(3-Iodo-benzyl)-2-methyl-morpholin-3-one (J-6)

The title compound was prepared as a single cis-stereoisomer from J-5 in analogy to the procedure described for H-8. LC-MS A: $t_R$=0.76 min; [M+H+MeCN]$^+$=373.04.

(2R,5R)-2-Methyl-5-(3-[1,2,3]triazol-2-yl-benzyl)-morpholin-3-one (J-7) and (2S,5R)-2-Methyl-5-(3-[1,2,3]triazol-2-yl-benzyl)-morpholin-3-one (J-8)

The title compounds were prepared from J-6 in analogy to the procedure described for H-9. J-7 LC-MS A: $t_R$=0.69 min; [M+H]$^+$=273.11. J-8 (minor product) LC-MS A: $t_R$=0.70 min; [M+H]$^+$=273.14.

(2R,5R)-2-Methyl-5-(3-[1,2,3]triazol-2-yl-benzyl)-morpholine (J-9)

The title compound was prepared from J-7 in analogy to the procedure described for A-12. LC-MS A: $t_R$=0.57 min; [M+H]$^+$=259.07.

(2S,5R)-2-Methyl-5-(3-[1,2,3]triazol-2-yl-benzyl)-morpholine (J-10)

The title compound was prepared from J-8 in analogy to the procedure described for A-12. LC-MS A: $t_R$=0.55 min; [M+H]$^+$=259.07.

(2R,5R)-2-Ethyl-5-(3-[1,2,3]triazol-2-yl-benzyl)-morpholine (J-11)

The title compound was prepared from A-8 and rac-2-chlorobutanoyl chloride in analogy to the sequence of reactions described for J-9. LC-MS A: $t_R$=0.59 min; [M+H]$^+$=273.17.

(2R,5R)-5-(2-Fluoro-5-[1,2,3]triazol-2-yl-benzyl)-2-methyl-morpholine (J-12)

The title compound was prepared from (R)-2-amino-3-(5-bromo-2-fluorophenyl)propan-1-ol (Chiral Quest) or G-30, in analogy to the sequence of reactions described for the preparation of J-9. LC-MS A: $t_R$=0.57 min; [M+H]$^+$=277.11.

(2R,5R)-5-(2-Fluoro-5-[1,2,3]triazol-1-yl-benzyl)-2-methyl-morpholine (J-13)

The title compound was prepared from (R)-2-amino-3-(5-bromo-2-fluorophenyl)propan-1-ol (Chiral Quest), in analogy to the sequence of reactions described for the preparation of J-9 and A-16. LC-MS A: $t_R$=0.50 min; [M+H+MeCN]$^+$=318.14.

(2R,5R)-2-Methyl-5-(3-pyrimidin-2-yl-benzyl)-morpholine hydrochloride (J-14)

The title compound was prepared from A-8 and rac-2-chloropropanoyl chloride, in analogy to the sequence of reactions described for the preparation of B-18. LC-MS A: $t_R$=0.53 min; [M+H]$^+$=270.14.

(2R,5R)-5-(2-Fluoro-5-pyrimidin-2-yl-benzyl)-2-methyl-morpholine hydrochloride (J-15)

The title compound was prepared from (R)-2-amino-3-(5-bromo-2-fluorophenyl)propan-1-ol (Chiral Quest) and rac-2-chloropropanoyl chloride, in analogy to the sequence of reactions described for the preparation of B-18. LC-MS A: $t_R$=0.56 min; [M+H]$^+$=288.24.

(2R,5R)-5-(2-Fluoro-5-pyridazin-3-yl-benzyl)-2-methyl-morpholine hydrochloride (J-16)

The title compound was prepared from (R)-2-amino-3-(5-bromo-2-fluorophenyl)propan-1-ol (Chiral Quest) and rac-2-chloropropanoyl chloride, in analogy to the sequence of reactions described for the preparation of B-18 substituting 2-bromopyrimidine for 3-bromopyridazine hydrobromide. LC-MS A: $t_R$=0.52 min; [M+H]$^+$=288.25.

General Method K for the Synthesis of 3-Benzyl Morpholines of Structure 1

[(R)-1-Hydroxymethyl-2-(3-iodo-phenyl)-ethyl]-carbamic acid tert-butyl ester (K-9)

A solution of Boc-3-iodo-D-phenylalanine (6.32 g, 16.2 mmol) and 4-methyl-morpholine (1.87 ml, 17 mol) in THF (13 mL) was added dropwise to a −15° C. solution of isobutyl chloroformate (2.22 mL, 17 mmol) in THF (13 mL) and the resulting suspension was stirred for 1 h. The cold reaction mixture was filtered and the filter cake was rinsed with THF. The filtrate was added dropwise to a 0° C. solution of NaBH$_4$ (0.92 g, 24.2 mmol) in dimethylacetamide (7 mL) and the resulting suspension was warmed to RT and stirred for 1 h. The reaction mixture was cooled back to 0° C. and quenched with 1M aq. citric acid. Additional water was added and the mixture was concentrated in vacuo. The remaining aqueous phase was acidified with 1M aq. HCl before being filtered. The filter cake was rinsed with water and dried under HV to give the title compound as an orange solid that was used further without purification. LC-MS A: $t_R$=0.84 min; [M-Me]$^+$=362.93.

[(R)-1-Formyl-2-(3-iodo-phenyl)-ethyl]-carbamic acid tert-butyl ester (K-10)

A solution of [(R)-1-hydroxymethyl-2-(3-iodo-phenyl)-ethyl]-carbamic acid tert-butyl ester K-9 (5.32 g, 14.1 mmol) in DCM (100 mL) was added dropwise to a RT suspension of DMP (6.78 g, 15.5 mmol) in DCM (40 mL) and the resulting mixture was stirred for 1.5 h. The reaction was quenched with 20% aq. NaHCO$_3$ and 10% aq. Na$_2$S$_2$O$_3$ and stirred for 1 h. The layers were separated and the aqueous layer was extracted with DCM (2×). The combined organic extracts were washed with 1M aq. HCl, brine, dried over Na$_2$SO$_4$, filtered and evaporated in vacuo. The crude product was subsequently triturated with a little DCM to give the title compound as an orange solid. LC-MS A: $t_R$=0.87 min; [M+H]$^+$=No ionisation.

[(1R,2S)-2-Hydroxy-1-(3-iodo-benzyl)-propyl]-carbamic acid tert-butyl ester and [(1R,2R)-2-Hydroxy-1-(3-iodo-benzyl)-propyl]-carbamic acid tert-butyl ester (K-11)

Methylmagnesium bromide 3.0 M soln. in Et$_2$O (8.4 mL, 25.2 mmol) was added dropwise to a −78° C. solution of [(R)-1-formyl-2-(3-iodo-phenyl)-ethyl]-carbamic acid tert-butyl ester K-10 (4.72 g, 12.6 mmol) in THF (100 mL) and the resulting mixture was warmed to 0° C. and stirred for 15 min. The reaction was quenched with sat. aq. NH$_4$Cl and the volatiles were removed in vacuo. The remaining aqueous phase was extracted with DCM (3×) and the combined organic extracts were washed with brine, dried over Na$_2$SO$_4$, filtered and evaporated in vacuo. The crude product purified by flash chromatography (eluting with 25% to 50% EtOAc in hexane) to give the title compounds as an ~1:1 mixture of diastereomers. LC-MS A: $t_R$=0.88 min; [M+H]$^+$=376.97.

(2S,3R)-3-Amino-4-(3-iodo-phenyl)-butan-2-ol hydrochloride and (2R,3R)-3-Amino-4-(3-iodo-phenyl)-butan-2-ol hydrochloride (K-12)

The title compounds were prepared from K-11 in analogy to the procedure described for A-7. LC-MS A: $t_R$=0.55 min; [M+H+MeCN]$^+$=333.10.

2-Chloro-N-[(1R,2S)-2-hydroxy-1-(3-iodo-benzyl)-propyl]-acetamide and 2-Chloro-N-[(1R,2R)-2-hydroxy-1-(3-iodo-benzyl)-propyl]-acetamide (K-13)

The title compounds were prepared from K-12 and chloroacetyl chloride in analogy to the procedure described for H-7. LC-MS A: $t_R$=0.75 min; [M($^{35}$Cl)+H]$^+$=367.91.

(5R,6S)-5-(3-Iodo-benzyl)-6-methyl-morpholin-3-one and (5R,6R)-5-(3-Iodo-benzyl)-6-methyl-morpholin-3-one (K-14)

The title compounds were prepared from K-13 in analogy to the procedure described for H-8. LC-MS A: $t_R$=0.76 min; [M+H+MeCN]$^+$=372.92.

(5R,6R)-6-Methyl-5-(3-[1,2,3]triazol-2-yl-benzyl)-morpholin-3-one and (5R,6S)-6-Methyl-5-(3-[1,2,3]triazol-2-yl-benzyl)-morpholin-3-one (K-15 & K-16)

The title compounds were prepared from K-14 in analogy to the procedure described for H-9 and the two diastereomers were subsequently separated by flash chromatography (eluting with a gradient of 50% to 70% EtOAc in hexane). K-15 or K16 LC-MS A: $t_R$=0.70 min; [M+H]$^+$=273.18. K-16 or K-15 LC-MS A: $t_R$=0.69 min; [M+H]$^+$=273.27.

(2R,3R)-2-Methyl-3-(3-[1,2,3]triazol-2-yl-benzyl)-morpholine (K-17)

The title compound was prepared from K-15 or K-16 in analogy to the procedure described for A-12. LC-MS A: $t_R$=0.55 min; [M+H]$^+$=259.21 or $t_R$=0.56 min; [M+H]$^+$=259.30.

(2S,3R)-2-Methyl-3-(3-[1,2,3]triazol-2-yl-benzyl)-morpholine (K-18)

The title compound was prepared from K-16 or K-15 in analogy to the procedure described for A-12. LC-MS A: $t_R$=0.56 min; [M+H]$^+$=259.30 or $t_R$=0.55 min; [M+H]$^+$=259.21.

General method L for the Synthesis of Example Compounds of Formula (I)

Rac-{3-[4-Methyl-3-(4,4,5,5-tetramethyl-[1,3,2]dioxaborolan-2-yl)-benzyl]-morpholin-4-yl}-(2-[1,2,3]triazol-2-yl-phenyl)-methanone (L-3)

The title compound was prepared from rac-2-tert-butoxycarbonylamino-3-(3-iodo-4-methyl-phenyl)-propionic acid G-36, in analogy to the sequence of reactions described for the preparation of D-8. LC-MS B: $t_R$=0.96 min; [M+H]$^+$=489.12.

Rac-{3-[4-Chloro-3-(4,4,5,5-tetramethyl-[1,3,2]dioxaborolan-2-yl)-benzyl]-morpholin-4-yl}-(2-[1,2,3]triazol-2-yl-phenyl)-methanone (L-4)

The title compound was prepared from rac-2-tert-Butoxycarbonylamino-3-(4-chloro-3-iodo-phenyl)-propionic acid G-37, in analogy to the sequence of reactions described for the preparation of D-8. LC-MS A: $t_R$=0.93 min; [M($^{35}$Cl)+H]$^+$=508.96.

Example Compounds 11 to 54

General Method F-1 for the Synthesis of Example Compounds of Formula (I)

TBTU (34 mg, 0.11 mmol) was added to a RT solution of the required acid 2 (0.1 mmol) and DIPEA (25 μL, 0.15 mmol) in DMF (0.5 mL) and after stirring for 5 min a solution of the required amine 1 as its free base or HCl salt (0.1 mmol) and DIPEA (25 μL, 0.15 mmol) in DMF (0.5 mL) was added. The resulting mixture was stirred for up to 4 d before being purified directly by prep. HPLC (method F) to furnish the desired product.

General Method F-2 for the Synthesis of Example Compounds of Formula (I)

A freshly prepared solution of the corresponding acid chloride of carboxylic acid 2 (0.11 mmol) in MeCN (0.5 mL) was added to a solution of the required amine 1 as its free base or HCl salt (0.1 mmol) and Et$_3$N (0.2 mmol) in MeCN (0.5 mL) and the resulting mixture was stirred at RT for up to 4 d. The reaction mixture was subsequently purified directly by prep. HPLC (method F) to furnish the desired product. Example compounds prepared according to General Method F-2 include Examples 68 to 74.

Listed in Tables 11 and 12 below are example compounds, prepared according to the above-mentioned methods F-1 and F-2, from the corresponding amine 1, prepared as described above and the corresponding carboxylic acid 2, prepared as described above.

TABLE 11

| Example No. | Amine 1 | Acid 2 | Compound of Formula (I) |
|---|---|---|---|
| 11 | A-15 | E-3 | (5-Methyl-2-[1,2,3]triazol-2-yl-phenyl)-[(R)-3-(3-[1,2,3]triazol-2-yl-benzyl)-morpholin-4-yl]-methanone; LC-MS D: $t_R$ = 0.85 min; [M + H]$^+$ = 430.05 |
| 12 | A-15 | E-2 | [(R)-3-(3-[1,2,3]Triazol-2-yl-benzyl)-morpholin-4-yl]-(2-[1,2,3]triazol-2-yl-phenyl)-methanone; LC-MS B: $t_R$ = 0.73 min; [M + H]$^+$ = 416.0 |
| 13 | A-26 | E-2 | [(S)-3-(3-[1,2,3]Triazol-2-yl-benzyl)-morpholin-4-yl]-(2-[1,2,3]triazol-2-yl-phenyl)-methanone; LC-MS D: $t_R$ = 0.85 min; [M + H]$^+$ = 416.05 |
| 14 | C-9 | E-2 | [(R)-3-(4-Methoxy-3-pyrazol-1-yl-benzyl)-morpholin-4-yl]-(2-[1,2,3]triazol-2-yl-phenyl)-methanone; LC-MS D: $t_R$ = 0.82 min; [M + H]$^+$ = 444.99 |
| 15 | A-16 | E-3 | (5-Methyl-2-[1,2,3]triazol-2-yl-phenyl)-[(R)-3-(3-[1,2,3]triazol-1-yl-benzyl)-morpholin-4-yl]-methanone; LC-MS D: $t_R$ = 0.79 min; [M + H]$^+$ = 430.00 |
| 16 | A-12 | E-2 | [(R)-3-(3-Pyrazol-1-yl-benzyl)-morpholin-4-yl]-(2-[1,2,3]triazol-2-yl-phenyl)-methanone; LC-MS D: $t_R$ = 0.83 min; [M + H]$^+$ = 415.07 |
| 17 | B-18 | E-3 | (5-Methyl-2-[1,2,3]triazol-2-yl-phenyl)-[(R)-3-(3-pyrimidin-2-yl-benzyl)-morpholin-4-yl]-methanone; LC-MS D: $t_R$ = 0.82 min; [M + H]$^+$ = 441.06 |
| 18 | B-18 | E-2 | [(R)-3-(3-Pyrimidin-2-yl-benzyl)-morpholin-4-yl]-(2-[1,2,3]triazol-2-yl-phenyl)-methanone; LC-MS D: $t_R$ = 0.82 min; [M + H]$^+$ = 426.96 |
| 19 | A-12 | E-3 | (5-Methyl-2-[1,2,3]triazol-2-yl-phenyl)-[(R)-3-(3-pyrazol-1-yl-benzyl)-morpholin-4-yl]-methanone; LC-MS D: $t_R$ = 0.83 min; [M + H]$^+$ = 429.04 |
| 20 | A-12 | E-7 | (5-Fluoro-2-[1,2,3]triazol-2-yl-phenyl)-[(R)-3-(3-pyrazol-1-yl-benzyl)-morpholin-4-yl]-methanone; LC-MS D: $t_R$ = 0.85 min; [M + H]$^+$ = 433.02 |
| 21 | A-12 | E-1 | (2-Fluoro-3-methyl-6-[1,2,3]triazol-2-yl-phenyl)-[(R)-3-(3-pyrazol-1-yl-benzyl)-morpholin-4-yl]-methanone; LC-MS D: $t_R$ = 0.90 min; [M + H]$^+$ = 447.02 |
| 22 | A-12 | E-4 | (4-Methyl-2-[1,2,3]triazol-2-yl-phenyl)-[(R)-3-(3-pyrazol-1-yl-benzyl)-morpholin-4-yl]-methanone; LC-MS D: $t_R$ = 0.83 min; [M + H]$^+$ = 429.02 |
| 23 | A-18 | E-3 | (5-Methyl-2-[1,2,3]triazol-2-yl-phenyl)-[(R)-3-(3-[1,2,4]triazol-1-yl-benzyl)-morpholin-4-yl]-methanone; LC-MS D: $t_R$ = 0.78 min; [M + H]$^+$ = 430.03 |
| 24 | B-19 | E-3 | (5-Methyl-2-[1,2,3]triazol-2-yl-phenyl)-[(R)-3-(3-pyridin-2-yl-benzyl)-morpholin-4-yl]-methanone; LC-MS D: $t_R$ = 0.84 min; [M + H]$^+$ = 440.04 |
| 25 | B-20 | E-3 | (5-Methyl-2-[1,2,3]triazol-2-yl-phenyl)-[(R)-3-(3-pyridin-3-yl-benzyl)-morpholin-4-yl]-methanone; LC-MS D: $t_R$ = 0.80 min; [M + H]$^+$ = 440.07 |
| 26 | A-15 | E-7 | (5-Fluoro-2-[1,2,3]triazol-2-yl-phenyl)-[(R)-3-(3-[1,2,3]triazol-2-yl-benzyl)-morpholin-4-yl]-methanone; LC-MS D: $t_R$ = 0.87 min; [M + H]$^+$ = 434.02 |
| 27 | A-15 | E-4 | (4-Methyl-2-[1,2,3]triazol-2-yl-phenyl)-[(R)-3-(3-[1,2,3]triazol-2-yl-benzyl)-morpholin-4-yl]-methanone; LC-MS D: $t_R$ = 0.87 min; [M + H]$^+$ = 430.05 |
| 28 | B-21 | E-3 | (5-Methyl-2-[1,2,3]triazol-2-yl-phenyl)-[(R)-3-(3-pyridin-4-yl-benzyl)-morpholin-4-yl]-methanone; LC-MS D: $t_R$ = 0.79 min; [M + H]$^+$ = 440.06 |
| 29 | A-15 | E-1 | (2-Fluoro-3-methyl-6-[1,2,3]triazol-2-yl-phenyl)-[(R)-3-(3-[1,2,3]triazol-2-yl-benzyl)-morpholin-4-yl]-methanone; LC-MS D: $t_R$ = 0.93 min; [M + H]$^+$ = 448.05 |
| 30 | A-15 | E-5 | (5-Chloro-2-[1,2,3]triazol-2-yl-phenyl)-[(R)-3-(3-[1,2,3]triazol-2-yl-benzyl)-morpholin-4-yl]-methanone; LC-MS D: $t_R$ = 0.87 min; [M($^{35}$Cl) + H]$^+$ = 449.99 |
| 31 | A-15 | E-13 | 4-[1,2,3]Triazol-2-yl-3-[(R)-3-(3-[1,2,3]triazol-2-yl-benzyl)-morpholine-4-carbonyl]-benzonitrile; LC-MS D: $t_R$ = 0.80 min; [M + H]$^+$ = 441.04 |
| 32 | A-15 | E-10 | (5-Methoxy-2-[1,2,3]triazol-2-yl-phenyl)-[(R)-3-(3-[1,2,3]triazol-2-yl-benzyl)-morpholin-4-yl]-methanone; LC-MS D: $t_R$ = 0.86 min; [M + H]$^+$ = 446.05 |
| 33 | A-15 | E-9 | (2-Fluoro-3-methoxy-6-[1,2,3]triazol-2-yl-phenyl)-[(R)-3-(3-[1,2,3]triazol-2-yl-benzyl)-morpholin-4-yl]-methanone; LC-MS D: $t_R$ = 0.86 min; [M + H]$^+$ = 464.07 |
| 34 | A-15 | E-12 | (4,5-Dimethoxy-2-[1,2,3]triazol-2-yl-phenyl)-[(R)-3-(3-[1,2,3]triazol-2-yl-benzyl)-morpholin-4-yl]-methanone; LC-MS D: $t_R$ = 0.81 min; [M + H]$^+$ = 476.09 |
| 35 | A-15 | E-6 | (4,5-Dimethyl-2-[1,2,3]triazol-2-yl-phenyl)-[(R)-3-(3-[1,2,3]triazol-2-yl-benzyl)-morpholin-4-yl]-methanone; LC-MS D: $t_R$ = 0.88 min; [M + H]$^+$ = 444.09 |

TABLE 11-continued

| Example No. | Amine 1 | Acid 2 | Compound of Formula (I) |
|---|---|---|---|
| 36 | A-15 | E-8 | (4-Fluoro-2-[1,2,3]triazol-2-yl-phenyl)-[(R)-3-(3-[1,2,3]triazol-2-yl-benzyl)-morpholin-4-yl]-methanone; LC-MS D: $t_R$ = 0.85 min; [M + H]$^+$ = 434.06 |
| 37 | A-15 | E-11 | (5-Methoxy-4-methyl-2-[1,2,3]triazol-2-yl-phenyl)-[(R)-3-(3-[1,2,3]triazol-2-yl-benzyl)-morpholin-4-yl]-methanone; LC-MS D: $t_R$ = 0.90 min; [M + H]$^+$ = 460.06 |
| 38 | A-20 | E-3 | (5-Methyl-2-[1,2,3]triazol-2-yl-phenyl)-[(R)-3-(3-pyrrol-1-yl-benzyl)-morpholin-4-yl]-methanone; LC-MS B: $t_R$ = 0.84 min; [M + H]$^+$ = 427.94 |
| 39 | B-22 | E-3 | {(R)-3-[3-(4-Methyl-pyrimidin-2-yl)-benzyl]-morpholin-4-yl}-(5-methyl-2-[1,2,3]triazol-2-yl-phenyl)-methanone; LC-MS D: $t_R$ = 0.86 min; [M + H]$^+$ = 455.07 |
| 40 | B-22 | E-2 | {(R)-3-[3-(4-Methyl-pyrimidin-2-yl)-benzyl]-morpholin-4-yl}-(2-[1,2,3]triazol-2-yl-phenyl)-methanone; LC-MS D: $t_R$ = 0.85 min; [M + H]$^+$ = 441.04 |
| 41 | B-23 | E-3 | (5-Methyl-2-[1,2,3]triazol-2-yl-phenyl)-[(R)-3-(3-pyrazin-2-yl-benzyl)-morpholin-4-yl]-methanone; LC-MS D: $t_R$ = 0.79 min; [M + H]$^+$ = 441.05 |
| 42 | B-24 | E-2 | [(R)-3-(3-Oxazol-2-yl-benzyl)-morpholin-4-yl]-(2-[1,2,3]triazol-2-yl-phenyl)-methanone; LC-MS D: $t_R$ = 0.81 min; [M + H]$^+$ = 416.04 |
| 43 | B-25 | E-3 | (5-Methyl-2-[1,2,3]triazol-2-yl-phenyl)-[(R)-3-(3-thiazol-2-yl-benzyl)-morpholin-4-yl]-methanone; LC-MS D: $t_R$ = 0.87 min; [M + H]$^+$ = 445.99 |
| 44 | B-25 | E-2 | [(R)-3-(3-Thiazol-2-yl-benzyl)-morpholin-4-yl]-(2-[1,2,3]triazol-2-yl-phenyl)-methanone; LC-MS D: $t_R$ = 0.85 min; [M + H]$^+$ = 432.00 |
| 45 | B-26 | E-3 | (5-Methyl-2-[1,2,3]triazol-2-yl-phenyl)-[(R)-3-(3-thiophen-2-yl-benzyl)-morpholin-4-yl]-methanone; LC-MS D: $t_R$ = 0.97 min; [M + H]$^+$ = 445.01 |
| 46 | B-26 | E-2 | [(R)-3-(3-Thiophen-2-yl-benzyl)-morpholin-4-yl]-(2-[1,2,3]triazol-2-yl-phenyl)-methanone; LC-MS D: $t_R$ = 0.94 min; [M + H]$^+$ = 431.00 |
| 47 | B-27 | E-3 | (5-Methyl-2-[1,2,3]triazol-2-yl-phenyl)-[(R)-3-(3-pyridazin-3-yl-benzyl)-morpholin-4-yl]-methanone; LC-MS D: $t_R$ = 0.78 min; [M + H]$^+$ = 441.05 |
| 48 | B-27 | E-2 | [(R)-3-(3-Pyridazin-3-yl-benzyl)-morpholin-4-yl]-(2-[1,2,3]triazol-2-yl-phenyl)-methanone; LC-MS D: $t_R$ = 0.75 min; [M + H]$^+$ = 426.92 |
| 49 | B-18 | E-1 | (2-Fluoro-3-methyl-6-[1,2,3]triazol-2-yl-phenyl)-[(R)-3-(3-pyrimidin-2-yl-benzyl)-morpholin-4-yl]-methanone; LC-MS D: $t_R$ = 0.85 min; [M + H]$^+$ = 458.93 |
| 50 | B-18 | E-10 | (5-Methoxy-2-[1,2,3]triazol-2-yl-phenyl)-[(R)-3-(3-pyrimidin-2-yl-benzyl)-morpholin-4-yl]-methanone; LC-MS D: $t_R$ = 0.83 min; [M + H]$^+$ = 456.96 |
| 51 | B-18 | E-5 | (5-Chloro-2-[1,2,3]triazol-2-yl-phenyl)-[(R)-3-(3-pyrimidin-2-yl-benzyl)-morpholin-4-yl]-methanone; LC-MS D: $t_R$ = 0.84 min; [M($^{35}$Cl) + H]$^+$ = 460.99 |
| 52 | A-15 | E-14 | (6-Methyl-3-[1,2,3]triazol-2-yl-pyridin-2-yl)-[(R)-3-(3-[1,2,3]triazol-2-yl-benzyl)-morpholin-4-yl]-methanone; LC-MS D: $t_R$ = 0.82 min; [M + H]$^+$ = 431.06 |
| 53 | A-12 | E-14 | (6-Methyl-3-[1,2,3]triazol-2-yl-pyridin-2-yl)-[(R)-3-(3-pyrazol-1-yl-benzyl)-morpholin-4-yl]-methanone; LC-MS D: $t_R$ = 0.80 min; [M + H]$^+$ = 430.03 |
| 54 | A-15 | E-15 | (3-Fluoro-2-[1,2,3]triazol-2-yl-phenyl)-[(R)-3-(3-[1,2,3]triazol-2-yl-benzyl)-morpholin-4-yl]-methanone; LC-MS D: $t_R$ = 0.84 min; [M + H]$^+$ = 434.04 |

Example Compound 55

[(R)-3-(4-Hydroxy-3-pyrimidin-2-yl-benzyl)-morpholin-4-yl]-(2-[1,2,3]triazol-2-yl-phenyl)-methanone Boron tribromide 1M soln. in DCM (0.8 mL, 0.8 mmol) was added to a −78° C. solution of [(R)-3-(4-methoxy-3-pyrimidin-2-yl-benzyl)-morpholin-4-yl]-(2-[1,2,3]triazol-2-yl-phenyl)-methanone Example 5 (72 mg, 0.16 mmol) in DCM (5 mL) and after complete addition the the reaction mixture was warmed to RT and stirred for 6 h. The reaction was quenched with sat. aq. NaHCO$_3$ and the layers were separated. The aqueous layer was extracted with DCM (2×) and the combined organic extracts were dried over Na$_2$SO$_4$, filtered and evaporated in vacuo. The crude product was purified by prep. HPLC (method F) to give the title compound as a white solid. LC-MS D: $t_R$=0.80 min; [M+H]$^+$=443.03.

Example Compounds 56 to 191

TABLE 12

| Example No. | Amine 1 | Acid 2 | Compound of Formula (I) |
|---|---|---|---|
| 56 | A-34 | E-3 | [(R)-3-(2-Fluoro-5-[1,2,3]triazol-2-yl-benzyl)-morpholin-4-yl]-(5-methyl-2-[1,2,3]triazol-2-yl-phenyl)-methanone; LC-MS D: $t_R$ = 0.87 min; $[M + H]^+$ = 448.07 |
| 57 | A-34 | E-2 | [(R)-3-(2-Fluoro-5-[1,2,3]triazol-2-yl-benzyl)-morpholin-4-yl]-(2-[1,2,3]triazol-2-yl-phenyl)-methanone; LC-MS D: $t_R$ = 0.86 min; $[M + H]^+$ = 434.06 |
| 58 | B-36 | E-3 | [(R)-3-(4-Methoxy-3-[1,2,4]oxadiazol-3-yl-benzyl)-morpholin-4-yl]-(5-methyl-2-[1,2,3]triazol-2-yl-phenyl)-methanone; LC-MS D: $t_R$ = 0.85 min; $[M + H]^+$ = 416.05 |
| 59 | B-36 | E-2 | [(R)-3-(4-Methoxy-3-[1,2,4]oxadiazol-3-yl-benzyl)-morpholin-4-yl]-(2-[1,2,3]triazol-2-yl-phenyl)-methanone; LC-MS D: $t_R$ = 0.78 min; $[M + H]^+$ = 447.04 |
| 60 | B-36 | E-4 | [(R)-3-(4-Methoxy-3-[1,2,4]oxadiazol-3-yl-benzyl)-morpholin-4-yl]-(4-methyl-2-[1,2,3]triazol-2-yl-phenyl)-methanone; LC-MS D: $t_R$ = 0.82 min; $[M + H]^+$ = 461.06 |
| 61 | B-36 | E-8 | (4-Fluoro-2-[1,2,3]triazol-2-yl-phenyl)-[(R)-3-(4-methoxy-3-[1,2,4]oxadiazol-3-yl-benzyl)-morpholin-4-yl]-methanone; LC-MS D: $t_R$ = 0.81 min; $[M + H]^+$ = 465.04 |
| 62 | A-34 | E-4 | [(R)-3-(2-Fluoro-5-[1,2,3]triazol-2-yl-benzyl)-morpholin-4-yl]-(4-methyl-2-[1,2,3]triazol-2-yl-phenyl)-methanone; LC-MS D: $t_R$ = 0.90 min; $[M + H]^+$ = 448.09 |
| 63 | B-36 | E-25 | [(R)-3-(4-Methoxy-3-[1,2,4]oxadiazol-3-yl-benzyl)-morpholin-4-yl]-(2-methyl-6-[1,2,3]triazol-2-yl-phenyl)-methanone; LC-MS D: $t_R$ = 0.75 min; $[M + H]^+$ = 461.07 |
| 64 | A-15 | E-27 | (3-Methyl-2-[1,2,3]triazol-2-yl-phenyl)-[(R)-3-(3-[1,2,3]triazol-2-yl-benzyl)-morpholin-4-yl]-methanone; LC-MS D: $t_R$ = 0.86 min; $[M + H]^+$ = 430.09 |
| 65 | A-40 | E-3 | [(R)-3-(4-Methyl-3-[1,2,3]triazol-2-yl-benzyl)-morpholin-4-yl]-(5-methyl-2-[1,2,3]triazol-2-yl-phenyl)-methanone; LC-MS D: $t_R$ = 0.87 min; $[M + H]^+$ = 444.06 |
| 66 | A-40 | E-2 | [(R)-3-(4-Methyl-3-[1,2,3]triazol-2-yl-benzyl)-morpholin-4-yl]-(2-[1,2,3]triazol-2-yl-phenyl)-methanone; LC-MS D: $t_R$ = 0.86 min; $[M + H]^+$ = 430.04 |
| 67 | A-40 | E-4 | [(R)-3-(4-Methyl-3-[1,2,3]triazol-2-yl-benzyl)-morpholin-4-yl]-(4-methyl-2-[1,2,3]triazol-2-yl-phenyl)-methanone; LC-MS D: $t_R$ = 0.88 min; $[M + H]^+$ = 444.10 |
| 68 | I-7 | E-2 | [(3R,5R)-3-Methyl-5-(3-[1,2,3]triazol-2-yl-benzyl)-morpholin-4-yl]-(2-[1,2,3]triazol-2-yl-phenyl)-methanone; LC-MS D: $t_R$ = 0.88 min; $[M + H]^+$ = 430.09 |
| 69 | I-7 | E-4 | [(3R,5R)-3-Methyl-5-(3-[1,2,3]triazol-2-yl-benzyl)-morpholin-4-yl]-(4-methyl-2-[1,2,3]triazol-2-yl-phenyl)-methanone; LC-MS D: $t_R$ = 0.92 min; $[M + H]^+$ = 444.13 |
| 70 | I-7 | E-27 | [(3R,5R)-3-Methyl-5-(3-[1,2,3]triazol-2-yl-benzyl)-morpholin-4-yl]-(3-methyl-2-[1,2,3]triazol-2-yl-phenyl)-methanone; LC-MS D: $t_R$ = 0.90 min; $[M + H]^+$ = 444.14 |
| 71 | I-8 | E-4 | [(3S,5R)-3-Methyl-5-(3-[1,2,3]triazol-2-yl-benzyl)-morpholin-4-yl]-(4-methyl-2-[1,2,3]triazol-2-yl-phenyl)-methanone; LC-MS D: $t_R$ = 0.92 min; $[M + H]^+$ = 444.08 |
| 72 | I-8 | E-27 | [(3S,5R)-3-Methyl-5-(3-[1,2,3]triazol-2-yl-benzyl)-morpholin-4-yl]-(3-methyl-2-[1,2,3]triazol-2-yl-phenyl)-methanone; LC-MS D: $t_R$ = 0.91 min; $[M + H]^+$ = 444.12 |
| 73 | I-8 | E-3 | [(3S,5R)-3-Methyl-5-(3-[1,2,3]triazol-2-yl-benzyl)-morpholin-4-yl]-(5-methyl-2-[1,2,3]triazol-2-yl-phenyl)-methanone; LC-MS D: $t_R$ = 0.92 min; $[M + H]^+$ = 444.15 |
| 74 | I-8 | E-6 | (4,5-Dimethyl-2-[1,2,3]triazol-2-yl-phenyl)-[(3S,5R)-3-methyl-5-(3-[1,2,3]triazol-2-yl-benzyl)-morpholin-4-yl]-methanone; LC-MS D: $t_R$ = 0.95 min; $[M + H]^+$ = 457.82 |
| 75 | A-15 | E-16 | (3,5-Dimethyl-2-[1,2,3]triazol-2-yl-phenyl)-[(R)-3-(3-[1,2,3]triazol-2-yl-benzyl)-morpholin-4-yl]-methanone; LC-MS D: $t_R$ = 0.90 min; $[M + H]^+$ = 444.14 |
| 76 | A-15 | E-21 | [(R)-3-(3-[1,2,3]Triazol-2-yl-benzyl)-morpholin-4-yl]-(2-[1,2,3]triazol-2-yl-4-trifluoromethyl-phenyl)-methanone; LC-MS D: $t_R$ = 0.92 min; $[M + H]^+$ = 484.13 |
| 77 | A-15 | E-17 | (4-Chloro-2-[1,2,3]triazol-2-yl-phenyl)-[(R)-3-(3-[1,2,3]triazol-2-yl-benzyl)-morpholin-4-yl]-methanone; LC-MS D: $t_R$ = 0.89 min; $[M(^{35}Cl) + H]^+$ = 450.07 |
| 78 | A-15 | E-19 | (4-Fluoro-5-methoxy-2-[1,2,3]triazol-2-yl-phenyl)-[(R)-3-(3-[1,2,3]triazol-2-yl-benzyl)-morpholin-4-yl]-methanone; LC-MS D: $t_R$ = 0.88 min; $[M + H]^+$ = 464.11 |
| 79* | B-41 | E-6 | (4,5-Dimethyl-2-[1,2,3]triazol-2-yl-phenyl)-[(R)-3-(4-methyl-3-[1,2,4]oxadiazol-3-yl-benzyl)-morpholin-4-yl]-methanone; LC-MS A: $t_R$ = 0.90 min; $[M + H]^+$ = 459.11 |

TABLE 12-continued

| Example No. | Amine 1 | Acid 2 | Compound of Formula (I) |
|---|---|---|---|
| 80 | B-39 | E-24 | (4,5-Difluoro-2-[1,2,3]triazol-2-yl-phenyl)-[(R)-3-(3-[1,2,4]oxadiazol-3-yl-benzyl)-morpholin-4-yl]-methanone; LC-MS A: $t_R$ = 0.85 min; [M + H]$^+$ = 453.07 |
| 81 | B-39 | E-4 | (4-Methyl-2-[1,2,3]triazol-2-yl-phenyl)-[(R)-3-(3-[1,2,4]oxadiazol-3-yl-benzyl)-morpholin-4-yl]-methanone; LC-MS A: $t_R$ = 0.85 min; [M + H]$^+$ = 431.10 |
| 82 | B-39 | E-15 | (3-Fluoro-2-[1,2,3]triazol-2-yl-phenyl)-[(R)-3-(3-[1,2,4]oxadiazol-3-yl-benzyl)-morpholin-4-yl]-methanone; LC-MS A: $t_R$ = 0.90 min; [M + H]$^+$ = 460.06 |
| 83 | B-39 | E-27 | (3-Methyl-2-[1,2,3]triazol-2-yl-phenyl)-[(R)-3-(3-[1,2,4]oxadiazol-3-yl-benzyl)-morpholin-4-yl]-methanone; LC-MS A: $t_R$ = 0.83 min; [M + H]$^+$ = 431.09 |
| 84 | B-39 | E-5 | (5-Chloro-2-[1,2,3]triazol-2-yl-phenyl)-[(R)-3-(3-[1,2,4]oxadiazol-3-yl-benzyl)-morpholin-4-yl]-methanone; LC-MS A: $t_R$ = 0.87 min; [M($^{35}$Cl) + H]$^+$ = 451.04 |
| 85 | B-39 | E-6 | (4,5-Dimethyl-2-[1,2,3]triazol-2-yl-phenyl)-[(R)-3-(3-[1,2,4]oxadiazol-3-yl-benzyl)-morpholin-4-yl]-methanone; LC-MS A: $t_R$ = 0.87 min; [M + H]$^+$ = 445.13 |
| 86 | B-39 | E-17 | (4-Chloro-2-[1,2,3]triazol-2-yl-phenyl)-[(R)-3-(3-[1,2,4]oxadiazol-3-yl-benzyl)-morpholin-4-yl]-methanone; LC-MS A: $t_R$ = 0.87 min; [M($^{35}$Cl) + H]$^+$ = 451.09 |
| 87 | B-39 | E-21 | [(R)-3-(3-[1,2,4]Oxadiazol-3-yl-benzyl)-morpholin-4-yl]-(2-[1,2,3]triazol-2-yl-4-trifluoromethyl-phenyl)-methanone; LC-MS A: $t_R$ = 0.89 min; [M + H]$^+$ = 485.09 |
| 88 | B-39 | E-7 | (5-Fluoro-2-[1,2,3]triazol-2-yl-phenyl)-[(R)-3-(3-[1,2,4]oxadiazol-3-yl-benzyl)-morpholin-4-yl]-methanone; LC-MS A: $t_R$ = 0.82 min; [M + H]$^+$ = 435.02 |
| 89 | B-39 | E-16 | (3,5-Dimethyl-2-[1,2,3]triazol-2-yl-phenyl)-[(R)-3-(3-[1,2,4]oxadiazol-3-yl-benzyl)-morpholin-4-yl]-methanone; LC-MS A: $t_R$ = 0.86 min; [M + H]$^+$ = 445.09 |
| 90* | B-42 | E-2 | [(R)-3-(4-Chloro-3-[1,2,4]oxadiazol-3-yl-benzyl)-morpholin-4-yl]-(2-[1,2,3]triazol-2-yl-phenyl)-methanone; LC-MS A: $t_R$ = 0.84 min; [M($^{35}$Cl) + H]$^+$ = 451.04 |
| 91 | A-15 | E-24 | (4,5-Difluoro-2-[1,2,3]triazol-2-yl-phenyl)-[(R)-3-(3-[1,2,3]triazol-2-yl-benzyl)-morpholin-4-yl]-methanone; LC-MS D: $t_R$ = 0.87 min; [M + H]$^+$ = 452.11 |
| 92 | A-15 | E-20 | (3,4-Dimethyl-2-[1,2,3]triazol-2-yl-phenyl)-[(R)-3-(3-[1,2,3]triazol-2-yl-benzyl)-morpholin-4-yl]-methanone; LC-MS D: $t_R$ = 0.89 min; [M + H]$^+$ = 444.16 |
| 93 | A-15 | E-18 | (4-Methoxy-2-[1,2,3]triazol-2-yl-phenyl)-[(R)-3-(3-[1,2,3]triazol-2-yl-benzyl)-morpholin-4-yl]-methanone; LC-MS D: $t_R$ = 0.85 min; [M + H]$^+$ = 446.13 |
| 94 | A-34 | E-20 | (3,4-Dimethyl-2-[1,2,3]triazol-2-yl-phenyl)-[(R)-3-(2-fluoro-5-[1,2,3]triazol-2-yl-benzyl)-morpholin-4-yl]-methanone; LC-MS D: $t_R$ = 0.90 min; [M + H]$^+$ = 462.17 |
| 95 | A-34 | E-18 | [(R)-3-(2-Fluoro-5-[1,2,3]triazol-2-yl-benzyl)-morpholin-4-yl]-(4-methoxy-2-[1,2,3]triazol-2-yl-phenyl)-methanone; LC-MS D: $t_R$ = 0.86 min; [M + H]$^+$ = 464.11 |
| 96 | J-10 | E-4 | [(2S,5R)-2-Methyl-5-(3-[1,2,3]triazol-2-yl-benzyl)-morpholin-4-yl]-(4-methyl-2-[1,2,3]triazol-2-yl-phenyl)-methanone; LC-MS D: $t_R$ = 0.90 min; [M + H]$^+$ = 444.18 |
| 97 | J-9 | E-27 | [(2R,5R)-2-Methyl-5-(3-[1,2,3]triazol-2-yl-benzyl)-morpholin-4-yl]-(3-methyl-2-[1,2,3]triazol-2-yl-phenyl)-methanone; LC-MS D: $t_R$ = 0.91 min; [M + H]$^+$ = 444.13 |
| 98 | J-9 | E-6 | (4,5-Dimethyl-2-[1,2,3]triazol-2-yl-phenyl)-[(2R,5R)-2-methyl-5-(3-[1,2,3]triazol-2-yl-benzyl)-morpholin-4-yl]-methanone; LC-MS D: $t_R$ = 0.91 min; [M + H]$^+$ = 458.00 |
| 99 | J-9 | E-20 | (3,4-Dimethyl-2-[1,2,3]triazol-2-yl-phenyl)-[(2R,5R)-2-methyl-5-(3-[1,2,3]triazol-2-yl-benzyl)-morpholin-4-yl]-methanone; LC-MS D: $t_R$ = 0.94 min; [M + H]$^+$ = 457.91 |
| 100 | J-9 | E-2 | [(2R,5R)-2-Methyl-5-(3-[1,2,3]triazol-2-yl-benzyl)-morpholin-4-yl]-(2-[1,2,3]triazol-2-yl-phenyl)-methanone; LC-MS D: $t_R$ = 0.86 min; [M + H]$^+$ = 430.17 |
| 101 | J-9 | E-4 | [(2R,5R)-2-Methyl-5-(3-[1,2,3]triazol-2-yl-benzyl)-morpholin-4-yl]-(4-methyl-2-[1,2,3]triazol-2-yl-phenyl)-methanone; LC-MS D: $t_R$ = 0.89 min; [M + H]$^+$ = 444.19 |
| 102* | H-10 | E-3 | [(R)-3-Methyl-3-(3-[1,2,3]triazol-2-yl-benzyl)-morpholin-4-yl]-(5-methyl-2-[1,2,3]triazol-2-yl-phenyl)-methanone; LC-MS A: $t_R$ = 0.94 min; [M + H]$^+$ = 444.11 |
| 103 | A-15 | E-28 | (5-Chloro-4-methyl-2-[1,2,3]triazol-2-yl-phenyl)-[(R)-3-(3-[1,2,3]triazol-2-yl-benzyl)-morpholin-4-yl]-methanone; LC-MS D: $t_R$ = 0.90 min; [M($^{35}$Cl) + H]$^+$ = 464.18 |
| 104 | A-15 | E-22 | (4-Chloro-5-methoxy-2-[1,2,3]triazol-2-yl-phenyl)-[(R)-3-(3-[1,2,3]triazol-2-yl-benzyl)-morpholin-4-yl]-methanone; LC-MS D: $t_R$ = 0.92 min; [M($^{35}$Cl) + H]$^+$ = 480.16 |

TABLE 12-continued

| Example No. | Amine 1 | Acid 2 | Compound of Formula (I) |
|---|---|---|---|
| 105 | A-37 | E-4 | [(R)-3-(3-Chloro-5-[1,2,3]triazol-2-yl-benzyl)-morpholin-4-yl]-(4-methyl-2-[1,2,3]triazol-2-yl-phenyl)-methanone; LC-MS D: $t_R$ = 0.95 min; [M($^{35}$Cl) + H]$^+$ = 464.16 |
| 106 | A-37 | E-27 | [(R)-3-(3-Chloro-5-[1,2,3]triazol-2-yl-benzyl)-morpholin-4-yl]-(3-methyl-2-[1,2,3]triazol-2-yl-phenyl)-methanone; LC-MS D: $t_R$ = 0.94 min; [M($^{35}$Cl) + H]$^+$ = 464.17 |
| 107 | A-15 | E-23 | (3-Chloro-2-[1,2,3]triazol-2-yl-phenyl)-[(R)-3-(3-[1,2,3]triazol-2-yl-benzyl)-morpholin-4-yl]-methanone; LC-MS D: $t_R$ = 0.87 min; [M($^{35}$Cl) + H]$^+$ = 449.73 |
| 108 | J-14 | E-2 | [(2R,5R)-2-Methyl-5-(3-pyrimidin-2-yl-benzyl)-morpholin-4-yl]-(2-[1,2,3]triazol-2-yl-phenyl)-methanone; LC-MS D: $t_R$ = 0.82 min; [M + H]$^+$ = 441.16 |
| 109 | J-14 | E-3 | [(2R,5R)-2-Methyl-5-(3-pyrimidin-2-yl-benzyl)-morpholin-4-yl]-(5-methyl-2-[1,2,3]triazol-2-yl-phenyl)-methanone; LC-MS D: $t_R$ = 0.86 min; [M + H]$^+$ = 455.15 |
| 110 | J-14 | E-4 | [(2R,5R)-2-Methyl-5-(3-pyrimidin-2-yl-benzyl)-morpholin-4-yl]-(4-methyl-2-[1,2,3]triazol-2-yl-phenyl)-methanone; LC-MS D: $t_R$ = 0.85 min; [M + H]$^+$ = 455.16 |
| 111 | J-14 | E-27 | [(2R,5R)-2-Methyl-5-(3-pyrimidin-2-yl-benzyl)-morpholin-4-yl]-(3-methyl-2-[1,2,3]triazol-2-yl-phenyl)-methanone; LC-MS D: $t_R$ = 0.88 min; [M + H]$^+$ = 455.14 |
| 112 | J-14 | E-20 | (3,4-Dimethyl-2-[1,2,3]triazol-2-yl-phenyl)-[(2R,5R)-2-methyl-5-(3-pyrimidin-2-yl-benzyl)-morpholin-4-yl]-methanone; LC-MS D: $t_R$ = 0.91 min; [M + H]$^+$ = 469.19 |
| 113 | J-14 | E-5 | (5-Chloro-2-[1,2,3]triazol-2-yl-phenyl)-[(2R,5R)-2-methyl-5-(3-pyrimidin-2-yl-benzyl)-morpholin-4-yl]-methanone; LC-MS D: $t_R$ = 0.87 min; [M($^{35}$Cl) + H]$^+$ = 475.13 |
| 114 | J-14 | E-17 | (4-Chloro-2-[1,2,3]triazol-2-yl-phenyl)-[(2R,5R)-2-methyl-5-(3-pyrimidin-2-yl-benzyl)-morpholin-4-yl]-methanone; LC-MS D: $t_R$ = 0.89 min; [M($^{35}$Cl) + H]$^+$ = 475.13 |
| 115 | J-12 | E-3 | [(2R,5R)-5-(2-Fluoro-5-[1,2,3]triazol-2-yl-benzyl)-2-methyl-morpholin-4-yl]-(5-methyl-2-[1,2,3]triazol-2-yl-phenyl)-methanone; LC-MS D: $t_R$ = 0.90 min; [M + H]$^+$ = 462.15 |
| 116 | J-12 | E-2 | [(2R,5R)-5-(2-Fluoro-5-[1,2,3]triazol-2-yl-benzyl)-2-methyl-morpholin-4-yl]-(2-[1,2,3]triazol-2-yl-phenyl)-methanone; LC-MS D: $t_R$ = 0.90 min; [M + H]$^+$ = 448.15 |
| 117 | J-12 | E-4 | [(2R,5R)-5-(2-Fluoro-5-[1,2,3]triazol-2-yl-benzyl)-2-methyl-morpholin-4-yl]-(4-methyl-2-[1,2,3]triazol-2-yl-phenyl)-methanone; LC-MS D: $t_R$ = 0.90 min; [M + H]$^+$ = 462.18 |
| 118 | J-12 | E-27 | [(2R,5R)-5-(2-Fluoro-5-[1,2,3]triazol-2-yl-benzyl)-2-methyl-morpholin-4-yl]-(3-methyl-2-[1,2,3]triazol-2-yl-phenyl)-methanone; LC-MS D: $t_R$ = 0.92 min; [M + H]$^+$ = 462.15 |
| 119 | A-36 | E-3 | [(R)-3-(2-Methyl-5-[1,2,3]triazol-2-yl-benzyl)-morpholin-4-yl]-(5-methyl-2-[1,2,3]triazol-2-yl-phenyl)-methanone; LC-MS D: $t_R$ = 0.90 min; [M + H]$^+$ = 4444.18 |
| 120 | A-35 | E-4 | [(R)-3-(2-Chloro-5-[1,2,3]triazol-2-yl-benzyl)-morpholin-4-yl]-(4-methyl-2-[1,2,3]triazol-2-yl-phenyl)-methanone; LC-MS D: $t_R$ = 0.92 min; [M($^{35}$Cl) + H]$^+$ = 464.07 |
| 121 | A-36 | E-2 | [(R)-3-(2-Methyl-5-[1,2,3]triazol-2-yl-benzyl)-morpholin-4-yl]-(2-[1,2,3]triazol-2-yl-phenyl)-methanone; LC-MS D: $t_R$ = 0.87 min; [M + H]$^+$ = 430.20 |
| 122 | A-35 | E-27 | [(R)-3-(2-Chloro-5-[1,2,3]triazol-2-yl-benzyl)-morpholin-4-yl]-(3-methyl-2-[1,2,3]triazol-2-yl-phenyl)-methanone; LC-MS D: $t_R$ = 0.92 min; [M($^{35}$Cl) + H]$^+$ = 464.11 |
| 123 | A-36 | E-4 | [(R)-3-(2-Methyl-5-[1,2,3]triazol-2-yl-benzyl)-morpholin-4-yl]-(4-methyl-2-[1,2,3]triazol-2-yl-phenyl)-methanone; LC-MS D: $t_R$ = 0.92 min; [M + H]$^+$ = 444.36 |
| 124 | A-36 | E-27 | [(R)-3-(2-Methyl-5-[1,2,3]triazol-2-yl-benzyl)-morpholin-4-yl]-(3-methyl-2-[1,2,3]triazol-2-yl-phenyl)-methanone; LC-MS D: $t_R$ = 0.90 min; [M + H]$^+$ = 444.22 |
| 125 | A-35 | E-3 | [(R)-3-(2-Chloro-5-[1,2,3]triazol-2-yl-benzyl)-morpholin-4-yl]-(5-methyl-2-[1,2,3]triazol-2-yl-phenyl)-methanone; LC-MS D: $t_R$ = 0.91 min; [M($^{35}$Cl) + H]$^+$ = 464.12 |
| 126 | A-35 | E-2 | [(R)-3-(2-Chloro-5-[1,2,3]triazol-2-yl-benzyl)-morpholin-4-yl]-(2-[1,2,3]triazol-2-yl-phenyl)-methanone; LC-MS D: $t_R$ = 0.89 min; [M($^{35}$Cl) + H]$^+$ = 450.09 |
| 127 | A-34 | E-27 | [(R)-3-(2-Fluoro-5-[1,2,3]triazol-2-yl-benzyl)-morpholin-4-yl]-(3-methyl-2-[1,2,3]triazol-2-yl-phenyl)-methanone; LC-MS D: $t_R$ = 0.88 min; [M + H]$^+$ = 448.14 |
| 128 | A-34 | E-6 | (4,5-Dimethyl-2-[1,2,3]triazol-2-yl-phenyl)-[(R)-3-(2-fluoro-5-[1,2,3]triazol-2-yl-benzyl)-morpholin-4-yl]-methanone; LC-MS D: $t_R$ = 0.90 min; [M + H]$^+$ = 462.14 |

TABLE 12-continued

| Example No. | Amine 1 | Acid 2 | Compound of Formula (I) |
|---|---|---|---|
| 129 | A-34 | E-5 | (5-Chloro-2-[1,2,3]triazol-2-yl-phenyl)-[(R)-3-(2-fluoro-5-[1,2,3]triazol-2-yl-benzyl)-morpholin-4-yl]-methanone; LC-MS D: $t_R$ = 0.89 min; [M($^{35}$Cl) + H]$^+$ = 468.10 |
| 130 | A-34 | E-17 | (4-Chloro-2-[1,2,3]triazol-2-yl-phenyl)-[(R)-3-(2-fluoro-5-[1,2,3]triazol-2-yl-benzyl)-morpholin-4-yl]-methanone; LC-MS D: $t_R$ = 0.90 min; [M($^{35}$Cl) + H]$^+$ = 468.09 |
| 131 | A-34 | E-10 | [(R)-3-(2-Fluoro-5-[1,2,3]triazol-2-yl-benzyl)-morpholin-4-yl]-(5-methoxy-2-[1,2,3]triazol-2-yl-phenyl)-methanone; LC-MS D: $t_R$ = 0.89 min; [M + H]$^+$ = 464.16 |
| 132 | A-34 | E-1 | (2-Fluoro-3-methyl-6-[1,2,3]triazol-2-yl-phenyl)-[(R)-3-(2-fluoro-5-[1,2,3]triazol-2-yl-benzyl)-morpholin-4-yl]-methanone; LC-MS D: $t_R$ = 0.89 min; [M + H]$^+$ = 466.15 |
| 133 | A-34 | E-9 | (2-Fluoro-3-methoxy-6-[1,2,3]triazol-2-yl-phenyl)-[(R)-3-(2-fluoro-5-[1,2,3]triazol-2-yl-benzyl)-morpholin-4-yl]-methanone; LC-MS D: $t_R$ = 0.87 min; [M + H]$^+$ = 482.16 |
| 134 | A-34 | E-11 | [(R)-3-(2-Fluoro-5-[1,2,3]triazol-2-yl-benzyl)-morpholin-4-yl]-(5-methoxy-4-methyl-2-[1,2,3]triazol-2-yl-phenyl)-methanone; LC-MS D: $t_R$ = 0.92 min; [M + H]$^+$ = 478.17 |
| 135 | A-34 | E-23 | (3-Chloro-2-[1,2,3]triazol-2-yl-phenyl)-[(R)-3-(2-fluoro-5-[1,2,3]triazol-2-yl-benzyl)-morpholin-4-yl]-methanone; LC-MS D: $t_R$ = 0.88 min; [M($^{35}$Cl) + H]$^+$ = 468.10 |
| 136 | A-34 | E-26 | [(R)-3-(2-Fluoro-5-[1,2,3]triazol-2-yl-benzyl)-morpholin-4-yl]-(2-fluoro-6-[1,2,3]triazol-2-yl-phenyl)-methanone; LC-MS D: $t_R$ = 0.87 min; [M + H]$^+$ = 452.08 |
| 137 | A-34 | E-24 | (4,5-Difluoro-2-[1,2,3]triazol-2-yl-phenyl)-[(R)-3-(2-fluoro-5-[1,2,3]triazol-2-yl-benzyl)-morpholin-4-yl]-methanone; LC-MS D: $t_R$ = 0.89 min; [M + H]$^+$ = 470.14 |
| 138 | A-34 | E-21 | [(R)-3-(2-Fluoro-5-[1,2,3]triazol-2-yl-benzyl)-morpholin-4-yl]-(2-[1,2,3]triazol-2-yl-4-trifluoromethyl-phenyl)-methanone; LC-MS D: $t_R$ = 0.93 min; [M + H]$^+$ = 502.11 |
| 139 | A-34 | E-22 | (4-Chloro-5-methoxy-2-[1,2,3]triazol-2-yl-phenyl)-[(R)-3-(2-fluoro-5-[1,2,3]triazol-2-yl-benzyl)-morpholin-4-yl]-methanone; LC-MS D: $t_R$ = 0.93 min; [M($^{35}$Cl) + H]$^+$ = 498.13 |
| 140 | J-13 | E-3 | [(2R,5R)-5-(2-Fluoro-5-[1,2,3]triazol-1-yl-benzyl)-2-methyl-morpholin-4-yl]-(5-methyl-2-[1,2,3]triazol-2-yl-phenyl)-methanone; LC-MS D: $t_R$ = 0.80 min; [M + H$_2$O]$^+$ = 479.20 |
| 141 | J-13 | E-4 | [(2R,5R)-5-(2-Fluoro-5-[1,2,3]triazol-1-yl-benzyl)-2-methyl-morpholin-4-yl]-(4-methyl-2-[1,2,3]triazol-2-yl-phenyl)-methanone; LC-MS D: $t_R$ = 0.81 min; [M + H$_2$O]$^+$ = 479.21 |
| 142 | J-11 | E-3 | [(2R,5R)-2-Ethyl-5-(3-[1,2,3]triazol-2-yl-benzyl)-morpholin-4-yl]-(5-methyl-2-[1,2,3]triazol-2-yl-phenyl)-methanone; LC-MS D: $t_R$ = 0.94 min; [M + H]$^+$ = 457.93 |
| 143 | J-11 | E-2 | [(2R,5R)-2-Ethyl-5-(3-[1,2,3]triazol-2-yl-benzyl)-morpholin-4-yl]-(2-[1,2,3]triazol-2-yl-phenyl)-methanone; LC-MS D: $t_R$ = 0.91 min; [M + H]$^+$ = 444.14 |
| 144 | J-11 | E-4 | [(2R,5R)-2-Ethyl-5-(3-[1,2,3]triazol-2-yl-benzyl)-morpholin-4-yl]-(4-methyl-2-[1,2,3]triazol-2-yl-phenyl)-methanone; LC-MS D: $t_R$ = 0.44 min; [M + H]$^+$ = 457.95 |
| 145* | A-38 | E-2 | [(R)-3-(3-Fluoro-5-[1,2,3]triazol-2-yl-benzyl)-morpholin-4-yl]-(2-[1,2,3]triazol-2-yl-phenyl)-methanone; LC-MS D: $t_R$ = 0.88 min; [M + H]$^+$ = 434.24 |
| 146* | A-38 | E-4 | [(R)-3-(3-Fluoro-5-[1,2,3]triazol-2-yl-benzyl)-morpholin-4-yl]-(4-methyl-2-[1,2,3]triazol-2-yl-phenyl)-methanone; LC-MS D: $t_R$ = 0.90 min; [M + H]$^+$ = 448.27 |
| 147 | J-15 | E-3 | [(2R,5R)-5-(2-Fluoro-5-pyrimidin-2-yl-benzyl)-2-methyl-morpholin-4-yl]-(5-methyl-2-[1,2,3]triazol-2-yl-phenyl)-methanone; LC-MS D: $t_R$ = 0.88 min; [M + H]$^+$ = 473.18 |
| 148 | J-15 | E-2 | [(2R,5R)-5-(2-Fluoro-5-pyrimidin-2-yl-benzyl)-2-methyl-morpholin-4-yl]-(2-[1,2,3]triazol-2-yl-phenyl)-methanone; LC-MS D: $t_R$ = 0.88 min; [M + H]$^+$ = 459.06 |
| 149 | J-15 | E-4 | [(2R,5R)-5-(2-Fluoro-5-pyrimidin-2-yl-benzyl)-2-methyl-morpholin-4-yl]-(4-methyl-2-[1,2,3]triazol-2-yl-phenyl)-methanone; LC-MS D: $t_R$ = 0.88 min; [M + H]$^+$ = 473.14 |
| 150 | J-15 | E-27 | [(2R,5R)-5-(2-Fluoro-5-pyrimidin-2-yl-benzyl)-2-methyl-morpholin-4-yl]-(3-methyl-2-[1,2,3]triazol-2-yl-phenyl)-methanone; LC-MS D: $t_R$ = 0.90 min; [M + H]$^+$ = 473.13 |
| 151 | J-15 | E-20 | (3,4-Dimethyl-2-[1,2,3]triazol-2-yl-phenyl)-[(2R,5R)-5-(2-fluoro-5-pyrimidin-2-yl-benzyl)-2-methyl-morpholin-4-yl]-methanone; LC-MS D: $t_R$ = 0.92 min; [M + H]$^+$ = 487.17 |
| 152 | J-15 | E-5 | (5-Chloro-2-[1,2,3]triazol-2-yl-phenyl)-[(2R,5R)-5-(2-fluoro-5-pyrimidin-2-yl-benzyl)-2-methyl-morpholin-4-yl]-methanone; LC-MS D: $t_R$ = 0.90 min; [M($^{35}$Cl) + H]$^+$ = 493.10 |

TABLE 12-continued

| Example No. | Amine 1 | Acid 2 | Compound of Formula (I) |
|---|---|---|---|
| 153 | J-15 | E-17 | (4-Chloro-2-[1,2,3]triazol-2-yl-phenyl)-[(2R,5R)-5-(2-fluoro-5-pyrimidin-2-yl-benzyl)-2-methyl-morpholin-4-yl]-methanone; LC-MS D: $t_R$ = 0.91 min; [M($^{35}$Cl) + H]$^+$ = 493.08 |
| 154 | J-15 | E-23 | (3-Chloro-2-[1,2,3]triazol-2-yl-phenyl)-[(2R,5R)-5-(2-fluoro-5-pyrimidin-2-yl-benzyl)-2-methyl-morpholin-4-yl]-methanone; LC-MS D: $t_R$ = 0.89 min; [M($^{35}$Cl) + H]$^+$ = 493.07 |
| 155 | B-43 | E-3 | [(R)-3-(2-Fluoro-5-pyrimidin-2-yl-benzyl)-morpholin-4-yl]-(5-methyl-2-[1,2,3]triazol-2-yl-phenyl)-methanone; LC-MS D: $t_R$ = 0.85 min; [M + H]$^+$ = 458.89 |
| 156 | B-43 | E-4 | [(R)-3-(2-Fluoro-5-pyrimidin-2-yl-benzyl)-morpholin-4-yl]-(4-methyl-2-[1,2,3]triazol-2-yl-phenyl)-methanone; LC-MS D: $t_R$ = 0.87 min; [M + H]$^+$ = 459.07 |
| 157 | B-43 | E-27 | [(R)-3-(2-Fluoro-5-pyrimidin-2-yl-benzyl)-morpholin-4-yl]-(3-methyl-2-[1,2,3]triazol-2-yl-phenyl)-methanone; LC-MS D: $t_R$ = 0.85 min; [M + H]$^+$ = 458.81 |
| 158 | B-43 | E-20 | (3,4-Dimethyl-2-[1,2,3]triazol-2-yl-phenyl)-[(R)-3-(2-fluoro-5-pyrimidin-2-yl-benzyl)-morpholin-4-yl]-methanone; LC-MS D: $t_R$ = 0.88 min; [M + H]$^+$ = 473.17 |
| 159 | B-43 | E-5 | (5-Chloro-2-[1,2,3]triazol-2-yl-phenyl)-[(R)-3-(2-fluoro-5-pyrimidin-2-yl-benzyl)-morpholin-4-yl]-methanone; LC-MS D: $t_R$ = 0.87 min; [M($^{35}$Cl) + H]$^+$ = 479.06 |
| 160 | B-43 | E-17 | (4-Chloro-2-[1,2,3]triazol-2-yl-phenyl)-[(R)-3-(2-fluoro-5-pyrimidin-2-yl-benzyl)-morpholin-4-yl]-methanone; LC-MS D: $t_R$ = 0.88 min; [M($^{35}$Cl) + H]$^+$ = 479.08 |
| 161 | B-43 | E-23 | (3-Chloro-2-[1,2,3]triazol-2-yl-phenyl)-[(R)-3-(2-fluoro-5-pyrimidin-2-yl-benzyl)-morpholin-4-yl]-methanone; LC-MS D: $t_R$ = 0.86 min; [M($^{35}$Cl) + H]$^+$ = 479.11 |
| 162 | K-18 | E-3 | [(2S,3R)-2-Methyl-3-(3-[1,2,3]triazol-2-yl-benzyl)-morpholin-4-yl]-(5-methyl-2-[1,2,3]triazol-2-yl-phenyl)-methanone or [(2R,3R)-2-Methyl-3-(3-[1,2,3]triazol-2-yl-benzyl)-morpholin-4-yl]-(5-methyl-2-[1,2,3]triazol-2-yl-phenyl)-methanone; LC-MS D: $t_R$ = 0.90 min; [M + H]$^+$ = 444.15 |
| 163 | K-18 | E-4 | [(2S,3R)-2-Methyl-3-(3-[1,2,3]triazol-2-yl-benzyl)-morpholin-4-yl]-(4-methyl-2-[1,2,3]triazol-2-yl-phenyl)-methanone or [(2R,3R)-2-Methyl-3-(3-[1,2,3]triazol-2-yl-benzyl)-morpholin-4-yl]-(4-methyl-2-[1,2,3]triazol-2-yl-phenyl)-methanone; LC-MS D: $t_R$ = 0.91 min; [M + H]$^+$ = 444.13 |
| 164 | K-18 | E-27 | [(2S,3R)-2-Methyl-3-(3-[1,2,3]triazol-2-yl-benzyl)-morpholin-4-yl]-(3-methyl-2-[1,2,3]triazol-2-yl-phenyl)-methanone or [(2R,3R)-2-Methyl-3-(3-[1,2,3]triazol-2-yl-benzyl)-morpholin-4-yl]-(3-methyl-2-[1,2,3]triazol-2-yl-phenyl)-methanone; LC-MS D: $t_R$ = 0.89 min; [M + H]$^+$ = 444.14 |
| 165 | J-16 | E-4 | [(2R,5R)-5-(2-Fluoro-5-pyridazin-3-yl-benzyl)-2-methyl-morpholin-4-yl]-(4-methyl-2-[1,2,3]triazol-2-yl-phenyl)-methanone; LC-MS D: $t_R$ = 0.79 min; [M + H]$^+$ = 473.16 |
| 166 | B-44 | E-4 | [(R)-3-(2-Fluoro-5-pyridazin-3-yl-benzyl)-morpholin-4-yl]-(4-methyl-2-[1,2,3]triazol-2-yl-phenyl)-methanone; LC-MS D: $t_R$ = 0.76 min; [M + H]$^+$ = 459.03 |
| 167 | K-17 | E-3 | [(2R,3R)-2-Methyl-3-(3-[1,2,3]triazol-2-yl-benzyl)-morpholin-4-yl]-(5-methyl-2-[1,2,3]triazol-2-yl-phenyl)-methanone or [(2S,3R)-2-Methyl-3-(3-[1,2,3]triazol-2-yl-benzyl)-morpholin-4-yl]-(5-methyl-2-[1,2,3]triazol-2-yl-phenyl)-methanone; LC-MS D: $t_R$ = 0.90 min; [M + H]$^+$ = 444.09 |
| 168 | K-17 | E-4 | [(2R,3R)-2-Methyl-3-(3-[1,2,3]triazol-2-yl-benzyl)-morpholin-4-yl]-(4-methyl-2-[1,2,3]triazol-2-yl-phenyl)-methanone or [(2S,3R)-2-Methyl-3-(3-[1,2,3]triazol-2-yl-benzyl)-morpholin-4-yl]-(4-methyl-2-[1,2,3]triazol-2-yl-phenyl)-methanone; LC-MS D: $t_R$ = 0.91 min; [M + H]$^+$ = 444.16 |
| 169 | A-35 | E-20 | [(R)-3-(2-Chloro-5-[1,2,3]triazol-2-yl-benzyl)-morpholin-4-yl]-(3,4-dimethyl-2-[1,2,3]triazol-2-yl-phenyl)-methanone; LC-MS D: $t_R$ = 0.94 min; [M($^{35}$Cl) + H]$^+$ = 478.11 |
| 170 | A-35 | E-17 | [(R)-3-(2-Chloro-5-[1,2,3]triazol-2-yl-benzyl)-morpholin-4-yl]-(4-chloro-2-[1,2,3]triazol-2-yl-phenyl)-methanone; LC-MS D: $t_R$ = 0.95 min; [M($^{35}$Cl) + H]$^+$ = 484.06 |
| 171 | A-35 | E-23 | [(R)-3-(2-Chloro-5-[1,2,3]triazol-2-yl-benzyl)-morpholin-4-yl]-(3-chloro-2-[1,2,3]triazol-2-yl-phenyl)-methanone; LC-MS D: $t_R$ = 0.91 min; [M($^{35}$Cl) + H]$^+$ = 484.03 |
| 172 | J-9 | E-23 | (3-Chloro-2-[1,2,3]triazol-2-yl-phenyl)-[(2R,5R)-2-methyl-5-(3-[1,2,3]triazol-2-yl-benzyl)-morpholin-4-yl]-methanone; LC-MS D: $t_R$ = 0.91 min; [M($^{35}$Cl) + H]$^+$ = 464.07 |
| 173 | J-12 | E-23 | (3-Chloro-2-[1,2,3]triazol-2-yl-phenyl)-[(2R,5R)-5-(2-fluoro-5-[1,2,3]triazol-2-yl-benzyl)-2-methyl-morpholin-4-yl]-methanone; LC-MS D: $t_R$ = 0.92 min; [M($^{35}$Cl) + H]$^+$ = 482.10 |

TABLE 12-continued

| Example No. | Amine 1 | Acid 2 | Compound of Formula (I) |
|---|---|---|---|
| 174 | B-40 | E-3 | [(R)-3-(2-Fluoro-5-[1,2,4]oxadiazol-3-yl-benzyl)-morpholin-4-yl]-(5-methyl-2-[1,2,3]triazol-2-yl-phenyl)-methanone; LC-MS A: $t_R$ = 0.85 min; [M + H]$^+$ = 449.11 |
| 175 | B-40 | E-4 | [(R)-3-(2-Fluoro-5-[1,2,4]oxadiazol-3-yl-benzyl)-morpholin-4-yl]-(4-methyl-2-[1,2,3]triazol-2-yl-phenyl)-methanone; LC-MS A: $t_R$ = 0.86 min; [M + H]$^+$ = 449.11 |
| 176 | B-40 | E-5 | (5-Chloro-2-[1,2,3]triazol-2-yl-phenyl)-[(R)-3-(2-fluoro-5-[1,2,4]oxadiazol-3-yl-benzyl)-morpholin-4-yl]-methanone; LC-MS A: $t_R$ = 0.86 min; [M($^{35}$Cl) + H]$^+$ = 469.07 |
| 177 | B-40 | E-27 | [(R)-3-(2-Fluoro-5-[1,2,4]oxadiazol-3-yl-benzyl)-morpholin-4-yl]-(3-methyl-2-[1,2,3]triazol-2-yl-phenyl)-methanone; LC-MS A: $t_R$ = 0.85 min; [M + H]$^+$ = 449.10 |
| 178 | B-40 | E17 | (4-Chloro-2-[1,2,3]triazol-2-yl-phenyl)-[(R)-3-(2-fluoro-5-[1,2,4]oxadiazol-3-yl-benzyl)-morpholin-4-yl]-methanone; LC-MS A: $t_R$ = 0.88 min; [M($^{35}$Cl) + H]$^+$ = 469.04 |
| 179 | B-40 | E-6 | (4,5-Dimethyl-2-[1,2,3]triazol-2-yl-phenyl)-[(R)-3-(2-fluoro-5-[1,2,4]oxadiazol-3-yl-benzyl)-morpholin-4-yl]-methanone; LC-MS A: $t_R$ = 0.88 min; [M + H]$^+$ = 463.11 |
| 180 | B-40 | E-23 | (3-Chloro-2-[1,2,3]triazol-2-yl-phenyl)-[(R)-3-(2-fluoro-5-[1,2,4]oxadiazol-3-yl-benzyl)-morpholin-4-yl]-methanone; LC-MS A: $t_R$ = 0.86 min; [M($^{35}$Cl) + H]$^+$ = 469.04 |
| 181 | B-40 | E-20 | (3,4-Dimethyl-2-[1,2,3]triazol-2-yl-phenyl)-[(R)-3-(2-fluoro-5-[1,2,4]oxadiazol-3-yl-benzyl)-morpholin-4-yl]-methanone; LC-MS A: $t_R$ = 0.88 min; [M + H]$^+$ = 463.12 |
| 182 | A-15 | E-29 | [(R)-3-(3-[1,2,3]Triazol-2-yl-benzyl)-morpholin-4-yl]-(2-[1,2,3]triazol-2-yl-3-trifluoromethyl-phenyl)-methanone; LC-MS D: $t_R$ = 0.89 min; [M + H]$^+$ = 484.18 |
| 183* | A-39 | E-4 | [(R)-3-(2-Fluoro-3-[1,2,3]triazol-2-yl-benzyl)-morpholin-4-yl]-(4-methyl-2-[1,2,3]triazol-2-yl-phenyl)-methanone; LC-MS D: $t_R$ = 0.82 min; [M + H]$^+$ = 448.14 |
| 184 | J-9 | E-5 | (5-Chloro-2-[1,2,3]triazol-2-yl-phenyl)-[(2R,5R)-2-methyl-5-(3-[1,2,3]triazol-2-yl-benzyl)-morpholin-4-yl]-methanone; LC-MS D: $t_R$ = 0.90 min; [M($^{35}$Cl) + H]$^+$ = 464.13 |
| 185 | J-9 | E-17 | (4-Chloro-2-[1,2,3]triazol-2-yl-phenyl)-[(2R,5R)-2-methyl-5-(3-[1,2,3]triazol-2-yl-benzyl)-morpholin-4-yl]-methanone; LC-MS D: $t_R$ = 0.92 min; [M($^{35}$Cl) + H]$^+$ = 464.14 |
| 186 | J-12 | E-5 | (5-Chloro-2-[1,2,3]triazol-2-yl-phenyl)-[(2R,5R)-5-(2-fluoro-5-[1,2,3]triazol-2-yl-benzyl)-2-methyl-morpholin-4-yl]-methanone; LC-MS D: $t_R$ = 0.92 min; [M($^{35}$Cl) + H]$^+$ = 482.13 |
| 187 | J-12 | E-17 | (4-Chloro-2-[1,2,3]triazol-2-yl-phenyl)-[(2R,5R)-5-(2-fluoro-5-[1,2,3]triazol-2-yl-benzyl)-2-methyl-morpholin-4-yl]-methanone; LC-MS D: $t_R$ = 0.93 min; [M($^{35}$Cl) + H]$^+$ = 482.10 |
| 188 | A-42 | E-3 | [(R)-3-(2-Methyl-5-pyrazol-1-yl-benzyl)-morpholin-4-yl]-(5-methyl-2-[1,2,3]triazol-2-yl-phenyl)-methanone; LC-MS D: $t_R$ = 0.85 min; [M + H]$^+$ = 443.16 |
| 189 | A-42 | E-4 | [(R)-3-(2-Methyl-5-pyrazol-1-yl-benzyl)-morpholin-4-yl]-(4-methyl-2-[1,2,3]triazol-2-yl-phenyl)-methanone; LC-MS D: $t_R$ = 0.87 min; [M + H]$^+$ = 443.14 |
| 190 | A-42 | E-27 | [(R)-3-(2-Methyl-5-pyrazol-1-yl-benzyl)-morpholin-4-yl]-(3-methyl-2-[1,2,3]triazol-2-yl-phenyl)-methanone; LC-MS D: $t_R$ = 0.86 min; [M + H]$^+$ = 443.18 |
| 191 | A-36 | E-17 | (4-Chloro-2-[1,2,3]triazol-2-yl-phenyl)-[(R)-3-(2-methyl-5-[1,2,3]triazol-2-yl-benzyl)-morpholin-4-yl]-methanone; LC-MS A: $t_R$ = 0.94 min; [M($^{35}$Cl) + H]$^+$ = 464.11 |

*Initially prepared as a racemate and isolated following prep. chiral HPLC

Example Compounds 192 to 194

Example 192

[(R)-3-(4-Methyl-3-pyrimidin-2-yl-benzyl)-morpholin-4-yl]-(2-[1,2,3]triazol-2-yl-phenyl)-methanone The title compound was prepared from L-3 in analogy to the procedure described for Example 5 and isolated following prep. chiral HPLC. LC-MS A: $t_R$=0.79 min; [M+H]$^+$=441.09.

Example 193

[(R)-3-(4-Methyl-3-thiazol-2-yl-benzyl)-morpholin-4-yl]-(2-[1,2,3]triazol-2-yl-phenyl)-methanone The title compound was prepared from L-3 in analogy to the procedure described for Example 8 and isolated following prep. chiral HPLC. LC-MS A: $t_R$=0.86 min; [M+H]$^+$=446.10.

Example 194

[(R)-3-(4-Chloro-3-pyrimidin-2-yl-benzyl)-morpholin-4-yl]-(2-[1,2,3]triazol-2-yl-phenyl)-methanone The title compound was prepared from L-4 in analogy to the procedure described for Example 5 and isolated following prep. chiral HPLC. LC-MS D: $t_R$=0.81 min; $[M+H]^+$=461.07.

Reference Compounds

Ref. compound 1

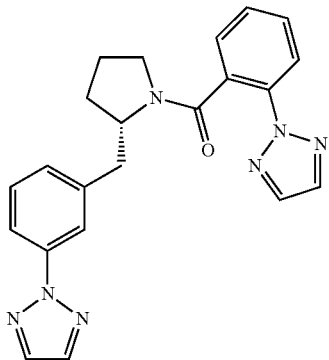

Ref. compound 2

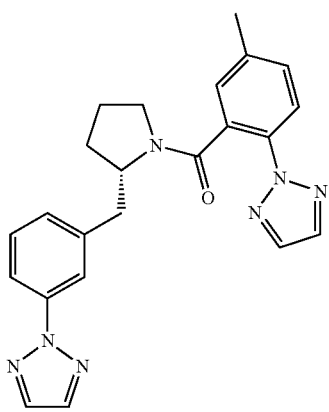

Ref. compound 3

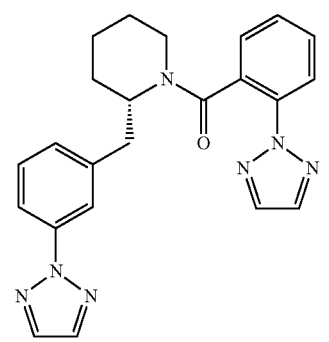

Ref. compound 4

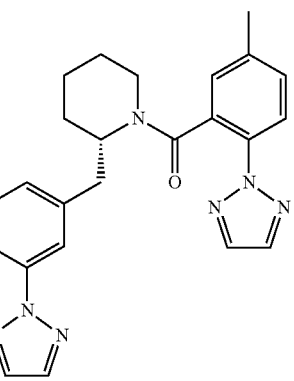

Reference Compound 1

[(S)-2-(3-[1,2,3]Triazol-2-yl-benzyl)-pyrrolidin-1-yl]-(2-[1,2,3]triazol-2-yl-phenyl)-methanone Step 1:
(S)-Tetrahydro-pyrrolo[1,2-c][1,2,3]oxathiazole 1,1-dioxide was prepared from commercially available L-prolinol following the procedure described for Example 2 in U.S. Pat. No. 5,130,432. $^1$H NMR (CDCl$_3$) $\delta_H$: 4.58 (dd, J$_1$=8.6 Hz, J$_2$=6.9 Hz, 1H), 4.30 (m, 1H), 4.07 (dd, J$_1$=8.7 Hz, J$_2$=6.0 Hz, 1H), 3.72 (m, 1H), 3.30 (dt, J$_1$=11.2 Hz, J$_2$=7.1 Hz, 1H), 2.21 (m, 1H), 1.99 (m, 2H), 1.85 (m, 1H).

Step 2:
(S)-2-(3-Iodo-benzyl)-pyrrolidine was prepared from 1,3-diiodobenzene and (S)-tetrahydro-pyrrolo[1,2-c][1,2,3]oxathiazole 1,1-dioxide in analogy to the procedure described for Example 4 in U.S. Pat. No. 5,130,432. LC-MS A: $t_R$=0.57 min; $[M+H]^+$=287.99.

Step 3:
(S)-2-(3-Iodo-benzyl)-pyrrolidine-1-carboxylic acid tert-butyl ester was prepared from (S)-2-(3-iodo-benzyl)-pyrrolidine in analogy to the procedure described for B-6. LC-MS A: $t_R$=1.02 min; $[M+H]^+$=387.91.

Step 4:
(S)-2-(3-[1,2,3]Triazol-2-yl-benzyl)-pyrrolidine-1-carboxylic acid tert-butyl ester was prepared from (S)-2-(3-iodo-benzyl)-pyrrolidine-1-carboxylic acid tert-butyl ester and 1H-1,2,3-triazole in analogy to the procedure described for A-13. LC-MS A: $t_R$=0.97 min; $[M+H-^tBu]^+$=273.16.

Step 5:
2-(3-(S)-1-Pyrrolidin-2-ylmethyl-phenyl)-2H-[1,2,3]triazole hydrochloride was prepared from (S)-2-(3-[1,2,3]triazol-2-yl-benzyl)-pyrrolidine-1-carboxylic acid tert-butyl ester in analogy to the procedure described for A-7. LC-MS A: $t_R$=0.55 min; $[M+H]^+$=229.19.

Step 6:
The title compound was prepared from 2-(3-(S)-1-pyrrolidin-2-ylmethyl-phenyl)-2H-[1,2,3]triazole hydrochloride and 2-(2H-1,2,3-triazol-2-yl)benzoic acid E-2 following the procedure described for B-28. LC-MS D: $t_R$=0.92 min; $[M+H]^+$=400.19.

Reference Compound 2

(5-Methyl-2-[1,2,3]triazol-2-yl-phenyl)-[(S)-2-(3-[1,2,3]triazol-2-yl-benzyl)-pyrrolidin-1-yl]-methanone The title compound was prepared from 2-(3-(S)-1-pyrrolidin-2-ylmethyl-phenyl)-2H-[1,2,3]triazole hydrochloride and 5-methyl-2-(2H-1,2,3-triazol-2-yl)benzoic acid E-3 following the procedure described for B-28. LC-MS D: $t_R$=0.96 min; [M+H]$^+$=414.21.

Reference Compound 3

[(S)-2-(3-[1,2,3]Triazol-2-yl-benzyl)-piperidin-1-yl]-(2-[1,2,3]triazol-2-yl-phenyl)-methanone Step 1:
(S)-2-Hydroxymethyl-piperidine-1-carboxylic acid benzyl ester was prepared from commercially available (S)-1-((benzyloxy)carbonyl)piperidine-2-carboxylic acid following the procedure described for A-8. LC-MS B: $t_R$=0.67 min; [M+H]$^+$=250.24.

Step 2:
(S)-1-Piperidin-2-yl-methanol; A solution of (S)-2-hydroxymethyl-piperidine-1-carboxylic acid benzyl ester (4.33 g, 17 mmol) in MeOH (50 mL) was degased with argon for 5 min before 10% palladium on activated charcoal (185 mg, 1 mol %) was added and the argon atmosphere was then replaced with hydrogen (hydrogen was bubbled through the reaction mixture for 5 min). The reaction mixture was stirred at RT for 4 h after which the mixture was filtered over a pad of celite washing with additional MeOH and the filtrate was evaporated in vacuo. The crude product appeared as a pale yellow oil and was not further purified. LC-MS B: $t_R$=0.12 min; [M+H]$^+$=116.22.

Step 3:
(S)-Hexahydro-[1,2,3]oxathiazolo[3,4-a]pyridine 1,1-dioxide was prepared from (S)-1-piperidin-2-yl-methanol in analogy to the procedure described for Example 2 in U.S. Pat. No. 5,130,432. $^1$H NMR (CDCl$_3$) $\delta_H$: 4.60 (m, 1H), 4.21 (m, 1H), 3.62 (m, 1H), 3.47 (m, 1H), 2.81 (m, 1H), 1.90 (m, 3H), 1.67 (m, 1H), 1.39 (m, 2H).

Step 4:
(S)-2-(3-Iodo-benzyl)-piperidine was prepared from 1,3-diiodobenzene and (S)-hexahydro-[1,2,3]oxathiazolo[3,4-a]pyridine 1,1-dioxide in analogy to the procedure described for Example 4 in U.S. Pat. No. 5,130,432. LC-MS B: $t_R$=0.54 min; [M+H]$^+$=302.07.

Step 5:
(S)-2-(3-Iodo-benzyl)-piperidine-1-carboxylic acid tert-butyl ester was prepared from (S)-2-(3-iodo-benzyl)-piperidine in analogy to the procedure described for B-6. LC-MS B: $t_R$=1.08 min; [M-Me]$^+$=386.86.

Step 6:
(S)-2-(3-[1,2,3]Triazol-2-yl-benzyl)-piperidine-1-carboxylic acid tert-butyl ester was prepared from (S)-2-(3-iodo-benzyl)-piperidine-1-carboxylic acid tert-butyl ester and 1H-1,2,3-triazole in analogy to the procedure described for A-13. LC-MS C: $t_R$=1.05 min; [M+H-$^t$Bu]$^+$=287.08.

Step 7:
(S)-2-(3-[1,2,3]Triazol-2-yl-benzyl)-piperidine hydrochloride was prepared from (S)-2-(3-[1,2,3]triazol-2-yl-benzyl)-piperidine-1-carboxylic acid tert-butyl ester in analogy to the procedure described for A-7. LC-MS C: $t_R$=0.90 min; [M+H]$^+$=243.17.

Step 8:
The title compound was prepared from (S)-2-(3-[1,2,3]triazol-2-yl-benzyl)-piperidine hydrochloride and 2-(2H-1,2,3-triazol-2-yl)benzoic acid E-2 following the procedure described for B-28. LC-MS D: $t_R$=0.91 min; [M+H]$^+$=414.05.

Reference Compound 4

(5-Methyl-2-[1,2,3]triazol-2-yl-phenyl)-[(S)-2-(3-[1,2,3]triazol-2-yl-benzyl)-piperidin-1-yl]-methanone The title compound was prepared from (S)-2-(3-[1,2,3]triazol-2-yl-benzyl)-piperidine hydrochloride and 5-methyl-2-(2H-1,2,3-triazol-2-yl)benzoic acid E-3 following the procedure described for B-28. LC-MS D: $t_R$=0.94 min; [M+H]$^+$=427.92.

II. Biological Assays

Antagonistic activities on both orexin receptors have been measured for each example compound using the following procedure:

In Vitro Assay: Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 µg/mL G418, 100 U/mL penicillin, 100 µg/mL streptomycin and 10% heat inactivated fetal calf serum (FCS). The cells are seeded at 20'000 cells/well into 384-well black clear bottom sterile plates (Greiner). The seeded plates are incubated overnight at 37° C. in 5% CO$_2$.

Human orexin-A as an agonist is prepared as 1 mM stock solution in MeOH: water (1:1), diluted in HBSS containing 0.1% bovine serum albumin (BSA), NaHCO$_3$: 0.375 g/L and 20 mM HEPES for use in the assay at a final concentration of 3 nM.

Antagonists are prepared as 10 mM stock solution in DMSO, then diluted in 384-well plates using DMSO followed by a transfer of the dilutions into in HBSS containing 0.1% bovine serum albumin (BSA), NaHCO$_3$: 0.375 g/L and 20 mM HEPES. On the day of the assay, 50 µL of staining buffer (HBSS containing 1% FCS, 20 mM HEPES, NaHCO$_3$: 0.375 g/L, 5 mM probenecid (Sigma) and 3 µM of the fluorescent calcium indicator fluo-4 AM (1 mM stock solution in DMSO, containing 10% pluronic) is added to each well. The 384-well cell-plates are incubated for 50 min at 37° C. in 5% CO$_2$ followed by equilibration at RT for 30 min before measurement.

Within the Fluorescent Imaging Plate Reader (FLIPR Tetra, Molecular Devices), antagonists are added to the plate in a volume of 10 µL/well, incubated for 120 min and finally 10 µL/well of agonist is added. Fluorescence is measured for each well at 1 second intervals, and the height of each fluorescence peak is compared to the height of the fluorescence peak induced by 3 nM orexin-A with vehicle in place of antagonist. The IC$_{50}$ value (the concentration of compound needed to inhibit 50% of the agonistic response) is determined and may be normalized using the obtained IC$_{50}$ value of an on-plate reference compound. Optimized conditions were achieved by adjustment of pipetting speed and cell splitting regime. The calculated IC$_{50}$ values may fluctuate depending on the daily cellular assay performance. Fluctuations of this kind are known to those skilled in the art. In the case where IC$_{50}$ values have been determined several times for the same compound, the geometric mean has been given. Antagonistic activities of example compounds are shown in Tables 13 and 14.

TABLE 13

| Example | IC$_{50}$ OX1 [nM] | IC$_{50}$ OX2 [nM] |
| --- | --- | --- |
| 1 | 40 | 803 |
| 2 | 7 | 406 |
| 3 | 4 | 3340 |
| 4 | 6 | 1880 |
| 5 | 4 | 2950 |
| 6 | 12 | 1940 |
| 7 | 26 | 6090 |
| 8 | 1 | 335 |
| 9 | 2 | 468 |
| 10 | 0.5 | 31 |
| 11 | 2 | 196 |
| 12 | 17 | 1235 |
| 13 | 966 | 4439 |
| 14 | 3 | 905 |
| 15 | 24 | 3160 |
| 16 | 30 | 1822 |
| 17 | 2 | 396 |
| 18 | 22 | 1892 |
| 19 | 2 | 369 |
| 20 | 25 | 1527 |
| 21 | 2 | 1649 |
| 22 | 3 | 318 |
| 23 | 34 | 4780 |
| 24 | 3 | 1030 |
| 25 | 11 | 1400 |
| 26 | 21 | 822 |
| 27 | 2 | 274 |
| 28 | 43 | 2107 |
| 29 | 4 | 333 |
| 30 | 4 | 199 |
| 31 | 33 | 360 |
| 32 | 7 | 489 |
| 33 | 14 | 1200 |
| 34 | 5 | 1230 |
| 35 | 1 | 25 |
| 36 | 41 | 889 |
| 37 | 4 | 209 |
| 38 | 1 | 131 |
| 39 | 5 | 231 |
| 40 | 34 | 762 |
| 41 | 8 | 1043 |
| 42 | 34 | 2009 |
| 43 | 0.3 | 273 |
| 44 | 2 | 457 |
| 45 | 0.1 | 119 |
| 46 | 0.5 | 163 |
| 47 | 13 | 2380 |
| 48 | 39 | 4440 |
| 49 | 3 | 582 |
| 50 | 2 | 942 |
| 51 | 3 | 229 |
| 52 | 43 | 1630 |
| 53 | 27 | 3404 |
| 54 | 46 | 1824 |
| Ref. 1 | 4 | 40 |
| Ref. 2 | 0.5 | 8 |
| Ref. 3 | 1 | 12 |
| Ref. 4 | 0.3 | 2 |

TABLE 14

| Example | IC$_{50}$ OX1 [nM] | IC$_{50}$ OX2 [nM] |
| --- | --- | --- |
| 55 | 27 | 2010 |
| 56 | 4 | 837 |
| 57 | 48 | 2736 |
| 58 | 0.7 | 42 |
| 59 | 1 | 80 |
| 60 | 0.7 | 34 |
| 61 | 1 | 60 |
| 62 | 3 | 404 |
| 63 | 9 | 49 |
| 64 | 6 | 784 |
| 65 | 2 | 261 |
| 66 | 16 | 992 |
| 67 | 2 | 274 |
| 68 | 16 | 1297 |
| 69 | 0.9 | 314 |
| 70 | 5 | 2610 |
| 71 | 35 | 2190 |
| 72 | 8 | 2460 |
| 73 | 10 | 1850 |
| 74 | 11 | 355 |
| 75 | 3 | 547 |
| 76 | 2 | 133 |
| 77 | 1 | 96 |
| 78 | 17 | 528 |
| 79 | 0.4 | 13 |
| 80 | 28 | 645 |
| 81 | 2 | 212 |
| 82 | 41 | 1140 |
| 83 | 7 | 403 |
| 84 | 5 | 246 |
| 85 | 1 | 21 |
| 86 | 42 | 2652 |
| 87 | 3 | 227 |
| 88 | 30 | 893 |
| 89 | 7 | 420 |
| 90 | 12 | 475 |
| 91 | 10 | 612 |
| 92 | 3 | 2633 |
| 93 | 5 | 2086 |
| 94 | 6 | 3578 |
| 95 | 11 | 1199 |
| 96 | 10 | 390 |
| 97 | 3 | 237 |
| 98 | 1 | 24 |
| 99 | 5 | 1223 |
| 100 | 6 | 289 |
| 101 | 2 | 155 |
| 102 | 25 | 1508 |
| 103 | 0.7 | 47 |
| 104 | 3 | 117 |
| 105 | 2 | 101 |
| 106 | 3 | 335 |
| 107 | 5 | 435 |
| 108 | 10 | 855 |
| 109 | 1 | 105 |
| 110 | 2 | 176 |
| 111 | 7 | 983 |
| 112 | 3 | 839 |
| 113 | 2 | 110 |
| 114 | 1 | 83 |
| 115 | 2 | 146 |
| 116 | 21 | 899 |
| 117 | 5 | 107 |
| 118 | 10 | 728 |
| 119 | 6 | 593 |
| 120 | 3 | 531 |
| 121 | 26 | 1640 |
| 122 | 6 | 1610 |
| 123 | 5 | 939 |
| 124 | 9 | 997 |
| 125 | 7 | 626 |
| 126 | 40 | 1480 |
| 127 | 26 | 1500 |
| 128 | 0.7 | 30 |
| 129 | 12 | 188 |
| 130 | 3 | 191 |
| 131 | 4 | 1131 |
| 132 | 8 | 1170 |
| 133 | 22 | 2600 |
| 134 | 11 | 336 |
| 135 | 16 | 1880 |
| 136 | 37 | 574 |
| 137 | 30 | 202 |
| 138 | 4 | 159 |

TABLE 14-continued

| Example | IC$_{50}$ OX1 [nM] | IC$_{50}$ OX2 [nM] |
|---|---|---|
| 139 | 10 | 191 |
| 140 | 27 | 1110 |
| 141 | 16 | 429 |
| 142 | 5 | 287 |
| 143 | 19 | 485 |
| 144 | 5 | 104 |
| 145 | 34 | 1514 |
| 146 | 3 | 282 |
| 147 | 3 | 171 |
| 148 | 39 | 1935 |
| 149 | 4 | 263 |
| 150 | 9 | 506 |
| 151 | 8 | 818 |
| 152 | 4 | 129 |
| 153 | 3 | 85 |
| 154 | 13 | 447 |
| 155 | 3 | 371 |
| 156 | 3 | 571 |
| 157 | 39 | 2590 |
| 158 | 3 | 2260 |
| 159 | 6 | 490 |
| 160 | 3 | 268 |
| 161 | 16 | 655 |
| 162 | 24 | 2530 |
| 163 | 22 | 1864 |
| 164 | 29 | 4040 |
| 165 | 14 | 1296 |
| 166 | 13 | 1395 |
| 167 | 19 | 2382 |
| 168 | 40 | 3505 |
| 169 | 5 | 2440 |
| 170 | 7 | 451 |
| 171 | 10 | 675 |
| 172 | 3 | 93 |
| 173 | 16 | 455 |
| 174 | 8 | 642 |
| 175 | 3 | 359 |
| 176 | 11 | 240 |
| 177 | 25 | 893 |
| 178 | 2 | 165 |
| 179 | 2 | 34 |
| 180 | 19 | 830 |
| 181 | 11 | 1567 |
| 182 | 7 | 371 |
| 183 | 15 | 2130 |
| 184 | 2 | 96 |
| 185 | 2 | 39 |
| 186 | 11 | 181 |
| 187 | 6 | 58 |
| 188 | 21 | 2130 |
| 189 | 12 | 1090 |
| 190 | 25 | 3770 |
| 191 | 12 | 1040 |
| 192 | 16 | 2606 |
| 193 | 1 | 238 |
| 194 | 33 | 2257 |

CYP3A4 Inhibition Assay

The CYP3A4 inhibition assay was performed using human liver microsomes and testosterone 6β-hydroxylation as a P450 isoform-specific marker. In a total volume of 150 μL, $^{14}$C-testosterone at a final concentration of 40 μM in a 100 mM phosphate buffer (pH 7.4) was incubated in a 96-well plate with 0.3 mg/mL of human liver microsomes in an Eppendorf thermomixer at 37° C. and 400 rpm. A 1.0 μL-aliquot of the 150-fold concentrated compound stock solution, prepared in DMSO, was added to yield final inhibitor concentrations of 0, 0.1, 0.5, 1.0, 5.0, 10, 25, and 50 μM. The reaction was initiated by addition of 15 μL of the NADPH-regenerating system containing the glucose-6-phosphate dehydrogenase and terminated after 7 min with a 75 μL-aliquot of methanol. After centrifugation at 465 g and 4° C. for 20 min, a 50 μL-aliquot of the supernatant was submitted to HPLC according to the method described below. The total concentration of DMSO in the assay including controls without inhibitor was 1%.

Nicardipine was run in parallel as a reference inhibitor of CYP3A4 activity at final concentrations of 0, 0.1, 0.5, 1.0, 5.0, 10, 25, and 50 μM. Stock solutions thereof were prepared in DMSO.

The chromatographic separation of testosterone and 6β-hydroxytestosterone was achieved on a Phenomenex Luna C18(2) column (5 μm, 2.0×10 mm) at RT with a flow rate of 0.6 mL/min. Mobile phases consisted of 1% aqueous formic acid (phase A) and methanol (phase B) using a gradient method with 0.9 min total run time. Using these chromatographic conditions, the 6β-hydroxy metabolite exhibited a retention time of 0.6 min.

The quantification of 6β-hydroxytestosterone was carried out using a quadrupole mass spectrometer equipped with an ionspray interface operating in positive ion mode. The parameters of the mass detector were set as follows: capillary voltage 5 kV, auxiliary gas 40 psi, collision gas 3 mTorr, and transfer capillary temperature 420° C. The mass transition used for 6β-hydroxytestosterone was 305.1 to 269.3 with a scan time of 30 ms.

Compounds of the present invention were tested in the above CYP3A4 assay and inhibition values for reference compounds and particular example compounds are given in Table 15.

TABLE 15

| Example | CYP3A4 IC$_{50}$ [μM] |
|---|---|
| 1 | >50 |
| 2 | 43 |
| 3 | 21 |
| 4 | 1.2 |
| 5 | >50 |
| 6 | 26 |
| 7 | >50 |
| 8 | 3.2 |
| 9 | 8.4 |
| 11 | 43 |
| 12 | 30 |
| 14 | >50 |
| 15 | 14 |
| 16 | 43 |
| 17 | 33 |
| 18 | 39 |
| 19 | 32 |
| 20 | 25 |
| 21 | 20 |
| 22 | 41 |
| 23 | 6 |
| 24 | >50 |
| 26 | 24 |
| 27 | 31 |
| 28 | 0.3 |
| 29 | 39 |
| 30 | 17 |
| 31 | >50 |
| 32 | >50 |
| 33 | >50 |
| 34 | >50 |
| 35 | 20 |
| 36 | 36 |
| 37 | 17 |
| 39 | 18 |
| 42 | 5.1 |
| 43 | 1.2 |
| 44 | 2 |
| 47 | 6 |
| 48 | 9.6 |
| 49 | 21 |

TABLE 15-continued

| Example | CYP3A4 IC$_{50}$ [μM] |
|---|---|
| 50 | >50 |
| 51 | 20 |
| 52 | >50 |
| 53 | >50 |
| 54 | >50 |
| 56 | 33 |
| 57 | 20 |
| 58 | 42 |
| 59 | 32 |
| 60 | 41 |
| 61 | 42 |
| 62 | 29 |
| 64 | 33 |
| 65 | 22 |
| 66 | 36 |
| 67 | 25 |
| 68 | 24 |
| 71 | 14 |
| 73 | 6.8 |
| 75 | 15 |
| 76 | 7.5 |
| 77 | 16 |
| 78 | 22 |
| 81 | 33 |
| 83 | 25 |
| 84 | 21 |
| 85 | 25 |
| 87 | 15 |
| 90 | 21 |
| 91 | 17 |
| 92 | 44 |
| 93 | >50 |
| 94 | 30 |
| 95 | 49 |
| 96 | 28 |
| 97 | 11 |
| 98 | 9.7 |
| 99 | 9.6 |
| 100 | 13 |
| 101 | 9.7 |
| 102 | 17 |
| 104 | 13 |
| 105 | 21 |
| 106 | 14 |
| 107 | 22 |
| 108 | 46 |
| 109 | 43 |
| 110 | >50 |
| 111 | 40 |
| 112 | >50 |
| 113 | 26 |
| 114 | 35 |
| 115 | 24 |
| 116 | 21 |
| 117 | 23 |
| 118 | 23 |
| 119 | 19 |
| 120 | 19 |
| 121 | 18 |
| 122 | 18 |
| 123 | 27 |
| 124 | 22 |
| 125 | 22 |
| 126 | 17 |
| 127 | 30 |
| 129 | 26 |
| 130 | 20 |
| 131 | 35 |
| 132 | 19 |
| 133 | 37 |
| 134 | 19 |
| 135 | 30 |
| 138 | 7.4 |
| 139 | 13 |
| 141 | 19 |
| 142 | 9.2 |
| 143 | 9.1 |
| 144 | 9.6 |
| 145 | 22 |
| 146 | 40 |
| 147 | 28 |
| 149 | 31 |
| 150 | 32 |
| 152 | 15 |
| 153 | 18 |
| 154 | 24 |
| 155 | 30 |
| 156 | >50 |
| 158 | 40 |
| 159 | 17 |
| 160 | 17 |
| 161 | 33 |
| 163 | 14 |
| 165 | 20 |
| 166 | 19 |
| 168 | 8.5 |
| 169 | 29 |
| 170 | 9.8 |
| 171 | 13 |
| 172 | 23 |
| 173 | 21 |
| 174 | 50 |
| 175 | 35 |
| 176 | 22 |
| 178 | 24 |
| 179 | 29 |
| 180 | 36 |
| 181 | 36 |
| 182 | 14 |
| 183 | >50 |
| 184 | 19 |
| 185 | 20 |
| 186 | 19 |
| 187 | 14 |
| 188 | 14 |
| 189 | 17 |
| 190 | 26 |
| 191 | 14 |
| 192 | >50 |
| 193 | 0.6 |
| Ref. 1 | 5.5 |
| Ref. 2 | 3.3 |
| Ref. 3 | 6.1 |
| Ref. 4 | 7.7 |

Measurement of Brain and Systemic Concentration after Oral Administration:

In order to assess brain penetration, the concentration of the compound is measured in plasma ([P]), and brain ([B]), sampled 1 h or 3 h (or at different time points) following oral administration (100 mg/kg) to male wistar rats (n=3). The compounds are formulated either in 100% PEG 400 or 10% PEG400/90% MC0.5%. Samples are collected in the same animal at the same time point (+/−5 min). Blood is sampled from the vena cava caudalis into containers with EDTA as anticoagulant and centrifuged to yield plasma. Brain is sampled after cardiac perfusion of 10 mL NaCl 0.9% and homogenized into one volume of cold phosphate buffer (pH 7.4). All samples are extracted with MeOH and analyzed by LC-MS/MS. Concentrations are determined with the help of calibration curves. Inter-individual variations between the three rats were limited. Particular compounds of the present invention tested as described above gave brain concentrations ([B]) as shown in Table 16 below; wherein the compounds of Examples 11-37 and 94 were formulated in 100% PEG400 and sampled at 3 h. All other examples below were formulated in 10% PEG400/90% MC0.5% and sampled at 1 h.

TABLE 16

| Example | [B] [ng/g] |
|---|---|
| 11 | 46 |
| 12 | 11888 |
| 16 | 160 |
| 21 | 36 |
| 27 | 5500 |
| 29 | 423 |
| 30 | 1869 |
| 35 | 59 |
| 37 | 881 |
| 62 | 4423 |
| 64 | 2371 |
| 76 | 1376 |
| 77 | 1609 |
| 87 | 1875 |
| 92 | 1971 |
| 94 | 654 |
| 100 | 529 |
| 116 | 5933 |
| 120 | 5133 |
| 130 | 5833 |
| 156 | 613 |

The invention claimed is:

1. A compound of formula (I)

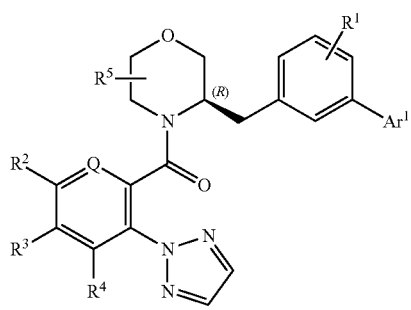

Formula (I)

wherein $Ar^1$ represents a 5- or 6-membered heteroaryl selected from the group consisting of pyrrolyl, pyrazolyl, triazolyl, oxazolyl, thiazolyl, oxadiazolyl, thiophenyl, pyridinyl, pyrimidinyl, pyrazinyl, and pyridazinyl; wherein said heteroaryl is unsubstituted, mono-, or di-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;

$R^1$ represents one optional substituent selected from $(C_{1-4})$alkyl, $(C_{1-4})$alkoxy, hydroxy, and halogen;

$R^2$ represents hydrogen, $(C_{1-4})$alkyl, $(C_{1-4})$alkoxy, halogen, or cyano;

$R^3$ represents hydrogen, $(C_{1-4})$alkyl, $(C_{1-4})$alkoxy, $(C_{1-3})$fluoroalkyl, or halogen;

$R^4$ represents hydrogen, $(C_{1-4})$alkyl, $(C_{1-3})$fluoroalkyl, or halogen;

$R^5$ represents one optional substituent on any ring carbon atom of the morpholine ring, wherein said substituent independently is methyl or ethyl; and Q represents $CR^6$; or, in case $R^2$ is $(C_{1-4})$alkyl or $(C_{1-4})$alkoxy, Q represents $CR^6$ or N; wherein $R^6$ represents hydrogen, fluoro or methyl;

or a pharmaceutically acceptable salt thereof.

2. A compound according to claim 1; wherein the morpholine ring of the compounds of formula (I):

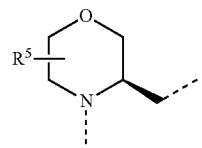

is a ring selected from the group consisting of:

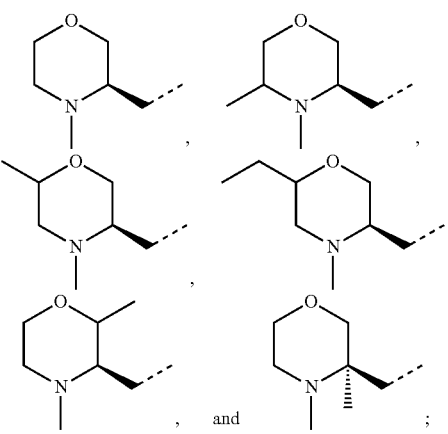

, and ;

$Ar^1$ represents a 5- or 6-membered heteroaryl selected from the group consisting of pyrrolyl, pyrazolyl, triazolyl, oxazolyl, thiazolyl, oxadiazolyl, thiophenyl, pyridinyl, pyrimidinyl, pyrazinyl, and pyridazinyl; wherein said heteroaryl is unsubstituted or mono-substituted with $(C_{1-4})$alkyl;

$R^1$ represents one optional substituent selected from methyl, methoxy, hydroxy, and halogen;

$R^2$ represents hydrogen, methyl, methoxy, halogen, or cyano;

$R^3$ represents hydrogen, methyl, methoxy, trifluoroalkyl, or halogen;

$R^4$ represents hydrogen, methyl, trifluoroalkyl, or halogen;

Q represents $CR^6$; or, in case $R^2$ is methyl, Q represents $CR^6$ or N; wherein $R^6$ represents hydrogen, fluoro or methyl;

or a pharmaceutically acceptable salt thereof.

3. A compound according to claim 1; wherein $Ar^1$ represents pyrazol-1-yl, [1,2,3]triazol-2-yl, [1,2,4]oxadiazol-3-yl, and or pyrimidin-2-yl, which groups are unsubstituted, or in case of pyrimidin-2-yl, optionally mono-substituted with methyl; or a pharmaceutically acceptable salt thereof.

4. A compound according to claim 1; wherein $R^2$ represents hydrogen, methyl, methoxy, cyano, fluoro, or chloro; $R^3$ represents hydrogen, methyl, trifluoromethyl, fluoro, or chloro; $R^4$ represent hydrogen, methyl, trifluoromethyl, or fluoro; and Q represents $CR^6$; or, in case $R^2$ is methyl, Q represents $CR^6$ or N; wherein $R^6$ represents hydrogen, fluoro or methyl;

or a pharmaceutically acceptable salt thereof.

5. A compound according to claim 1; wherein Q represents CH;

or a pharmaceutically acceptable salt thereof.

6. A compound according to claim 1; wherein $R^2$ represents hydrogen or chloro; $R^3$ represents hydrogen, chloro, methyl or trifluoromethyl, R⁴ represent hydrogen or methyl; and Q represents CH;
or a pharmaceutically acceptable salt thereof.
7. A compound according to claim 1; wherein the group
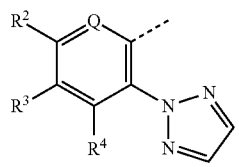
is a group independently selected from the following groups A) to F):
A)
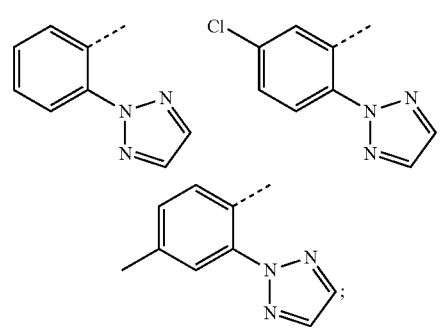
B)
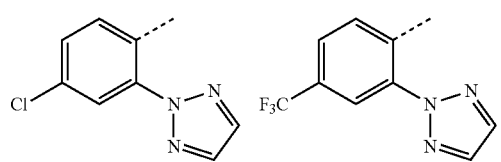
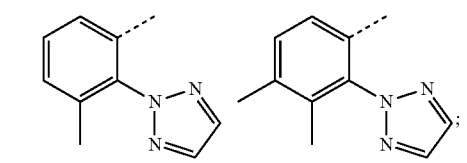
C)
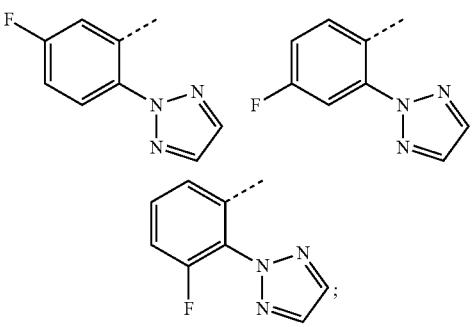
D)
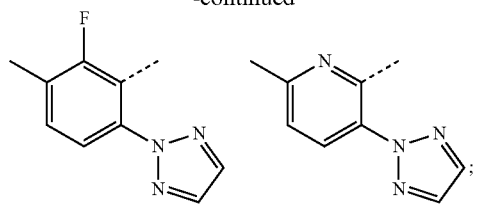
E)
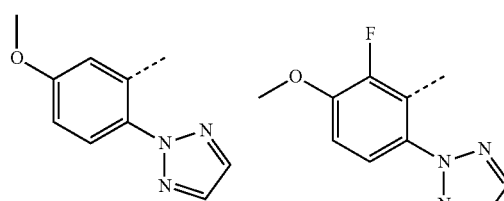
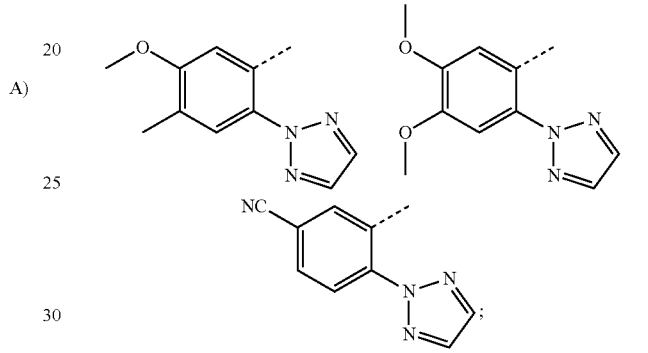
F)
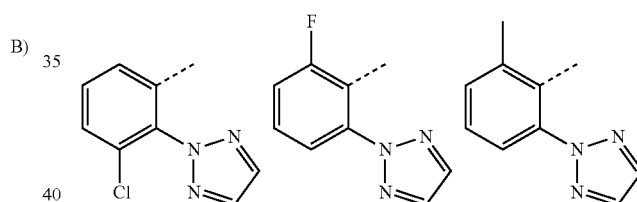
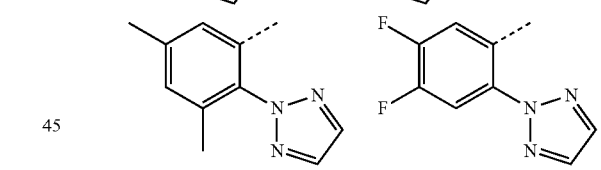
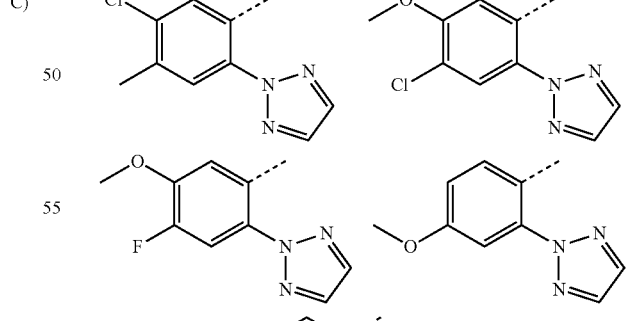
or a pharmaceutically acceptable salt thereof.

8. A compound according to claim 1; wherein the group
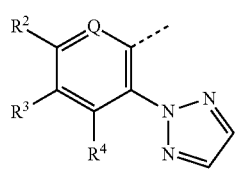
is a group selected from the group consisting of the following groups A) and B):
A)
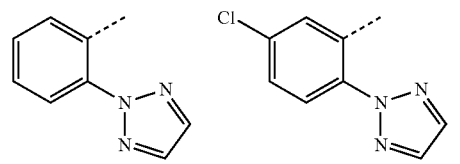
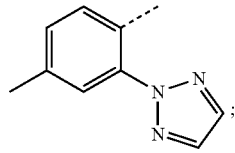
;
B)
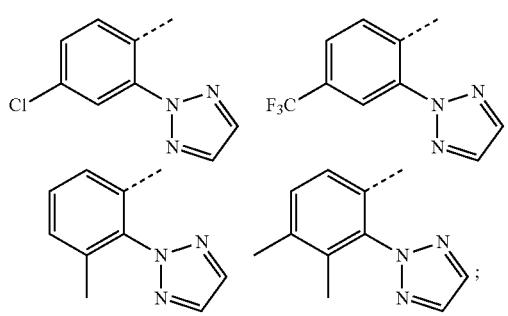
;
or a pharmaceutically acceptable salt thereof.
9. A compound according to claim 1; wherein the group
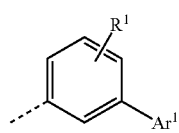
is a group independently selected from the following groups A) to H):
A)
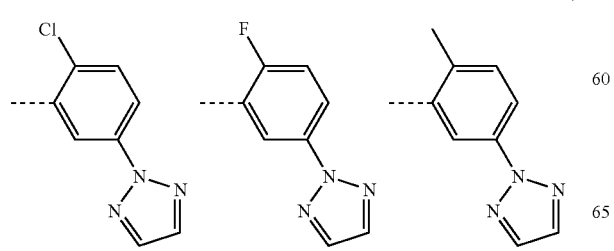
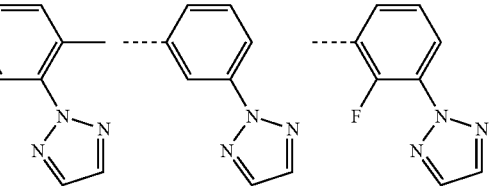
B)
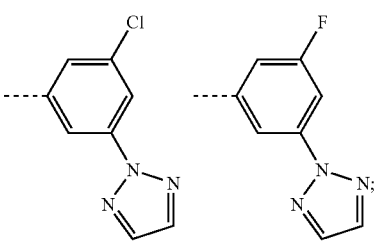
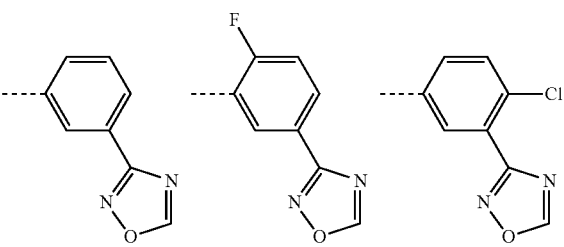
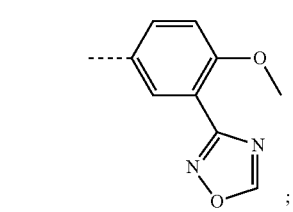
;
C)
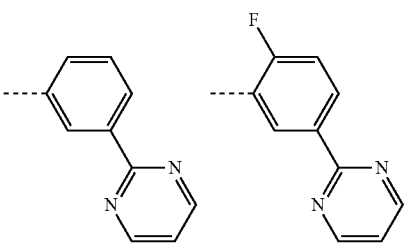
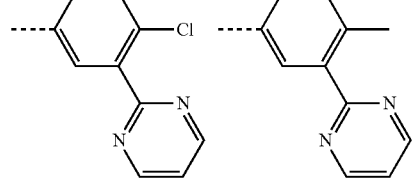
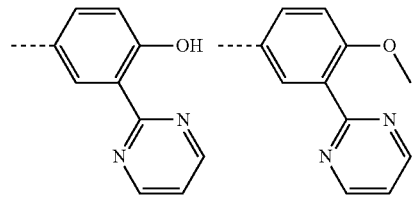

or a pharmaceutically acceptable salt thereof.

10. A compound according to claim 1; wherein the group

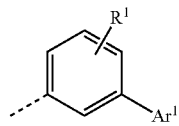

is a group selected from the group consisting of the following groups A) and B):

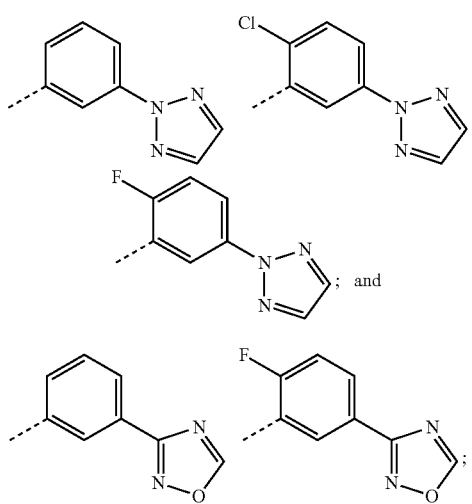

or a pharmaceutically acceptable salt thereof.

11. A compound according to claim 1 selected from the group consisting of:
[(R)-3-(3-[1,2,4]Oxadiazol-3-yl-benzyl)-morpholin-4-yl]-(2-[1,2,3]triazol-2-yl-phenyl)-methanone;
(5-Methyl-2-[1,2,3]triazol-2-yl-phenyl)-[(R)-3-(3-[1,2,4]oxadiazol-3-yl-benzyl)-morpholin-4-yl]-methanone;
[(R)-3-(4-Methoxy-3-pyridin-2-yl-benzyl)-morpholin-4-yl]-(2-[1,2,3]triazol-2-yl-phenyl)-methanone;
[(R)-3-(4-Methoxy-3-pyridin-3-yl-benzyl)-morpholin-4-yl]-(2-[1,2,3]triazol-2-yl-phenyl)-methanone;
[(R)-3-(4-Methoxy-3-pyrimidin-2-yl-benzyl)-morpholin-4-yl]-(2-[1,2,3]triazol-2-yl-phenyl)-methanone;
[(R)-3-(4-Methoxy-3-pyrazin-2-yl-benzyl)-morpholin-4-yl]-(2-[1,2,3]triazol-2-yl-phenyl)-methanone;
[(R)-3-(4-Methoxy-3-pyridazin-3-yl-benzyl)-morpholin-4-yl]-(2-[1,2,3]triazol-2-yl-phenyl)-methanone;
[(R)-3-(4-Methoxy-3-thiazol-2-yl-benzyl)-morpholin-4-yl]-(2-[1,2,3]triazol-2-yl-phenyl)-methanone;
[(R)-3-(4-Methoxy-3-oxazol-2-yl-benzyl)-morpholin-4-yl]-(2-[1,2,3]triazol-2-yl-phenyl)-methanone;
[(R)-3-(4-Methoxy-3-thiophen-2-yl-benzyl)-morpholin-4-yl]-(2-[1,2,3]triazol-2-yl-phenyl)-methanone;
(5-Methyl-2-[1,2,3]triazol-2-yl-phenyl)-[(R)-3-(3-[1,2,3]triazol-2-yl-benzyl)-morpholin-4-yl]-methanone;
[(R)-3-(3-[1,2,3]Triazol-2-yl-benzyl)-morpholin-4-yl]-(2-[1,2,3]triazol-2-yl-phenyl)-methanone;
[(S)-3-(3-[1,2,3]Triazol-2-yl-benzyl)-morpholin-4-yl]-(2-[1,2,3]triazol-2-yl-phenyl)-methanone;
[(R)-3-(4-Methoxy-3-pyrazol-1-yl-benzyl)-morpholin-4-yl]-(2-[1,2,3]triazol-2-yl-phenyl)-methanone;
(5-Methyl-2-[1,2,3]triazol-2-yl-phenyl)-[(R)-3-(3-[1,2,3]triazol-1-yl-benzyl)-morpholin-4-yl]-methanone;
[(R)-3-(3-Pyrazol-1-yl-benzyl)-morpholin-4-yl]-(2-[1,2,3]triazol-2-yl-phenyl)-methanone;
(5-Methyl-2-[1,2,3]triazol-2-yl-phenyl)-[(R)-3-(3-pyrimidin-2-yl-benzyl)-morpholin-4-yl]-methanone;
[(R)-3-(3-Pyrimidin-2-yl-benzyl)-morpholin-4-yl]-(2-[1,2,3]triazol-2-yl-phenyl)-methanone;
(5-Methyl-2-[1,2,3]triazol-2-yl-phenyl)-[(R)-3-(3-pyrazol-1-yl-benzyl)-morpholin-4-yl]-methanone;
(5-Fluoro-2-[1,2,3]triazol-2-yl-phenyl)-[(R)-3-(3-pyrazol-1-yl-benzyl)-morpholin-4-yl]-methanone;
(2-Fluoro-3-methyl-6-[1,2,3]triazol-2-yl-phenyl)-[(R)-3-(3-pyrazol-1-yl-benzyl)-morpholin-4-yl]-methanone;
(4-Methyl-2-[1,2,3]triazol-2-yl-phenyl)-[(R)-3-(3-pyrazol-1-yl-benzyl)-morpholin-4-yl]-methanone;
(5-Methyl-2-[1,2,3]triazol-2-yl-phenyl)-[(R)-3-(3-[1,2,4]triazol-1-yl-benzyl)-morpholin-4-yl]-methanone;
(5-Methyl-2-[1,2,3]triazol-2-yl-phenyl)-[(R)-3-(3-pyridin-2-yl-benzyl)-morpholin-4-yl]-methanone;
(5-Methyl-2-[1,2,3]triazol-2-yl-phenyl)-[(R)-3-(3-pyridin-3-yl-benzyl)-morpholin-4-yl]-methanone;
(5-Fluoro-2-[1,2,3]triazol-2-yl-phenyl)-[(R)-3-(3-[1,2,3]triazol-2-yl-benzyl)-morpholin-4-yl]-methanone;
(4-Methyl-2-[1,2,3]triazol-2-yl-phenyl)-[(R)-3-(3-[1,2,3]triazol-2-yl-benzyl)-morpholin-4-yl]-methanone;
(5-Methyl-2-[1,2,3]triazol-2-yl-phenyl)-[(R)-3-(3-pyridin-4-yl-benzyl)-morpholin-4-yl]-methanone;
(2-Fluoro-3-methyl-6-[1,2,3]triazol-2-yl-phenyl)-[(R)-3-(3-[1,2,3]triazol-2-yl-benzyl)-morpholin-4-yl]-methanone;
(5-Chloro-2-[1,2,3]triazol-2-yl-phenyl)-[(R)-3-(3-[1,2,3]triazol-2-yl-benzyl)-morpholin-4-yl]-methanone;
4-[1,2,3]Triazol-2-yl-3-[(R)-3-(3-[1,2,3]triazol-2-yl-benzyl)-morpholine-4-carbonyl]-benzonitrile;
(5-Methoxy-2-[1,2,3]triazol-2-yl-phenyl)-[(R)-3-(3-[1,2,3]triazol-2-yl-benzyl)-morpholin-4-yl]-methanone;
(2-Fluoro-3-methoxy-6-[1,2,3]triazol-2-yl-phenyl)-[(R)-3-(3-[1,2,3]triazol-2-yl-benzyl)-morpholin-4-yl]-methanone;
(4,5-Dimethoxy-2-[1,2,3]triazol-2-yl-phenyl)-[(R)-3-(3-[1,2,3]triazol-2-yl-benzyl)-morpholin-4-yl]-methanone;
(4,5-Dimethyl-2-[1,2,3]triazol-2-yl-phenyl)-[(R)-3-(3-[1,2,3]triazol-2-yl-benzyl)-morpholin-4-yl]-methanone;
(4-Fluoro-2-[1,2,3]triazol-2-yl-phenyl)-[(R)-3-(3-[1,2,3]triazol-2-yl-benzyl)-morpholin-4-yl]-methanone;
(5-Methoxy-4-methyl-2-[1,2,3]triazol-2-yl-phenyl)-[(R)-3-(3-[1,2,3]triazol-2-yl-benzyl)-morpholin-4-yl]-methanone;
(5-Methyl-2-[1,2,3]triazol-2-yl-phenyl)-[(R)-3-(3-pyrrol-1-yl-benzyl)-morpholin-4-yl]-methanone;
{(R)-3-[3-(4-Methyl-pyrimidin-2-yl)-benzyl]-morpholin-4-yl}-(5-methyl-2-[1,2,3]triazol-2-yl-phenyl)-methanone;
{(R)-3-[3-(4-Methyl-pyrimidin-2-yl)-benzyl]-morpholin-4-yl}-(2-[1,2,3]triazol-2-yl-phenyl)-methanone;
(5-Methyl-2-[1,2,3]triazol-2-yl-phenyl)-[(R)-3-(3-pyrazin-2-yl-benzyl)-morpholin-4-yl]-methanone;
[(R)-3-(3-Oxazol-2-yl-benzyl)-morpholin-4-yl]-(2-[1,2,3]triazol-2-yl-phenyl)-methanone;
(5-Methyl-2-[1,2,3]triazol-2-yl-phenyl)-[(R)-3-(3-thiazol-2-yl-benzyl)-morpholin-4-yl]-methanone;
[(R)-3-(3-Thiazol-2-yl-benzyl)-morpholin-4-yl]-(2-[1,2,3]triazol-2-yl-phenyl)-methanone;
(5-Methyl-2-[1,2,3]triazol-2-yl-phenyl)-[(R)-3-(3-thiophen-2-yl-benzyl)-morpholin-4-yl]-methanone;

[(R)-3-(3-Thiophen-2-yl-benzyl)-morpholin-4-yl]-(2-[1,2,3]triazol-2-yl-phenyl)-methanone;

(5-Methyl-2-[1,2,3]triazol-2-yl-phenyl)-[(R)-3-(3-pyridazin-3-yl-benzyl)-morpholin-4-yl]-methanone;

[(R)-3-(3-Pyridazin-3-yl-benzyl)-morpholin-4-yl]-(2-[1,2,3]triazol-2-yl-phenyl)-methanone;

(2-Fluoro-3-methyl-6-[1,2,3]triazol-2-yl-phenyl)-[(R)-3-(3-pyrimidin-2-yl-benzyl)-morpholin-4-yl]-methanone;

(5-Methoxy-2-[1,2,3]triazol-2-yl-phenyl)-[(R)-3-(3-pyrimidin-2-yl-benzyl)-morpholin-4-yl]-methanone;

(5-Chloro-2-[1,2,3]triazol-2-yl-phenyl)-[(R)-3-(3-pyrimidin-2-yl-benzyl)-morpholin-4-yl]-methanone;

(6-Methyl-3-[1,2,3]triazol-2-yl-pyridin-2-yl)-[(R)-3-(3-pyrazol-1-yl-benzyl)-morpholin-4-yl]-methanone;

(6-Methyl-3-[1,2,3]triazol-2-yl-pyridin-2-yl)-[(R)-3-(3-[1,2,3]triazol-2-yl-benzyl)-morpholin-4-yl]-methanone; and (3-Fluoro-2-[1,2,3]triazol-2-yl-phenyl)-[(R)-3-(3-[1,2,3]triazol-2-yl-benzyl)-morpholin-4-yl]-methanone;

or a pharmaceutically acceptable salt thereof.

12. A compound according to claim 1 selected from the group consisting of:

[(R)-3-(4-Hydroxy-3-pyrimidin-2-yl-benzyl)-morpholin-4-yl]-(2-[1,2,3]triazol-2-yl-phenyl)-methanone;

[(R)-3-(2-Fluoro-5-[1,2,3]triazol-2-yl-benzyl)-morpholin-4-yl]-(5-methyl-2-[1,2,3]triazol-2-yl-phenyl)-methanone;

[(R)-3-(2-Fluoro-5-[1,2,3]triazol-2-yl-benzyl)-morpholin-4-yl]-(2-[1,2,3]triazol-2-yl-phenyl)-methanone;

[(R)-3-(4-Methoxy-3-[1,2,4]oxadiazol-3-yl-benzyl)-morpholin-4-yl]-(5-methyl-2-[1,2,3]triazol-2-yl-phenyl)-methanone;

[(R)-3-(4-Methoxy-3-[1,2,4]oxadiazol-3-yl-benzyl)-morpholin-4-yl]-(2-[1,2,3]triazol-2-yl-phenyl)-methanone;

[(R)-3-(4-Methoxy-3-[1,2,4]oxadiazol-3-yl-benzyl)-morpholin-4-yl]-(4-methyl-2-[1,2,3]triazol-2-yl-phenyl)-methanone;

(4-Fluoro-2-[1,2,3]triazol-2-yl-phenyl)-[(R)-3-(4-methoxy-3-[1,2,4]oxadiazol-3-yl-benzyl)-morpholin-4-yl]-methanone;

[(R)-3-(2-Fluoro-5-[1,2,3]triazol-2-yl-benzyl)-morpholin-4-yl]-(4-methyl-2-[1,2,3]triazol-2-yl-phenyl)-methanone;

[(R)-3-(4-Methoxy-3-[1,2,4]oxadiazol-3-yl-benzyl)-morpholin-4-yl]-(2-methyl-6-[1,2,3]triazol-2-yl-phenyl)-methanone;

(3-Methyl-2-[1,2,3]triazol-2-yl-phenyl)-[(R)-3-(3-[1,2,3]triazol-2-yl-benzyl)-morpholin-4-yl]-methanone;

[(R)-3-(4-Methyl-3-[1,2,3]triazol-2-yl-benzyl)-morpholin-4-yl]-(5-methyl-2-[1,2,3]triazol-2-yl-phenyl)-methanone;

[(R)-3-(4-Methyl-3-[1,2,3]triazol-2-yl-benzyl)-morpholin-4-yl]-(2-[1,2,3]triazol-2-yl-phenyl)-methanone;

[(R)-3-(4-Methyl-3-[1,2,3]triazol-2-yl-benzyl)-morpholin-4-yl]-(4-methyl-2-[1,2,3]triazol-2-yl-phenyl)-methanone;

[(3R,5R)-3-Methyl-5-(3-[1,2,3]triazol-2-yl-benzyl)-morpholin-4-yl]-(2-[1,2,3]triazol-2-yl-phenyl)-methanone;

[(3R,5R)-3-Methyl-5-(3-[1,2,3]triazol-2-yl-benzyl)-morpholin-4-yl]-(4-methyl-2-[1,2,3]triazol-2-yl-phenyl)-methanone;

[(3R,5R)-3-Methyl-5-(3-[1,2,3]triazol-2-yl-benzyl)-morpholin-4-yl]-(3-methyl-2-[1,2,3]triazol-2-yl-phenyl)-methanone;

[(3S,5R)-3-Methyl-5-(3-[1,2,3]triazol-2-yl-benzyl)-morpholin-4-yl]-(4-methyl-2-[1,2,3]triazol-2-yl-phenyl)-methanone;

[(3S,5R)-3-Methyl-5-(3-[1,2,3]triazol-2-yl-benzyl)-morpholin-4-yl]-(3-methyl-2-[1,2,3]triazol-2-yl-phenyl)-methanone;

[(3S,5R)-3-Methyl-5-(3-[1,2,3]triazol-2-yl-benzyl)-morpholin-4-yl]-(5-methyl-2-[1,2,3]triazol-2-yl-phenyl)-methanone;

(4,5-Dimethyl-2-[1,2,3]triazol-2-yl-phenyl)-[(3S,5R)-3-methyl-5-(3-[1,2,3]triazol-2-yl-benzyl)-morpholin-4-yl]-methanone;

(3,5-Dimethyl-2-[1,2,3]triazol-2-yl-phenyl)-[(R)-3-(3-[1,2,3]triazol-2-yl-benzyl)-morpholin-4-yl]-methanone;

[(R)-3-(3-[1,2,3]Triazol-2-yl-benzyl)-morpholin-4-yl]-(2-[1,2,3]triazol-2-yl-4-trifluoromethyl-phenyl)-methanone;

(4-Chloro-2-[1,2,3]triazol-2-yl-phenyl)-[(R)-3-(3-[1,2,3]triazol-2-yl-benzyl)-morpholin-4-yl]-methanone;

(4-Fluoro-5-methoxy-2-[1,2,3]triazol-2-yl-phenyl)-[(R)-3-(3-[1,2,3]triazol-2-yl-benzyl)-morpholin-4-yl]-methanone;

(4,5-Dimethyl-2-[1,2,3]triazol-2-yl-phenyl)-[(R)-3-(4-methyl-3-[1,2,4]oxadiazol-3-yl-benzyl)-morpholin-4-yl]-methanone;

(4,5-Difluoro-2-[1,2,3]triazol-2-yl-phenyl)-[(R)-3-(3-[1,2,4]oxadiazol-3-yl-benzyl)-morpholin-4-yl]-methanone;

(4-Methyl-2-[1,2,3]triazol-2-yl-phenyl)-[(R)-3-(3-[1,2,4]oxadiazol-3-yl-benzyl)-morpholin-4-yl]-methanone;

(3-Fluoro-2-[1,2,3]triazol-2-yl-phenyl)-[(R)-3-(3-[1,2,4]oxadiazol-3-yl-benzyl)-morpholin-4-yl]-methanone;

(3-Methyl-2-[1,2,3]triazol-2-yl-phenyl)-[(R)-3-(3-[1,2,4]oxadiazol-3-yl-benzyl)-morpholin-4-yl]-methanone;

(5-Chloro-2-[1,2,3]triazol-2-yl-phenyl)-[(R)-3-(3-[1,2,4]oxadiazol-3-yl-benzyl)-morpholin-4-yl]-methanone;

(4,5-Dimethyl-2-[1,2,3]triazol-2-yl-phenyl)-[(R)-3-(3-[1,2,4]oxadiazol-3-yl-benzyl)-morpholin-4-yl]-methanone;

(4-Chloro-2-[1,2,3]triazol-2-yl-phenyl)-[(R)-3-(3-[1,2,4]oxadiazol-3-yl-benzyl)-morpholin-4-yl]-methanone;

[(R)-3-(3-[1,2,4]Oxadiazol-3-yl-benzyl)-morpholin-4-yl]-(2-[1,2,3]triazol-2-yl-4-trifluoromethyl-phenyl)-methanone;

(5-Fluoro-2-[1,2,3]triazol-2-yl-phenyl)-[(R)-3-(3-[1,2,4]oxadiazol-3-yl-benzyl)-morpholin-4-yl]-methanone;

(3,5-Dimethyl-2-[1,2,3]triazol-2-yl-phenyl)-[(R)-3-(3-[1,2,4]oxadiazol-3-yl-benzyl)-morpholin-4-yl]-methanone;

[(R)-3-(4-Chloro-3-[1,2,4]oxadiazol-3-yl-benzyl)-morpholin-4-yl]-(2-[1,2,3]triazol-2-yl-phenyl)-methanone;

(4,5-Difluoro-2-[1,2,3]triazol-2-yl-phenyl)-[(R)-3-(3-[1,2,3]triazol-2-yl-benzyl)-morpholin-4-yl]-methanone;

(3,4-Dimethyl-2-[1,2,3]triazol-2-yl-phenyl)-[(R)-3-(3-[1,2,3]triazol-2-yl-benzyl)-morpholin-4-yl]-methanone;

(4-Methoxy-2-[1,2,3]triazol-2-yl-phenyl)-[(R)-3-(3-[1,2,3]triazol-2-yl-benzyl)-morpholin-4-yl]-methanone;

(3,4-Dimethyl-2-[1,2,3]triazol-2-yl-phenyl)-[(R)-3-(2-fluoro-5-[1,2,3]triazol-2-yl-benzyl)-morpholin-4-yl]-methanone;

[(R)-3-(2-Fluoro-5-[1,2,3]triazol-2-yl-benzyl)-morpholin-4-yl]-(4-methoxy-2-[1,2,3]triazol-2-yl-phenyl)-methanone;

[(2S,5R)-2-Methyl-5-(3-[1,2,3]triazol-2-yl-benzyl)-morpholin-4-yl]-(4-methyl-2-[1,2,3]triazol-2-yl-phenyl)-methanone;

[(2R,5R)-2-Methyl-5-(3-[1,2,3]triazol-2-yl-benzyl)-morpholin-4-yl]-(3-methyl-2-[1,2,3]triazol-2-yl-phenyl)-methanone;
(4,5-Dimethyl-2-[1,2,3]triazol-2-yl-phenyl)-[(2R,5R)-2-methyl-5-(3-[1,2,3]triazol-2-yl-benzyl)-morpholin-4-yl]-methanone;
(3,4-Dimethyl-2-[1,2,3]triazol-2-yl-phenyl)-[(2R,5R)-2-methyl-5-(3-[1,2,3]triazol-2-yl-benzyl)-morpholin-4-yl]-methanone;
[(2R,5R)-2-Methyl-5-(3-[1,2,3]triazol-2-yl-benzyl)-morpholin-4-yl]-(2-[1,2,3]triazol-2-yl-phenyl)-methanone;
[(2R,5R)-2-Methyl-5-(3-[1,2,3]triazol-2-yl-benzyl)-morpholin-4-yl]-(4-methyl-2-[1,2,3]triazol-2-yl-phenyl)-methanone;
[(R)-3-Methyl-3-(3-[1,2,3]triazol-2-yl-benzyl)-morpholin-4-yl]-(5-methyl-2-[1,2,3]triazol-2-yl-phenyl)-methanone;
(5-Chloro-4-methyl-2-[1,2,3]triazol-2-yl-phenyl)-[(R)-3-(3-[1,2,3]triazol-2-yl-benzyl)-morpholin-4-yl]-methanone;
(4-Chloro-5-methoxy-2-[1,2,3]triazol-2-yl-phenyl)-[(R)-3-(3-[1,2,3]triazol-2-yl-benzyl)-morpholin-4-yl]-methanone;
[(R)-3-(3-Chloro-5-[1,2,3]triazol-2-yl-benzyl)-morpholin-4-yl]-(4-methyl-2-[1,2,3]triazol-2-yl-phenyl)-methanone;
[(R)-3-(3-Chloro-5-[1,2,3]triazol-2-yl-benzyl)-morpholin-4-yl]-(3-methyl-2-[1,2,3]triazol-2-yl-phenyl)-methanone;
(3-Chloro-2-[1,2,3]triazol-2-yl-phenyl)-[(R)-3-(3-[1,2,3]triazol-2-yl-benzyl)-morpholin-4-yl]-methanone;
[(2R,5R)-2-Methyl-5-(3-pyrimidin-2-yl-benzyl)-morpholin-4-yl]-(2-[1,2,3]triazol-2-yl-phenyl)-methanone;
[(2R,5R)-2-Methyl-5-(3-pyrimidin-2-yl-benzyl)-morpholin-4-yl]-(5-methyl-2-[1,2,3]triazol-2-yl-phenyl)-methanone;
[(2R,5R)-2-Methyl-5-(3-pyrimidin-2-yl-benzyl)-morpholin-4-yl]-(4-methyl-2-[1,2,3]triazol-2-yl-phenyl)-methanone;
[(2R,5R)-2-Methyl-5-(3-pyrimidin-2-yl-benzyl)-morpholin-4-yl]-(3-methyl-2-[1,2,3]triazol-2-yl-phenyl)-methanone;
(3,4-Dimethyl-2-[1,2,3]triazol-2-yl-phenyl)-[(2R,5R)-2-methyl-5-(3-pyrimidin-2-yl-benzyl)-morpholin-4-yl]-methanone;
(5-Chloro-2-[1,2,3]triazol-2-yl-phenyl)-[(2R,5R)-2-methyl-5-(3-pyrimidin-2-yl-benzyl)-morpholin-4-yl]-methanone;
(4-Chloro-2-[1,2,3]triazol-2-yl-phenyl)-[(2R,5R)-2-methyl-5-(3-pyrimidin-2-yl-benzyl)-morpholin-4-yl]-methanone;
[(2R,5R)-5-(2-Fluoro-5-[1,2,3]triazol-2-yl-benzyl)-2-methyl-morpholin-4-yl]-(5-methyl-2-[1,2,3]triazol-2-yl-phenyl)-methanone;
[(2R,5R)-5-(2-Fluoro-5-[1,2,3]triazol-2-yl-benzyl)-2-methyl-morpholin-4-yl]-(2-[1,2,3]triazol-2-yl-phenyl)-methanone;
[(2R,5R)-5-(2-Fluoro-5-[1,2,3]triazol-2-yl-benzyl)-2-methyl-morpholin-4-yl]-(4-methyl-2-[1,2,3]triazol-2-yl-phenyl)-methanone;
[(2R,5R)-5-(2-Fluoro-5-[1,2,3]triazol-2-yl-benzyl)-2-methyl-morpholin-4-yl]-(3-methyl-2-[1,2,3]triazol-2-yl-phenyl)-methanone;
[(R)-3-(2-Methyl-5-[1,2,3]triazol-2-yl-benzyl)-morpholin-4-yl]-(5-methyl-2-[1,2,3]triazol-2-yl-phenyl)-methanone;
[(R)-3-(2-Chloro-5-[1,2,3]triazol-2-yl-benzyl)-morpholin-4-yl]-(4-methyl-2-[1,2,3]triazol-2-yl-phenyl)-methanone;
[(R)-3-(2-Methyl-5-[1,2,3]triazol-2-yl-benzyl)-morpholin-4-yl]-(2-[1,2,3]triazol-2-yl-phenyl)-methanone;
[(R)-3-(2-Chloro-5-[1,2,3]triazol-2-yl-benzyl)-morpholin-4-yl]-(3-methyl-2-[1,2,3]triazol-2-yl-phenyl)-methanone;
[(R)-3-(2-Methyl-5-[1,2,3]triazol-2-yl-benzyl)-morpholin-4-yl]-(4-methyl-2-[1,2,3]triazol-2-yl-phenyl)-methanone;
[(R)-3-(2-Methyl-5-[1,2,3]triazol-2-yl-benzyl)-morpholin-4-yl]-(3-methyl-2-[1,2,3]triazol-2-yl-phenyl)-methanone;
[(R)-3-(2-Chloro-5-[1,2,3]triazol-2-yl-benzyl)-morpholin-4-yl]-(5-methyl-2-[1,2,3]triazol-2-yl-phenyl)-methanone;
[(R)-3-(2-Chloro-5-[1,2,3]triazol-2-yl-benzyl)-morpholin-4-yl]-(2-[1,2,3]triazol-2-yl-phenyl)-methanone;
[(R)-3-(2-Fluoro-5-[1,2,3]triazol-2-yl-benzyl)-morpholin-4-yl]-(3-methyl-2-[1,2,3]triazol-2-yl-phenyl)-methanone;
(4,5-Dimethyl-2-[1,2,3]triazol-2-yl-phenyl)-[(R)-3-(2-fluoro-5-[1,2,3]triazol-2-yl-benzyl)-morpholin-4-yl]-methanone;
(5-Chloro-2-[1,2,3]triazol-2-yl-phenyl)-[(R)-3-(2-fluoro-5-[1,2,3]triazol-2-yl-benzyl)-morpholin-4-yl]-methanone;
(4-Chloro-2-[1,2,3]triazol-2-yl-phenyl)-[(R)-3-(2-fluoro-5-[1,2,3]triazol-2-yl-benzyl)-morpholin-4-yl]-methanone;
[(R)-3-(2-Fluoro-5-[1,2,3]triazol-2-yl-benzyl)-morpholin-4-yl]-(5-methoxy-2-[1,2,3]triazol-2-yl-phenyl)-methanone;
(2-Fluoro-3-methyl-6-[1,2,3]triazol-2-yl-phenyl)-[(R)-3-(2-fluoro-5-[1,2,3]triazol-2-yl-benzyl)-morpholin-4-yl]-methanone;
(2-Fluoro-3-methoxy-6-[1,2,3]triazol-2-yl-phenyl)-[(R)-3-(2-fluoro-5-[1,2,3]triazol-2-yl-benzyl)-morpholin-4-yl]-methanone;
[(R)-3-(2-Fluoro-5-[1,2,3]triazol-2-yl-benzyl)-morpholin-4-yl]-(5-methoxy-4-methyl-2-[1,2,3]triazol-2-yl-phenyl)-methanone;
(3-Chloro-2-[1,2,3]triazol-2-yl-phenyl)-[(R)-3-(2-fluoro-5-[1,2,3]triazol-2-yl-benzyl)-morpholin-4-yl]-methanone;
[(R)-3-(2-Fluoro-5-[1,2,3]triazol-2-yl-benzyl)-morpholin-4-yl]-(2-fluoro-6-[1,2,3]triazol-2-yl-phenyl)-methanone;
(4,5-Difluoro-2-[1,2,3]triazol-2-yl-phenyl)-[(R)-3-(2-fluoro-5-[1,2,3]triazol-2-yl-benzyl)-morpholin-4-yl]-methanone;
[(R)-3-(2-Fluoro-5-[1,2,3]triazol-2-yl-benzyl)-morpholin-4-yl]-(2-[1,2,3]triazol-2-yl-4-trifluoromethyl-phenyl)-methanone;
(4-Chloro-5-methoxy-2-[1,2,3]triazol-2-yl-phenyl)-[(R)-3-(2-fluoro-5-[1,2,3]triazol-2-yl-benzyl)-morpholin-4-yl]-methanone;
[(2R,5R)-5-(2-Fluoro-5-[1,2,3]triazol-1-yl-benzyl)-2-methyl-morpholin-4-yl]-(5-methyl-2-[1,2,3]triazol-2-yl-phenyl)-methanone;
[(2R,5R)-5-(2-Fluoro-5-[1,2,3]triazol-1-yl-benzyl)-2-methyl-morpholin-4-yl]-(4-methyl-2-[1,2,3]triazol-2-yl-phenyl)-methanone;
[(2R,5R)-2-Ethyl-5-(3-[1,2,3]triazol-2-yl-benzyl)-morpholin-4-yl]-(5-methyl-2-[1,2,3]triazol-2-yl-phenyl)-methanone;

[(2R,5R)-2-Ethyl-5-(3-[1,2,3]triazol-2-yl-benzyl)-morpholin-4-yl]-(2-[1,2,3]triazol-2-yl-phenyl)-methanone;
[(2R,5R)-2-Ethyl-5-(3-[1,2,3]triazol-2-yl-benzyl)-morpholin-4-yl]-(4-methyl-2-[1,2,3]triazol-2-yl-phenyl)-methanone;
[(R)-3-(3-Fluoro-5-[1,2,3]triazol-2-yl-benzyl)-morpholin-4-yl]-(2-[1,2,3]triazol-2-yl-phenyl)-methanone;
[(R)-3-(3-Fluoro-5-[1,2,3]triazol-2-yl-benzyl)-morpholin-4-yl]-(4-methyl-2-[1,2,3]triazol-2-yl-phenyl)-methanone;
[2R,5R)-5-(2-Fluoro-5-pyrimidin-2-yl-benzyl)-2-methyl-morpholin-4-yl]-(5-methyl-2-[1,2,3]triazol-2-yl-phenyl)-methanone;
[2R,5R)-5-(2-Fluoro-5-pyrimidin-2-yl-benzyl)-2-methyl-morpholin-4-yl]-(2-[1,2,3]triazol-2-yl-phenyl)-methanone;
[2R,5R)-5-(2-Fluoro-5-pyrimidin-2-yl-benzyl)-2-methyl-morpholin-4-yl]-(4-methyl-2-[1,2,3]triazol-2-yl-phenyl)-methanone;
[2R,5R)-5-(2-Fluoro-5-pyrimidin-2-yl-benzyl)-2-methyl-morpholin-4-yl]-(3-methyl-2-[1,2,3]triazol-2-yl-phenyl)-methanone;
(3,4-Dimethyl-2-[1,2,3]triazol-2-yl-phenyl)-[(2R,5R)-5-(2-fluoro-5-pyrimidin-2-yl-benzyl)-2-methyl-morpholin-4-yl]-methanone;
(5-Chloro-2-[1,2,3]triazol-2-yl-phenyl)-[(2R,5R)-5-(2-fluoro-5-pyrimidin-2-yl-benzyl)-2-methyl-morpholin-4-yl]-methanone;
(4-Chloro-2-[1,2,3]triazol-2-yl-phenyl)-[(2R,5R)-5-(2-fluoro-5-pyrimidin-2-yl-benzyl)-2-methyl-morpholin-4-yl]-methanone;
(3-Chloro-2-[1,2,3]triazol-2-yl-phenyl)-[(2R,5R)-5-(2-fluoro-5-pyrimidin-2-yl-benzyl)-2-methyl-morpholin-4-yl]-methanone;
[(R)-3-(2-Fluoro-5-pyrimidin-2-yl-benzyl)-morpholin-4-yl]-(5-methyl-2-[1,2,3]triazol-2-yl-phenyl)-methanone;
[(R)-3-(2-Fluoro-5-pyrimidin-2-yl-benzyl)-morpholin-4-yl]-(4-methyl-2-[1,2,3]triazol-2-yl-phenyl)-methanone;
[(R)-3-(2-Fluoro-5-pyrimidin-2-yl-benzyl)-morpholin-4-yl]-(3-methyl-2-[1,2,3]triazol-2-yl-phenyl)-methanone;
(3,4-Dimethyl-2-[1,2,3]triazol-2-yl-phenyl)-[(R)-3-(2-fluoro-5-pyrimidin-2-yl-benzyl)-morpholin-4-yl]-methanone;
(5-Chloro-2-[1,2,3]triazol-2-yl-phenyl)-[(R)-3-(2-fluoro-5-pyrimidin-2-yl-benzyl)-morpholin-4-yl]-methanone;
(4-Chloro-2-[1,2,3]triazol-2-yl-phenyl)-[(R)-3-(2-fluoro-5-pyrimidin-2-yl-benzyl)-morpholin-4-yl]-methanone;
(3-Chloro-2-[1,2,3]triazol-2-yl-phenyl)-[(R)-3-(2-fluoro-5-pyrimidin-2-yl-benzyl)-morpholin-4-yl]-methanone;
[(2S,3R)-2-Methyl-3-(3-[1,2,3]triazol-2-yl-benzyl)-morpholin-4-yl]-(5-methyl-2-[1,2,3]triazol-2-yl-phenyl)-methanone;
[(2S,3R)-2-Methyl-3-(3-[1,2,3]triazol-2-yl-benzyl)-morpholin-4-yl]-(4-methyl-2-[1,2,3]triazol-2-yl-phenyl)-methanone;
[(2S,3R)-2-Methyl-3-(3-[1,2,3]triazol-2-yl-benzyl)-morpholin-4-yl]-(3-methyl-2-[1,2,3]triazol-2-yl-phenyl)-methanone;
[(2R,5R)-5-(2-Fluoro-5-pyridazin-3-yl-benzyl)-2-methyl-morpholin-4-yl]-(4-methyl-2-[1,2,3]triazol-2-yl-phenyl)-methanone;
[(R)-3-(2-Fluoro-5-pyridazin-3-yl-benzyl)-morpholin-4-yl]-(4-methyl-2-[1,2,3]triazol-2-yl-phenyl)-methanone;
[(2R,3R)-2-Methyl-3-(3-[1,2,3]triazol-2-yl-benzyl)-morpholin-4-yl]-(5-methyl-2-[1,2,3]triazol-2-yl-phenyl)-methanone;
[(2R,3R)-2-Methyl-3-(3-[1,2,3]triazol-2-yl-benzyl)-morpholin-4-yl]-(4-methyl-2-[1,2,3]triazol-2-yl-phenyl)-methanone;
[(R)-3-(2-Chloro-5-[1,2,3]triazol-2-yl-benzyl)-morpholin-4-yl]-(3,4-dimethyl-2-[1,2,3]triazol-2-yl-phenyl)-methanone;
[(R)-3-(2-Chloro-5-[1,2,3]triazol-2-yl-benzyl)-morpholin-4-yl]-(4-chloro-2-[1,2,3]triazol-2-yl-phenyl)-methanone;
[(R)-3-(2-Chloro-5-[1,2,3]triazol-2-yl-benzyl)-morpholin-4-yl]-(3-chloro-2-[1,2,3]triazol-2-yl-phenyl)-methanone;
(3-Chloro-2-[1,2,3]triazol-2-yl-phenyl)-[(2R,5R)-2-methyl-5-(3-[1,2,3]triazol-2-yl-benzyl)-morpholin-4-yl]-methanone;
(3-Chloro-2-[1,2,3]triazol-2-yl-phenyl)-[(2R,5R)-5-(2-fluoro-5-[1,2,3]triazol-2-yl-benzyl)-2-methyl-morpholin-4-yl]-methanone;
[(R)-3-(2-Fluoro-5-[1,2,4]oxadiazol-3-yl-benzyl)-morpholin-4-yl]-(5-methyl-2-[1,2,3]triazol-2-yl-phenyl)-methanone;
[(R)-3-(2-Fluoro-5-[1,2,4]oxadiazol-3-yl-benzyl)-morpholin-4-yl]-(4-methyl-2-[1,2,3]triazol-2-yl-phenyl)-methanone;
(5-Chloro-2-[1,2,3]triazol-2-yl-phenyl)-[(R)-3-(2-fluoro-5-[1,2,4]oxadiazol-3-yl-benzyl)-morpholin-4-yl]-methanone;
[(R)-3-(2-Fluoro-5-[1,2,4]oxadiazol-3-yl-benzyl)-morpholin-4-yl]-(3-methyl-2-[1,2,3]triazol-2-yl-phenyl)-methanone;
(4-Chloro-2-[1,2,3]triazol-2-yl-phenyl)-[(R)-3-(2-fluoro-5-[1,2,4]oxadiazol-3-yl-benzyl)-morpholin-4-yl]-methanone;
(4,5-Dimethyl-2-[1,2,3]triazol-2-yl-phenyl)-[(R)-3-(2-fluoro-5-[1,2,4]oxadiazol-3-yl-benzyl)-morpholin-4-yl]-methanone;
(3-Chloro-2-[1,2,3]triazol-2-yl-phenyl)-[(R)-3-(2-fluoro-5-[1,2,4]oxadiazol-3-yl-benzyl)-morpholin-4-yl]-methanone;
(3,4-Dimethyl-2-[1,2,3]triazol-2-yl-phenyl)-[(R)-3-(2-fluoro-5-[1,2,4]oxadiazol-3-yl-benzyl)-morpholin-4-yl]-methanone;
[(R)-3-(3-[1,2,3]Triazol-2-yl-benzyl)-morpholin-4-yl]-(2-[1,2,3]triazol-2-yl-3-trifluoromethyl-phenyl)-methanone;
[(R)-3-(2-Fluoro-3-[1,2,3]triazol-2-yl-benzyl)-morpholin-4-yl]-(4-methyl-2-[1,2,3]triazol-2-yl-phenyl)-methanone;
(5-Chloro-2-[1,2,3]triazol-2-yl-phenyl)-[(2R,5R)-2-methyl-5-(3-[1,2,3]triazol-2-yl-benzyl)-morpholin-4-yl]-methanone;
(4-Chloro-2-[1,2,3]triazol-2-yl-phenyl)-[(2R,5R)-2-methyl-5-(3-[1,2,3]triazol-2-yl-benzyl)-morpholin-4-yl]-methanone;
(5-Chloro-2-[1,2,3]triazol-2-yl-phenyl)-[(2R,5R)-5-(2-fluoro-5-[1,2,3]triazol-2-yl-benzyl)-2-methyl-morpholin-4-yl]-methanone;
(4-Chloro-2-[1,2,3]triazol-2-yl-phenyl)-[(2R,5R)-5-(2-fluoro-5-[1,2,3]triazol-2-yl-benzyl)-2-methyl-morpholin-4-yl]-methanone;
[(R)-3-(2-Methyl-5-pyrazol-1-yl-benzyl)-morpholin-4-yl]-(5-methyl-2-[1,2,3]triazol-2-yl-phenyl)-methanone;

[(R)-3-(2-Methyl-5-pyrazol-1-yl-benzyl)-morpholin-4-yl]-(4-methyl-2-[1,2,3]triazol-2-yl-phenyl)-methanone;

[(R)-3-(2-Methyl-5-pyrazol-1-yl-benzyl)-morpholin-4-yl]-(3-methyl-2-[1,2,3]triazol-2-yl-phenyl)-methanone;

(4-Chloro-2-[1,2,3]triazol-2-yl-phenyl)-[(R)-3-(2-methyl-5-[1,2,3]triazol-2-yl-benzyl)-morpholin-4-yl]-methanone;

[(R)-3-(4-Methyl-3-pyrimidin-2-yl-benzyl)-morpholin-4-yl]-(2-[1,2,3]triazol-2-yl-phenyl)-methanone;

[(R)-3-(4-Methyl-3-thiazol-2-yl-benzyl)-morpholin-4-yl]-(2-[1,2,3]triazol-2-yl-phenyl)-methanone; and

[(R)-3-(4-Chloro-3-pyrimidin-2-yl-benzyl)-morpholin-4-yl]-(2-[1,2,3]triazol-2-yl-phenyl)-methanone;

or a pharmaceutically acceptable salt thereof.

13. A pharmaceutical composition comprising, as active principle, one or more compounds according to claim 1, or a pharmaceutically acceptable salt thereof, and at least one therapeutically inert excipient.

14. A method of treatment of a disease treatable by antagonizing an orexin receptor, wherein the disease is selected from the group consisting of anxiety disorders, addiction disorders, mood disorders, and appetite disorders; comprising administering to a patient an effective amount of a compound of formula (I) as defined in claim 1, in free or pharmaceutically acceptable salt form.

15. The compound according to claim 1 which is (4-methyl-2-[1,2,3]triazol-2-yl-phenyl)-[(R)-3-(3-[1,2,3]triazol-2-yl-benzyl)-morpholin-4-yl]-methanone;

or a pharmaceutically acceptable salt thereof.

16. The compound according to claim 1, wherein the morpholine ring of the compounds of formula (I):

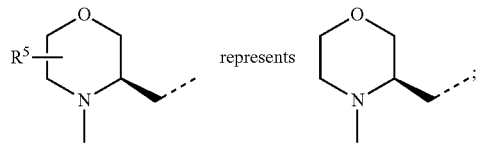

represents or a pharmaceutically acceptable salt thereof.

17. A compound according to claim 16, wherein the group

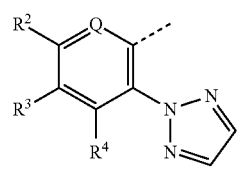

is a group independently selected from the following groups A) to F):

A)

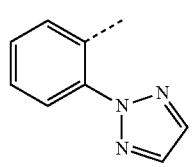 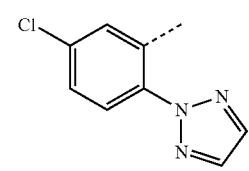

B)

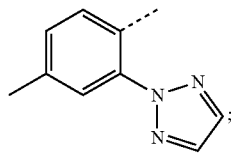

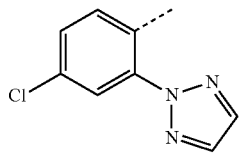 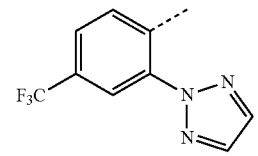

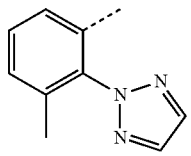 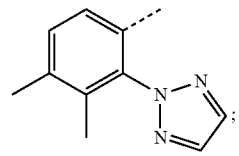

C)

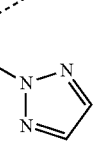 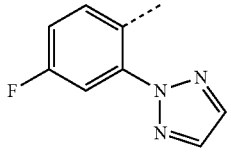

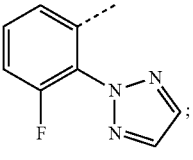

D)

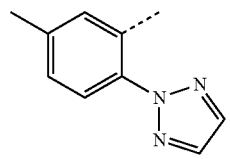 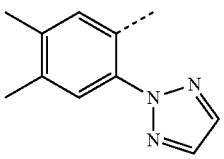

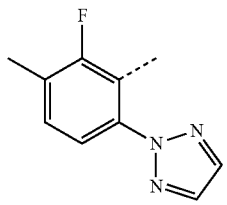 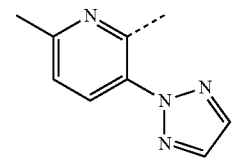

E)

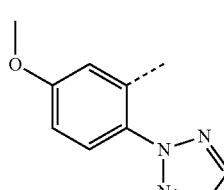 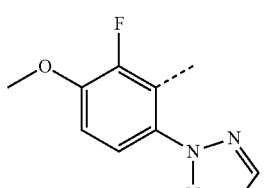

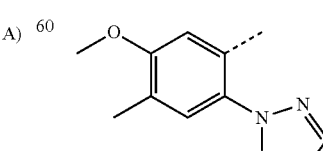 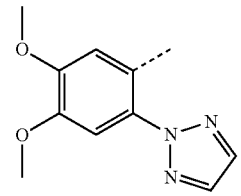

-continued
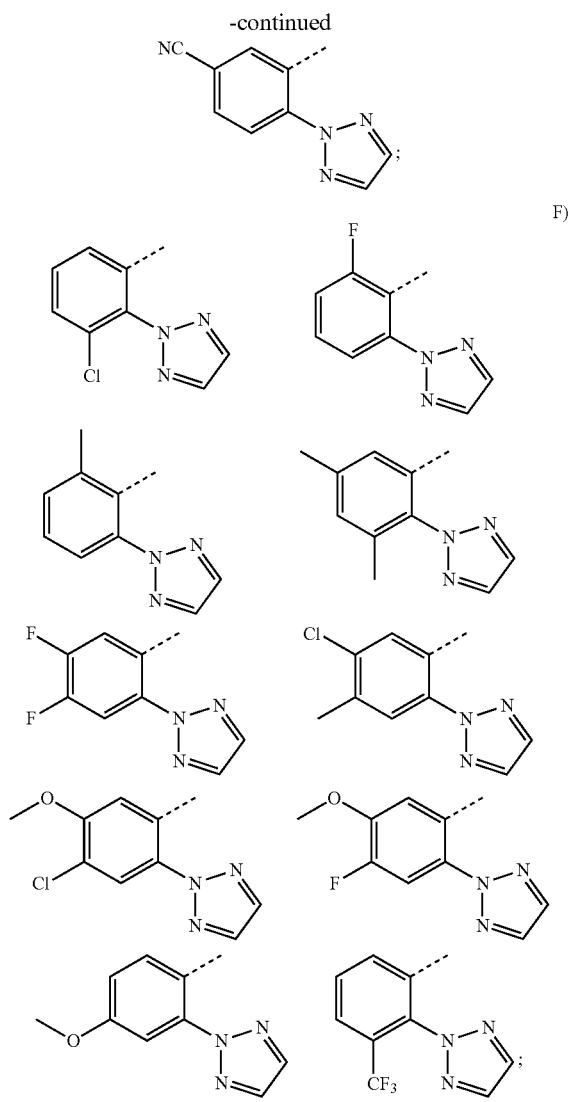
or a pharmaceutically acceptable salt thereof.
18. A compound according to claim 16, wherein the group
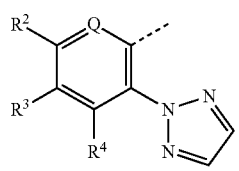
is a group selected from the group consisting of the following groups A) and B):
A)
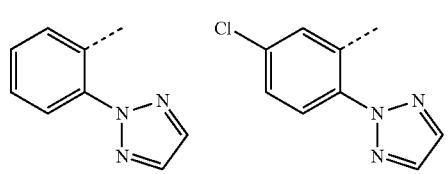
-continued
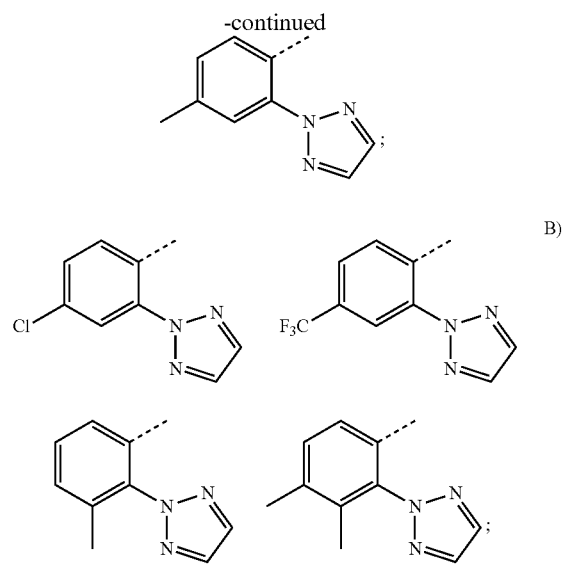
or a pharmaceutically acceptable salt thereof.
19. A compound according to claim 17, wherein the group
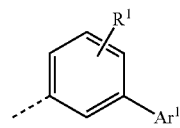
is a group independently selected from the following groups A) to H):
A)
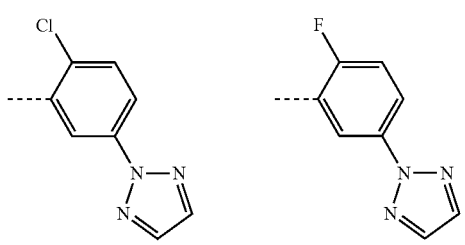
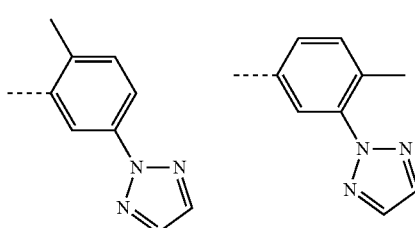
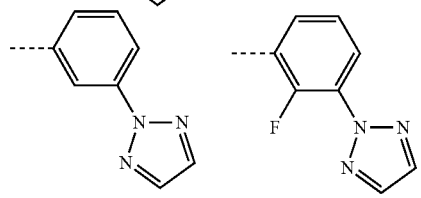

-continued
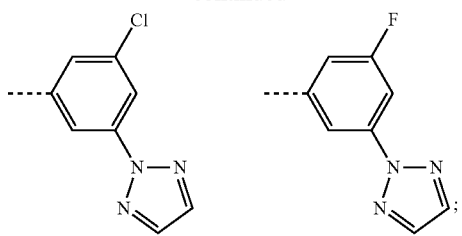
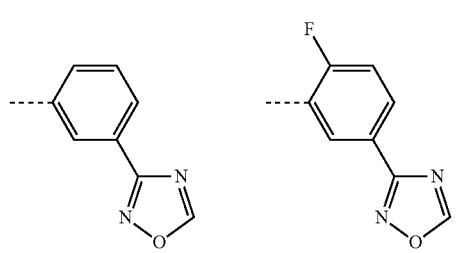
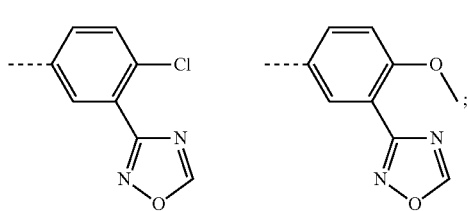
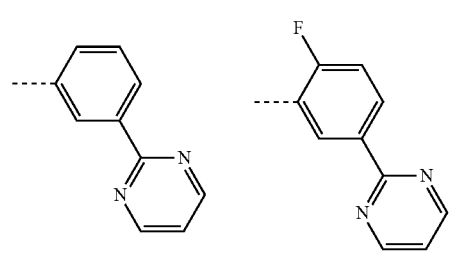
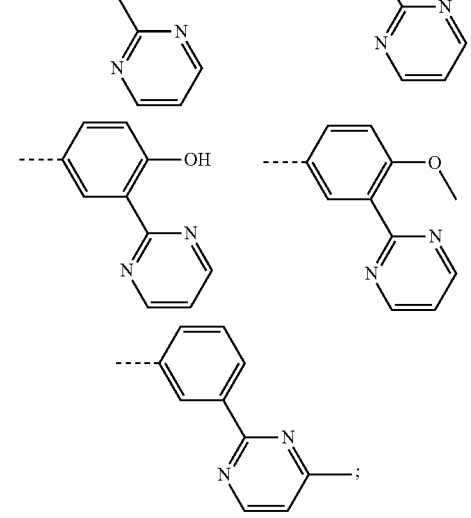
-continued
B)
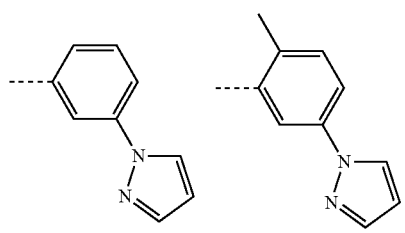
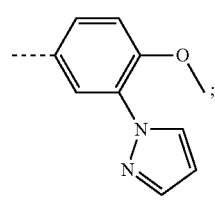
C)
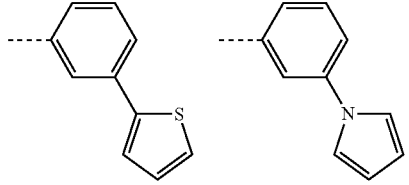
D)
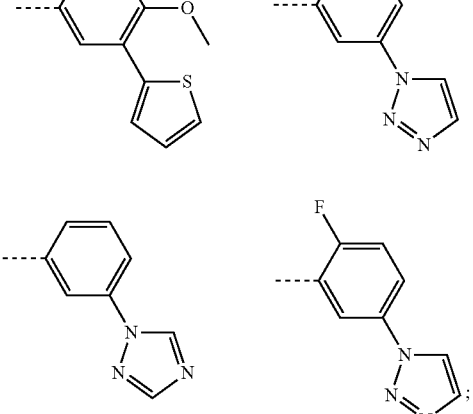
E)
F)
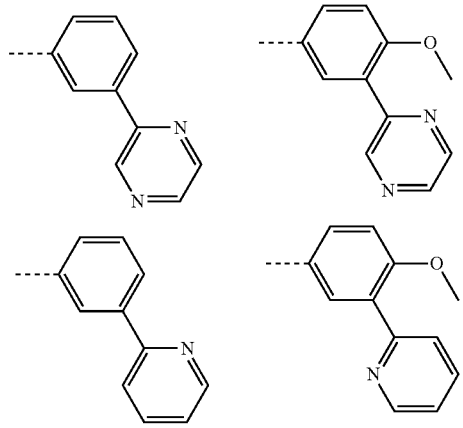

-continued

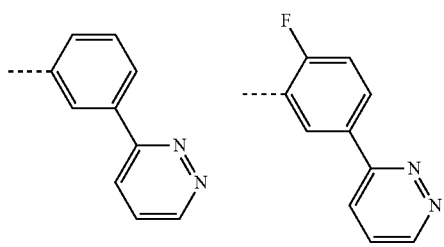

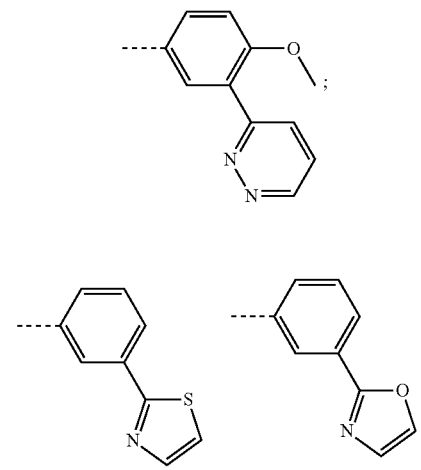

or a pharmaceutically acceptable salt thereof.

20. A compound according to claim 18, wherein the group

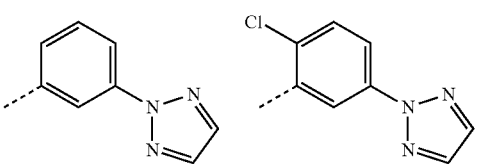

is a group selected from the group consisting of the following groups A) and B):

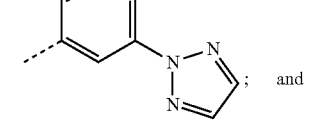

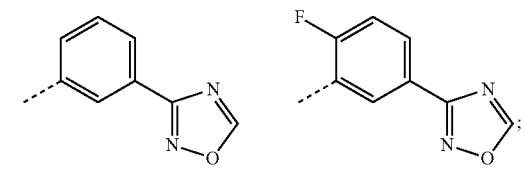

or a pharmaceutically acceptable salt thereof.

21. A pharmaceutical composition comprising, as active principle, the compound according to claim 15, or a pharmaceutically acceptable salt thereof, and at least one therapeutically inert excipient.

22. A pharmaceutical composition comprising, as active principle, a compound according to claim 19, or a pharmaceutically acceptable salt thereof, and at least one therapeutically inert excipient.

23. A pharmaceutical composition comprising, as active principle, a compound according to claim 20, or a pharmaceutically acceptable salt thereof, and at least one therapeutically inert excipient.

24. A method of treatment of a disease treatable by antagonizing an orexin receptor, wherein the disease is selected from the group consisting of anxiety disorders, addiction disorders, mood disorders, and appetite disorders; comprising administering to a patient an effective amount of a compound as defined in claim 20, in free or pharmaceutically acceptable salt form.

25. A method of treatment of a disease treatable by antagonizing an orexin receptor, wherein the disease is an anxiety disorder or an addiction disorder; comprising administering to a patient an effective amount of the compound of claim 15, in free or pharmaceutically acceptable salt form.

26. A method of treatment of a circumscribed threat induced anxiety disorder; comprising administering to a patient an effective amount of the compound of claim 15, in free or pharmaceutically acceptable salt form.

27. The method of claim 26, wherein the circumscribed threat induced anxiety disorder is a phobic anxiety disorder or a post-traumatic stress disorder.

* * * * *